(12) United States Patent
Judd et al.

(10) Patent No.: US 10,676,485 B2
(45) Date of Patent: Jun. 9, 2020

(54) MACROCYCLIC MCL-1 INHIBITORS AND METHODS OF USE

(71) Applicants: AbbVie Inc., North Chicago, IL (US); AbbVie Deutschland GmbH & Co. KG, Wiesbaden (DE)

(72) Inventors: Andrew S. Judd, Grayslake, IL (US); Aaron R. Kunzer, Arlington Heights, IL (US); Chunqiu Lai, Libertyville, IL (US); Andrew J. Souers, Libertyville, IL (US); Zhi-Fu Tao, Vernon Hills, IL (US); Anthony Mastracchio, Vernon Hills, IL (US); Xilu Wang, Libertyville, IL (US); Cheng Ji, Buffalo Grove, IL (US); Michael D. Wendt, Vernon Hills, IL (US); Xiaohong Song, Grayslake, IL (US); George A. Doherty, Libertyville, IL (US); Thomas D. Penning, Elmhurst, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/998,789

(22) Filed: Aug. 15, 2018

(65) Prior Publication Data

US 2019/0144465 A1 May 16, 2019

Related U.S. Application Data

(60) Provisional application No. 62/545,853, filed on Aug. 15, 2017, provisional application No. 62/555,475, filed on Sep. 7, 2017, provisional application No. 62/692,663, filed on Jun. 30, 2018.

(51) Int. Cl.
| | |
|---|---|
| *A61K 31/395* | (2006.01) |
| *A61P 35/02* | (2006.01) |
| *C07D 495/16* | (2006.01) |
| *C07D 495/18* | (2006.01) |
| *A61K 45/06* | (2006.01) |
| *C07D 495/22* | (2006.01) |
| *C07D 491/18* | (2006.01) |
| *A61K 31/519* | (2006.01) |
| *C07D 491/22* | (2006.01) |
| *A61P 35/00* | (2006.01) |

(52) U.S. Cl.
CPC .......... *C07D 495/16* (2013.01); *A61K 31/519* (2013.01); *A61K 45/06* (2013.01); *A61P 35/00* (2018.01); *A61P 35/02* (2018.01); *C07D 491/18* (2013.01); *C07D 491/22* (2013.01); *C07D 495/18* (2013.01); *C07D 495/22* (2013.01)

(58) Field of Classification Search
CPC ...... A61K 31/395; A61P 35/02; C07D 495/16
See application file for complete search history.

(56) References Cited

U.S. PATENT DOCUMENTS

| | | |
|---|---|---|
| 2009/0275533 A1 | 11/2009 | Hsieh et al. |
| 2015/0175623 A1 | 6/2015 | Kotschy et al. |
| 2019/0055264 A1 | 2/2019 | Brady et al. |

FOREIGN PATENT DOCUMENTS

| | | |
|---|---|---|
| CN | 107573360 A | 1/2018 |
| EP | 2886545 A1 | 6/2015 |
| WO | WO-2015097123 A1 | 7/2015 |
| WO | WO-2016207216 A1 | 12/2016 |
| WO | WO-2016207217 A1 | 12/2016 |
| WO | WO-2016207225 A1 | 12/2016 |
| WO | WO-2016207226 A1 | 12/2016 |
| WO | WO-2017125224 A1 | 7/2017 |
| WO | WO-2017182625 A1 | 10/2017 |

(Continued)

OTHER PUBLICATIONS

Ashkenazi A., et al., "From Basic Apoptosis Discoveries to Advanced Selective BCL-2 Family Inhibitors," Nature Reviews Drug Discovery, Feb. 17, 2017, vol. 16(4), pp. 273-284.

(Continued)

*Primary Examiner* — Brenda L Coleman

(74) *Attorney, Agent, or Firm* — Laura E. Johannes

(57) ABSTRACT

The present disclosure provides for compounds of formula (I)

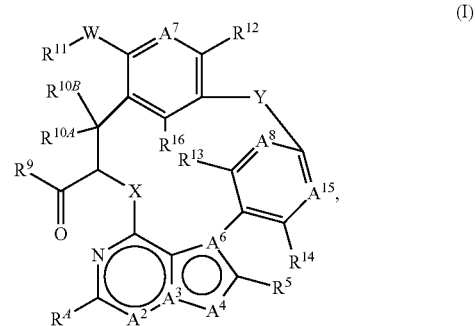

wherein $A^2$, $A^3$, $A^4$, $A^6$, $A^7$, $A^8$, $A^{15}$, $R^4$, $R^5$, $R^9$, $R^{10A}$, $R^{10B}$, $R^{11}$, $R^{12}$, $R^{13}$, $R^{14}$, $R^{16}$, W, X, and Y have any of the values defined in the specification, and pharmaceutically acceptable salts thereof, that are useful as agents in the treatment of diseases and conditions, including cancer. Also provided are pharmaceutical compositions comprising compounds of formula (I).

2 Claims, No Drawings

Specification includes a Sequence Listing.

(56) References Cited

FOREIGN PATENT DOCUMENTS

| WO | WO-2018015526 A1 | 1/2018 |
|----|------------------|--------|
| WO | WO-2018078064 A1 | 5/2018 |
| WO | WO-2018126898 A1 | 7/2018 |
| WO | WO-2018127575 A1 | 7/2018 |
| WO | WO-2019035899 A1 | 2/2019 |
| WO | WO-2019035914 A1 | 2/2019 |
| WO | WO-2019035927 A1 | 2/2019 |

OTHER PUBLICATIONS

Berge S.M., et al., "Pharmaceutical Salts," Journal of Pharmaceutical Sciences, 1977, vol. 66(1), pp. 1-19.
Beroukhim R., et al., "The Landscape of Somatic Copy-Number Alteration Across Human Cancers," Nature, Feb. 18, 2010, vol. 463(7283), pp. 899-905.
Bringmann G., et al., "Atroposelective Synthesis of Axially Chiral Biaryl Compounds," Angewandte Chemie International Edition in English, Aug. 2005, vol. 44(34), pp. 5384-5427.
Chen L., et al., "MCL-1 Inhibitors: a Patent Review," Expert Opinions on Therapeutic Patents, Feb. 2017, vol. 27 (2), pp. 163-178.
Derenne S., et al., "Antisense Strategy Shows that Mcl-1 rather than Bcl-2 or Bcl-xL is an Essential Survival Protein of Human Myeloma Cells," Blood, 2002, vol. 100, pp. 194-199.
Furniss B.S., et al., Vogel's Textbook of Practical Organic Chemistry, 5th Edition, Longman Scientific & Technical, 1989, Essex CM20 2JE, England, Table of Contents.
Glaser S.P., et al., "Anti-apoptotic Mcl-1 is Essential for the Development and Sustained Growth of Acute Myeloid Leukemia," Genes & Development, Jan. 2012, vol. 26(2), pp. 120-125.
Greene T.W., et al., Protective Groups in Organic Synthesis, 3rd Edition, John Wiley and Sons, Inc., 1999, Preface, Table of Contents, Abbreviations.
Gregory G.P., et al., "CDK9 Inhibition by Dinaciclib Potently Suppresses Mcl-1 to Induce Durable Apoptotic Responses in Aggressive MYC-driven B-cell Lymphoma in Vivo," Leukemia, Jun. 2015, vol. 29(6), pp. 1437-1441.
Hanahan D., et al., "The Hallmarks of Cancer," Cell, 2000, vol. 100 (1), pp. 57-70.
International Search Report and Written Opinion for Application No. PCT/US2018/00180, dated Nov. 5, 2018, 6 pages.
IUPAC 1974 Recommendations for Section E, Fundamental Stereochemistry, Pure and Applied Chemistry, 1976, vol. 45, pp. 13-30.
Kelly G.L., et al., "Targeting of MCL-1 kills MYC-driven Mouse and Human Lymphomas Even when they Bear Mutations in p53," Genes & Development, Jan. 2014, vol. 28(1), pp. 58-70.
Kim W., et al., "Alvocidib Potentiates the Activity of Azacytidine in an MCL-1-Dependent Fashion," Blood, 2015, vol. 126, p. 1343.
Kotschy A., et al., "The MCL1 Inhibitor S63845 is Tolerable and Effective in Diverse Cancer Models," Nature, Oct. 2016, vol. 538(7626), pp. 477-482.
Stoermer R., et al., "Synthese Aromatischer Alkohole Mit Formaldehyd," Mittheilungen, Aug. 1901, vol. 34(2), pp. 2455-2460.
Taygerly J.P., et al., "Small-Molecule Antagonists of MCL-1," Medicinal Chemistry Reviews, Nov. 2017, vol. 52 (14), pp. 263-277.
Wang, Z. X., "An Exact Mathematical Expression for Describing Competitive Binding of Two Different Ligands to a Protein Molecule," FEBS Letters, 1995, vol. 360 (2), pp. 111-114.
Wertz I.E., "Sensitivity to Antitubulin Chemotherapeutics is Regulated by MCL1 and FBW7," Nature, Mar. 2011, vol. 471(7336), pp. 110-114.
Youle R.J. et al., "The BCL-2 Protein Family: Opposing Activities that Mediate Cell Death," Nature Reviews Molecular Cell Biology, Jan. 2008, vol. 9(1), pp. 47-59.
Co-pending U.S. Appl. No. 16/575,114, filed Sep. 18, 2019.
International Search Report and Written Opinion for Application No. PCT/US2018/00167, dated Jan. 9, 2019, 5 pages.
International Search Report and Written Opinion for Application No. PCT/US2018/00183, dated Dec. 13, 2018, 5 pages.
International Search Report and Written Opinion for Application No. PCT/US2018/00196, dated Feb. 21, 2019, 6 pages.
European Search Report for Application No. EP18846737 dated Apr. 03, 2020, 4 pages.

MACROCYCLIC MCL-1 INHIBITORS AND METHODS OF USE

BACKGROUND

Technical Field

This disclosure relates to inhibitors of induced myeloid leukemia cell differentiation protein (MCL-1), compositions containing compounds described herein, and methods of treatment thereof.

SEQUENCE LISTING

The instant application contains a Sequence Listing which has been submitted electronically in ASCII format and is hereby incorporated by reference in its entirety. Said ASCII copy, created on Feb. 4, 2019, is named ABV12392USO1_SEQUENCE_LISTING and is 728 bytes in size.

Description of Related Technology

Apoptosis, a type of programmed cell death, is critical for normal development and for preservation of cellular homeostasis. Dysregulation of apoptosis is recognized to play an important role in the development of various diseases. For example, blocks in apoptotic signaling are a common requirement for oncogenesis, tumor maintenance and chemoresistance (Hanahan, D. et al. Cell 2000, 100, 57). Apoptotic pathways can be divided into two categories, intrinsic and extrinsic, depending on the origin of the death signal. The intrinsic pathway, or mitochondrial apoptotic pathway, is initiated by intracellular signals that ultimately lead to mitochondrial outer membrane permeabilization (MOMP), caspase activation and cell death.

The intrinsic mitochondrial apoptotic pathway is highly regulated, and the dynamic binding interactions between the pro-apoptotic (e.g. BAX, BAK, BAD, BIM, NOXA) and anti-apoptotic (e.g. BCL-2, BCL-XL, MCL-1) BCL-2 family members control commitment to cell death (Youle, R. J, et al. Nat. Rev. Mol. Cell Biol. 2008, 9, 47). BAK and BAX are essential mediators that upon conformational activation cause MOMP, an irreversible event that subsequently leads to cytochrome c release, caspase activation and cell death. Anti-apoptotic BCL-2 family members such as BCL-2, BCL-XL and MCL-1 can bind and sequester their pro-apoptotic counterparts, thus preventing BAX/BAK activation and promoting cell survival.

BCL-2 plays a dominant role in the survival of several hematological malignancies where it is frequently overexpressed, whereas BCL-XL is a key survival protein in some hematological and solid tumors. The related anti-apoptotic protein MCL-1 is implicated in mediating malignant cell survival in a number of primary tumor types (Ashkenazi, A, et al. Nature Rev Drug Discovery 2017, 16, 273). MCL-1 gene amplifications are frequently found in human cancers, including breast cancer and non-small cell lung cancer (Beroukhim, R, et al. Nature 2010, 463, 899), and the MCL-1 protein has been shown to mediate survival in models of multiple myeloma (Derenn, S, et al. Blood 2002, 100, 194), acute myeloid leukemia (Glaser, S, et al. Genes Dev 2012, 26, 120) and MYC-driven lymphomas (Kelly, G, et al. Genes Dev 2014, 28, 58). Specific compounds that broadly inhibit gene transcription (e.g., CDK9 inhibitors) exert their cytotoxic effects on tumor cells, at least in part, by down-regulating MCL-1 (Kotschy, A, et al. Nature 2016, 538.477); alvocidib (Kim. W, et al. Blood 2015, 126, 1343) and dinaciclib (Gregory-, G, et al. Leukemia 2015, 29, 1437) are two examples that have demonstrated clinical proof-of-concept in patients with hematological malignancies. Literature data supports a role for MCL-1 as a resistance factor to anticancer therapies such gemcitabine, vincristine and taxol (Wertz, I. E. et al. Nature 2011, 471, 110). Accordingly, there is a need in the therapeutic arts for compounds which inhibit the activity of the MCL-1 protein.

SUMMARY

In embodiments the present disclosure provides for compounds of formula (I) or a pharmaceutically acceptable salt thereof.

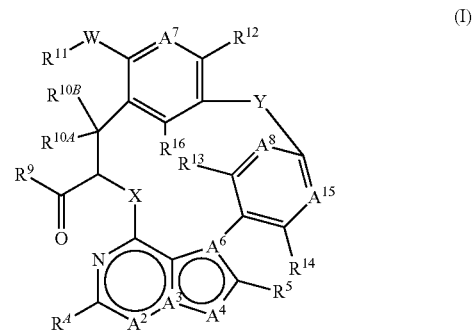

(I)

wherein
$A^2$ is $CR^2$, $A^3$ is N, $A^4$ is $CR^{4a}$, and $A^6$ is C; or
$A^2$ is $CR^2$, $A^3$ is N, $A^4$ is O or S, and $A^6$ is C; or
$A^2$ is $CR^2$, $A^3$ is C, $A^4$ is O or S and $A^6$ is C; or
$A^2$ is N, $A^3$ is C, $A^4$ is O or S and $A^6$ is C; or
$A^2$ is N, $A^3$ is C, $A^4$ is $CR^{4a}$, and $A^6$ is N;
$R^A$ is hydrogen, $CH_3$, halogen, CN, $CH_2F$, $CHF_2$, or $CF_3$;
X is O, or $N(R^{x2})$; wherein $R^{x2}$ is hydrogen, $C_1$-$C_3$ alkyl, or unsubstituted cyclopropyl;
Y is $(CH_2)_m$, —CH=CH—$(CH_2)_n$—, —$(CH_2)_p$—CH=CH—, or —$(CH_2)_q$—CH=CH—$(CH_2)_r$; wherein 0, 1, 2, or 3 $CH_2$ groups are each independently replaced by O, $N(R^{ya})$, $C(R^{ya})(R^{yb})$, C(O), NC(O)$R^{ya}$, or $S(O)_2$;
m is 2, 3, 4, or 5;
n is 1, 2, or 3;
p is 1, 2, or 3;
q is 1 or 2; and
r is 1 or 2; wherein the sum of q and r is 2 or 3;
$R^{ya}$, at each occurrence, is independently hydrogen, $C_2$-$C_6$ alkenyl, $C_2$-$C_6$ alkynyl, $G^1$, $C_1$-$C_6$ alkyl, or $C_1$-$C_6$ haloalkyl; wherein the $C_2$-$C_6$ alkenyl, $C_2$-$C_6$ alkynyl, $C_1$-$C_6$ alkyl, and $C_1$-$C_6$ haloalkyl are optionally substituted with 1 or 2 substituents independently selected from the group consisting of oxo, —$N(R^{yd})(R^{ye})$, $G^1$, —$OR^{yf}$, —$SR^{yg}$, —$S(O)_2N(R^{yd})(R^{ye})$, and —$S(O)_2$-$G^1$; and
$R^{yb}$ is $C_2$-$C_6$ alkenyl, $C_2$-$C_6$ alkynyl, $G^1$, $C_1$-$C_6$ alkyl, or $C_1$-$C_6$ haloalkyl; wherein the $C_2$-$C_6$ alkenyl, $C_2$-$C_6$ alkynyl, $C_1$-$C_6$ alkyl, and $C_1$-$C_6$ haloalkyl are optionally substituted with 1 or 2 substituents independently selected from the group consisting of oxo, —$N(R^{yd})(R^{ye})$, $G^1$, —$OR^{yf}$, —$SR^{yg}$, —$S(O)_2N(R^{yd})(R^{ye})$, and —$S(O)_2$-$G^1$; or
$R^{ya}$ and $R^{yb}$, together with the carbon atom to which they are attached, form a $C_3$-$C_7$ monocyclic cycloalkyl, $C_4$-$C_7$ monocyclic cycloalkenyl, or a 4-7 membered monocyclic heterocycle; wherein the $C_3$-$C_7$ monocyclic cycloalkyl, $C_4$-$C_7$ monocyclic cycloalkenyl, and the 4-7 membered monocyclic heterocycle are each optionally substituted with 1 —$OR^m$ and 0, 1, 2, or 3 independently selected $R^s$ groups;

$R^{yd}$, $R^{ye}$, $R^{yf}$, and $R^{yg}$, at each occurrence, are each independently hydrogen, $G^1$, $C_1$-$C_6$ alkyl, or $C_1$-$C_6$ haloalkyl; wherein the $C_1$-$C_6$ alkyl and the $C_1$-$C_6$ haloalkyl are optionally substituted with one substituent selected from the group consisting of $G^1$, —$OR^{yh}$, —$SR^{yh}$, —$SO_2R^{yh}$, and —$N(R^{yi})(R^{yk})$;

$G^1$, at each occurrence, is piperazinyl, piperidinyl, pyrrolidinyl, thiomorpholinyl, tetrahydropyranyl, morpholinyl, oxetanyl, 1,3-dioxolanyl, 1,3-dioxanyl, 1,4-dioxanyl, 1,3-dioxepanyl, or 1,4-dioxepanyl; wherein each $G^1$ is optionally substituted with 1 —$OR^m$ and 0, 1, 2, or 3 substituents independently selected from the group consisting of $G^2$, —($C_1$-$C_6$ alkylenyl)-$G^2$, and $R^s$;

$G^2$, at each occurrence, is a $C_3$-$C_7$ monocyclic cycloalkyl, $C_4$-$C_7$ monocyclic cycloalkenyl, oxetanyl, morpholinyl, 1,3-dioxolanyl, 1,3-dioxanyl, 1,4-dioxanyl, 1,3-dioxepanyl, or 1,4-dioxepanyl; wherein each $G^2$ is optionally substituted with 1 —$OR^m$ and 0, 1, or 2 independently selected $R^t$ groups;

$R^2$ is independently hydrogen, halogen, $CH_3$, or CN;

$R^{4a}$, at each occurrence, is independently hydrogen, halogen, CN, $C_2$-$C_4$ alkenyl, $C_2$-$C_4$ alkynyl, $C_1$-$C_4$ alkyl, $C_1$-$C_4$ haloalkyl, $G^4$, $C_1$-$C_4$ alkyl-$G^4$, or $C_1$-$C_4$ alkyl-O-$G^4$; wherein each $G^4$ is independently $C_6$-$C_{10}$ aryl, $C_3$-$C_7$ monocyclic cycloalkyl, $C_4$-$C_7$ monocyclic cycloalkenyl, or 4-7 membered heterocycle; wherein each $G^4$ is optionally substituted with 1, 2, or 3 $R^u$ groups;

$R^5$ is independently hydrogen, halogen, $G^3$, $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, and $C_2$-$C_6$ alkynyl are each optionally substituted with one $G^3$;

$G^3$, at each occurrence, is independently $C_6$-$C_{10}$ aryl, 5-11 membered heteroaryl, $C_3$-$C_{11}$ cycloalkyl, $C_4$-$C_{11}$ cycloalkenyl, oxetanyl, 2-oxaspiro[3.3]heptanyl, 1,3-dioxolanyl, 1,3-dioxanyl, 1,4-dioxanyl, 1,3-dioxepanyl, 2,3-dihydro-1,4-dioxinyl, or 1,4-dioxepanyl; wherein each $G^3$ is optionally substituted with 1, 2, or 3 $R^v$ groups;

$A^7$ is N or $CR^7$;
$A^8$ is N or $CR^8$;
$A^{15}$ is N or $CR^{15}$;

$R^7$, $R^{12}$ and $R^{16}$ are each independently hydrogen, halogen, $C_1$-$C_4$ alkyl, $C_1$-$C_4$ haloalkyl, —CN, —$OR^{7a}$, —$SR^{7a}$, or —$N(R^{7b})(R^{7c})$;

$R^8$, $R^{13}$, $R^{14}$, and $R^{15}$ are each independently hydrogen, halogen, $C_1$-$C_4$ alkyl, $C_1$-$C_4$ haloalkyl, —CN, —$OR^{8a}$, —$SR^{8a}$, —$N(R^{8b})(R^{8c})$, or $C_3$-$C_4$ monocyclic cycloalkyl; wherein the $C_3$-$C_4$ monocyclic cycloalkyl is optionally substituted with one or two substituents independently selected from the group consisting of halogen, $C_1$-$C_3$ alkyl, and $C_1$-$C_3$ haloalkyl; or $R^8$ and $R^{13}$ are each independently hydrogen, halogen, $C_1$-$C_4$ alkyl, $C_1$-$C_4$ haloalkyl, —CN, —$OR^{8a}$, —$SR^{8a}$, —$N(R^{8b})(R^{8c})$, or $C_3$-$C_4$ monocyclic cycloalkyl; wherein the $C_3$-$C_4$ monocyclic cycloalkyl is optionally substituted with one or two substituents independently selected from the group consisting of halogen, $C_1$-$C_3$ alkyl, and $C_1$-$C_3$ haloalkyl; and $R^{14}$ and $R^{15}$, together with the carbon atoms to which they are attached, form a monocyclic ring selected from the group consisting of benzene, cyclobutane, cyclopentane, and pyridine; wherein the monocyclic ring is optionally substituted with 1, 2, or 3 substituents independently selected from the group consisting of halogen, $C_1$-$C_4$ alkyl, $C_1$-$C_4$ haloalkyl, —CN, —$OR^{8a}$, —$SR^{8a}$, and —$N(R^{8b})(R^{8c})$;

$R^9$ is —OH, —O—$C_1$-$C_4$ alkyl, —O—$CH_2$—OC(O)($C_1$-$C_6$ alkyl), —NHOH,

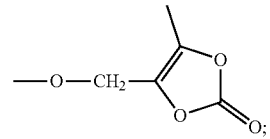

or —N(H)S(O)$_2$—($C_1$-$C_6$ alkyl);

$R^{10A}$ and $R^{10B}$, are each independently hydrogen, $C_1$-$C_3$ alkyl, or $C_1$-$C_3$ haloalkyl; or $R^{10A}$ and $R^{10B}$, together with the carbon atom to which they are attached, form a cyclopropyl; wherein the cyclopropyl is optionally substituted with one or two substituents independently selected from the group consisting of halogen and $CH_3$;

W is —CH=CH—, $C_1$-$C_4$ alkyl, —O—CHF—, -$L^1$-$CH_2$—, or —$CH_2$-$L^1$-; wherein $L^1$ at each occurrence, is independently O, S, S(O), S(O)$_2$, S(O)$_2$N(H), N(H), or N($C_1$-$C_3$ alkyl);

$R^{11}$ is a $C_6$-$C_{10}$ aryl or a 5-11 membered heteroaryl; wherein each $R^{11}$ is optionally substituted with 1, 2, or 3 independently selected $R^W$ groups;

$R^W$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{11a}$, —$SR^{11b}$, —$S(O)_2R^{11b}$, —$S(O)_2N(R^{11c})_2$, —$C(O)R^{11a}$, —$C(O)N(R^{11c})_2$, —$N(R^{11c})_2$, —$N(R^{11c})C(O)R^{11b}$, —$N(R^{11c})S(O)_2R^{11b}$, —$N(R^{11c})C(O)O(R^{11b})$, —$N(R^{11c})C(O)N(R^{11c})_2$, $G^4$, —($C_1$-$C_6$ alkylenyl)-$OR^{11a}$, —($C_1$-$C_6$ alkylenyl)-OC(O)N($R^{11c})_2$, —($C_1$-$C_6$ alkylenyl)-$SR^{11a}$, —($C_1$-$C_6$ alkylenyl)-$S(O)_2R^{11b}$, —($C_1$-$C_6$ alkylenyl)-$S(O)_2N(R^{11c})_2$, —($C_1$-$C_6$ alkylenyl)-$C(O)R^{11a}$, —($C_1$-$C_6$ alkylenyl)-$C(O)N(R^{11c})_2$, —($C_1$-$C_6$ alkylenyl)-$N(R^{11c})_2$, —($C_1$-$C_6$ alkylenyl)-$N(R^{11c})C(O)R^{11b}$, —($C_1$-$C_6$ alkylenyl)-$N(R^{11c})S(O)_2R^{11b}$, —($C_1$-$C_6$ alkylenyl)-$N(R^{11c})C(O)O(R^{11b})$, —($C_1$-$C_6$ alkylenyl)-$N(R^{11c})C(O)N(R^{11c})_2$, —($C_1$-$C_6$ alkylenyl)-CN, or —($C_1$-$C_6$ alkylenyl)-$G^4$;

$R^{11a}$ and $R^{11c}$, at each occurrence, are each independently hydrogen, $C_1$-$C_6$ alkyl, $C_2$-$C_6$ alkenyl, $C_1$-$C_6$ haloalkyl, $G^4$, —($C_2$-$C_6$ alkylenyl)-$OR^{11d}$, —($C_2$-$C_6$ alkylenyl)-N($R^{11e})_2$, or —($C_2$-$C_6$ alkylenyl)-$G^4$;

$R^{11b}$, at each occurrence, is independently $C_1$-$C_6$ alkyl, $C_2$-$C_6$ alkenyl, $C_1$-$C_6$ haloalkyl, $G^4$, —($C_2$-$C_6$ alkylenyl)-$OR^{11d}$, —($C_2$-$C_6$ alkylenyl)-N($R^{11e})_2$, or —($C_2$-$C_6$ alkylenyl)-$G^4$;

$G^4$, at each occurrence, is independently phenyl, monocyclic heteroaryl, $C_3$-$C_{11}$ cycloalkyl, $C_4$-$C_{11}$ cycloalkenyl, oxetanyl, tetrahydrofuranyl, tetrahydropyranyl, 2,6-dioxa-9-azaspiro[4.5]decanyl, 2-oxa-5-azabicyclo[2.2.1]heptanyl, 3-oxa-8-azabicyclo[3.2.1]octanyl, piperidinyl, piperazinyl, azetidinyl, morpholinyl, dihydropyranyl, tetrahydropyridinyl, dihydropyrrolyl, pyrrolidinyl, 2,3-dihydrodioxinyl, 1,3-dioxolanyl, 1,3-dioxanyl, 1,4-dioxanyl, 1,3-dioxepanyl, or 1,4-dioxepanyl; wherein each $G^4$ is optionally substituted with 1 —OR$^m$ and 0, 1, 2, or 3 substituents independently selected from the group consisting of G$^5$, R$^y$, —(C$_1$-C$_6$ alkylenyl)-G$^5$, —(C$_1$-C$_6$ alkylenyl)-L$^2$-(C$_1$-C$_6$ alkylenyl)-G$^5$, and -L$^2$-(C$_1$-C$_6$ alkylenyl)$_s$-G$^5$;

L$^2$ is O, C(O), N(H), N(C$_1$-C$_6$ alkyl), NHC(O), C(O)O, S, S(O), or S(O)$_2$;

s is 0 or 1;

G$^5$, at each occurrence, is independently phenyl, monocyclic heteroaryl, C$_3$-C$_7$ monocyclic cycloalkyl, C$_4$-C$_7$ monocyclic cycloalkenyl, piperazine, 1,3-dioxolanyl, 1,3-dioxanyl, 1,4-dioxanyl, 1,3-dioxepanyl, or 1,4-dioxepanyl; wherein each G$^5$ is optionally substituted with 1 independently selected —OR$^m$ or 0, 1, 2, or 3 R$^z$ groups;

R$^s$, R$^t$, R$^u$, R$^v$, R$^y$, and R$^z$, at each occurrence, are each independently C$_1$-C$_6$ alkyl, C$_2$-C$_6$ alkenyl, C$_2$-C$_6$ alanyl, halogen, C$_1$-C$_6$ haloalkyl, —CN, oxo, NO$_2$, P(O)(R$^k$)$_2$, —OC(O)R$^k$, —OC(O)N(R$^j$)$_2$, —SR$^j$, —S(O)$_2$R$^k$, —S(O)$_2$N(R$^j$)$_2$, —C(O)R$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)C)(R$^k$), —N(R$^j$)C(O)N(R$^j$)$_2$, —(C$_1$-C$_6$ alkylenyl)-OR$^j$, (C$_1$-C$_6$ alkylenyl)-OC(O)N(R$^j$)$_2$, —(C$_1$-C$_6$ alkylenyl)-SR$^j$, —(C$_1$-C$_6$ alkylenyl)-S(O)$_2$R$^k$, —(C$_1$-C$_6$ alkylenyl)-S(O)$_2$N(R$^j$)$_2$, —(C$_1$-C$_6$ alkylenyl)-C(O)R$^j$, —(C$_1$-C$_6$ alkylenyl)-C(O)N(R$^j$)$_2$, —(C$_1$-C$_6$ alkylenyl)-N(R$^j$)$_2$, —(C$_1$-C$_6$ alkylenyl)-N(R$^j$)C(O)R$^k$, —(C$_1$-C$_6$ alkylenyl)-N(R$^j$)S(O)$_2$R$^k$, —(C$_1$-C$_6$ alkylenyl)-N(R$^j$)C(O)O(R$^k$), —(C$_1$-C$_6$ alkylenyl)-N(R$^j$)C(O)N(R$^j$)$_2$, or —(C$_1$-C$_6$ alkylenyl)-CN;

R$^m$ is hydrogen, C$_1$-C$_6$ alkyl, C$_1$-C$_6$ haloalkyl, —(C$_2$-C$_6$ alkylenyl)-OR$^j$, or —(C$_2$-C$_6$ alkylenyl)-N(R$^j$)$_2$;

R$^{yh}$, R$^{vi}$, R$^{yk}$, R$^{7a}$, R$^{7b}$, R$^{7c}$, R$^{8a}$, R$^{8b}$, R$^{8c}$, R$^{11d}$, R$^{11e}$, and R$^j$, at occurrence, are each independently hydrogen, C$_1$-C$_6$ alkyl, or C$_1$-C$_6$ haloalkyl; and R$^k$, at each occurrence, is independently C$_1$-C$_6$ alkyl or C$_1$-C$_6$ haloalkyl;

wherein at least one of G$^1$, G$^2$, G$^3$, G$^4$, and G$^5$ is 2,2-dimethyl-1,3-dioxolanyl, 2,3-dihydro-1,4-dioxinyl, 1,3-dioxolanyl, 1,3-dioxanyl, 1,4-dioxanyl, 1,3-dioxepanyl, or 1,4-dioxepanyl.

In embodiments, the present disclosure provides for methods of treating or preventing disorders that are amenable to inhibition of MCL-1. Such methods comprise administering to the subject a therapeutically effective amount of a compound of formula (I), alone, or in combination with a pharmaceutically acceptable carrier.

In embodiments, some methods are directed to treating or preventing cancer. That is, in embodiments, die present disclosure provides for methods for treating or preventing cancer, wherein such methods comprise administering to the subject a therapeutically effective amount of a compound of formula (I), alone, or in combination with a pharmaceutically acceptable carrier.

In embodiments, the present disclosure relates to methods of treating cancer in a subject comprising administering a therapeutically effective amount of a compound of formula (I), or a pharmaceutically acceptable salt thereof, to a subject in need thereof. In certain embodiments, the cancer is multiple myeloma. In certain embodiments, the methods further comprise administering a therapeutically effective amount of at least one additional therapeutic agent.

In embodiments, the present disclosure provides the use of a compound of formula (I), alone or in combination with at least one additional therapeutic agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with at least one additional therapeutic agent, are also provided.

DETAILED DESCRIPTION

In embodiments, the present disclosure provides for compounds of Formula (I), or a pharmaceutically acceptable salt thereof,

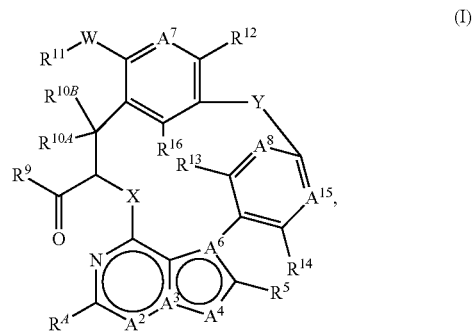

(I)

wherein A$^2$, A$^3$, A$^4$, A$^6$, A$^7$, A$^8$, A$^{15}$, R$^4$, R$^5$, R$^9$, R$^{10A}$, R$^{10B}$, R$^{11}$, R$^{12}$, R$^{13}$, R$^{14}$, R$^{16}$, W, X, and Y are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a." "an," and "the" include plural referents unless the context clearly dictates otherwise. Thus, for example, reference to "a compound" includes a single compound as well as one or more of the same or different compounds, reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "C$_2$-C$_6$ alkenyl" and "C$_2$-C$_4$ alkenyl" means an alkenyl group containing 2-6 carbon atoms and 2-4 carbon atoms respectively. Non-limiting examples of alkenyl include buta-1,3-dienyl, ethenyl, 2-propenyl, 2-methyl-2-propenyl, 3-butenyl, 4-pentenyl, and 5-hexenyl. The terms "alkenyl," "C$_2$-C$_6$ alkenyl," and "C$_2$-C$_4$ alkenyl" used herein are unsubstituted, unless otherwise indicated.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms, "$C_1$-$C_4$ alkyl" means an alkyl substituent containing from 1 to 4 carbon atoms, and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_1$-$C_4$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms ($C_1$-$C_4$ alkylenyl) or of 1 to 3 carbon atoms ($C_1$-$C_3$ alkylenyl) or of 2 to 6 carbon atoms ($C_2$-$C_6$ alkylenyl). Examples of alkylenyl include, but are not limited to, —$CH_2$—, —$CH_2CH_2$—, —$C((CH_3)_2)$—$CH_2CH_2CH_2$—, —$C((CH_3)_2)$—$CH_2CH_2$—, —$CH_2CH_2CH_2CH_2$—, and —$CH_2CH(CH_3)CH_2$—.

The term "$C_2$-$C_6$ alkynyl" and "$C_2$-$C_4$ alkynyl" as used herein, means a straight or branched chain hydrocarbon radical containing from 2 to 6 carbon atoms and 2 to 4 carbon atoms respectively, and containing at least one carbon-carbon triple bond. Representative examples of $C_2$-$C_6$ alkynyl and $C_2$-$C_4$ alkynyl include, but are not limited, to acetylenyl, 1-propynyl, 2-propynyl, 3-butynyl, 2-pentynyl, and 1-butynyl. The terms "alkynyl," "$C_2$-$C_6$ alkynyl," and "$C_2$-$C_4$ alkynyl" used herein are unsubstituted, unless otherwise indicated.

The term "$C_6$-$C_{10}$ aryl" as used herein, means phenyl or a bicyclic aryl. The bicyclic aryl is naphthyl, or a phenyl fused to a $C_3$-$C_6$ monocyclic cycloalkyl, or a phenyl fused to a $C_4$-$C_6$ monocyclic cycloalkenyl. Non-limiting examples of the aryl groups include dihydroindenyl, indenyl, naphthyl, dihydronaphthalenyl, and tetrahydronaphthalenyl.

The term "$C_3$-$C_{11}$ cycloalkyl" as used herein, means a hydrocarbon ring radical containing 3-11 carbon atoms, zero heteroatom, and zero double bond. The $C_3$-$C_{11}$ cycloalkyl group may be a single-ring (monocyclic) or have two or more rings (polycyclic or bicyclic). Monocyclic cycloalkyl groups typically contain from 3 to 8 carbon ring atoms ($C_3$-$C_8$ monocyclic cycloalkyl) or 3 to 7 carbon ring atoms ($C_3$-$C_7$ monocyclic cycloalkyl), and even more typically 3-6 carbon ring atoms ($C_3$-$C_6$ monocyclic cycloalkyl). Examples of monocyclic cycloalkyls include cyclopropyl, cyclobutyl, cyclopentyl, cyclohexyl, cycloheptyl, and cyclooctyl. Polycyclic cycloalkyl groups contain two or more rings, and bicyclic cycloalkyls contain two rings. In certain embodiments, the polycyclic cycloalkyl groups contain 2 or 3 rings. The rings within the polycyclic and the bicyclic cycloalkyl groups may be in a bridged, fused, or spiro orientation, or combinations thereof. In a spirocyclic cycloalkyl, one atom is common to two different rings. An example of a spirocyclic cycloalkyl is spiro[4.5]decane. In a bridged cycloalkyl, the rings share at least two non-adjacent atoms. Examples of bridged cycloalkyls include, but are not limited to, bicyclo[1.1.1]pentanyl, bicyclo[2.2.2]octanyl, bicyclo[3.2.1]octanyl, bicyclo[3.1.1]heptyl, bicyclo[2.2.1] heptyl, bicyclo[3.2.2]nonyl, bicyclo[3.3.1]nonyl, bicyclo [4.2.1]nonyl, tricyclo[3.3.1.0$^{3,7}$]nonyl (octahydro-2,5-methanopentalenyl or noradamantyl), tricyclo[3.3.1.1$^{3,7}$] decyl (adamantyl), and tricyclo[4.3.1.1$^{3,8}$]undecyl (homoadamantyl). In a fused ring cycloalkyl, the rings share one common bond. Example of fused-ring cycloalkyl include, but are not limited to, decalin (decahydronaphthyl).

The term "$C_3$-$C_7$ monocyclic cycloalkyl" as used herein, means cyclopropyl, cyclobutyl, cyclopentyl, cyclohexyl, and cycloheptyl.

The term "$C_4$-$C_{11}$ cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic and bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and the bicyclic cycloalkenyls, including exemplary rings, are optionally substituted unless otherwise indicated. The monocyclic cycloalkenyl and bicyclic cycloalkenyl are attached to the parent molecular moiety through any substitutable atom contained within the ring systems.

The term "$C_3$-$C_6$ monocyclic cycloalkyl" as used herein, means cyclopropyl, cyclobutyl, cyclopentyl, and cyclohexyl.

The term "$C_3$-$C_4$ monocyclic cycloalkyl" as used herein, means cyclopropyl and cyclobutyl.

The term "$C_4$-$C_6$ monocyclic cycloalkenyl" as used herein, means cyclobutenyl, cyclopentenyl, and cyclohexenyl.

The term "halo" or "halogen" as used herein, means Cl, Br, I, and F.

The term "haloalkyl" as used herein, means an alkyl group, as defined herein, in which one, two, three, four, five, or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_4$ haloalkyl" means a $C_1$-$C_4$ alkyl group, as defined herein, in which one, two, three, four, or five hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl. The terms "haloalkyl," "$C_1$-$C_6$ haloalkyl," "$C_1$-$C_4$ haloalkyl," and "$C_1$-$C_3$ haloalkyl," as used herein are unsubstituted, unless otherwise indicated.

The term "5-11 membered heteroaryl" as used herein, means a monocyclic heteroaryl and a bicyclic heteroaryl. The monocyclic heteroaryl is a five- or six-membered hydrocarbon ring wherein at least one carbon ring atom is replaced by heteroatom independently selected from the group consisting of O, N, and S. The five-membered ring contains two double bonds. The five membered ring may have one heteroatom selected from O or S; or one, two, three, or four nitrogen atoms and optionally one oxygen or one sulfur atom. The six-membered ring contains three double bonds and one, two, three or four nitrogen atoms. Examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic $C_3$-$C_6$ cycloalkyl, or a monocyclic heteroaryl fused to $C_4$-$C_6$ monocyclic cycloalkenyl, or a monocyclic heteroaryl fused to a monocyclic heteroaryl, or a monocyclic heteroaryl fused to a 4-7 membered monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazol[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolol[5,4-c]pyridin-2-yl, thiazolo[5,4-c]pyrimidin-2-yl, and 5,6,7,8-tetrahydroquinolin-5-yl.

The term "4-11 membered heterocycle" as used herein, means a hydrocarbon ring radical of 4-11 carbon ring atoms wherein at least one carbon ring atom is replaced by atoms independently selected from the group consisting of O, N, S. $P(=O)$, and Si. The 4-11 membered heterocycle ring may be a single ring (monocyclic) or have two or more rings (bicyclic or polycyclic). In certain embodiments, the monocyclic heterocycle is a four-, five-, six-, or seven-, membered hydrocarbon ring wherein at least one carbon ring atom is replaced by atoms independently selected from the group consisting of O, N, S, $P(=O)$, and Si. In certain embodiments, the monocyclic heterocycle is a 4-6 membered hydrocarbon ring wherein at least one carbon ring atom is replaced by atoms independently selected from the group consisting of O, N, S, $P(=O)$, and Si. A four-membered monocyclic heterocycle contains zero or one double bond, and one carbon ring atom replaced by an atom selected from the group consisting of O, N, and S. A five-membered monocyclic heterocycle contains zero or one double bond and one, two, or three carbon ring atoms replaced by atoms selected from the group consisting of O, N, S, $P(=O)$, and Si. Examples of five-membered monocyclic heterocycles include those containing in the ring: 1 O; 1 S; 1 N; 1 $P(=O)$; 1 Si; 2 N; 3 N; 1 S and 1 N; 1 S, and 2 N; 1 O and 1 N; or 1 O and 2 N. Non-limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, isothiazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three carbon ring atoms replaced by heteroatoms selected from the group consisting of O, N, S, $P(=O)$, and Si. Examples of six-membered monocyclic heterocycles include diose containing in the ring: 1 $P(=O)$; 1 Si; 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include 1,3-oxazinanyl, tetrahydropyranyl, dihydropyranyl, 1,6-dihydropyridazinyl, 1,2-dihydropyrimidinyl, 1,6-dihydropyrimidinyl, dioxanyl, 1,4-dithianyl, hexahydropyrimidinyl, morpholinyl, piperazinyl, piperidinyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three carbon ring atoms replaced by heteroatoms selected from the group consisting of O, N, and S. Examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,6-dihydropyridazinyl, 1,2-dihydropyrimidinyl, 1,6-dihydropyrimidinyl, hexahydropyrimidinyl, imidazolinyl, imidazolidinyl, isoindolinyl, isothiazolinyl, isothiazolidinyl, isoxazolinyl, isoxazolidinyl, morpholinyl, oxadiazolinyl, oxadiazolidinyl, 1,3-oxazinanyl, oxazolinyl, 1,3-oxazolidinyl, oxetanyl, piperazinyl, piperidinyl, pyranyl pyrazolinyl, pyrazolidinyl, pyrrolinyl, pyrrolidinyl, 1,2-dihydropyridinyl, tetrahydrofuranyl, tetrahydropyridinyl, tetrahydropyrimidinyl, tetrahydropyranyl, tetrahydrothienyl, thiadiazolinyl, thiadiazolidinyl, thiazolinyl, thiazolidinyl, thiomorpholinyl, thiopyranyl, and trithianyl. Polycyclic heterocycle groups contain two or more rings, and bicyclic heterocycles contain two rings. In certain embodiments, the polycyclic heterocycle groups contain 2 or 3 rings. The rings within the polycyclic and the bicyclic heterocycle groups are in a bridged, fused, or spiro orientation, or combinations thereof. In a spirocyclic heterocycle, one atom is common to two different rings. Non limiting examples of spirocyclic heterocycles include 4,6-diazaspiro[2.4]heptanyl, 6-azaspiro[3.4]octane, 2-oxa-6-azaspiro[3.4]octan-6-yl, and 2,7-diazaspiro[4.4]nonane. In a fused ring heterocycle, the rings share one common bond. Examples of fused bicyclic heterocycles are a 4-6 membered monocyclic heterocycle fused to a phenyl group, or a 4-6 membered monocyclic heterocycle fused to a monocyclic $C_3$-$C_6$ cycloalkyl, or a 4-6 membered monocyclic heterocycle fused to a $C_4$-$C_6$ monocyclic cycloalkenyl, or a 4-6 membered monocyclic heterocycle fused to a 4-6 membered monocyclic heterocycle. Examples of fused bicyclic heterocycles include, but are not limited to hexahydropyrano[3,4-b][1,4]oxazin-1(5H)-yl, hexahydropyrrolo[3,4-c]pyrrol-2(1H)-yl, hexahydro-1H-imidazo[5,1-c][1,4]oxazinyl, hexahydro-1H-pyrrolo[1,2-c]imidazolyl, hexahydrocyclopenta[c]pyrrol-3a(1H)-yl, and 3-azabicyclo[3.1.0]hexanyl. In a bridged heterocycle, the rings share at least two non-adjacent atoms. Examples of such bridged heterocycles include, but are not limited to, azabicyclo[2.2.1]heptyl (including 2-azabicyclo[2.2.1]hept-2-yl), 8-azabicyclo[3.2.1]oct-8-yl, octahydro-2,5-epoxypentalene, hexahydro-1H-1,4-methanocyclopenta[r]furan, aza-admantane (1-azatricyclo[3.3.1.1$^{3,7}$]decane), and oxa-adamantane (2-oxatricyclo[3.3.1.1$^{3,7}$]decane).

The term "4-7 membered monocyclic heterocycle" as used herein, means a four-, five-, six-, or seven-membered monocyclic heterocycle, as defined herein above.

The phenyl, the aryls, the cycloalkyls, the cycloalkenyls, the heteroaryls, and the heterocycles, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "oxo" as used herein, means a =O group.

The term "radiolabel" means a compound of the present disclosure in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^{3}$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat." "treating." and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

Compounds

Compounds of the present disclosure have the general Formula (I) as described above.

Particular values of variable groups are as follows. Such values may be used where appropriate with any of the other values, definitions, claims or embodiments defined hereinbefore or hereinafter.

Formula (I)

In embodiments, the present disclosure pertains to compounds of Formula (I), or pharmaceutically acceptable salts thereof.

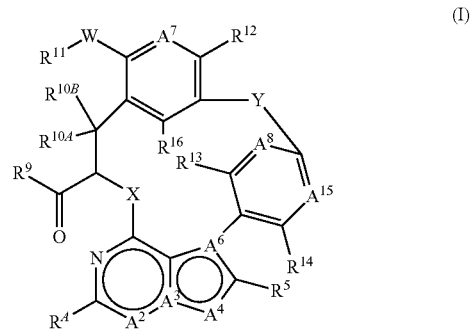

(I)

wherein
$A^2$ is $CR^2$, $A^3$ is N, $A^4$ is $CR^{4a}$, and $A^6$ is C; or
$A^2$ is $CR^2$, $A^3$ is N, $A^4$ is O or S, and $A^6$ is C; or
$A^2$ is $CR^2$, $A^3$ is C, $A^4$ is O or S and $A^6$ is C; or
$A^2$ is N, $A^3$ is C, $A^4$ is O or S and $A^6$ is C; or
$A^2$ is N, $A^3$ is C, $A^4$ is $CR^{4a}$, and $A^6$ is N;
$R^4$ is hydrogen, $CH_3$, halogen, CN, $CH_2F$, $CHF_2$, or $CF_3$;
X is O, or $N(R^{x2})$; wherein $R^{x2}$ is hydrogen, $C_1$-$C_3$ alkyl, or unsubstituted cyclopropyl;
Y is $(CH_2)_m$, —CH═CH—$(CH_2)_n$—, —$(CH_2)_p$—CH═CH—, or —$(CH_2)_q$—CH═CH—$(CH_2)_r$; wherein 0, 1, 2, or 3 $CH_2$ groups are each independently replaced by O, $N(R^{ya})$, $C(R^{ya})(R^{yb})$, C(O), $NC(O)R^{ya}$, or $S(O)_2$;
m is 2, 3, 4, or 5;
n is 1, 2, or 3;
p is 1, 2, or 3;
q is 1 or 2; and
r is 1 or 2; wherein the sum of q and r is 2 or 3;
$R^{ya}$, at each occurrence, is independently hydrogen, $C_2$-$C_6$ alkenyl, $C_2$-$C_6$ alkynyl, $G^1$, $C_1$-$C_6$ alkyl, or $C_1$-$C_6$ haloalkyl; wherein the $C_2$-$C_6$ alkenyl, $C_2$-$C_6$ alkynyl, $C_1$-$C_6$ alkyl, and $C_1$-$C_6$ haloalkyl are optionally substituted with 1 or 2 substituents independently selected from the group consisting of oxo, —N($R^{yd}$)($R^{ye}$), $G^1$, —$OR^{yf}$, —$SR^{yg}$, —$S(O)_2N(R^{yd})(R^{ye})$, and —$S(O)_2$-$G^1$; and
$R^{yb}$ is $C_2$-$C_6$ alkenyl, $C_2$-$C_6$ alkynyl, $G^1$, $C_1$-$C_6$ alkyl, or $C_1$-$C_6$ haloalkyl; wherein the $C_2$-$C_6$ alkenyl, $C_2$-$C_6$ alkynyl, $C_1$-$C_6$ alkyl, and $C_1$-$C_6$ haloalkyl are optionally substituted with 1 or 2 substituents independently selected from the group consisting of oxo, —N(R$^{yd}$)(R$^{ye}$), G$^1$, —OR$^{yf}$, —SR$^{yg}$, —S(O)$_2$N(R$^{yd}$)(R$^{ye}$), and —S(O)$_2$-G$^1$; or R$^{ya}$ and R$^{yb}$, together with the carbon atom to which they are attached, form a C$_3$-C$_7$ monocyclic cycloalkyl, C$_4$-C$_7$ monocyclic cycloalkenyl, or a 4-7 membered monocyclic heterocycle; wherein the C$_3$-C$_7$ monocyclic cycloalkyl, C$_4$-C$_7$ monocyclic cycloalkenyl, and the 4-7 membered monocyclic heterocycle are each optionally substituted with 1 —OR$^m$ and 0, 1, 2, or 3 independently selected R$^s$ groups;

R$^{yd}$, R$^{ye}$, R$^{yf}$, and R$^{yg}$, at each occurrence, are each independently hydrogen, G$^1$, C$_1$-C$_6$ alkyl, or C$_1$-C$_6$ haloalkyl; wherein the C$_1$-C$_6$ alkyl and the C$_1$-C$_6$ haloalkyl are optionally substituted with one substituent selected from the group consisting of G$^1$, —OR$^{yh}$, —SR$^{yh}$, —SO$_2$R$^{yh}$, and —N(R$^{yi}$)(R$^{yk}$);

G$^1$, at each occurrence, is piperazinyl, piperidinyl, pyrrolidinyl, thiomorpholinyl, tetrahydropyranyl, morpholinyl, oxetanyl, 1,3-dioxolanyl, 1,3-dioxanyl, 1,4-dioxanyl, 1,3-dioxepanyl, or 1,4-dioxepanyl; wherein each G$^1$ is optionally substituted with 1 —OR$^m$ and 0, 1, 2, or 3 substituents independently selected from the group consisting of G$^2$, —(C$_1$-C$_6$ alkylenyl)-G$^2$, and R$^s$;

G$^2$, at each occurrence, is a C$_3$-C$_7$ monocyclic cycloalkyl, C$_4$-C$_7$ monocyclic cycloalkenyl, oxetanyl, morpholinyl, 1,3-dioxolanyl, 1,3-dioxanyl, 1,4-dioxanyl, 1,3-dioxepanyl, or 1,4-dioxepanyl; wherein each G$^2$ is optionally substituted with 1 —OR$^m$ and 0, 1, or 2 independently selected R$^t$ groups;

R$^2$ is independently hydrogen, halogen, CH$_3$, or CN;

R$^{4a}$, at each occurrence, is independently hydrogen, halogen, CN, C$_2$-C$_4$ alkenyl, C$_2$-C$_4$ alkynyl, C$_1$-C$_4$ alkyl, C$_1$-C$_4$ haloalkyl, G$^4$, C$_1$-C$_4$ alkyl-G$^4$, or C$_1$-C$_4$ alkyl-O-G$^4$; wherein each G$^4$ is independently C$_6$-C$_{10}$ aryl, C$_3$-C$_7$ monocyclic cycloalkyl, C$_4$-C$_7$ monocyclic cycloalkenyl, or 4-7 membered heterocycle; wherein each G$^4$ is optionally substituted with 1, 2, or 3 R$^u$ groups;

R$^5$ is independently hydrogen, halogen, G$^3$, C$_1$-C$_6$ alkyl, C$_2$-C$_6$ alkenyl, or C$_2$-C$_6$ alkynyl; wherein the C$_1$-C$_6$ alkyl, C$_2$-C$_6$ alkenyl, and C$_2$-C$_6$ alkynyl are each optionally substituted with one G$^3$;

G$^3$, at each occurrence, is independently C$_6$-C$_{10}$ aryl, 5-11 membered heteroaryl, C$_3$-C$_{11}$ cycloalkyl, C$_4$-C$_{11}$ cycloalkenyl, oxetanyl, 2-oxaspiro[3.3]heptanyl, 1,3-dioxolanyl, 1,3-dioxanyl, 1,4-dioxanyl, 1,3-dioxepanyl, 2,3-dihydro-1,4-dioxinyl, or 1,4-dioxepanyl; wherein each G$^3$ is optionally substituted with 1, 2, or 3 R$^v$ groups;

A$^7$ is N or CR$^7$;
A$^8$ is N or CR$^8$;
A$^{15}$ is N or CR$^{15}$;

R$^7$, R$^{12}$ and R$^{16}$ are each independently hydrogen, halogen, C$_1$-C$_4$ alkyl, C$_1$-C$_4$ haloalkyl, —CN, —OR$^{7a}$, —SR$^{7a}$, or —N(R$^{7b}$)(R$^{7c}$);

R$^8$, R$^{13}$, R$^{14}$, and R$^{15}$ are each independently hydrogen, halogen, C$_1$-C$_4$ alkyl, C$_1$-C$_4$ haloalkyl, —CN, —OR$^{8a}$, —SR$^{8a}$, —N(R$^{8b}$)(R$^{8c}$), or C$_3$-C$_4$ monocyclic cycloalkyl; wherein the C$_3$-C$_4$ monocyclic cycloalkyl is optionally substituted with one or two substituents independently selected from the group consisting of halogen, C$_1$-C$_3$ alkyl, and C$_1$-C$_3$ haloalkyl; or R$^8$ and R$^{13}$ are each independently hydrogen, halogen, C$_1$-C$_4$ alkyl, C$_1$-C$_4$ haloalkyl, —CN, —OR$^{8a}$, —SR$^{8a}$, —N(R$^{8b}$)(R$^{8c}$), or C$_3$-C$_4$ monocyclic cycloalkyl; wherein the C$_3$-C$_4$ monocyclic cycloalkyl is optionally substituted with one or two substituents independently selected from the group consisting of halogen, C$_1$-C$_3$ alkyl, and C$_1$-C$_3$ haloalkyl; and R$^{14}$ and R$^{15}$, together with the carbon atoms to which they are attached, form a monocyclic ring selected from the group consisting of benzene, cyclobutane, cyclopentane, and pyridine; wherein the monocyclic ring is optionally substituted with 1, 2, or 3 substituents independently selected from the group consisting of halogen, C$_1$-C$_4$ alkyl, C$_1$-C$_4$ haloalkyl, —CN, —OR$^{8a}$, —SR$^{8a}$, and —N(R$^{8b}$)(R$^{8c}$);

R$^9$ is —OH, —O—C$_1$-C$_4$ alkyl, —O—CH$_2$—OC(O)(C$_1$-C$_6$ alkyl), —NHOH,

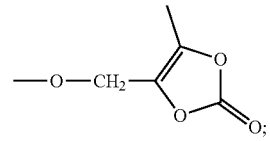

or —N(H)S(O)$_2$—(C$_1$-C$_6$ alkyl);

R$^{10A}$ and R$^{10B}$, are each independently hydrogen, C$_1$-C$_3$ alkyl, or C$_1$-C$_3$ haloalkyl; or R$^{10A}$ and R$^{10B}$, together with the carbon atom to which they are attached, form a cyclopropyl; wherein the cyclopropyl is optionally substituted with one or two substituents independently selected from the group consisting of halogen and CH$_3$;

W is —CH=CH—, C$_1$-C$_4$ alkyl, —O—CHF—, -L$^1$-CH$_2$—, or —CH$_2$-L$^1$-; wherein L$^1$ at each occurrence, is independently O, S, S(O), S(O)$_2$, S(O)$_2$N(H), N(H), or N(C$_1$-C$_3$ alkyl);

R$^{11}$ is a C$_6$-C$_{10}$ aryl or a 5-11 membered heteroaryl; wherein each R$^{11}$ is optionally substituted with 1, 2, or 3 independently selected R$^W$ groups;

R$^W$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{11a}$, —SR$^{11b}$, —S(O)$_2$R$^{11b}$, —S(O)$_2$N(R$^{11c}$)$_2$, —C(O)R$^{11a}$, —C(O)N(R$^{11c}$)$_2$, —N(R$^{11c}$)$_2$, —N(R$^{11c}$)C(O)R$^{11b}$, —N(R$^{11c}$)S(O)$_2$R$^{11b}$, —N(R$^{11c}$)C(O)O(R$^{11b}$), —N(R$^{11c}$)C(O)N(R$^{11c}$)$_2$, G$^4$, —(C$_1$-C$_6$ alkylenyl)-OR$^{11a}$, —(C$_1$-C$_6$ alkylenyl)-OC(O)N(R$^{11c}$)$_2$, —(C$_1$-C$_6$ alkylenyl)-SR$^{11a}$, —(C$_1$-C$_6$ alkylenyl)-S(O)$_2$R$^{11b}$, —(C$_1$-C$_6$ alkylenyl)-S(O)$_2$N(R$^{11c}$)$_2$, —(C$_1$-C$_6$ alkylenyl)-C(O)R$^{11a}$, —(C$_1$-C$_6$ alkylenyl)-C(O)N(R$^{11c}$)$_2$, —(C$_1$-C$_6$ alkylenyl)-N(R$^{11c}$)$_2$, —(C$_1$-C$_6$ alkylenyl)-N(R$^{11c}$)C(O)R$^{11b}$, —(C$_1$-C$_6$ alkylenyl)-N(R$^{11c}$)S(O)$_2$R$^{11b}$, —(C$_1$-C$_6$ alkylenyl)-N(R$^{11c}$)C(O)O(R$^{11b}$), —(C$_1$-C$_6$ alkylenyl)-N(R$^{11c}$)C(O)N(R$^{11c}$)$_2$, —(C$_1$-C$_6$ alkylenyl)-CN, or —(C$_1$-C$_6$ alkylenyl)-G$^4$;

R$^{11a}$ and R$^{11c}$, at each occurrence, are each independently hydrogen, C$_1$-C$_6$ alkyl, C$_2$-C$_6$ alkenyl, C$_1$-C$_6$ haloalkyl, G$^4$, —(C$_2$-C$_6$ alkylenyl)-OR$^{11d}$, —(C$_2$-C$_6$ alkylenyl)-N(R$^{11e}$)$_2$, or —(C$_2$-C$_6$ alkylenyl)-G$^4$;

R$^{11b}$, at each occurrence, is independently C$_1$-C$_6$ alkyl, C$_2$-C$_6$ alkenyl, C$_1$-C$_6$ haloalkyl, G$^4$, —(C$_2$-C$_6$ alkylenyl)-OR$^{11d}$, —(C$_2$-C$_6$ alkylenyl)-N(R$^{11e}$)$_2$, or —(C$_2$-C$_6$ alkylenyl)-G$^4$;

G$^4$, at each occurrence, is independently phenyl, monocyclic heteroaryl, C$_3$-C$_{11}$ cycloalkyl, C$_4$-C$_{11}$ cycloalkenyl, oxetanyl, tetrahydrofuranyl, tetrahydropyranyl, 2,6-dioxa-9-azaspiro[4.5]decanyl, 2-oxa-5-azabicyclo[2.2.1]heptanyl, 3-oxa-8-azabicyclo[3.2.1]octanyl, piperidinyl, piperazinyl, azetidinyl, morpholinyl, dihydropyranyl, tetrahydropyridinyl, dihydropyrrolyl, pyrrolidinyl, 2,3-dihydrodioxinyl, 1,3-dioxolanyl, 1,3-dioxanyl, 1,4-dioxanyl, 1,3-dioxepanyl, or 1,4-dioxepanyl; wherein each $G^4$ is optionally substituted with 1 —$OR^m$ and 0, 1, 2, or 3 substituents independently selected from the group consisting of $G^5$, $R^v$, —($C_1$-$C_6$ alkylenyl)-$G^5$, —($C_1$-$C_6$ alkylenyl)-$L^2$-($C_1$-$C_6$ alkylenyl)-$G^5$, and -$L^2$-($C_1$-$C_6$ alkylenyl)$_s$-$G^5$;

$L^2$ is O, C(O), N(H), N($C_1$-$C_6$ alkyl), NHC(O), C(O)O, S, S(O), or S(O)$_2$;

s is 0 or 1;

$G^5$, at each occurrence, is independently phenyl, monocyclic heteroaryl, $C_3$-$C_7$ monocyclic cycloalkyl, $C_4$-$C_7$ monocyclic cycloalkenyl, piperazine, 1,3-dioxolanyl, 1,3-dioxanyl, 1,4-dioxanyl, 1,3-dioxepanyl, or 1,4-dioxepanyl; wherein each $G^5$ is optionally substituted with 1 independently selected —$OR^m$ or 0, 1, 2, or 3 $R^z$ groups;

$R^s$, $R^t$, $R^u$, $R^v$, $R^y$, and $R^z$, at each occurrence, are each independently $C_1$-$C_6$ alkyl, $C_2$-$C_6$ alkenyl, $C_2$-$C_6$ alanyl, halogen, $C_1$-$C_6$ haloalkyl, —CN, oxo, $NO_2$, P(O)($R^k$)$_2$, —OC(O)$R^k$, —OC(O)N($R^j$)$_2$, —$SR^j$, —S(O)$_2$$R^k$, —S(O)$_2$N($R^j$)$_2$, —C(O)$R^j$, —C(O)N($R^j$)$_2$, —N($R^j$)$_2$, —N($R^j$)C(O)$R^k$, —N($R^j$)S(O)$_2$$R^k$, —N($R^j$)C(O)C)($R^k$), —N($R^j$)C(O)N($R^j$)$_2$, —($C_1$-$C_6$ alkylenyl)-$OR^j$, ($C_1$-$C_6$ alkylenyl)-OC(O)N($R^j$)$_2$, —($C_1$-$C_6$ alkylenyl)-$SR^j$, —($C_1$-$C_6$ alkylenyl)-S(O)$_2$$R^k$, —($C_1$-$C_6$ alkylenyl)-S(O)$_2$N($R^j$)$_2$, —($C_1$-$C_6$ alkylenyl)-C(O)$R^j$, —($C_1$-$C_6$ alkylenyl)-C(O)N($R^j$)$_2$, —($C_1$-$C_6$ alkylenyl)-N($R^j$)$_2$, —($C_1$-$C_6$ alkylenyl)-N($R^j$)C(O)$R^k$, —($C_1$-$C_6$ alkylenyl)-N($R^j$)S(O)$_2$$R^k$, —($C_1$-$C_6$ alkylenyl)-N($R^j$)C(O)O($R^k$), —($C_1$-$C_6$ alkylenyl)-N($R^j$)C(O)N($R^j$)$_2$, or —($C_1$-$C_6$ alkylenyl)-CN;

$R^m$ is hydrogen, $C_1$-$C_6$ alkyl, $C_1$-$C_6$ haloalkyl, —($C_2$-$C_6$ alkylenyl)-$OR^j$, or —($C_2$-$C_6$ alkylenyl)-N($R^j$)$_2$;

$R^{yh}$, $R^{yi}$, $R^{yk}$, $R^{7a}$, $R^{7b}$, $R^{7c}$, $R^{8a}$, $R^{8b}$, $R^{8c}$, $R^{11d}$, $R^{11e}$, and $R^j$, at occurrence, are each independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl;

wherein at least one of $G^1$, $G^2$, $G^1$, $G^4$, and $G^5$ is 2,2-dimethyl-1,3-dioxolanyl, 2,3-dihydro-1,4-dioxinyl, 1,3-dioxolanyl, 1,3-dioxanyl, 1,4-dioxanyl, 1,3-dioxepanyl, or 1,4-dioxepanyl.

In one embodiment of Formula (I), $A^2$ is $CR^2$, $A^3$ is N, $A^4$ is $CR^{4a}$, and $A^6$ is C; or $A^2$ is $CR^2$, $A^3$ is N, $A^4$ is O or S, and $A^6$ is C; or $A^2$ is N, $A^3$ is C, $A^4$ is O or S and $A^6$ is C; or $A^2$ is $CR^2$, $A^3$ is C, $A^4$ is O or S and $A^6$ is C; or $A^2$ is N, $A^3$ is C, $A^4$ is $CR^{4a}$, and $A^6$ is N. In another embodiment of Formula (I), $A^2$ is $CR^2$, $A^3$ is N, $A^4$ is $CR^{4a}$, and $A^6$ is C. In another embodiment of Formula (I), $A^2$ is CH, $A^3$ is N, $A^4$ is CH, and $A^6$ is C. In another embodiment of Formula (I), $A^2$ is $CR^2$, $A^3$ is N, $A^4$ is $CR^{4a}$, $A^6$ is C, $R^2$ is H, and $R^{4a}$ is halogen. In another embodiment of Formula (I), $A^2$ is $CR^2$, $A^3$ is N, $A^4$ is $CR^{4a}$, $A^6$ is C, $R^2$ is H, and $R^{4a}$ is Cl. In another embodiment of Formula (I), $A^2$ is $CR^2$, $A^3$ is N, $A^4$ is O or S, and $A^6$ is C. In another embodiment of Formula (I), $A^2$ is N, $A^3$ is C, $A^4$ is O, and $A^6$ is C. In another embodiment of Formula (I), $A^2$ is N, $A^3$ is C, $A^4$ is S, and $A^6$ is C. In another embodiment of Formula (I), $A^2$ is N, $A^3$ is C, $A^4$ is $CR^{4a}$, and $A^6$ is N. In another embodiment of Formula (I), $A^2$ is $CR^2$, $A^3$ is C, $A^4$ is O or S and $A^6$ is C.

In one embodiment of Formula (I), $R^4$ is hydrogen, $CH_3$, halogen, CN, $CH_2F$, $CHF_2$, or $CF_3$. In another embodiment of Formula (I), $R^4$ is hydrogen.

In one embodiment of Formula (I), X is O, or N($R^{x2}$); wherein $R^{x2}$ is hydrogen, $C_1$-$C_3$ alkyl, or unsubstituted cyclopropyl. In another embodiment of Formula (I), X is O.

In one embodiment of Formula (I), Y is $(CH_2)_m$, —CH=CH—$(CH_2)_n$—, —$(CH_2)_p$—CH=CH—, or —$(CH_2)_q$—CH=CH—$(CH_2)_r$; wherein 0, 1, 2, or 3 $CH_2$ groups are each independently replaced by O, N($R^{ya}$), C($R^{ya}$)($R^{yb}$), C(O), NC(O)$R^{ya}$, or S(O)$_2$; and m is 2, 3, 4, or 5. In another embodiment of Formula (I), Y is $(CH_2)_m$; wherein 1, 2, or 3 $CH_2$ groups are each independently replaced by O, N($R^{ya}$), C($R^{ya}$)($R^{yb}$), C(O), or NC(O)$R^{ya}$; and m is 3 or 4. In another embodiment of Formula (I), Y is $(CH_2)_m$; wherein 1 $CH_2$ group is independently replaced by N($R^{ya}$); and m is 3. In another embodiment of Formula (I), Y is $(CH_2)_m$; wherein 2 $CH_2$ groups are each independently replaced by O and 1 $CH_2$ group is replaced by C($R^{ya}$)($R^{yb}$); and m is 4. In another embodiment of Formula (I), Y is

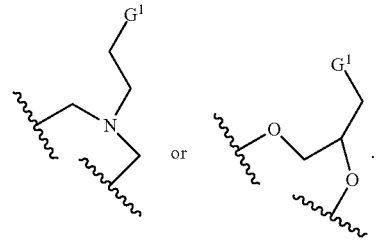

another embodiment of Formula (I), Y is

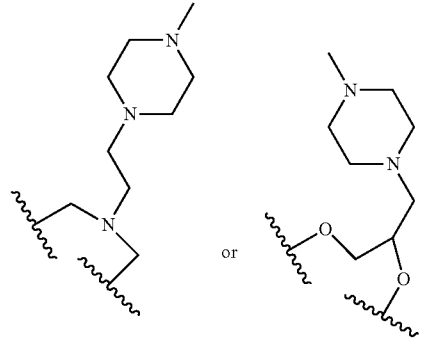

In another embodiment of Formula (I), Y is

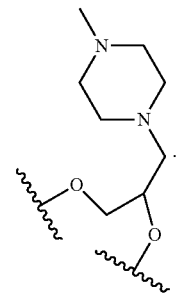 [SMILES: *OCC(CN1CCN(C)CC1)O*]

In one embodiment of Formula (I), $R^{ya}$, at each occurrence, is independently hydrogen, $C_2$-$C_6$ alkenyl, $C_2$-$C_6$ alkynyl, $G^1$, $C_1$-$C_6$ alkyl, or $C_1$-$C_6$ haloalkyl; wherein the $C_2$-$C_6$ alkenyl, $C_2$-$C_6$ alkynyl, $C_1$-$C_6$ alkyl, and $C_1$-$C_6$ haloalkyl are optionally substituted with 1 or 2 substituents independently selected from the group consisting of oxo, —N($R^{yd}$)($R^{ye}$), $G^1$, —O$R^{yf}$, —S$R^{yg}$, —S(O)$_2$N($R^{yd}$)($R^{ye}$), and —S(O)$_2$-$G^1$; and $R^{yb}$ is $C_2$-$C_6$ alkenyl, $C_2$-$C_6$ alkynyl, $G^1$, $C_1$-$C_6$ alkyl, or $C_1$-$C_6$ haloalkyl; wherein the $C_2$-$C_6$ alkenyl, $C_2$-$C_6$ alkynyl, $C_1$-$C_6$ alkyl, and $C_1$-$C_6$ haloalkyl are optionally substituted with 1 or 2 substituents independently selected from the group consisting of oxo, —N($R^{yd}$)($R^{ye}$), $G^1$, —O$R^{yf}$, —S$R^{yg}$, —S(O)$_2$N($R^{yd}$)($R^{ye}$), and —S(O)$_2$-$G^1$; or $R^{ya}$ and $R^{yb}$, together with the carbon atom to which they are attached, form a $C_3$-$C_7$ monocyclic cycloalkyl, $C_4$-$C_7$ monocyclic cycloalkenyl, or a 4-7 membered monocyclic heterocycle; wherein the $C_3$-$C_7$ monocyclic cycloalkyl, $C_4$-$C_7$ monocyclic cycloalkenyl, and the 4-7 membered monocyclic heterocycle are each optionally substituted with 1 —O$R^m$ and 0, 1, 2, or 3 independently selected $R^s$ groups; and $R^{yd}$, $R^{ye}$, $R^{yf}$, and $R^{yg}$, at each occurrence, are each independently hydrogen, $G^1$, $C_1$-$C_6$ alkyl, or $C_1$-$C_6$ haloalkyl; wherein the $C_1$-$C_6$ alkyl and the $C_1$-$C_6$ haloalkyl are optionally substituted with one substituent selected from the group consisting of $G^1$, —O$R^{yh}$, —S$R^{yh}$, —SO$_2$$R^{yh}$, and —N($R^{yi}$)($R^{ya}$). In another embodiment of Formula (I), $R^{ya}$, at each occurrence, is independently hydrogen, or $C_1$-$C_6$ alkyl; wherein the $C_1$-$C_6$ alkyl is optionally substituted with 1 or 2 substituents independently selected from the group consisting of —N($R^{yd}$)($R^{ye}$), $G^1$, —O$R^{yf}$, or $C_1$-$C_6$, alkyl; and $R^{yb}$ is $C_1$-$C_6$ alkyl; wherein the $C_1$-$C_6$ alkyl is optionally substituted with 1 or 2 substituents independently selected from the group consisting of —N($R^{yd}$)($R^{ye}$), $G^1$, and —O$R^{yf}$; and $R^{yd}$, $R^{ye}$, and $R^{yf}$, at each occurrence, are each independently hydrogen, or $C_1$-$C_6$ alkyl; wherein the $C_1$-$C_6$ alkyl is optionally substituted with one substituent selected from the group consisting of $G^1$, —O$R^{yh}$, and SO$_2$$R^{yh}$. In another embodiment of Formula (I), $R^{ya}$, at each occurrence, is independently hydrogen; and $R^{yb}$ is $C_1$-$C_6$ alkyl; wherein the $C_1$-$C_6$ alkyl is substituted with 1 $G^1$.

In one embodiment of Formula (I), $G^1$ at each occurrence, is piperazinyl, piperidinyl, pyrrolidinyl, thiomorpholinyl, tetrahydropyranyl, morpholinyl, oxetanyl, 1,3-dioxolanyl, 1,3-dioxanyl, 1,4-dioxanyl, 1,3-dioxepanyl, or 1,4-dioxepanyl; wherein each $G^1$ is optionally substituted with 1 —O$R^m$ and 0, 1, 2, or 3 substituents independently selected from the group consisting of $G^2$, —($C_1$-$C_6$ alkylenyl)-$G^2$, and $R^s$. In another embodiment of Formula (I), $G^1$ is piperazinyl optionally substituted with 1 —O$R^m$ and 0, 1, 2, or 3 substituents independently selected from the group consisting of $G^2$, —($C_1$-$C_6$ alkylenyl)-$G^2$, and $R^s$. In another embodiment of Formula (I), $G^1$ is piperazinyl substituted with 1 $R^s$. In another embodiment of Formula (I), $G^1$ is piperazinyl substituted with 1 $R^s$; and $R^s$ is $C_1$-$C_6$ alkyl. In another embodiment of Formula (I), $G^1$ is piperazinyl substituted with 1 $R^s$; and $R^s$ is $CH_3$.

In one embodiment of Formula (I), $G^2$, at each occurrence, is a $C_3$-$C_7$ monocyclic cycloalkyl, $C_4$-$C_7$ monocyclic cycloalkenyl, oxetanyl, morpholinyl, 1,3-dioxolanyl, 1,3-dioxanyl, 1,4-dioxanyl, 1,3-dioxepanyl, or 1,4-dioxepanyl; wherein each $G^2$ is optionally substituted with 1 independently selected $R^1$ groups. In another embodiment of Formula (I), $G^2$, at each occurrence, is a $C_3$-$C_7$ monocyclic cycloalkyl. In another embodiment of Formula (I), $G^2$, at each occurrence, is morpholinyl.

In one embodiment of Formula (I), $R^2$ is independently hydrogen, halogen, $CH_3$, or $CN$. In another embodiment of Formula (I), $R^2$ is independently hydrogen.

In one embodiment of Formula (I), $R^{4a}$, at each occurrence, is independently hydrogen, halogen, $CN$, $C_2$-$C_4$ alkenyl, $C_2$-$C_4$ alkynyl, $C_1$-$C_4$ alkyl, $C_1$-$C_4$ haloalkyl, G $C_1$-$C_4$ alkyl-$G^A$, or $C_1$-$C_4$ alkyl-O-$G^A$; wherein each $G^A$ is independently $C_6$-$C_{10}$ aryl, $C_3$-$C_7$ monocyclic cycloalkyl, $C_4$-$C_7$ monocyclic cycloalkenyl, or 4-7 membered heterocycle; wherein each $G^A$ is optionally substituted with 1, 2, or 3 $R^u$ groups. In another embodiment of Formula (I), $R^{4a}$, at each occurrence, is independently halogen.

In one embodiment of Formula (I), $R^5$ is independently hydrogen, halogen, G $C_1$-$C_6$ alkyl, $C_2$-$C_6$ alkenyl, or $C_2$-$C_6$ alkynyl; wherein the $C_1$-$C_6$ alkyl, $C_2$-$C_6$, alkenyl, and $C_2$-$C_6$ alkynyl are each optionally substituted with one $G^3$; and $G^3$, at each occurrence, is independently $C_6$-$C_{10}$ aryl, 5-11 membered heteroaryl, $C_3$-$C_{11}$ cycloalkyl, $C_4$-$C_{11}$ cycloalkenyl, oxetanyl, 2-oxaspiro[3.3]heptanyl, 1,3-dioxolanyl, 1,3-dioxanyl, 1,4-dioxanyl, 1,3-dioxepanyl, 2,3-dihydro-1,4-dioxinyl, or 1,4-dioxepanyl; wherein each $G^3$ is optionally substituted with 1, 2, or 3 $R^v$ groups. In another embodiment of Formula (I), $R^5$ is independently hydrogen, $G^3$, or $C_2$-$C_6$ alkynyl; and $G^3$, at each occurrence, is independently $C_6$-$C_{10}$ aryl, or $C_3$-$C_{11}$ cycloalkyl; wherein each $G^3$ is optionally substituted with 1, 2, or 3 $R^v$ groups. In another embodiment of Formula (I), $R^5$ is independently $C_1$-$C_6$ alkyl; wherein the $C_1$-$C_6$ alkyl is optionally substituted with one $G^3$; and $G^3$, at each occurrence, is independently $C_6$-$C_{10}$ aryl, 5-11 membered heteroaryl, $C_3$-$C_{11}$ cycloalkyl, $C_4$-$C_{11}$ cycloalkenyl, oxetanyl, 2-oxaspiro[3.3]heptanyl, 1,3-dioxolanyl, 1,3-dioxanyl, 1,4-dioxanyl, 1,3-dioxepanyl, 2,3-dihydro-1,4-dioxinyl, or 1,4-dioxepanyl; wherein each $G^3$ is optionally substituted with 1, 2, or 3 $R^v$ groups. In another embodiment of Formula (I), $R^5$ is independently $C_1$-$C_6$ alkyl; wherein the $C_1$-$C_6$ alkyl is optionally substituted with one $G^3$; and $G^3$, at each occurrence, is independently 1,4-dioxanyl. In another embodiment of Formula (I), $R^5$ is independently $G^3$; and $G^3$, at each occurrence, is independently $C_3$-$C_{11}$ cycloalkyl; wherein each $G^3$ is optionally substituted with 1, 2, or 3 $R^v$ groups. In another embodiment of Formula (I), $R^5$ is independently $G^3$; and $G^3$, at each occurrence, is independently $C_4$-$C_{11}$ cycloalkenyl; wherein each $G^3$ is optionally substituted with 1, 2, or 3 $R^v$ groups. In another embodiment of Formula (I), $R^5$ is independently $G^3$; and $G^3$, at each occurrence, is independently 2,3-dihydro-1,4-dioxinyl; wherein each $G^3$ is optionally substituted with 1, 2, or 3 $R^v$ groups.

In another embodiment of Formula (I), $R^5$ is independently $G^3$; and $G^3$, at each occurrence, is independently $C_6$-$C_{10}$ aryl; wherein each $G^3$ is optionally substituted with 1 $R^v$ groups. In another embodiment of Formula (I), $R^5$ is independently $G^3$; and $G^3$, at each occurrence, is independently phenyl; wherein each $G^3$ is optionally substituted with 1 $R^v$ groups; and $R^v$ is halogen. In another embodiment of Formula (I), $R^5$ is independently $G^3$; and $G^3$, at each occurrence, is independently phenyl; wherein $G^3$ is optionally substituted with 1 $R^v$ groups; and $R^v$ is F.

In one embodiment of Formula (I), $A^7$ is N or $CR^7$; $A^8$ is N or $CR^8$; and $A^{15}$ is N or $CR^{15}$. In another embodiment of Formula (I), $R^7$, $R^{12}$ and $R^{16}$ are each independently hydrogen, halogen, $C_1$-$C_4$ alkyl, $C_1$-$C_4$ haloalkyl, —CN, —O$R^{7a}$, —S$R^{73}$, or —N($R^{7b}$)($R^{7c}$); and $R^8$, $R^{13}$, $R^{14}$, and $R^{15}$, are each independently hydrogen, halogen, $C_1$-$C_4$ alkyl, $C_1$-$C_4$ haloalkyl, —CN, —O$R^{8a}$, —S$R^{8a}$, —N($R^{8b}$)($R^{8c}$), or $C_3$-$C_4$ monocyclic cycloalkyl; wherein the $C_3$-$C_4$ monocyclic cycloalkyl is optionally substituted with one or two substituents independently selected from the group consisting of halogen, $C_1$-$C_3$ alkyl, and $C_1$-$C_3$ haloalkyl. In another embodiment of Formula (I), $R^7$, $R^{12}$ and $R^{16}$ are each independently hydrogen. In another embodiment of Formula (I), $A^7$ is CH; $A^8$ is $CR^8$; $A^{15}$ is $CR^{15}$; and $R^8$ and $R^{15}$ are each independently hydrogen, halogen, $C_1$-$C_4$ alkyl, or —OR$^{8a}$. In another embodiment of Formula (I), A$^7$ is CH; A$^8$ is CR$^8$; A$^{15}$ is CR$^{15}$; and R$^8$ and R$^{15}$ are each independently hydrogen, halogen, or C$_1$-C$_4$ alkyl. In another embodiment of Formula (I), A$^7$ is CH; A$^8$ is CR$^8$; A$^{15}$ is CR$^{15}$; and R$^8$ and R$^{15}$ are each independently hydrogen, Cl, or CH$_3$.

In one embodiment of Formula (I), R$^8$ and R$^{13}$ are each independently hydrogen, halogen, C$_1$-C$_4$ alkyl, C$_1$-C$_4$ haloalkyl, —CN, —OR$^{8a}$, —SR$^{8a}$, —N(R$^{8b}$)(R$^{8c}$), or C$_3$-C$_4$ monocyclic cycloalkyl; wherein the C$_3$-C$_4$ monocyclic cycloalkyl is optionally substituted with one or two substituents independently selected from the group consisting of halogen, C$_1$-C$_3$ alkyl, and C$_1$-C$_3$ haloalkyl; and R$^{14}$ and R$^{15}$, together with the carbon atoms to which they are attached, form a monocyclic ring selected from the group consisting of benzene, cyclobutane, cyclopentane, and pyridine; wherein the monocyclic ring is optionally substituted with 1, 2, or 3 substituents independently selected from the group consisting of halogen, C$_1$-C$_4$ alkyl, C$_1$-C$_4$ haloalkyl, —CN, —OR$^{8a}$, —SR$^{8a}$, and —N(R$^{8b}$)(R$^{8c}$). In another embodiment of Formula (I), R$^8$ and R$^{13}$ are each independently hydrogen, and R$^{14}$ and R$^{15}$, together with the carbon atoms to which they are attached form benzine.

In one embodiment of Formula (I), R$^9$ is —OH, —O—C$_1$-C$_4$ alkyl, —O—CH$_2$—OC(O)(C$_1$-C$_6$ alkyl), —NHOH,

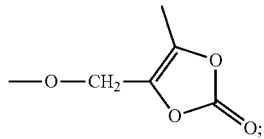

or —N(H)S(O)$_2$—(C$_1$-C$_6$ alkyl). In another embodiment of Formula (I), R$^9$ is —OH.

In one embodiment of Formula (I), R$^{10A}$ and R$^{10B}$, are each independently hydrogen, C$_1$-C$_3$ alkyl, or C$_1$-C$_3$ haloalkyl; or R$^{10A}$ and R$^{10B}$, together with the carbon atom to which they are attached, form a cyclopropyl; wherein the cyclopropyl is optionally substituted with one or two substituents independently selected from the group consisting of halogen and CH$_3$. In another embodiment of Formula (I), R$^{10A}$ and R$^{10B}$ are each independently hydrogen.

In one embodiment of Formula (I),
R$^A$ is hydrogen;
R$^9$ is —OH;
R$^{10A}$ and R$^{10B}$, are each independently hydrogen; and
R$^7$, R$^{12}$ and R$^{16}$ are each independently hydrogen.

In one embodiment of Formula (I), W is —CH═CH—, C$_1$-C$_4$ alkyl, —O—CHF—, -L$^1$-CH$_2$—, or —CH$_2$-L$^1$-; wherein L$^1$ at each occurrence, is independently O, S, S(O), S(O)$_2$, S(O)$_2$N(H), N(H), or N(C$_1$-C$_3$ alkyl). In another embodiment of Formula (I), W is —O—CHF—, or -L$^1$-CH$_2$—; wherein L$^1$ at each occurrence, is independently O. In another embodiment of Formula (I), W is -L$^1$-CH$_2$—; wherein L$^1$ at each occurrence, is independently O.

In one embodiment of Formula (I), R$^{11}$ is a C$_6$-C$_{10}$ aryl or a 5-11 membered heteroaryl; wherein each R$^{11}$ is optionally substituted with 1, 2, or 3 independently selected R$^W$ groups. In another embodiment of Formula (I), R$^{11}$ is a C$_6$-C$_{10}$ aryl or a 5-11 membered heteroaryl; wherein each R$^{11}$ is optionally substituted with 1 or 2 independently selected R$^W$ groups. In another embodiment of Formula (I), W is —O—CH$_2$—, and R$^{11}$ is pyrimidinyl, optionally substituted with 1, 2, or 3 independently selected R$^W$ groups. In another embodiment of Formula (I), W is —O—CH$_2$—; and R$^{11}$ is pyrimidinyl, optionally substituted with 1, 2, or 3 independently selected R$^W$ groups; and R$^W$, at each occurrence, is independently C$_1$-C$_6$ alkyl, —OR$^{11a}$, or G$^4$. In another embodiment of Formula (I), W is —O—CH$_2$—; and R$^{11}$ is pyrimidinyl, optionally substituted with 1, 2, or 3 independently selected R$^W$ groups; and R$^W$, at each occurrence, is independently —OR$^{11a}$ or G$^4$.

In one embodiment of Formula (I), R$^{11a}$ and R$^{11c}$, at each occurrence, are each independently hydrogen, C$_1$-C$_6$ alkyl, C$_2$-C$_6$ alkenyl, C$_1$-C$_6$ haloalkyl. G$^4$, —(C$_2$-C$_6$ alkylenyl)-OR$^{11d}$, —(C$_2$-C$_6$ alkylenyl)-N(R$^{11e}$)$_2$, or —(C$_2$-C$_6$ alkylenyl)-G$^4$; and R$^{11b}$, at each occurrence, is independently C$_1$-C$_6$ alkyl. C$_2$-C$_6$ alkenyl, C$_1$-C$_6$ haloalkyl, G$^4$, —(C$_2$-C$_6$ alkylenyl)-OR$^{11d}$, —(C$_2$-C$_6$ alkylenyl)-N(R$^{11e}$)$_2$, or —(C$_2$-C$_6$ alkylenyl)-G$^4$. In another embodiment of Formula (I), R$^{11a}$ is C$_1$-C$_6$ alkyl or C$_1$-C$_6$ haloalkyl. In another embodiment of Formula (I), R$^{11a}$ is —(C$_2$-C$_6$ alkylenyl)-G$^4$.

In one embodiment of Formula (I), G$^4$, at each occurrence, is independently phenyl, monocyclic heteroaryl, C$_3$-C$_{11}$ cycloalkyl, C$_4$-C$_{11}$ cycloalkenyl, oxetanyl, tetrahydrofuranyl, tetrahydropyranyl, 2,6-dioxa-9-azaspiro[4.5]decanyl, 2-oxa-5-azabicyclo[2.2.1]heptanyl, 3-oxa-8-azabicyclo[3.2.1]octanyl, piperidinyl, piperazinyl, azetidinyl, morpholinyl, dihydropyranyl, tetrahydropyridinyl, dihydropyrrolyl, pyrrolidinyl, 2,3-dihydrodioxinyl, 1,3-dioxolanyl, 1,3-dioxanyl, 1,4-dioxanyl, 1,3-dioxepanyl, or 1,4-dioxepanyl; wherein each G$^4$ is optionally substituted with 1 —OR$^m$ and 0, 1, 2, or 3 substituents independently selected from the group consisting of G$^5$, R$^y$, —(C$_1$-C$_6$ alkylenyl)-G$^5$, —(C$_1$-C$_6$ alkylenyl)-L$^2$-(C$_1$-C$_6$ alkylenyl)-G$^5$, and -L$^2$-(C$_1$-C$_6$ alkylenyl)$_s$-G$^5$; L$^2$ is O, C(O). N(H), N(C$_1$-C$_6$ alkyl), NHC(O), C(O)O, S, S(O), or S(O)$_2$; and s is 0 or 1.

In embodiments of Formula (I), G$^4$, at each occurrence, is independently phenyl, monocyclic heteroaryl, C$_3$-C$_{11}$ cycloalkyl, C$_4$-C$_{11}$ cycloalkenyl, oxetanyl, tetrahydrofuranyl, tetrahydropyranyl, morpholinyl, 2,6-dioxa-9-azaspiro[4.5]decanyl, 2-oxa-5-azabicyclo[2.2.1]heptanyl, 3-oxa-8-azabicyclo[3.2.1]octanyl, piperidinyl, azetidinyl, dihydropyranyl, tetrahydropyridinyl, dihydropyrrolyl, pyrrolidinyl, 2,3-dihydrodioxinyl, 1,3-dioxolanyl, 1,3-dioxanyl, 1,4-dioxanyl, 1,3-dioxepanyl, or 1,4-dioxepanyl; wherein each G$^4$ is optionally substituted with 1 —OR$^m$ and 0, 1, 2.3, or 4 substituents independently selected from the group consisting of G$^5$, R$^y$, —(C$_1$-C$_6$ alkylenyl)-G$^5$, —(C$_1$-C$_6$ alkylenyl)-L$^2$-(C$_1$-C$_6$ alkylenyl)-G$^5$, and -L$^2$-(C$_1$-C$_6$ alkylenyl)$_s$-G$^5$; and L$^2$ is O, C(O), N(H), N(C$_1$-C$_6$ alkyl). NHC(O), C(O)O, S, S(O), or S(O)$_2$; and s is 0 or 1. In another embodiment of Formula (I), G$^4$, at each occurrence, is independently phenyl, monocyclic heteroaryl, C$_3$-C$_{11}$ cycloalkyl, oxetanyl, tetrahydrofuranyl, tetrahydropyranyl, morpholinyl, 2,6-dioxa-9-azaspiro[4.5]decanyl, 2-oxa-5-azabicyclo[2.2.1]heptanyl, 3-oxa-8-azabicyclo[3.2.1]octanyl, pyrrolidinyl, 2,3-dihydrodioxinyl, 1,3-dioxolanyl, 1,3-dioxanyl, 1,4-dioxanyl, 1,3-dioxepanyl, or 1,4-dioxepanyl; wherein each G$^4$ is optionally substituted with 1 —OR$^m$ and 0, 1, 2, 3, or 4 substituents independently selected from the group consisting of R$^y$, —(C$_1$-C$_6$ alkylenyl)-L$^2$-(C$_1$-C$_6$ alkylenyl)-G$^5$, and -L$^2$-(C$_1$-C$_6$ alkylenyl)$_s$-G$^5$; L$^2$ is O or C(O)O; and s is 0 or 1. In another embodiment of Formula (I), G$^4$, at each occurrence, is independently phenyl optionally substituted with 1 —OR$^m$ and 0, 1, 2, 3, or 4 substituents independently selected from the group consisting of R$^y$, —(C$_1$-C$_6$ alkylenyl)-L$^2$-(C$_1$-C$_6$ alkylenyl)-G$^5$, and -L$^2$-(C$_1$-C$_6$ alkylenyl)$_s$-G$^5$; L$^2$ is O or C(O)O; and s is 0 or 1. In another embodiment of Formula (I), G$^4$, at each occurrence, is independently phenyl optionally substituted with -L$^2$-(C$_1$-

$C_6$ alkylenyl)$_s$-$G^5$. In another embodiment of Formula (I), $G^4$, at each occurrence, is independently phenyl optionally substituted with -$L^2$-($C_1$-$C_6$ alkylenyl)$_s$-$G^5$; $L^2$ is O; and s is 1. In another embodiment of Formula (I), $G^4$, at each occurrence, is independently phenyl, monocyclic heteroaryl, $C_3$-$C_{11}$ cycloalkyl, $C_4$-$C_{11}$ cycloalkenyl, piperidinyl, piperazinyl, azetidinyl, morpholinyl, 1,4-dioxanyl, or 1,4-dioxepanyl; wherein each $G^4$ is optionally substituted with 1 —$OR^m$ and 0, 1, 2, or 3 substituents independently selected from the group consisting of $R^y$, —($C_1$-$C_6$ alkylenyl)-$L^2$-($C_1$-$C_6$ alkylenyl)-$G^5$, and -$L^2$-($C_1$-$C_6$ alkylenyl)$_s$-$G^5$; $L^2$ is O, or $S(O)_2$; and s is 0 or 1. In another embodiment of Formula (I), $G^4$, at each occurrence, is independently phenyl; wherein each $G^4$ is optionally substituted with 1 —$OR^m$ and 0, 1, 2, or 3 substituents independently selected from the group consisting of $R^y$, —($C_1$-$C_6$ alkylenyl)-$L^2$-($C_1$-$C_6$ alkylenyl)-$G^5$, and -$L^2$-($C_1$-$C_6$ alkylenyl)$_s$-$G^4$; $L^2$ is O, or $S(O)_2$; and s is 0 or 1. In another embodiment of Formula (I), $G^5$, at each occurrence, is independently monocyclic heteroaryl; wherein each $G^4$ is optionally substituted with 1 —$OR^m$ and 0, 1, 2, or 3 substituents independently selected from the group consisting of $R^y$—($C_1$-$C_6$ alkylenyl)-$L^2$-($C_1$-$C_6$ alkylenyl)-$G^5$, and -$L^2$-($C_1$-$C_6$ alkylenyl)$_s$-$G^5$; $L^2$ is O, or $S(O)_2$; and s is 0 or 1. In another embodiment of Formula (I), $G^4$, at each occurrence, is independently $C_3$-$C_{11}$ cycloalkyl; wherein each $G^4$ is optionally substituted with 1 —$OR^m$ and 0, 1, 2, or 3 substituents independently selected from the group consisting of $R^y$, —($C_1$-$C_6$ alkylenyl)-$L^2$-($C_1$-$C_6$ alkylenyl)-$G^5$, and -$L^2$-($C_1$-$C_6$ alkylenyl)$_s$-$G^5$; $L^2$ is O, or $S(O)_2$; and s is 0 or 1. In another embodiment of Formula (I), $G^4$, at each occurrence, is independently $C_4$-$C_{11}$ cycloalkenyl; wherein each $G^4$ is optionally substituted with 1 —$OR^m$ and 0, 1, 2, or 3 substituents independently selected from the group consisting of $R^y$, —($C_1$-$C_6$ alkylenyl)-$L^2$-($C_1$-$C_6$ alkylenyl)-$G^5$, and -$L^2$-($C_1$-$C_6$ alkylenyl)$_s$-$G^5$; $L^2$ is O, or $S(O)_2$; and s is 0 or 1. In another embodiment of Formula (I), $G^4$, at each occurrence, is independently piperidinyl, piperazinyl, azetidinyl, morpholinyl, 1,4-dioxanyl, or 1,4-dioxepanyl; wherein each $G^4$ is optionally substituted with 1 —$OR^m$ and 0, 1, 2, or 3 substituents independently selected from the group consisting of $R^y$, —($C_1$-$C_6$ alkylenyl)-$L^2$-($C_1$-$C_6$ alkylenyl)-$G^5$, and -$L^2$-($C_1$-$C_6$ alkylenyl)$_s$-$G^5$; $L^2$ is O, or $S(O)_2$; and s is 0 or 1.

In one embodiment of Formula (I), $G^5$, at each occurrence, is independently phenyl, monocyclic heteroaryl, $C_1$-$C_7$ monocyclic cycloalkyl, $C_4$-$C_7$ monocyclic cycloalkenyl, piperazine, 1,3-dioxolanyl, 1,3-dioxanyl, 1,4-dioxanyl, 1,3-dioxepanyl, or 1,4-dioxepanyl; wherein each $G^5$ is optionally substituted with 1 independently selected —$OR^m$ or 0, 1, 2, or 3 $R^z$ groups. In another embodiment of Formula (I), $G^5$, at each occurrence, is independently 1,3-dioxolanyl optionally substituted with 2 independently selected $R^z$ groups. In another embodiment of Formula (I), $G^5$, at each occurrence, is independently 1,4-dioxanyl optionally substituted with 2 independently selected $R^z$ groups.

In one embodiment of Formula (I),
$A^2$ is CH;
$A^3$ is N;
$A^4$ is CH;
$A^6$ is C;
$R^A$ is hydrogen;
X is O;
$R^9$ is —OH;
$R^{10A}$ and $R^{10B}$, are each independently hydrogen; and
$R^7$, $R^{12}$ and $R^{16}$ are each independently hydrogen.
In one embodiment of Formula (I),
$A^2$ is N;
$A^3$ is C;
$A^4$ is O;
$A^6$ is C;
$R^A$ is hydrogen;
X is O;
$R^9$ is —OH;
$R^{10A}$ and $R^{10B}$, are each independently hydrogen; and
$R^7$, $R^{12}$ and $R^{16}$ are each independently hydrogen.
In one embodiment of Formula (I),
$A^2$ is N;
$A^3$ is C;
$A^4$ is S;
$A^6$ is C;
$R^A$ is hydrogen;
X is O;
$R^9$ is —OH;
$R^{10A}$ and $R^{10B}$, are each independently hydrogen; and
$R^7$, $R^{12}$ and $R^{16}$ are each independently hydrogen.
In one embodiment of Formula (I),
$A^2$ is N;
$A^3$ is C;
$A^4$ is S;
$A^6$ is C;
$R^A$ is hydrogen;
X is O;
$R^9$ is —OH;
$R^{10A}$ and $R^{10B}$, are each independently hydrogen;
$R^7$, $R^{12}$ and $R^{16}$ are each independently hydrogen;
Y is $(CH_2)_m$; wherein 1 $CH_2$ group is independently replaced by N($R^{ya}$); and
m is 3.
In one embodiment of Formula (I),
$A^2$ is N;
$A^3$ is C;
$A^4$ is S;
$A^6$ is C;
$R^A$ is hydrogen;
X is O;
$R^9$ is —OH;
$R^{10A}$ and $R^{10B}$, are each independently hydrogen;
$R^7$, $R^{12}$ and $R^{16}$ are each independently hydrogen;
Y is $(CH_2)_m$; wherein 2 $CH_2$ groups are each independently replaced by O and 1 $CH_2$ group is replaced by C($R^{ya}$)($R^{yb}$); and
m is 4.
In one embodiment of Formula (I),
$A^2$ is CH;
$A^3$ is N;
$A^4$ is CH;
$A^6$ is C;
$R^A$ is hydrogen;
X is O;
$R^9$ is —OH;
$R^{10A}$ and $R^{10B}$, are each independently hydrogen;
$R^7$, $R^{12}$ and $R^{16}$ are each independently hydrogen;
Y is $(CH_2)_m$; wherein 1 $CH_2$ group is independently replaced by N($R^{ya}$);
m is 3; and
$G^1$ is piperazinyl substituted with 1 $R^s$.
In one embodiment of Formula (I),
$A^2$ is CH;
$A^3$ is N;
$A^4$ is CH;
$A^6$ is C;
$R^A$ is hydrogen;
X is O;
$R^9$ is —OH;

$R^{10A}$ and $R^{10B}$, are each independently hydrogen;
$R^7$, $R^{12}$ and $R^{16}$ are each independently hydrogen;
Y is $(CH_2)_m$; wherein 2 $CH_2$ groups are each independently replaced by O and 1 $CH_2$ group is replaced by $C(R^{ya})(R^{yb})$;
m is 4; and
$G^1$ is piperazinyl substituted with 1 $R^s$.

In one embodiment of Formula (I),
$A^2$ is CH;
$A^3$ is N;
$A^4$ is CH;
$A^6$ is C;
$R^A$ is hydrogen;
X is O;
$R^9$ is —OH;
$R^{10A}$ and $R^{10B}$, are each independently hydrogen;
$R^7$, $R^{12}$ and $R^{16}$ are each independently hydrogen;
Y is $(CH_2)_m$; wherein 1 $CH_2$ group is independently replaced by $N(R^{ya})$;
m is 3;
$G^1$ is piperazinyl substituted with 1 $R^s$;
W is -$L^1$-$CH_2$—; and
$L^1$ is independently O.

In one embodiment of Formula (I),
$A^2$ is CH;
$A^3$ is N;
$A^4$ is CH;
$A^6$ is C;
$R^A$ is hydrogen;
X is O;
$R^9$ is —OH;
$R^{10A}$ and $R^{10B}$, are each independently hydrogen;
$R^7$, $R^{12}$ and $R^{16}$ are each independently hydrogen;
Y is $(CH_2)_m$; wherein 2 $CH_2$ groups are each independently replaced by O and 1 $CH_2$ group is replaced by $C(R^{ya})(R^{yb})$;
m is 4;
$G^1$ is piperazinyl substituted with 1 $R^s$;
W is -$L^1$-$CH_2$—; and
$L^1$ is independently O.

In one embodiment of Formula (I),
$A^2$ is CH;
$A^3$ is N;
$A^4$ is CH;
$A^6$ is C;
$R^A$ is hydrogen;
X is O;
$R^9$ is —OH;
$R^{10A}$ and $R^{10B}$, are each independently hydrogen;
$R^7$, $R^{12}$ and $R^{16}$ are each independently hydrogen;
Y is $(CH_2)_m$; wherein 1 $CH_2$ group is independently replaced by $N(R^{ye})$;
m is 3;
$G^1$ is piperazinyl substituted with 1 $R^s$;
W is -$L^1$-$CH_2$—;
$L^1$ is independently O;
W is —O—$CH_2$—, and
$R^{11}$ is pyrimidinyl, optionally substituted with 1, 2, or 3 independently selected $R^W$ groups.

One embodiment pertains to compounds of Formula (I), or pharmaceutically acceptable salts thereof,
wherein
$A^2$ is N, $A^3$ is C, $A^4$ is S and $A^6$ is C;
$R^A$ is hydrogen;
X is O;
Y is $(CH_2)_m$; wherein 3 $CH_2$ groups are each independently replaced by O, or $C(R^{ya})(R^{yb})$;

m is 4;
$R^{ya}$, at each occurrence, is independently hydrogen;
$R^{yb}$ is $C_1$-$C_6$ alkyl; wherein the $C_1$-$C_6$ alkyl is optionally substituted with 1 $G^1$;
$G^1$, at each occurrence, is piperazinyl; wherein each $G^1$ is optionally substituted with $R^s$;
$R^5$ is independently $G^3$;
$G^3$, at each occurrence, is independently $C_6$-$C_{10}$ aryl optionally substituted with 1 $R^v$ group;
$A^7$ is $CR^7$;
$A^8$ is $CR^8$;
$A^{15}$ is $CR^{15}$;
$R^7$, $R^{12}$ and $R^{16}$ are each independently hydrogen;
$R^8$, $R^{13}$, $R^{14}$, and $R^{15}$, are each independently hydrogen, halogen, $C_1$-$C_4$ alkyl;
$R^9$ is —OH;
$R^{10A}$ and $R^{10B}$, are each independently hydrogen;
W is -$L^1$-$CH_2$—; wherein $L^1$ is independently O;
$R^{11}$ is a 5-11 membered heteroaryl; wherein each $R^{11}$ is optionally substituted with 1, 2, or 3 independently selected $R^W$ groups;
$R^W$, at each occurrence, is independently $G^4$;
$G^4$, at each occurrence, is independently phenyl substituted with -$L^2$-$(C_1$-$C_6$ alkylenyl$)_s$-$G^3$;
$L^2$ is O;
s is 1;
$G^5$, at each occurrence, is independently 1,3-dioxolanyl, 1,3-dioxanyl, 1,4-dioxanyl, 1,3-dioxepanyl, or 1,4-dioxepanyl; wherein each $G^1$ is optionally substituted with 1 independently selected —$OR^m$ or 0, 1, 2, or 3 $R^z$ groups;
$R^s$, $R^v$, and $R^z$, at each occurrence, are each independently $C_1$-$C_6$ alkyl; and
$R^m$ is hydrogen, $C_1$-$C_6$ alkyl, $C_1$-$C_6$ haloalkyl, —$(C_2$-$C_6$ alkylenyl)-$OR^j$, or —$(C_2$-$C_6$ alkylenyl)-$N(R^j)_2$.

One embodiment pertains to compounds of Formula (I), or pharmaceutically acceptable salts thereof,
wherein
$A^2$ is N, $A^3$ is C, $A^4$ is S and $A^6$ is C;
$R^A$ is hydrogen;
X is O,
Y is $(CH_2)_m$; wherein 3 GHz groups are each independently replaced by O or $C(R^{ya})(R^{yb})$;
m is 4;
$R^{ya}$, at each occurrence, is independently hydrogen;
$R^{yb}$ is $C_1$-$C_6$ alkyl; wherein the $C_1$-$C_0$ alkyl is optionally substituted with $G^1$;
$G^1$ is piperazinyl; wherein each $G^1$ is optionally substituted with $R^s$;
$R^5$ is independently $G^3$;
$G^3$, at each occurrence, is independently $C_6$-$C_{10}$ aryl; wherein each $G^3$ is optionally substituted with 1 $R^v$ groups;
$A^7$ is $CR^7$;
$A^8$ is $CR^8$;
$A^{15}$ is $CR^{15}$;
$R^7$, $R^{12}$ and $R^{16}$ are each independently hydrogen;
$R^8$, $R^{13}$, $R^{14}$, and $R^{15}$, are each independently halogen or $C_1$-$C_4$ alkyl;
$R^9$ is —OH;
$R^{10A}$ and $R^{10B}$, are each independently hydrogen;
W is -$L^1$-$CH_2$; wherein $L^1$ at each occurrence, is independently O;
$R^{11}$ is 5-11 membered heteroaryl; wherein each $R^{11}$ is optionally substituted with 1 independently selected $R^W$ group;
$R^W$, at each occurrence, is independently $G^4$;

G$^4$, at each occurrence, is independently phenyl or C$_3$-C$_{11}$ cycloalkyl; wherein each G$^4$ is optionally substituted with 1 substituent independently selected from the group consisting of —(C$_1$-C$_6$ alkylenyl)-L$^2$-(C$_1$-C$_6$ alkylenyl)-G$^5$, and -L$^2$-(C$_1$-C$_6$ alkylenyl)$_s$-G$^5$;

L$^2$ is O;

s is 1;

G$^5$, at each occurrence, is independently 1,4-dioxanyl; and

R$^s$ and R$^v$, at each occurrence, are each independently C$_1$-C$_6$ alkyl or halogen.

One embodiment pertains to compounds of Formula (I), or pharmaceutically acceptable salts thereof, wherein A$^2$ is N, A$^3$ is C, A$^4$ is S and A$^6$ is C;

R$^4$ is hydrogen;

X is O;

Y is (CH$_2$)$_m$; wherein 3 CH$_2$ groups are each independently replaced by O or C(R$^{ya}$)(R$^{yb}$;

m is 4;

R$^{ya}$, at each occurrence, is independently hydrogen;

R$^{yb}$ is C$_1$-C$_6$ alkyl; wherein the C$_1$-C$_6$ alkyl is optionally substituted with G$^1$;

G$^1$ is piperazinyl; wherein each G$^1$ is optionally substituted with R$^s$;

R$^5$ is independently G$^3$;

G$^3$, at each occurrence, is independently C$_6$-C$_{10}$ aryl; wherein each G$^3$ is optionally substituted with 1 R$^v$ groups;

A$^7$ is CR$^7$;

A$^8$ is CR$^8$;

A$^{15}$ is CR$^{15}$;

R$^7$, R$^{12}$ and R$^{16}$ are each independently hydrogen;

R$^8$, R$^{13}$, R$^{14}$, and R$^{15}$, are each independently halogen or C$_1$-C$_4$ alkyl;

R$^9$ is —OH;

R$^{10A}$ and R$^{10b}$, are each independently hydrogen;

W is -L$^1$-CH$_2$; wherein L$^1$ at each occurrence, is independently O;

R$^{11}$ is 5-11 membered heteroaryl; wherein each R$^{11}$ is optionally substituted with 1 independently selected R$^W$ group;

R$^W$, at each occurrence, is independently G$^4$;

G$^4$, at each occurrence, is independently phenyl; wherein each G$^4$ is optionally substituted with -L$^2$-(C$_1$-C$_6$ alkylenyl)$_s$-G$^5$.

L$^2$ is O;

s is 1;

G$^5$, at each occurrence, is independently 1,4-dioxanyl; and

R$^s$ and R$^v$, at each occurrence, are each independently C$_1$-C$_6$ alkyl or halogen.

One embodiment pertains to compounds of Formula (I), or pharmaceutically acceptable salts thereof, wherein A$^2$ is N, A$^3$ is C, A$^4$ is S and A$^6$ is C;

R$^4$ is hydrogen;

X is O;

Y is (CH$_2$)$_m$; wherein 3 CH$_2$ groups are each independently replaced by O or C(R$^{ya}$)(R$^{yb}$;

m is 4;

R$^{ya}$, at each occurrence, is independently hydrogen;

R$^{yb}$ is C$_1$-C$_6$ alkyl; wherein the C$_1$-C$_6$ alkyl is optionally substituted with G$^1$;

G$^1$ is piperazinyl; wherein each G$^1$ is optionally substituted with R$^s$;

R$^5$ is independently G$^3$;

G$^3$, at each occurrence, is independently C$_6$-C$_{10}$ aryl; wherein each G$^3$ is optionally substituted with 1 R$^v$ groups;

A$^7$ is CR$^7$;

A$^8$ is CR$^8$;

A$^{15}$ is CR$^{15}$;

R$^7$, R$^{12}$ and R$^{16}$ are each independently hydrogen;

R$^8$, R$^{13}$, R$^{14}$, and R$^{15}$, are each independently halogen or C$_1$-C$_4$ alkyl;

R$^9$ is —OH;

R$^{10A}$ and R$^{10B}$, are each independently hydrogen;

W is -L$^1$-CH$_2$; wherein L$^1$ at each occurrence, is independently O;

R$^{11}$ is 5-11 membered heteroaryl; wherein each R$^{11}$ is optionally substituted with 1 independently selected R$^W$ group;

R$^W$, at each occurrence, is independently G$^4$;

G$^4$, at each occurrence, is independently C$_3$-C$_{11}$ cycloalkyl; wherein each G$^4$ is optionally substituted with -L$^2$-(C$_1$-C$_6$ alkylenyl)$_s$-G$^5$;

L$^2$ is O;

s is 1;

G$^5$, at each occurrence, is independently 1,4-dioxanyl; and

R$^s$ and R$^v$, at each occurrence, are each independently C$_1$-C$_6$ alkyl or halogen.

One embodiment pertains to compounds of Formula (I), or pharmaceutically acceptable salts thereof, wherein A$^2$ is N, A$^3$ is C, A$^4$ is S and A$^6$ is C;

R$^4$ is hydrogen;

X is O;

Y is (CH$_2$)$_m$; wherein 3 CH$_2$ groups are each independently replaced by O or C(R$^{ya}$)(R$^{yb}$;

m is 4;

R$^{ya}$ at each occurrence, is independently hydrogen;

R$^{yb}$ is C$_1$-C$_6$ alkyl; wherein the C$_1$-C$_6$ alkyl is optionally substituted with G$^1$;

G$^1$ is piperazinyl; wherein each G$^1$ is optionally substituted with R$^s$;

R$^5$ is independently G$^3$;

G$^3$, at each occurrence, is independently C$_6$-C$_{10}$ aryl; wherein each G$^3$ is optionally substituted with 1 R$^v$ groups;

A$^7$ is CR$^7$;

A$^8$ is CR$^8$;

A$^{15}$ is CR$^{15}$;

R$^7$, R$^{12}$ and R$^{16}$ are each independently hydrogen;

R$^8$, R$^{13}$, R$^{14}$, and R$^{15}$, are each independently halogen or C$_1$-C$_4$ alkyl;

R$^9$ is —OH;

R$^{10A}$ and R$^{10B}$, are each independently hydrogen;

W is -L$^1$-CH$_2$; wherein L$^1$ at each occurrence, is independently O;

R$^{11}$ is 5-11 membered heteroaryl; wherein each R$^{11}$ is optionally substituted with 1 independently selected R$^W$ group;

R$^W$, at each occurrence, is independently G$^4$;

G$^4$, at each occurrence, is independently C$_3$-C$_{11}$ cycloalkyl; wherein each G$^4$ is optionally substituted with —(C$_1$-C$_6$ alkylenyl)-L$^2$-(C$_1$-C$_6$ alkylenyl)-G$^5$;

L$^2$ is O;

s is 1;

G$^5$, at each occurrence, is independently 1,4-dioxanyl; and

R$^s$ and R$^v$, at each occurrence, are each independently C$_1$-C$_6$ alkyl or halogen.

One embodiment pertains to compounds of Formula (I), or pharmaceutically acceptable salts thereof, wherein $A^2$ is N, $A^3$ is C, $A^4$ is O or S and $A^6$ is C;
$R^A$ is hydrogen;
X is O;
Y is $(CH_2)_m$; wherein 3 $CH_2$ groups are each independently replaced by O, or $C(R^{ya})(R^{yb})$;
m is 4;
$R^{ya}$, at each occurrence, is independently hydrogen;
$R^{yb}$ is $C_1$-$C_6$ alkyl; wherein the $C_1$-$C_6$ alkyl is optionally substituted with $G^1$;
$G^1$, at each occurrence, is piperazinyl; wherein each $G^1$ is optionally substituted with 1 $R^s$;
$R^s$ is independently $G^3$ and $C_1$-$C_6$ alkyl; wherein the $C_1$-$C_6$ alkyl is optionally substituted with one $G^3$;
$G^3$, at each occurrence, is independently $C_6$-$C_{10}$ aryl, $C_3$-$C_{11}$ cycloalkyl, $C_4$-$C_{11}$ cycloalkenyl, 1,4-dioxanyl, or 2,3-dihydro-1,4-dioxinyl; wherein each $G^3$ is optionally substituted with 1 3 $R^v$ groups;
$A^7$ is $CR^7$;
$A^8$ is $CR^8$;
$A^{15}$ is $CR^{15}$;
$R^7$, $R^{12}$ and $R^{16}$ are each independently hydrogen;
$R^8$, $R^{13}$, $R^{14}$, and $R^{15}$, are each independently hydrogen, halogen, or $C_1$-$C_4$ alkyl;
$R^9$ is —OH;
$R^{10A}$ and $R^{10B}$, are each independently hydrogen;
W is -$L^1$-$CH_2$—; wherein $L^1$ at each occurrence, is independently O;
$R^{11}$ is 5-11 membered heteroaryl; wherein each $R^{11}$ is optionally substituted with 1 or 2 independently selected $R^W$ groups;
$R^W$, at each occurrence, is independently —$OR^{11a}$ or $G^4$;
$R^{11a}$, at each occurrence, are each independently –$(C_2$-$C_6$ alkylenyl)-$G^4$;
$G^4$, at each occurrence, is independently phenyl, monocyclic heteroaryl, $C_3$-$C_{11}$ cycloalkyl, $C_4$-$C_{11}$ cycloalkenyl, piperidinyl, piperazinyl, azetidinyl, morpholinyl, 1,4-dioxanyl, or 1,4-dioxepanyl; wherein each $G^4$ is optionally substituted with 1 —$OR^m$ and 1 or 2 substituents independently selected from the group consisting of $R^y$, —$(C_1$-$C_6$ alkylenyl)-$L^2$-$(C_1$-$C_6$ alkylenyl)-$G^5$, and -$L^2$-$(C_1$-$C_6$ alkylenyl)$_s$-$G^5$;
$L^2$ is O, or $S(O)_2$;
s is 1;
$G^5$, at each occurrence, is independently 1,3-dioxolanyl, or 1,4-dioxanyl; wherein each $G^5$ is substituted with 0, 1, or 2 $R^z$ groups;
$R^s$, $R^v$, $R^y$, and $R^z$, at each occurrence, are each independently $C_1$-$C_6$ alkyl, or halogen; and
$R^m$ is $C_1$-$C_6$ alkyl;
wherein at least one of $G^3$, $G^4$, and $G^5$ is 2,3-dihydro-1,4-dioxinyl, 1,3-dioxolanyl, 1,4-dioxanyl, or 1,4-dioxepanyl.

Exemplary compounds of Formula (I) include, but are not limited to:

(7R,16R)-19,23-dichloro-10-{[2-(4-{[(4S)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(2-{[(4R)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R,21S)-19-chloro-10-{[2-(1,4-dioxan-2-yl)pyrimidin-4-yl]methoxy}-1-(4-fluorophenyl)-20-methyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(6-{[(2R)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(6-{[(2S)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(4-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[4-({[(2S)-1,4-dioxan-2-yl]methoxy}methyl)-4-fluoropiperidin-1-yl]pyrimidin-1-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1R,4r)-4-{[(2R)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(4-{[(2R)-1,4-dioxan-2-yl]methoxy}piperidin-1-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[1-({[(2S)-1,4-dioxan-2-yl]methoxy}methyl)cyclobutyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[3-({[(2S)-1,4-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid;

(7R,16R)-19,23-dichloro-10-({2-[3-({[(2R)-1,4-dioxan-2-yl]methoxy}methylazetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid;

(7R,16R)-19,23-dichloro-10-[(2-{(1r,4r)-4-[(1,3-dioxolan-4-yl)methoxy]cyclohexyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-[(2-{(1s,4s)-4-[(1,4-dioxan-2-yl)methoxy]cyclohexyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[6-(4-{[(2R)-1,4-dioxan-2-yl]methoxy}phenyl)pyrazin-2-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-cyclohexyl-10-{[2-(4-{[(2S)-1,4-dioxan-2-yl]methoxy}phenyl)pyrimidin-4-yl]methoxy}-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid;

(7R,16R)-19,23-dichloro-1-{[(2R)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-{[(2S)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(2R)-2-{[(1,4-dioxan-2-yl)methoxy]methyl}morpholin-4-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(3-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(3-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[4-(4-{[(2R)-1,4-dioxan-2-yl]methoxy}phenyl)pyrimidin-2-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-[(2-{[(2S)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid;

(7R,16R)-19,23-dichloro-10-[(2-{[(2R)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid;

(7R,16R)-19,23-dichloro-10-[(2-{4-[(1,4-dioxan-2-yl)methanesulfonyl]piperazin-1-yl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-<5,6-dihydro-1,4-dioxin-2-yl)-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1R,4s)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-cyclobutyl-10-[(2-{(1r,4r)-4-[(1,4-dioxan-2-yl)methoxy]cyclohexyl}pyrimidin-4-yl)methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[2-(1,4-dioxepan-6-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[6-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-[(2-{(1r,4r)-4-[(1,4-dioxan-2-yl)methoxy]cyclohexyl}pyrimidin-4-yl)methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-({2-[(1R,4s)-4-({[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-({2-[(4S)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-({2-[(4S)-4-({[(2S)-1,4-dioxan-2-yl]methoxy}methyl)-4-fluorocyclohex-1-en-1-yl]pyrimidin-4-yl}methoxy)-20, 22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[6-({[(2S)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-({2-[(1S,4r)-4-({[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-({2-[(4R)-4-({[(2S)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1S,4S)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(4S)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[6-({[(2R)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(4R)-4-({[(2S)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(4R)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1S,4r)-4-{[(2S)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(4S)-4-({[(2S)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1S,4r)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1R,4r)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-(cyclopent-1-en-1-yl)-10-({2-[(4R)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1S,4r)-4-({[(2R)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1S,4R)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-({2-[(1R,4r)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-1-cyclobutyl-10-({2-[(1R,4r)-4-{[(2R)-1,4-dioxan-2-yl]methoxy}cyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid;

(7R,16R)-19,23-dichloro-10-{[3-{[(2S)-1,4-dioxan-2-yl]methoxy}-6-(2-methoxyphenyl)pyridin-2-yl]methoxy}-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid; and pharmaceutically acceptable salts thereof.

Formula (II)

One embodiment pertains to compounds of Formula (IIa), (IIb), (IIc), (IId), or pharmaceutically acceptable salts thereof.

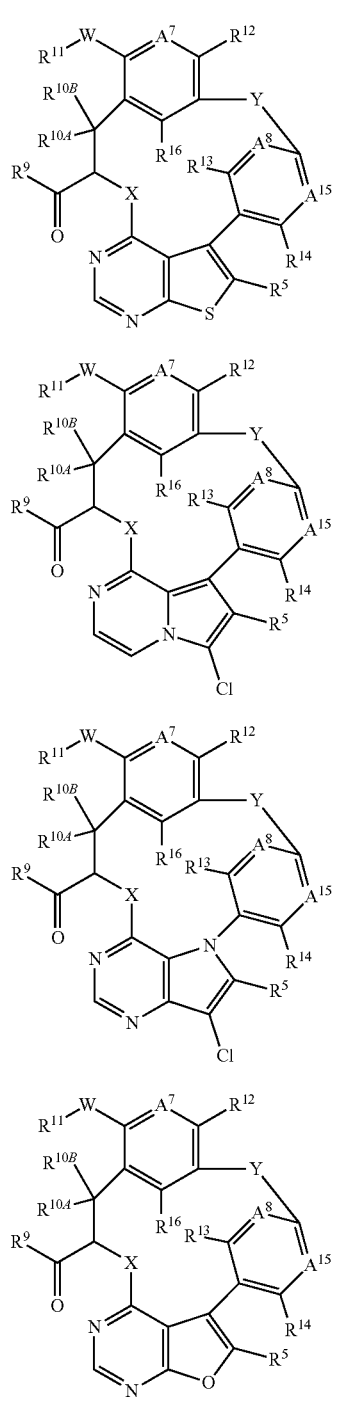

wherein $A^7$, $A^8$, $A^{15}$, $R^5$, $R^9$, $R^{10A}$, $R^{10B}$, $R^{11}$, $R^{12}$, $R^{13}$, $R^{14}$, $R^{16}$, W, X, and Y are as described in embodiments of Formula (I) herein.

Exemplary compounds of Formula (IIa), (IIb), (IIc), and (IId) include, but are not limited to: Examples 1-53; and pharmaceutically acceptable salts thereof.

Formula (III)

One embodiment pertains to compounds of Formula (IIIa), (IIIb), (IIIc), (IId), or pharmaceutically acceptable salts thereof, wherein $A^8$, $A^{15}$, $R^5$, $R^{11}$, $R^{13}$, $R^{14}$, W, and Y are as described in embodiments of Formula (I) herein.

Exemplary compounds of Formula IIIa), (IIIb), (IIIc), and (IIId) include, but are not limited to: Examples 1-53; and pharmaceutically acceptable salts thereof.

Formula (IV)

One embodiment pertains to compounds of Formula (IVa), (IVb), (IVc), (IVd), or pharmaceutically acceptable salts thereof, (IVa)

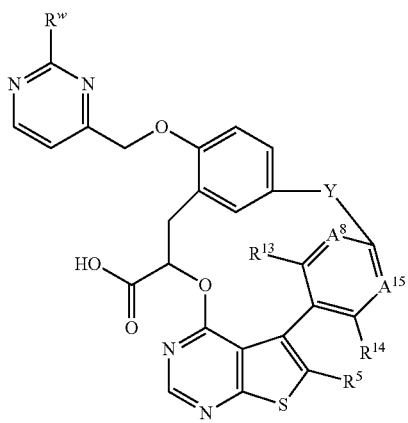

(IVb)

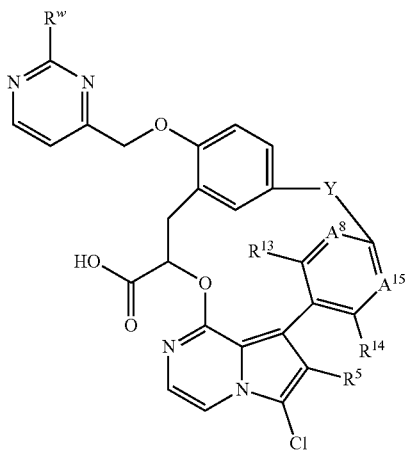

(IVc)

(IVd)

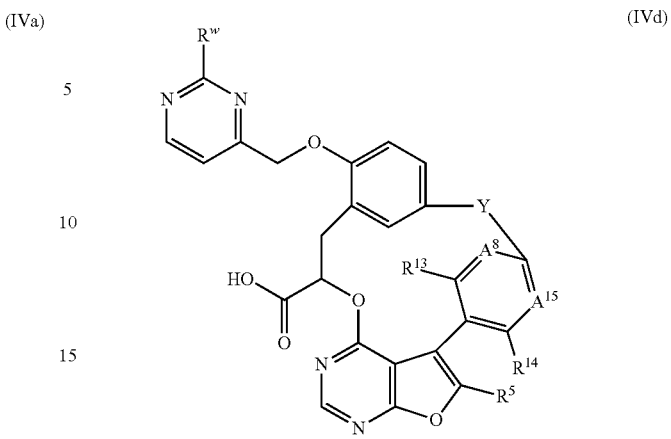

wherein $A^8$, $A^{15}$, $R^5$, $R^{13}$, $R^{14}$, $R^W$, and Y are as described in embodiments of Formula (I) herein.

One embodiment pertains to compounds of Formula (IVa), (IVb), (IVc), and (IVd) wherein $R^W$ is tetrahydrofuranyl, tetrahydropyranyl, or phenyl, substituted with one -$L^2$-$(C_1$-$C_6$ alkylenyl$)_s$-$G^5$.

One embodiment pertains to compounds of Formula (IVa), (IVb), (IVc), and (IVd) wherein $R^W$ is phenyl, substituted with one -$L^2$-$(C_1$-$C_6$ alkylenyl$)_s$-$G^5$.

One embodiment pertains to compounds of Formula (IVa), (IVb). (IVc), and (IVd) wherein $R^W$ is phenyl, substituted with one -$L^2$-$(C_1$-$C_6$ alkylenyl$)_s$-$G^5$; and $R^5$ is 4-fluorophenyl or cyclopropyl.

Exemplary compounds of Formula (IVa), (IVb), (IVc), (IVd) include, but are not limited to: Examples 1, 2, 3, 4, 5, 6, 7, 8, 9, 10, 11, 12, 13, 14, 15, 17, 18, 19, 20, 21, 22, 24, 25, 26, 27, 28, 29, 30, 32, 33, 34, 35, 36, 37, 38, 39, 40, 41, 42, 43, 44, 45, 46, 47, 48, 49, 50, 51, 52, and pharmaceutically acceptable salts thereof.

Formula (V)

One embodiment pertains to compounds of Formula (Va), (Vb), (Vc), (Vd), or pharmaceutically acceptable salts thereof, (Va)

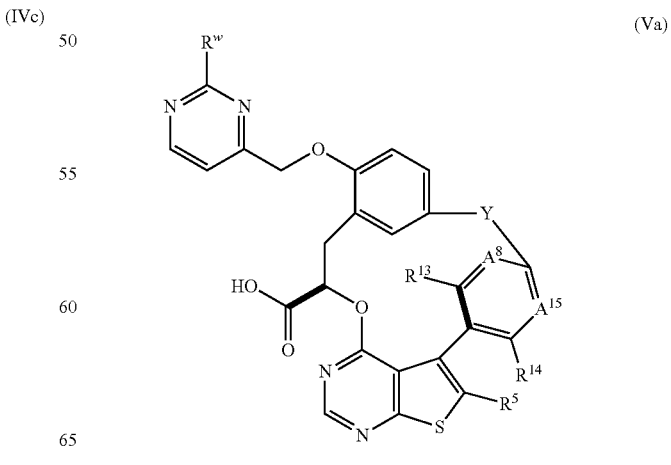

-continued (Vb)

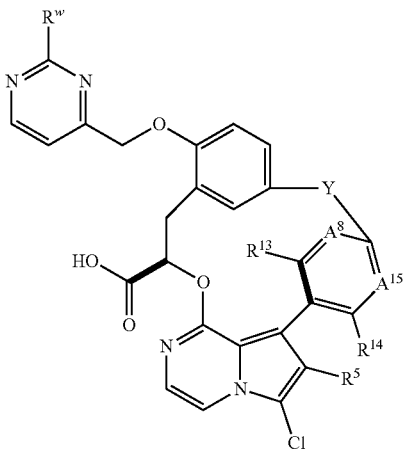

(Vc)

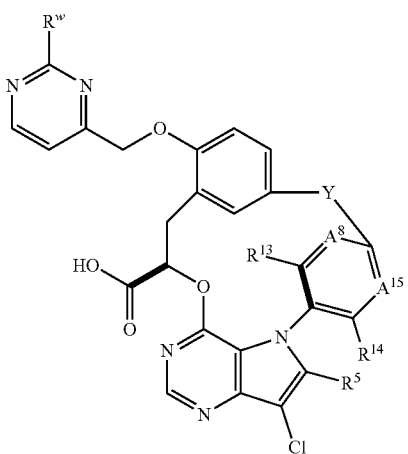

(Vd)

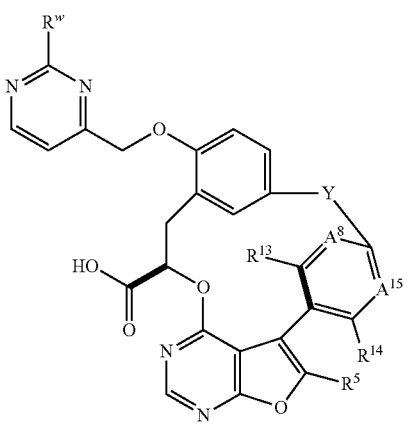

wherein $A^8$, $A^{15}$, $R^5$, $R^{13}$, $R^{14}$, $R^W$, and Y are as described in embodiments of Formula (I) herein.

One embodiment pertains to compounds of Formula (Va), (Vb), (Vc), and (Vd) wherein $R^W$ is tetrahydrofuranyl, tetrahydropyranyl, or phenyl, substituted with one -$L^2$-($C_1$-$C_6$ alkylenyl)$_s$-$G^5$.

One embodiment pertains to compounds of Formula (Va), (Vb), (Vc), and (Vd) wherein $R^W$ is phenyl, substituted with one -$L^2$-($C_1$-$C_6$ alkylenyl)$_s$-$G^5$.

One embodiment pertains to compounds of Formula (Va), (Vb), (Vc), and (Vd) wherein $R^W$ is phenyl, substituted with one -$L^2$-($C_1$-$C_6$ alkylenyl)$_s$-$G^5$; and $R^5$ is 4-fluorophenyl or cyclopropyl.

Exemplary compounds of Formula (Va), (Vb), (Vc), (Vd), include, but are not limited to: Example 4, and pharmaceutically acceptable salts thereof.

Compound names are assigned by using Name 2016.1.1 (File Version N30E41, Build 86668) or Name 2017.2.1 (File Version N40E41, Build 96719) naming algorithm by Advanced Chemical Development or Struct=Name naming algorithm as part of CHEMDRAW® ULTRA v. 12.0.2.1076 or Professional Version 15.0.0.106.

Compounds of the disclosure may exist as atropisomers, resulting from hindered rotation about a single bond, when energy differences due to steric strain or other contributors create a barrier to rotation that is high enough to allow for isolation of individual conformers. See, e.g., Bringmann. G, et al., Atroposelective Synthesis of Axially Chiral Biaryl Compounds. Angew. Chem., Int. Ed., 2005, 44: 5384-5428. In some instances, the barrier of rotation is high enough that the different atropisomers may be separated and isolated, such as by chromatography on a chiral stationary phase. It is to be understood that the stereochemistry of the atropisomers is included in the compound names only when compounds are assayed as being pure (at least 95%) or are predominantly (at least 80%) one isomer. Where there is no atropisomer stereochemistry noted for a compound, then it is to be understood that either the stereochemistry is undetermined, or it was determined to be a near-equal mixture of atropisomers. In addition, where there is a discrepancy between the name of the compound and the structure found in Table 1, the structure depicted in Table 1 shall prevail.

Compounds of the present disclosure may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The present disclosure contemplates various stereoisomers and mixtures thereof and these are specifically included within the scope of this disclosure. Stereoisomers include enantiomers and diastereomers, and mixtures of enantiomers or diastereomers. Individual stereoisomers of compounds of the present disclosure may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by precipitation or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical. Essex CM20 2JE, England, or (2) direct separation of the mixture of optical enantiomers on chiral chromatographic columns or (3) fractional recrystallization methods. It is to be understood that an asterisk (*) at a particular stereocenter in a structure of a chiral compound, indicates an arbitrary assignment of stereochemical configuration at that stereocenter. Moreover, an asterisk (*) following a stereochemical descriptor in the name of such a compound designates an arbitrary assignment of stereochemical configuration at that stereocenter.

Compounds of the present disclosure may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the present disclosure may be prepared synthetically from commercially available starting materials using selective organic transformations, or prepared in single isomeric form by purification of mixtures of the cis and trans isomers. Such methods are well-known to those of ordinary skill in the art, and may include separation of isomers by precipitation or chromatography.

It should be understood that the compounds of the present disclosure may possess tautomeric forms, as well as geometric isomers, and that these also constitute an aspect of the disclosure.

The present disclosure includes all pharmaceutically acceptable isotopically-labeled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the present disclosure encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to, the compounds shown in Table 1 below. It is to be understood that when there is a discrepancy between the name of the compound found herein and the structure found in Table 1, the structure in Table 1 shall prevail. In addition, it is to be understood that an asterisk (*), at a particular stereocenter in a structure, indicates an arbitrary assignment of stereochemical configuration at that stereocenter.

TABLE 1

| EXAMPLE | STRUCTURE |
|---------|-----------|
| 1 | 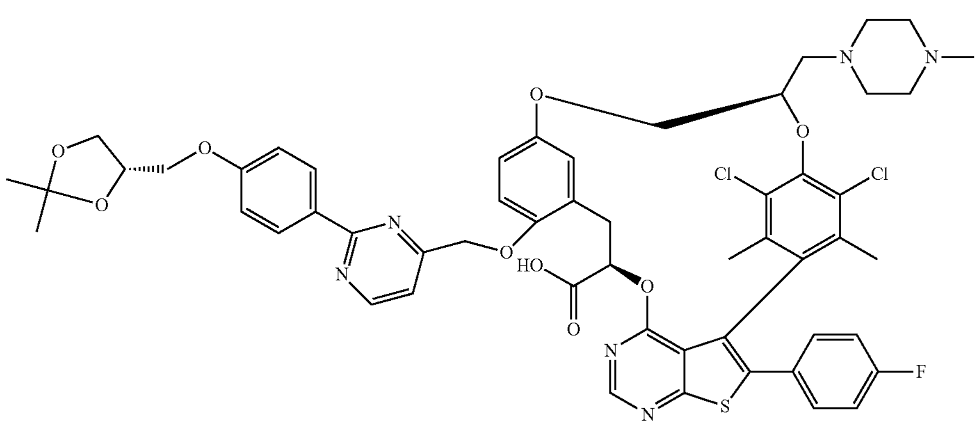 |

TABLE 1-continued
| EXAMPLE | STRUCTURE |
|---|---|
| 2 | 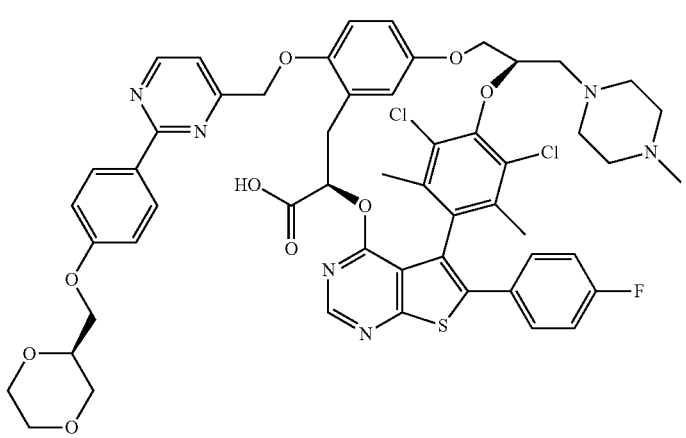 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3ccc(OC[C@H]4COCCO4)cc3)n1)OC[C@@H](CN1CCN(C)CC1)O2] |
| 3 | 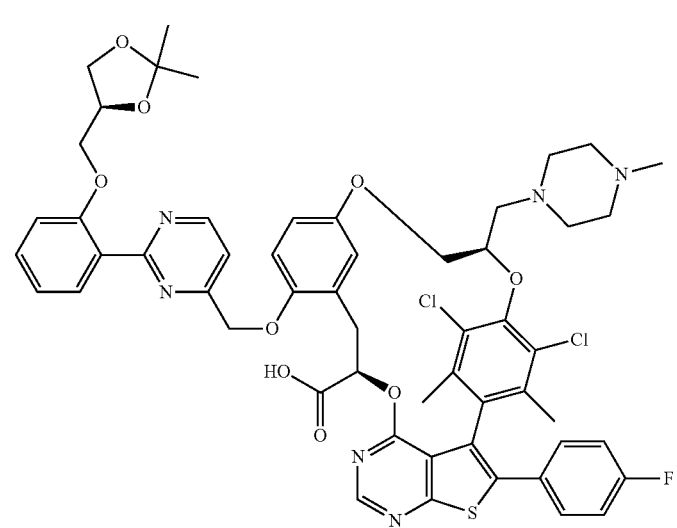 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3ccccc3OC[C@H]3COC(C)(C)O3)n1)OC[C@@H](CN1CCN(C)CC1)O2] |
| 4 | 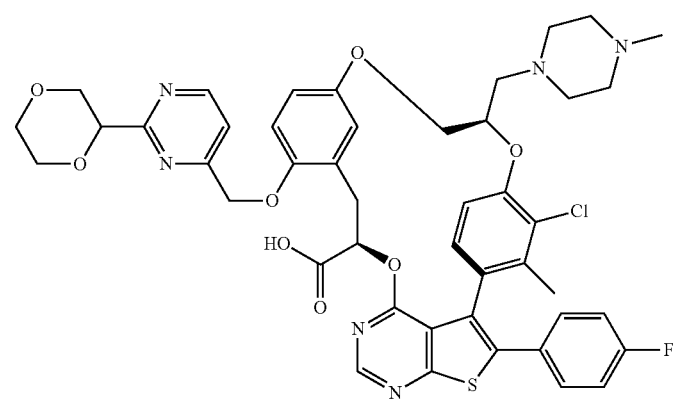 |

TABLE 1-continued

| EXAMPLE | STRUCTURE |
|---|---|
| 5 | 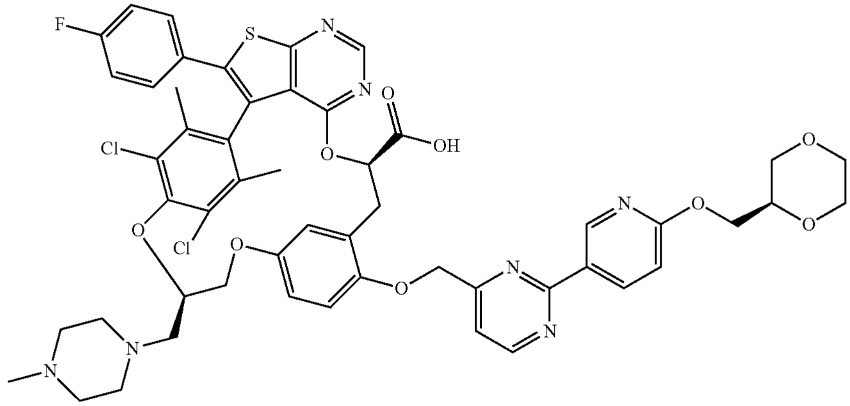 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3ccc(OC[C@H]4COCCO4)nc3)n1)OC[C@@H](CN1CCN(C)CC1)O2] |
| 6 | 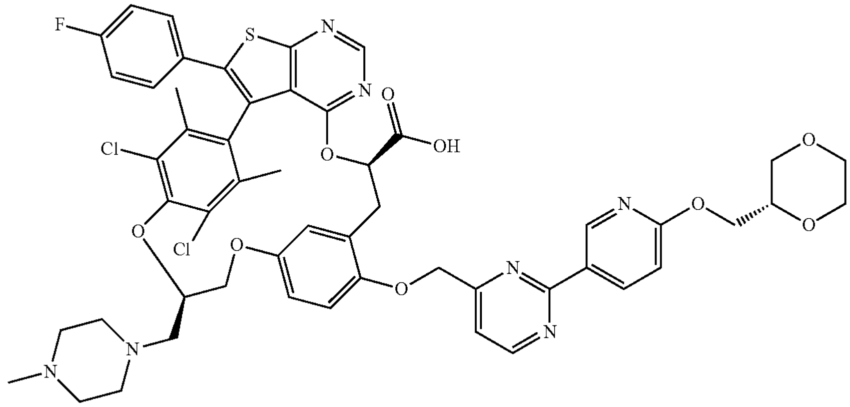 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3ccc(OC[C@@H]4COCCO4)nc3)n1)OC[C@@H](CN1CCN(C)CC1)O2] |
| 7 | 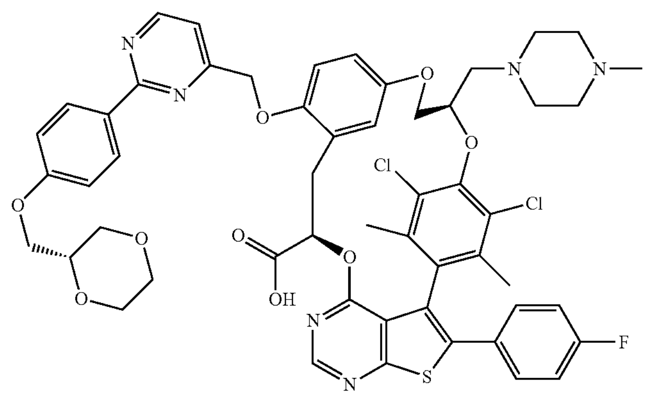 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3ccc(OC[C@@H]4COCCO4)cc3)n1)OC[C@@H](CN1CCN(C)CC1)O2] |
| 8 | 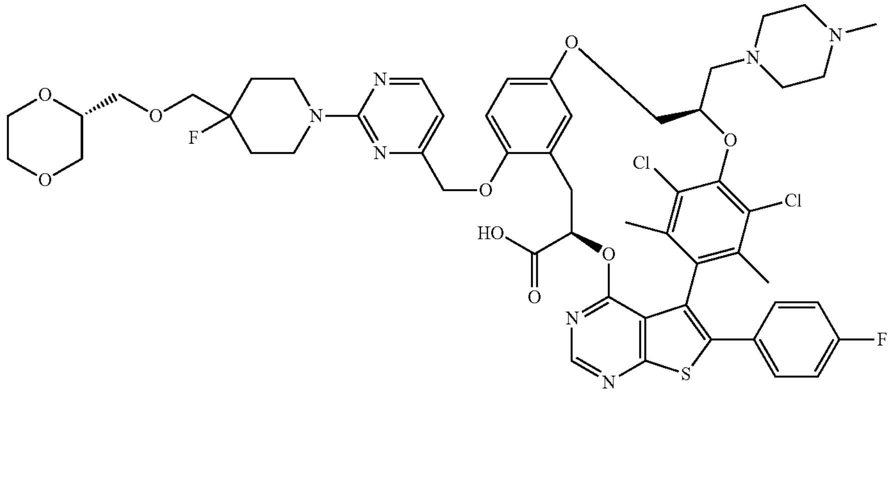 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(N3CCC(F)(COC[C@@H]4COCCO4)CC3)n1)OC[C@@H](CN1CCN(C)CC1)O2] |

TABLE 1-continued
| EXAMPLE | STRUCTURE |
|---|---|
| 9 | 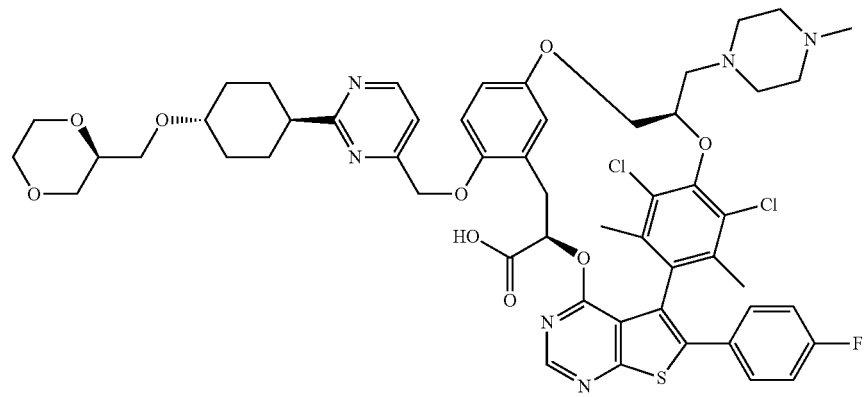 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@H](OC[C@H]4COCCO4)CC3)n1)OC[C@@H](CN1CCN(C)CC1)O2] |
| 10 | 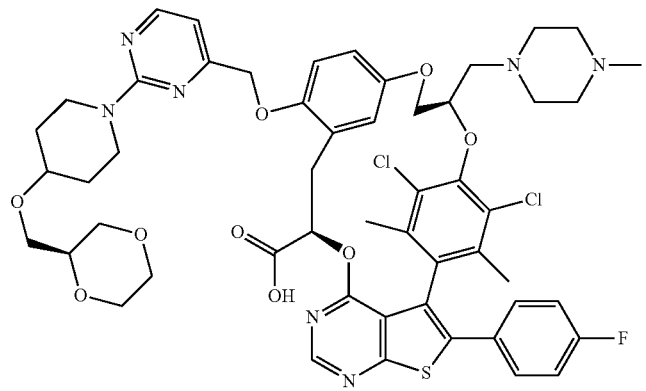 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(N3CCC(OC[C@H]4COCCO4)CC3)n1)OC[C@@H](CN1CCN(C)CC1)O2] |
| 11 | 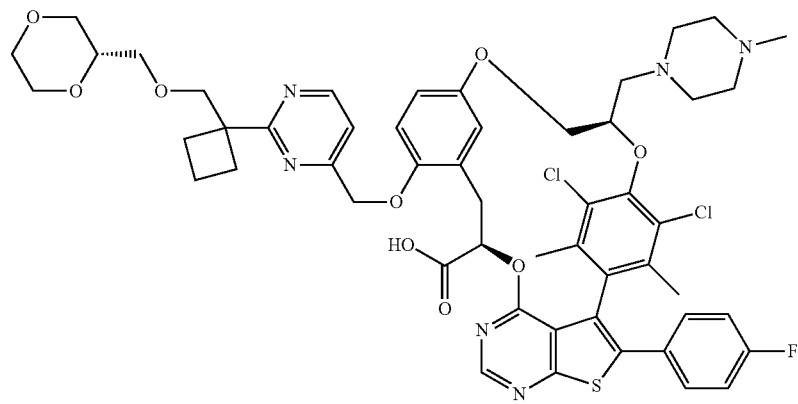 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(C3(COC[C@H]4COCCO4)CCC3)n1)OC[C@@H](CN1CCN(C)CC1)O2] |

TABLE 1-continued

| EXAMPLE | STRUCTURE |
|---|---|
| 12 | 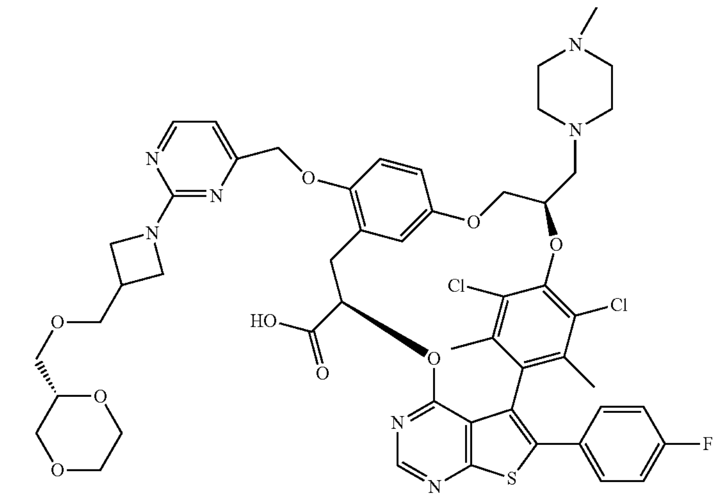 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(N3CC(COC[C@H]4COCCO4)C3)n1)OC[C@@H](CN1CCN(C)CC1)O2] |
| 13 | 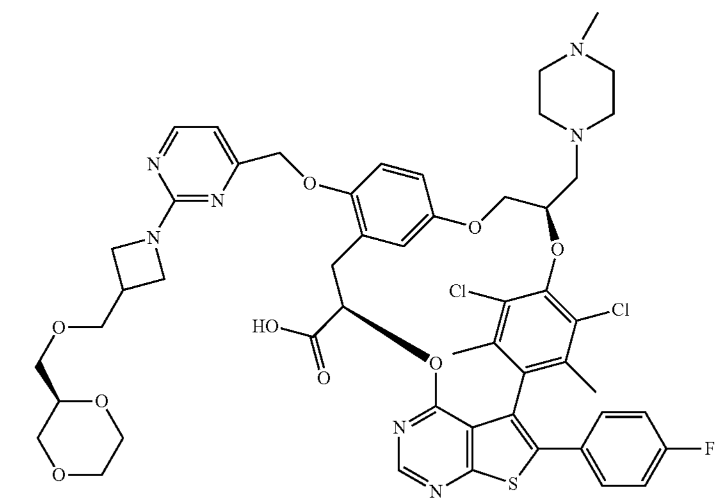 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(N3CC(COC[C@@H]4COCCO4)C3)n1)OC[C@@H](CN1CCN(C)CC1)O2] |
| 14 | 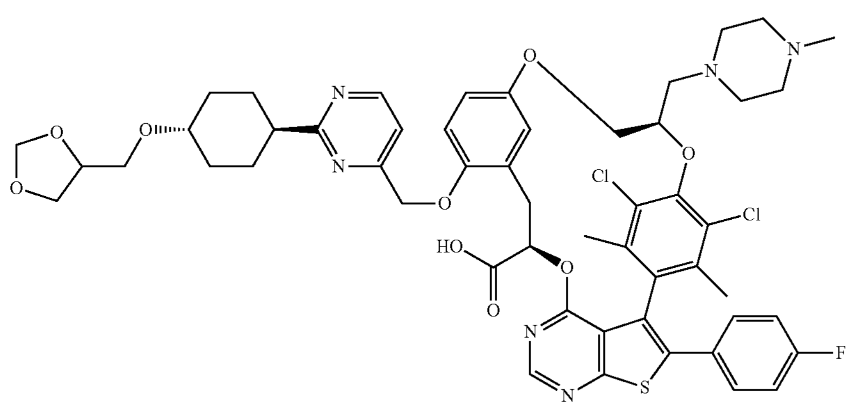 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@H](OCC4COCO4)CC3)n1)OC[C@@H](CN1CCN(C)CC1)O2] |

TABLE 1-continued
| EXAMPLE | STRUCTURE |
|---|---|
| 15 | 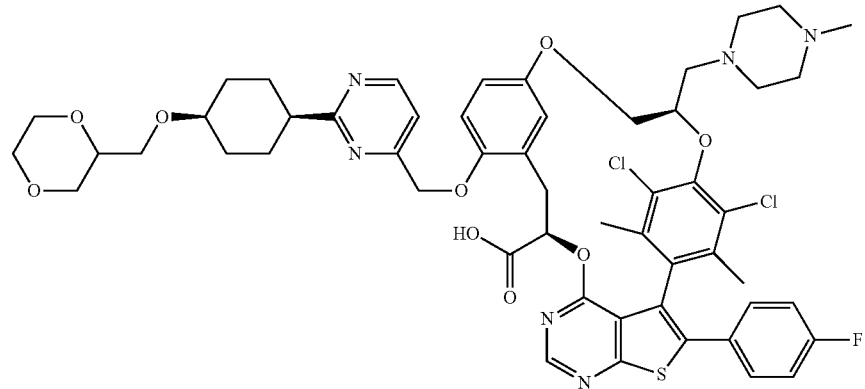 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@@H](OCC4COCCO4)CC3)n1)OC[C@@H](CN1CCN(C)CC1)O2] |
| 16 | 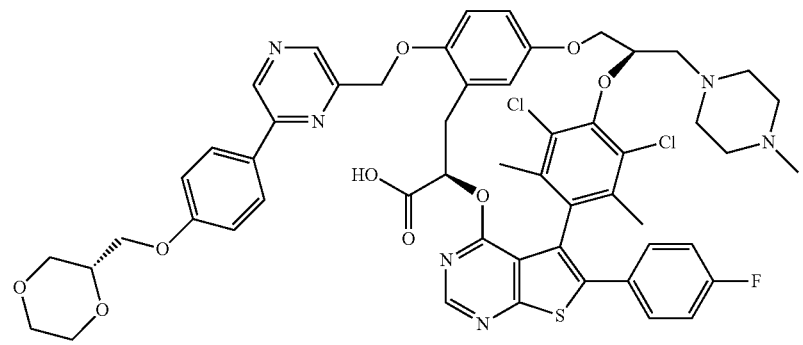 [SMILES: Cc1c(Cl)c2c(Cl)c(C)c1-c1c(-c3ccc(F)cc3)sc3ncnc(c13)O[C@@H](C(=O)O)Cc1cc(ccc1OCc1cncc(-c3ccc(OC[C@H]4COCCO4)cc3)n1)OC[C@@H](CN1CCN(C)CC1)O2] |
| 17 | 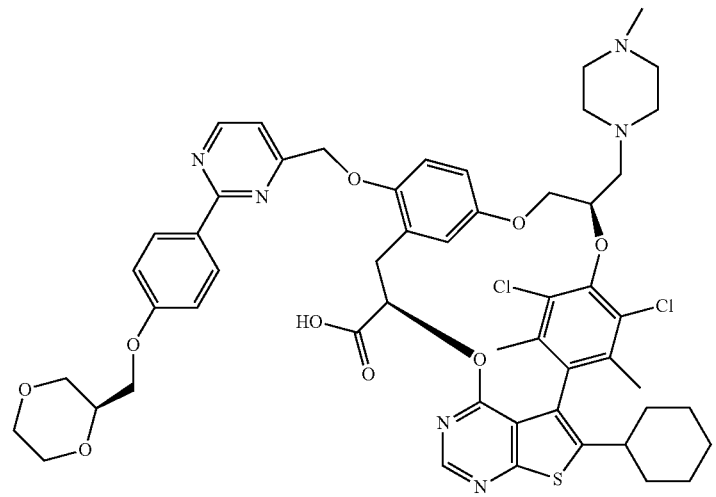 [SMILES: Cc1c(Cl)c2c(Cl)c(C)c1-c1c(C3CCCCC3)sc3ncnc(c13)O[C@@H](C(=O)O)Cc1cc(ccc1OCc1ccnc(-c3ccc(OC[C@@H]4COCCO4)cc3)n1)OC[C@@H](CN1CCN(C)CC1)O2] |

US 10,676,485 B2
TABLE 1-continued
| EXAMPLE | STRUCTURE |
|---|---|
| 18 | 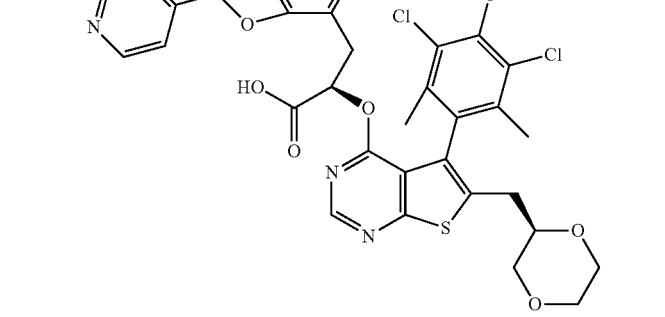 |
| 19 | 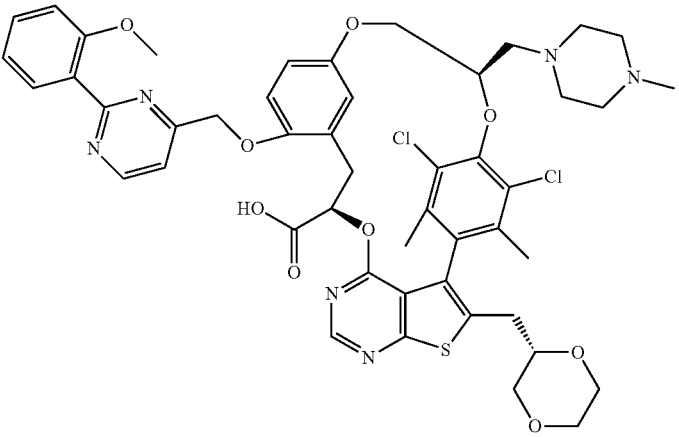 [SMILES: COc1ccccc1-c1nccc(COc2ccc3cc2C[C@H](C(=O)O)Oc2ncnc4sc(C[C@H]5COCCO5)c(c24)-c2c(C)c(Cl)c(c(Cl)c2C)O[C@H](CN2CCN(C)CC2)CO3)n1] |
| 20 | 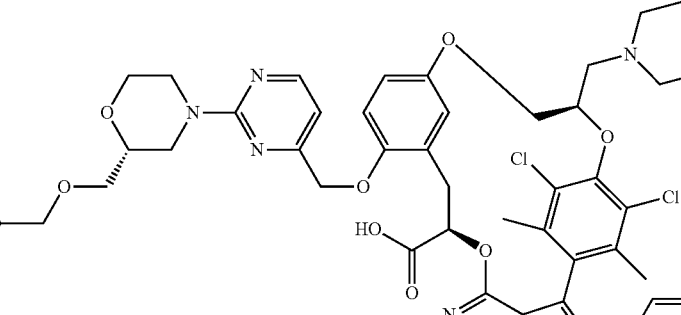 |

TABLE 1-continued

| EXAMPLE | STRUCTURE |
|---|---|
| 21 | 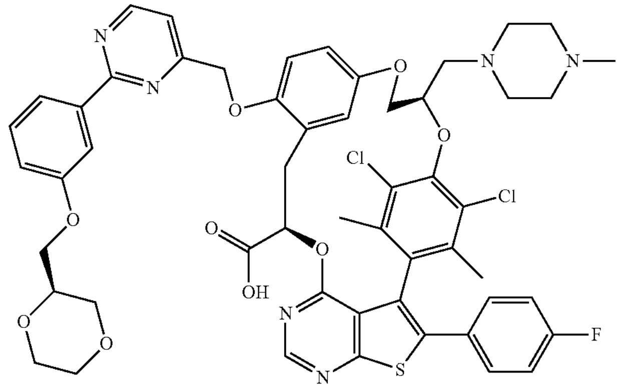 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3cccc(OC[C@H]4COCCO4)c3)n1)OC[C@@H](CN1CCN(C)CC1)O2] |
| 22 | 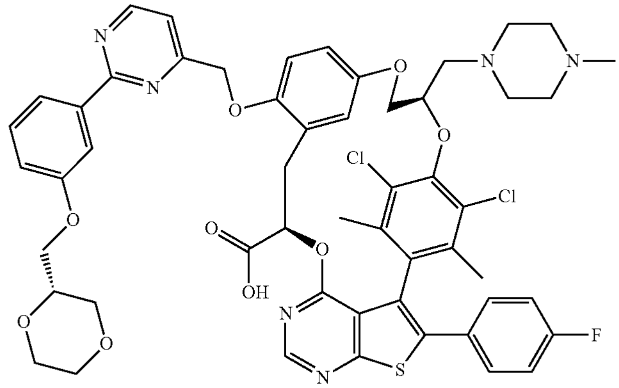 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3cccc(OC[C@@H]4COCCO4)c3)n1)OC[C@@H](CN1CCN(C)CC1)O2] |
| 23 | 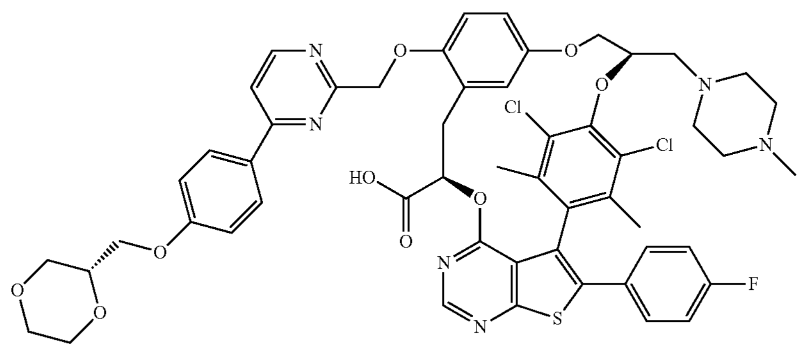 |
| 24 | 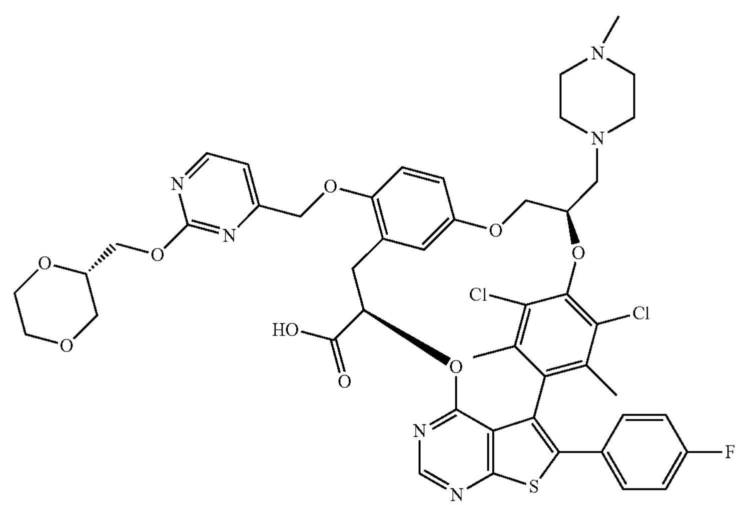 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(OC[C@@H]3COCCO3)n1)OC[C@@H](CN1CCN(C)CC1)O2] |

TABLE 1-continued
| EXAMPLE | STRUCTURE |
|---|---|
| 25 | 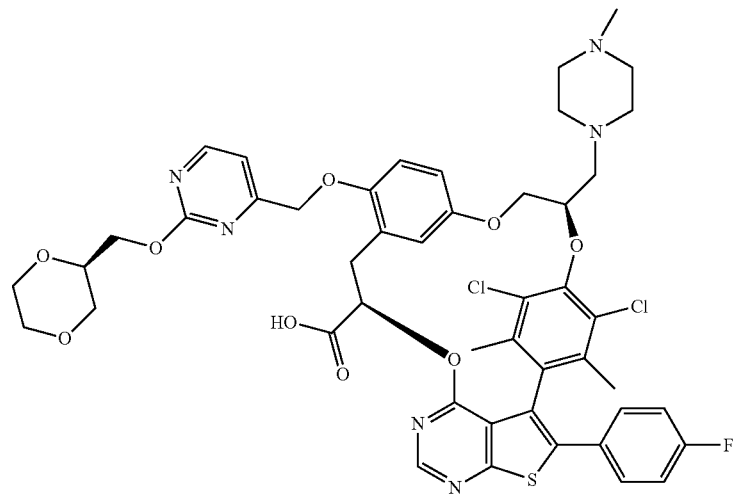 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(OC[C@H]3COCCO3)n1)OC[C@@H](CN1CCN(C)CC1)O2] |
| 26 | 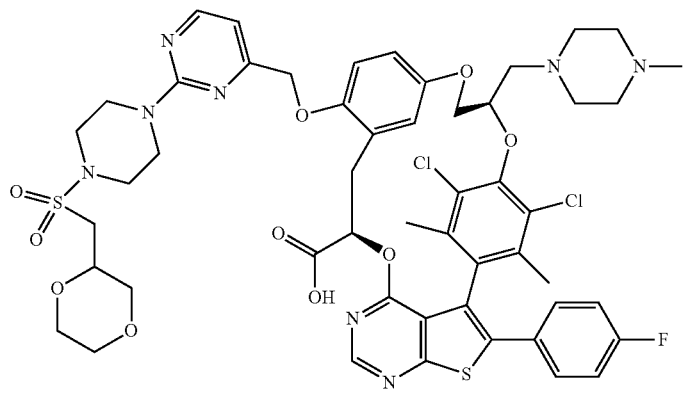 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(N3CCN(S(=O)(=O)CC4COCCO4)CC3)n1)OC[C@@H](CN1CCN(C)CC1)O2] |
| 27 | 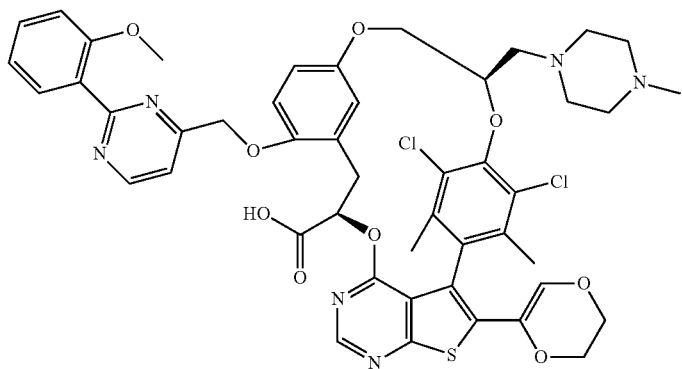 [SMILES: COc1ccccc1-c1nccc(COc2ccc3cc2C[C@H](C(=O)O)Oc2ncnc4sc(C5=COCCO5)c(c24)-c2c(C)c(Cl)c(c(Cl)c2C)O[C@H](CN2CCN(C)CC2)CO3)n1] |

TABLE 1-continued
| EXAMPLE | STRUCTURE |
|---|---|
| 28 | 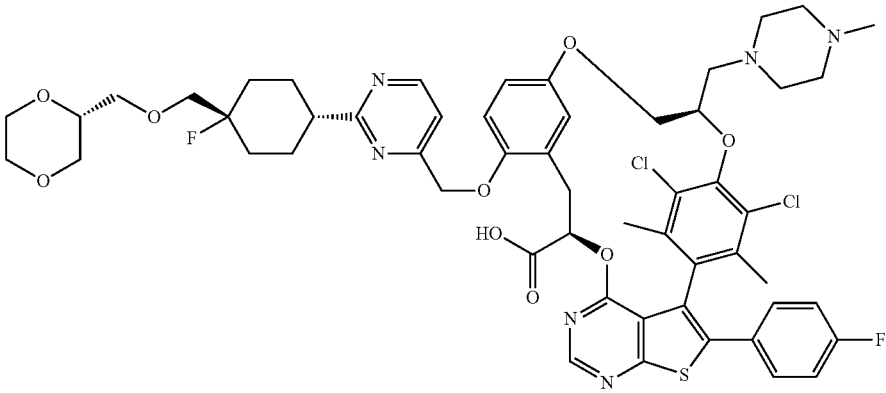 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@](F)(COC[C@@H]4COCCO4)CC3)n1)OC[C@@H](CN1CCN(C)CC1)O2] |
| 29 | 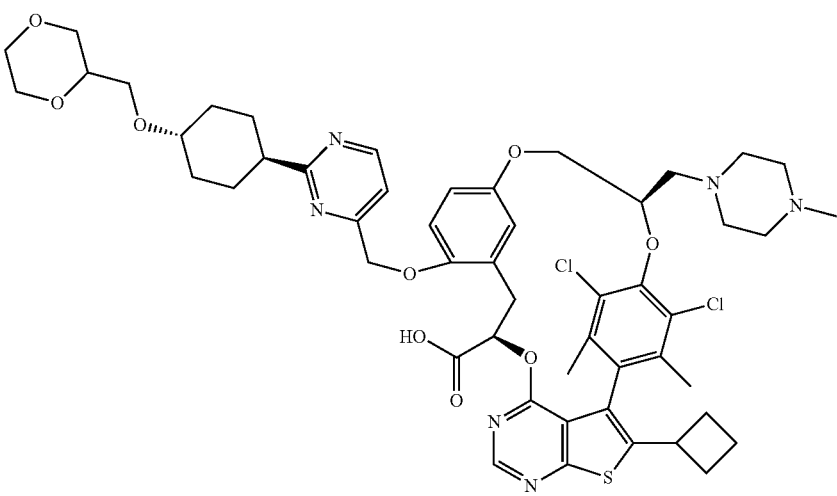 [SMILES: Cc1c(Cl)c2c(Cl)c(C)c1-c1c(C3CCC3)sc3ncnc(c13)O[C@@H](C(=O)O)Cc1cc(ccc1OCc1ccnc([C@H]3CC[C@H](OCC4COCCO4)CC3)n1)OC[C@@H](CN1CCN(C)CC1)O2] |
| 30 | 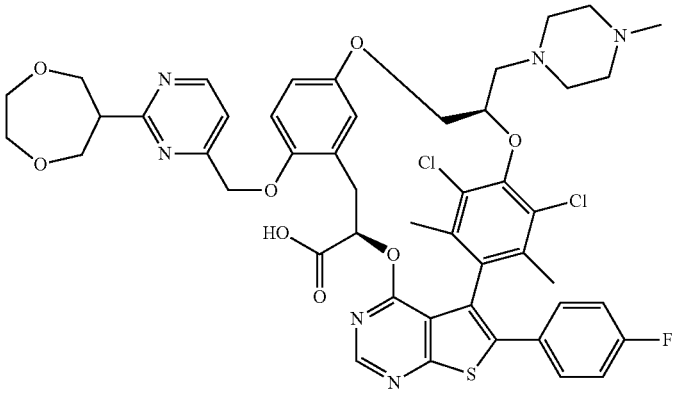 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(C3COCCOC3)n1)OC[C@@H](CN1CCN(C)CC1)O2] |

TABLE 1-continued
| EXAMPLE | STRUCTURE |
|---|---|
| 31 | 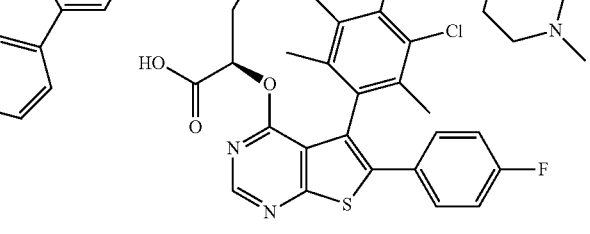 |
| 32 | 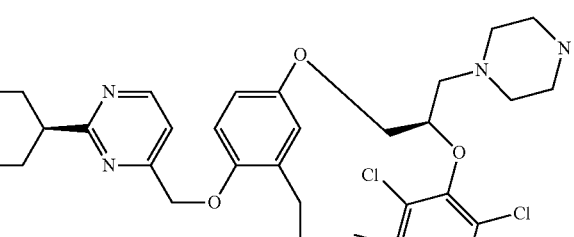 |
| 33 | 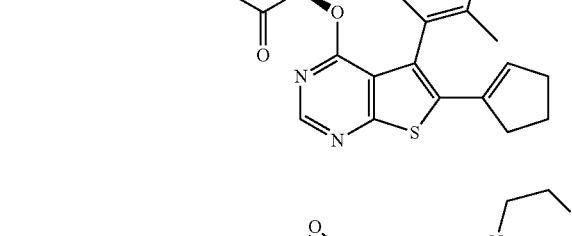 |
| 34 | 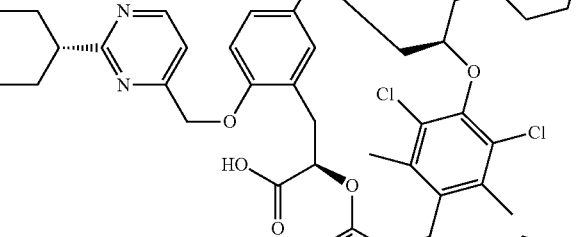 |

TABLE 1-continued
| EXAMPLE | STRUCTURE |
|---|---|
| 35 | 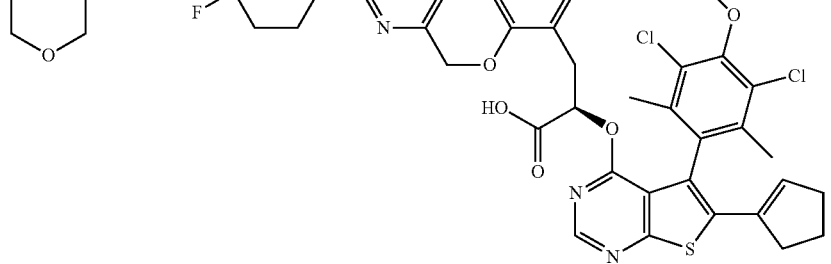 |
| 36 | 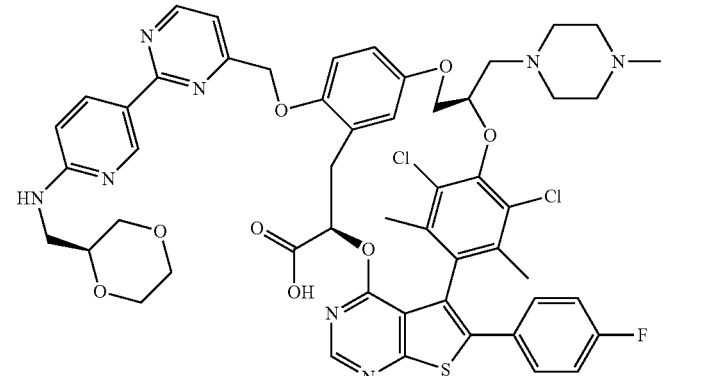 |
| 37 | 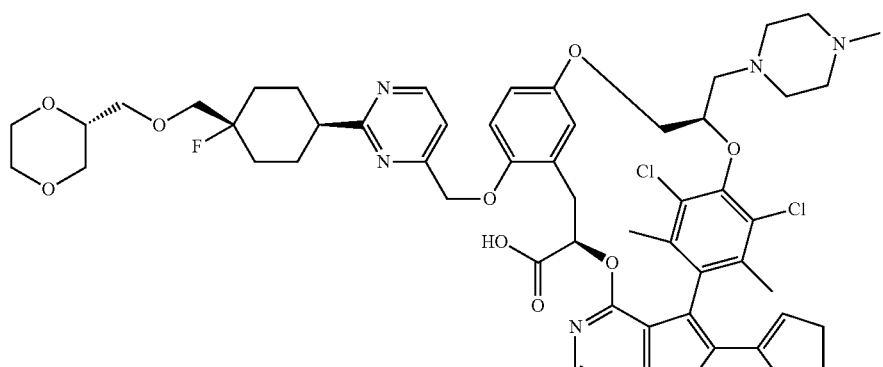 |
| 38 | 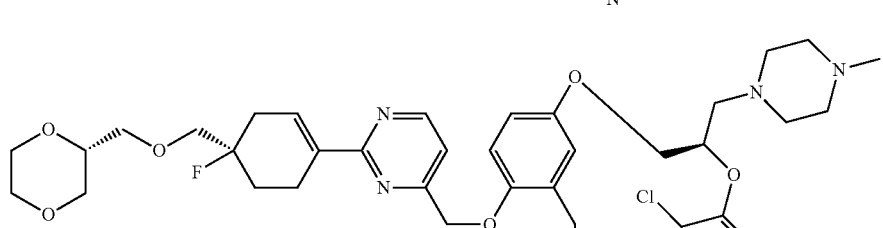 |

TABLE 1-continued
| EXAMPLE | STRUCTURE |
|---|---|
| 39 | 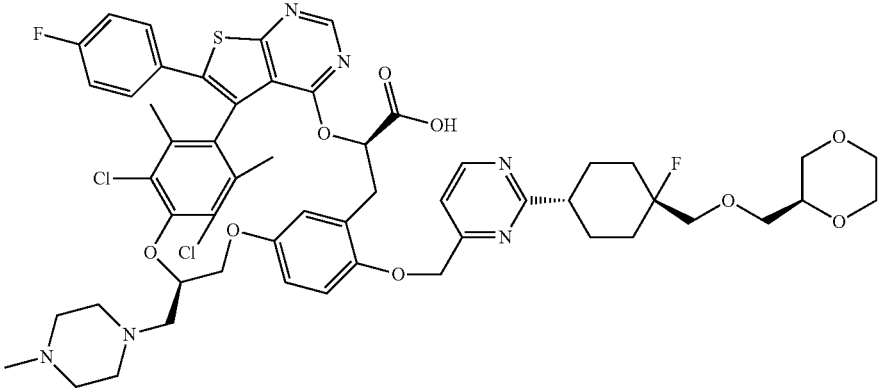 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@](F)(COC[C@H]4COCCO4)CC3)n1)OC[C@@H](CN1CCN(C)CC1)O2] |
| 40 | 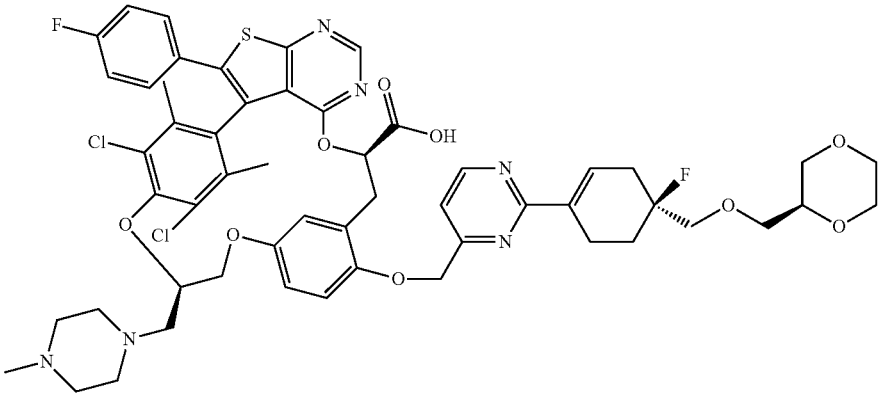 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(C3=CC[C@](F)(COC[C@H]4COCCO4)CC3)n1)OC[C@@H](CN1CCN(C)CC1)O2] |
| 41 | 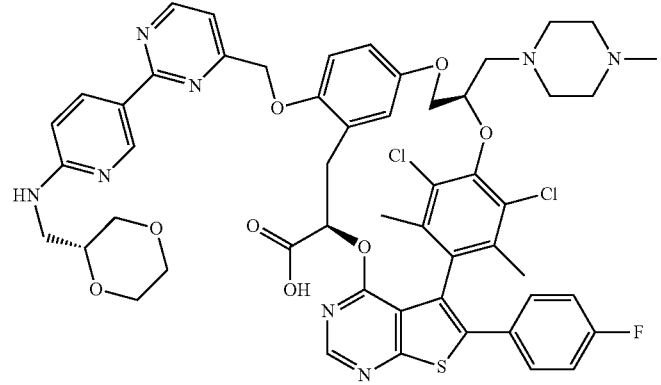 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(-c3ccc(NC[C@@H]4COCCO4)nc3)n1)OC[C@@H](CN1CCN(C)CC1)O2] |
| 42 | 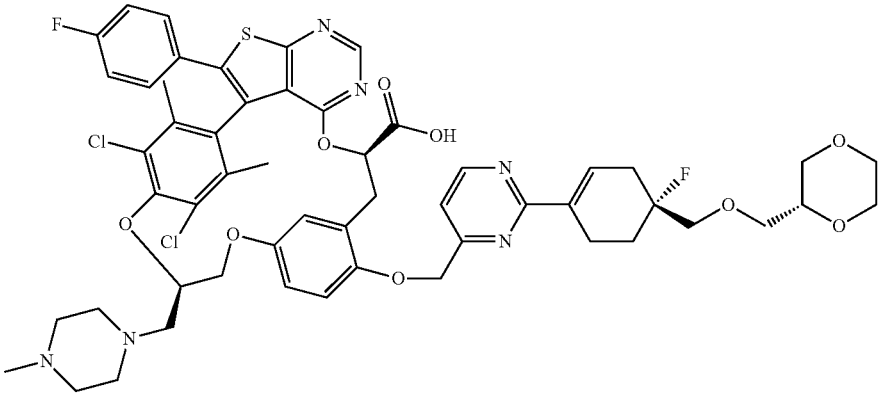 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(C3=CC[C@@](F)(COC[C@@H]4COCCO4)CC3)n1)OC[C@@H](CN1CCN(C)CC1)O2] |

TABLE 1-continued

| EXAMPLE | STRUCTURE |
| --- | --- |
| 43 | 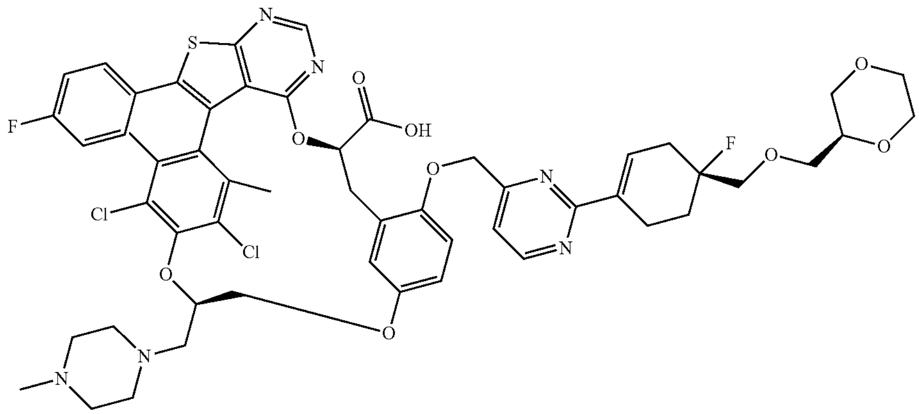 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(C3=CC[C@@](F)(COC[C@H]4COCCO4)CC3)n1)OC[C@@H](CN1CCN(C)CC1)O2] |
| 44 | 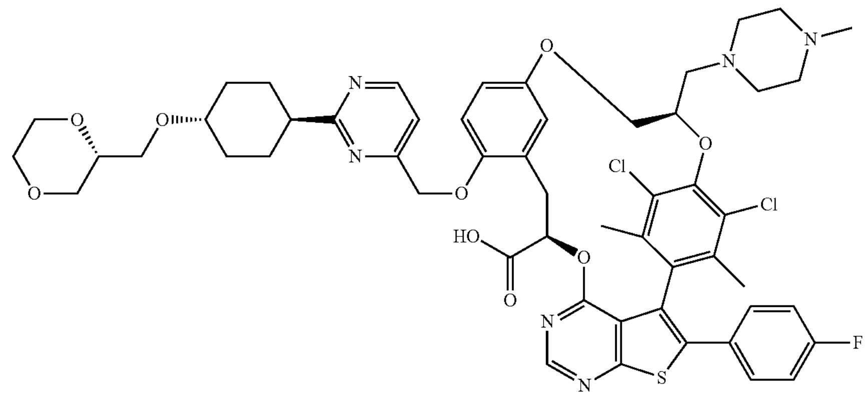 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@H](OC[C@@H]4COCCO4)CC3)n1)OC[C@@H](CN1CCN(C)CC1)O2] |
| 45 | 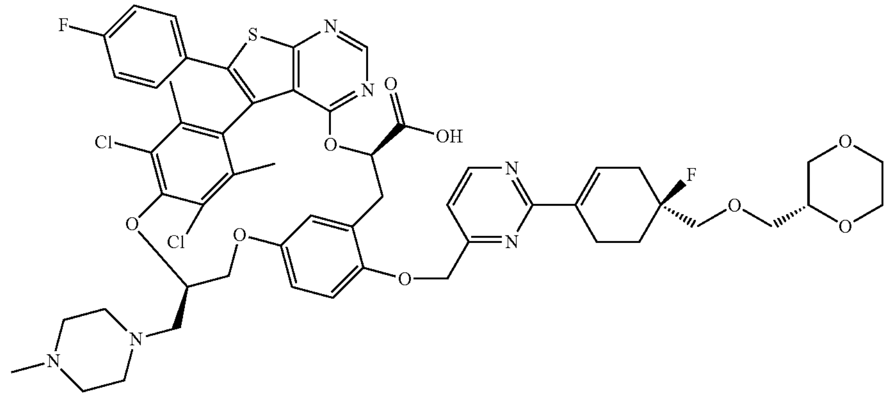 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc(C3=CC[C@](F)(COC[C@@H]4COCCO4)CC3)n1)OC[C@@H](CN1CCN(C)CC1)O2] |
| 46 | 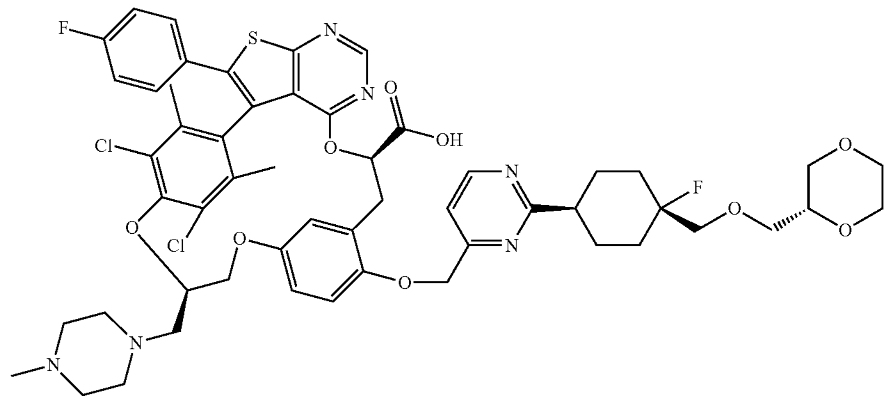 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@@](F)(COC[C@@H]4COCCO4)CC3)n1)OC[C@@H](CN1CCN(C)CC1)O2] |

TABLE 1-continued

| EXAMPLE | STRUCTURE |
| --- | --- |
| 47 | 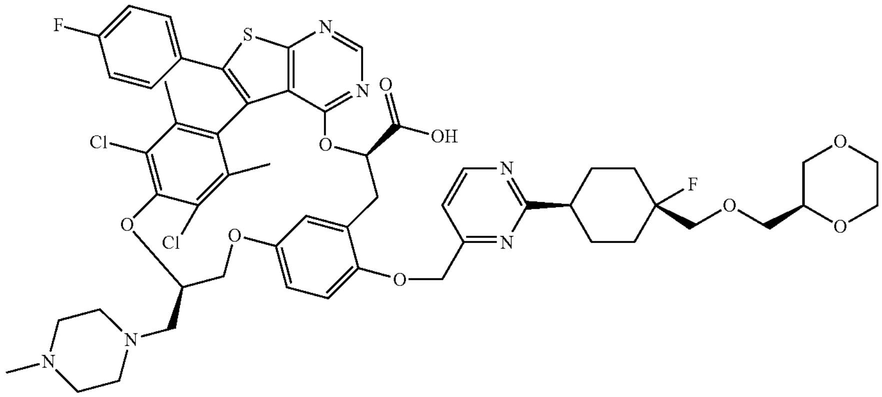 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@@](F)(COC[C@H]4COCCO4)CC3)n1)OC[C@@H](CN1CCN(C)CC1)O2] |
| 48 | 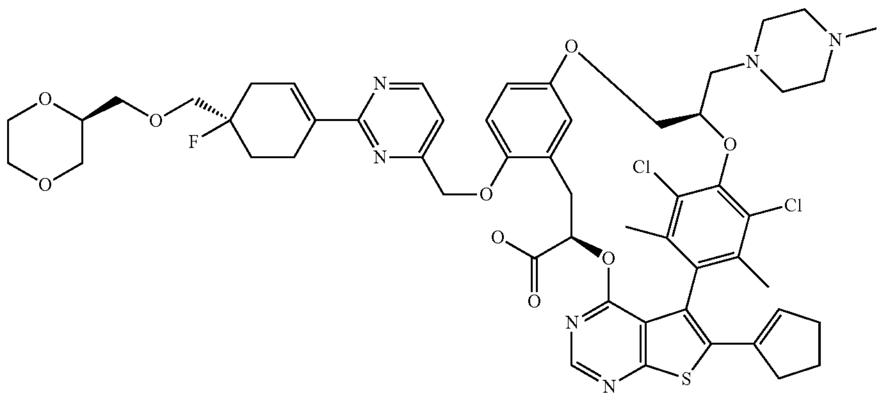 [SMILES: Cc1c(Cl)c2c(Cl)c(C)c1-c1c(C3=CCCC3)sc3ncnc(c13)O[C@@H](C(=O)O)Cc1cc(ccc1OCc1ccnc(C3=CC[C@@](F)(COC[C@H]4COCCO4)CC3)n1)OC[C@@H](CN1CCN(C)CC1)O2] |
| 49 | 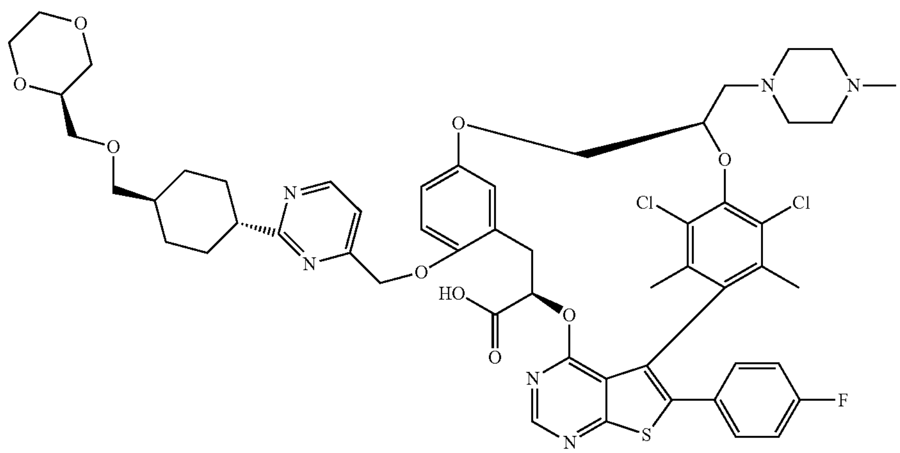 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@H](COC[C@@H]4COCCO4)CC3)n1)OC[C@@H](CN1CCN(C)CC1)O2] |

TABLE 1-continued
| EXAMPLE | STRUCTURE |
|---|---|
| 50 | 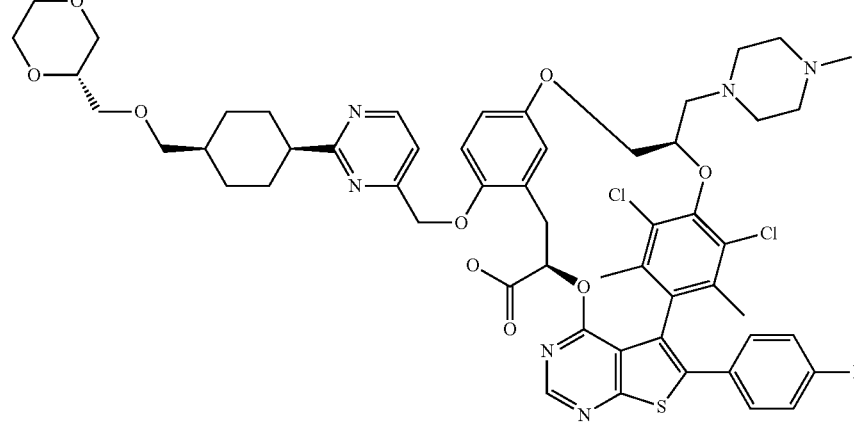 |
| 51 | 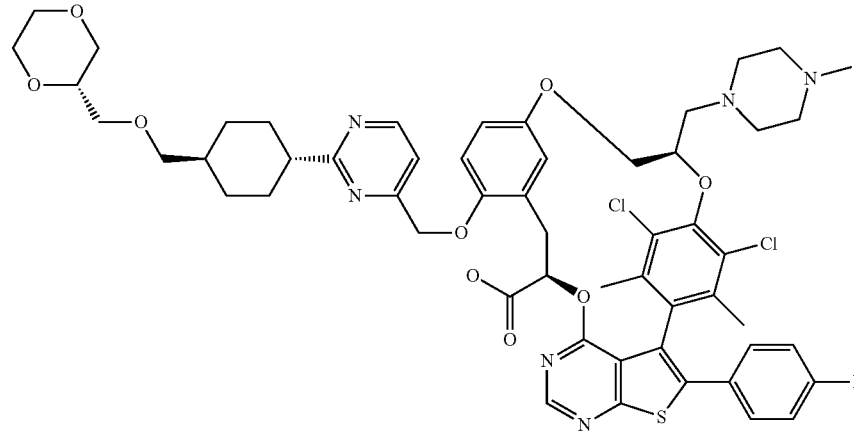 |
| 52 | 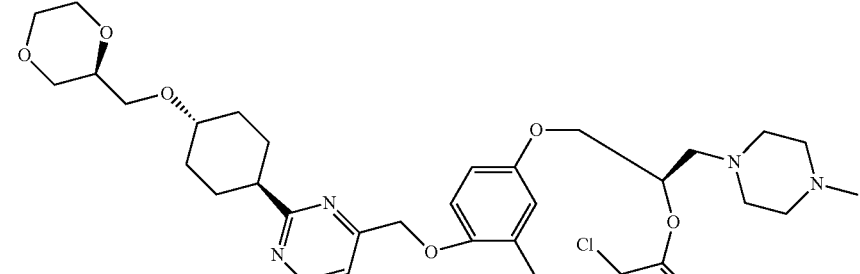 |

TABLE 1-continued

| EXAMPLE | STRUCTURE |
|---|---|
| 53 | 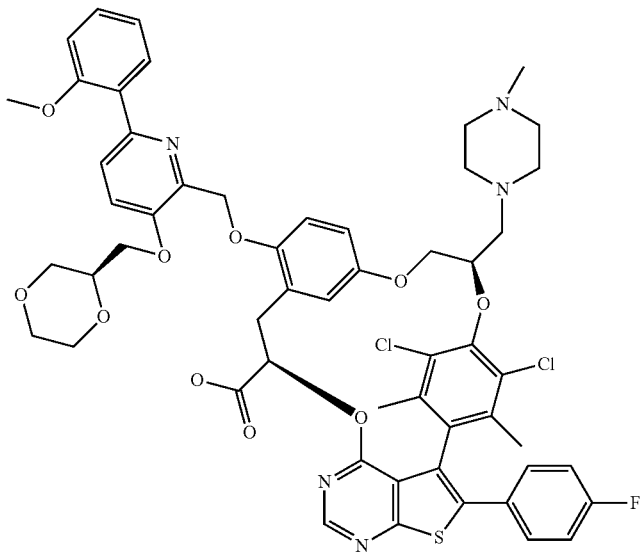 [SMILES: COc1ccccc1-c1ccc(OC[C@@H]2COCCO2)c(COc2ccc3cc2C[C@H](C(=O)O)Oc2ncnc4sc(-c5ccc(F)cc5)c(c24)-c2c(C)c(Cl)c(c(Cl)c2C)O[C@H](CN2CCN(C)CC2)CO3)n1] |

One embodiment pertains to Example 2, and pharmaceutically acceptable salts thereof:

2 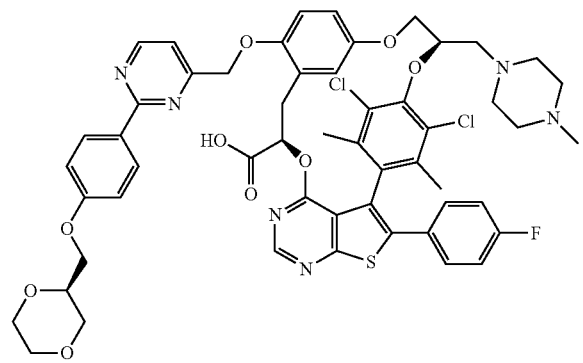

That is, in embodiments, the compound of Formula (I) is (7R,16R)-19,23-dichloro-10-{[2-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

One embodiment pertains to Example 9, and pharmaceutically acceptable salts thereof:

9 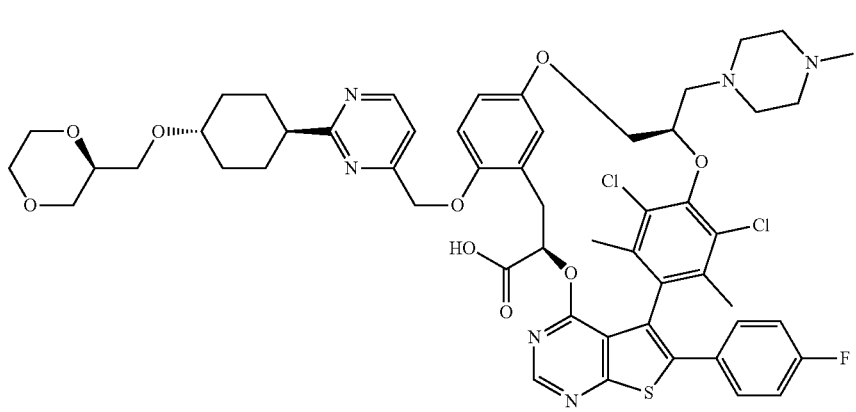

That is, in embodiments, the compound of Formula (I) is (7R,16R)-19,23-dichloro-10-({2-[(1R,4r)-4-{[(2R)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

One embodiment pertains to Example 28, and pharmaceutically acceptable salts thereof:

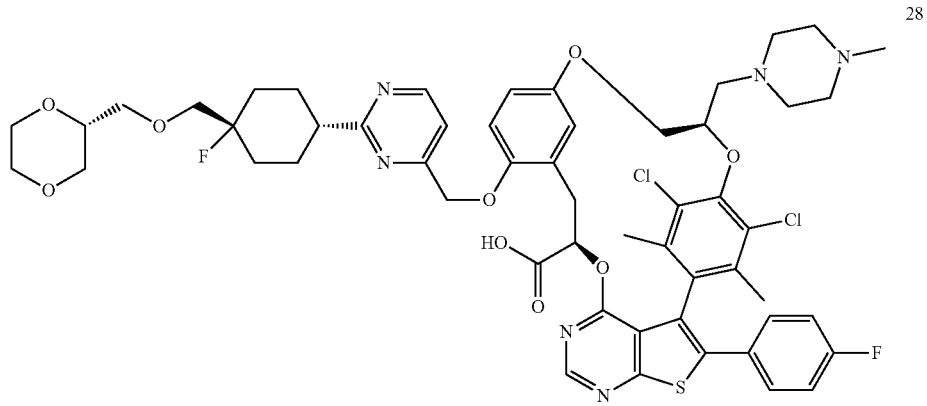 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@](F)(COC[C@@H]4COCCO4)CC3)n1)OC[C@@H](CN1CCN(C)CC1)O2]

28

That is, in embodiments, the compound of Formula (I) is (7R,16R)-19,23-dichloro-10-({2-[(1R,4s)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

One embodiment pertains to Example 39, and pharmaceutically acceptable salts thereof:

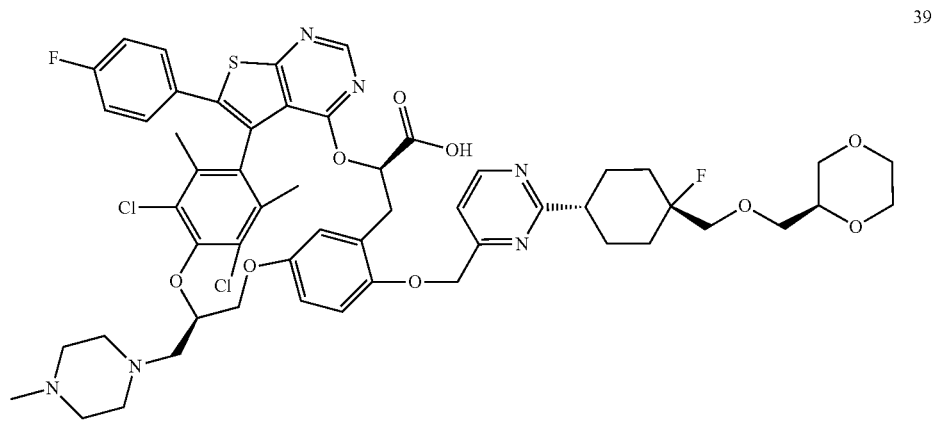 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@](F)(COC[C@H]4COCCO4)CC3)n1)OC[C@@H](CN1CCN(C)CC1)O2]

39

That is, in embodiments, the compound of Formula (I) is (7R,16R)-19,23-dichloro-10-({2-[(1S,4s)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

One embodiment pertains to Example 44, and pharmaceutically acceptable salts thereof:

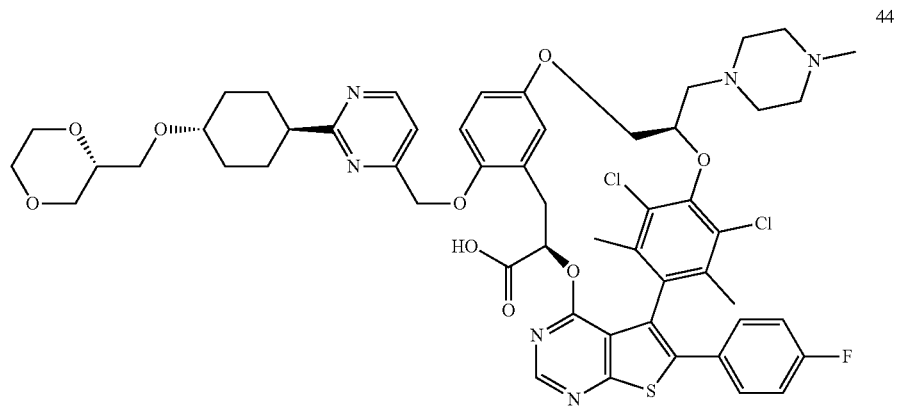 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@H](OC[C@@H]4COCCO4)CC3)n1)OC[C@@H](CN1CCN(C)CC1)O2]

That is, in embodiments, the compound of Formula (I) is (7R,16R)-19,23-dichloro-10-({2-[(1S,4r)-4-{[(2S)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

One embodiment pertains to Example 49, and pharmaceutically acceptable salts thereof:

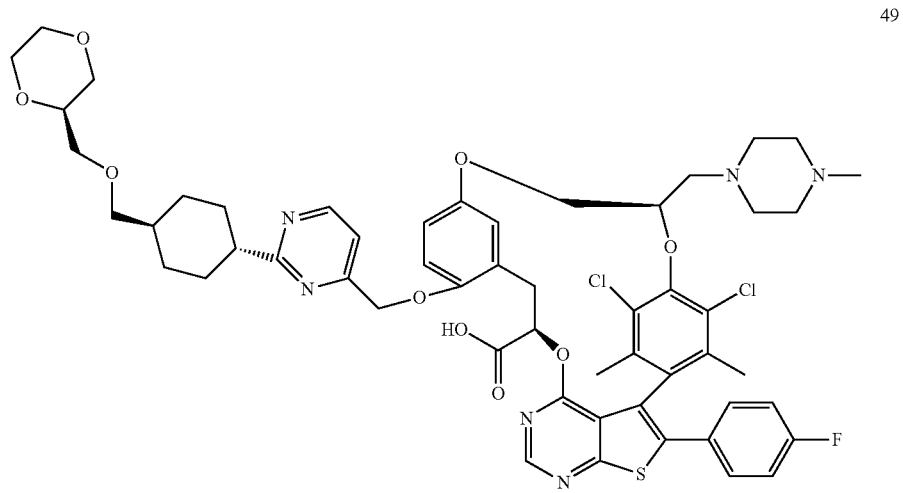 [SMILES: Cc1c(Cl)c2c(Cl)c(C)c1-c1c(-c3ccc(F)cc3)sc3ncnc(c13)O[C@@H](C(=O)O)Cc1cc(ccc1OCc1ccnc([C@H]3CC[C@H](COC[C@@H]4COCCO4)CC3)n1)OC[C@@H](CN1CCN(C)CC1)O2]

That is, in embodiments, the compound of Formula (I) is (7R,16R)-19,23-dichloro-10-({2-[(1S,4r)-4-({[(2R)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

One embodiment pertains to Example 51, and pharmaceutically acceptable salts thereof:

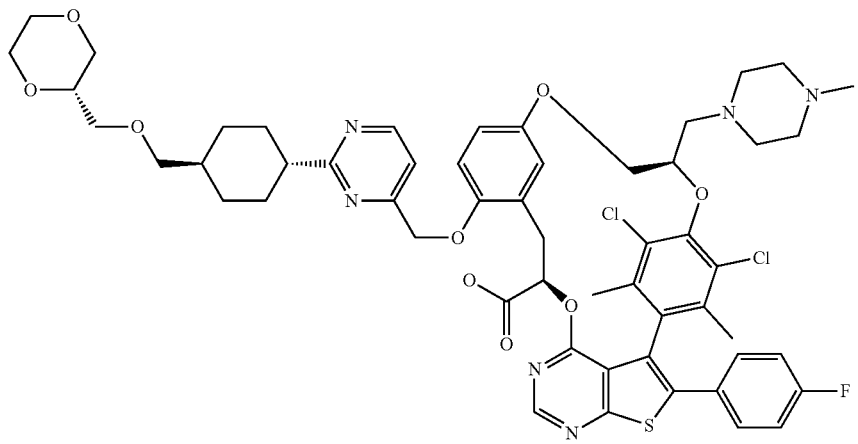

51

That is, in embodiments, the compound of Formula (I) is (7R,16R)-19,23-dichloro-10-({2-[(1R,4r)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid, or pharmaceutically acceptable salts thereof.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and may be converted to a pharmaceutically acceptable salt, when desired, by using a suitable acid or base.

The salts may be prepared in situ during the final isolation and purification of the compounds of the present disclosure.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this disclosure by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

Synthesis

The compounds described herein, including compounds of general formula (I) and specific examples, may be prepared, for example, through the reaction routes depicted in schemes 1-9. The variables $A^2$, $A^3$, $A^4$, $A^6$, $A^7$, $A^8$, $A^{15}$, $R^4$, $R^5$, $R^9$, $R^{10A}$, $R^{10B}$, $R^{11}$, $R^{12}$, $R^{13}$, $R^{14}$, $R^{15}$, $R^{16}$, W, X, and Y used in the following schemes have the meanings as set forth in the Summary and Detailed Description sections unless otherwise noted.

Abbreviations that may be used in the descriptions of the schemes and the specific examples have the meanings listed in the table below.

| Abbreviation | Definition |
|---|---|
| μL | microliter |
| Boc | tert-butoxycarbonyl |
| br s | broad singlet |
| d | duplet |
| DCI | desorption chemical ionization |
| DCM | dichloromethane |
| dd | double duplet |
| DIEA | N,N-Diisopropylethylamine |
| DMAP | dimethylaminopyridine |
| DMF | N,N-dimethylformamide |
| DMSO | dimethyl sulfoxide |
| eq or equiv | equivalents |
| ESI | electrospray ionization |
| Et | ethyl |
| g | gram |
| h | hours |
| HATU | 1-[bis(dimethylamino)methylene]-1H-1,2,3-triazolo[4,5-b]pyridinium 3-oxid hexafluorophosphate |
| HOBt | 1-hydroxybenzotriazole hydrate |

| Abbreviation | Definition |
| --- | --- |
| HPLC | high performance liquid chromatography or high pressure liquid chromatography |
| kg | kilogram |
| LC/MS or LCMS | liquid chromatography-mass spectrometry |
| m | multiplet |
| Me | methyl |
| MeOH | methanol |
| mg | milligram |
| min | minute |
| mL | milliliter |
| mmol | millimoles |
| MPLC | medium pressure liquid chromatography |
| MS | mass spectrum |
| NMP | N-methylpyrrolidone |
| NMR | nuclear magnetic resonance |
| Ph | phenyl |
| ppm | parts per million |
| psi | pounds per square inch |
| s | singlet |
| SFC | supercritical fluid chromatography |
| tBuOH or t-BuOH | tert-butanol |
| TFA | trifluoroacetic acid |
| THF | tetrahydrofuran |
| TLC | thin layer chromatography |
| XPhos | 2-dicyclohexylphosphino-2',4',6'-triisopropylbiphenyl |

Scheme 1

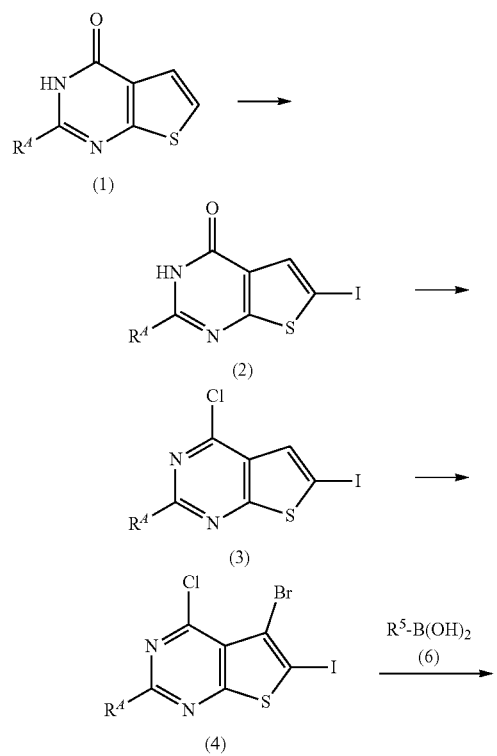

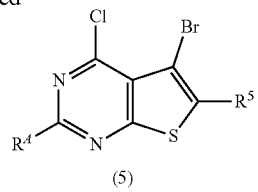

The synthesis of thienopyrimidine intermediates of formula (5) is described in Scheme 1. Thieno[2,3-d]pyrimidine-4(3H)-ones of formula (1), wherein $R^A$ is as described herein, can be treated with periodic acid and iodine to provide 6-iodothieno[2,3-d]pyrimidin-4(3H)-ones of formula (2). The reaction is typically performed at an elevated temperature, for example from 60° C. to 70° C., in a solvent system such as, but not limited to, acetic acid, sulfuric acid and water. 4-Chloro-6-iodothieno[2,3-d]pyrimidines of formula (3) can be prepared by treating 6-iodothieno[2,3-d]pyrimidin-4(3H)-ones of formula (2) with phosphorous oxychloride. The reaction is typically carried out in a solvent such as, but not limited to, N,N-dimethylaniline at an elevated temperature. 5-Bromo-4-chloro-6-iodothieno[2,3-d]pyrimidines of formula (4) can be prepared by the treatment of 4-chloro-6-iodothieno[2,3-d]pyrimidines of formula (3) with N-bromosuccinimide in the presence of tetrafluoroboric acid-dimethyl ether complex. The reaction is typically performed at ambient temperature in a solvent such as, but not limited to, acetonitrile. Compounds of formula (5) can be prepared by reacting 5-bromo-4-chloro-6-iodothieno[2,3-d]pyrimidines of formula (4) with a boronic acid (or the equivalent boronate ester) of formula (6), wherein $R^5$ is $G^3$ as described herein, under Suzuki Coupling conditions described herein, known to those skilled in the art, or widely available in the literature.

Scheme 2

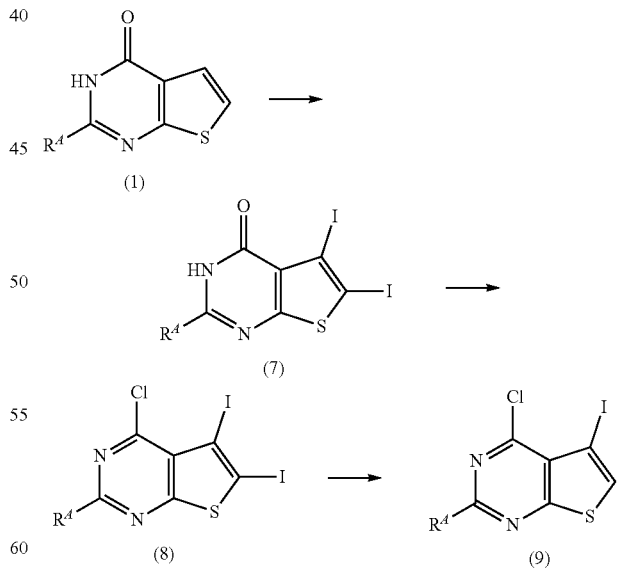

The synthesis of thienopyrimidine intermediates of formula (9) is described in Scheme 2. Thieno[2,3-d]pyrimidine-4(3H)-ones of formula (1), wherein $R^A$ is as described herein, can be treated with periodic acid and iodine to provide 5,6-diiodothieno[2,3-d]pyrimidin-4(3H)-ones of formula (7). The reaction is typically performed at an elevated temperature, for example from 60° C. to 100° C., in a solvent system such as, but not limited to, acetic acid, sulfuric acid and water. 4-Chloro-5,6-diiodothieno[2,3-d]pyrimidines of formula (8) can be prepared by treating 5,6-diiodothieno[2,3-d]pyrimidin-4(3H)-ones of formula (7) with phosphorous oxychloride. The reaction is typically carried out in a solvent such as, but not limited to, N,N-dimethylaniline at an elevated temperature. 4-Chloro-5,6-diiodothieno[2,3-d]pyrimidines of formula (8) can be treated with tert-butylmagnesium chloride to provide compounds of formula (9). The reaction is typically performed at a low temperature in a solvent, such as, but not limited to, tetrahydrofuran.

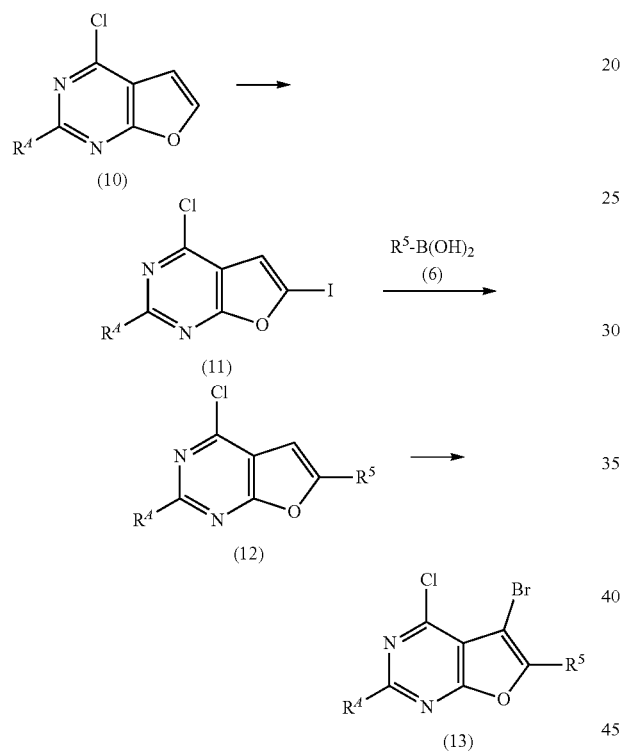

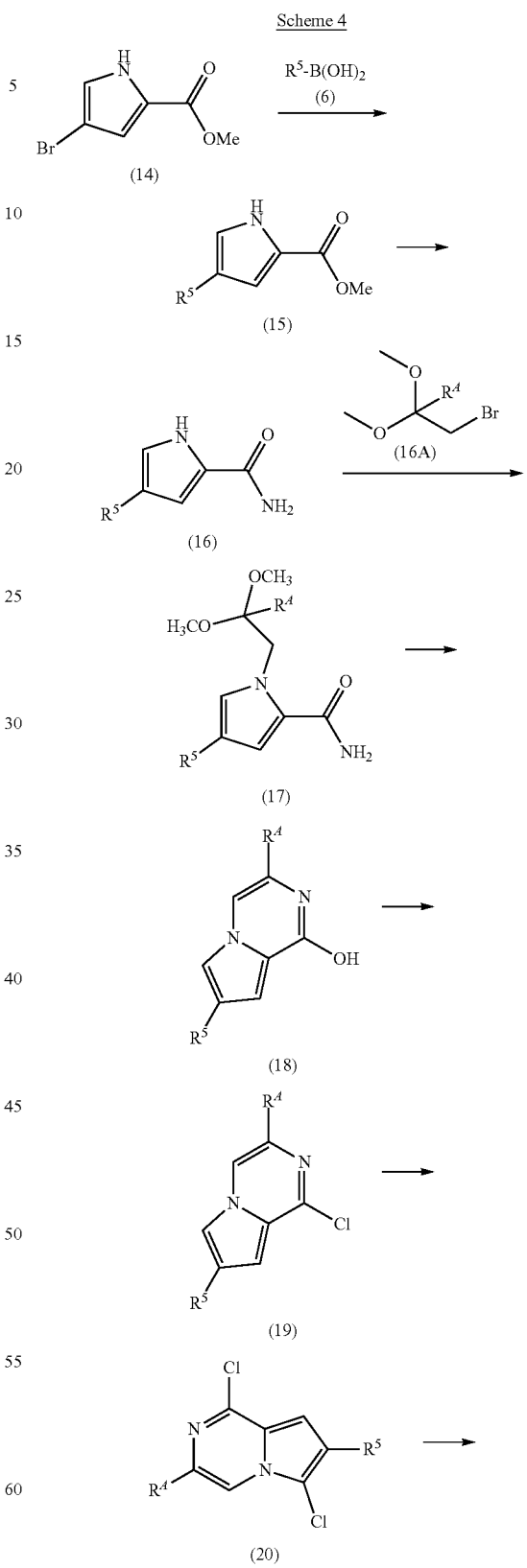

Scheme 3 describes the synthesis of Aminopyrimidine intermediates of formula (13). 4-Chlorofuro[2,3-d]pyrimidines (10), wherein $R^A$ is as described herein, can be treated with lithium diisopropylamide followed by iodine, in a solvent such as, but not limited to, tetrahydrofuran, to provide 4-chloro-6-iodofuro[2,3-d]pyrimidines of formula (11). The reaction is typically performed by first incubating a compound of formula (10) with lithium diisopropylamide at a low temperature, such as −78° C., followed by the addition of iodine and subsequent warming to ambient temperature. Compounds of formula (12) can be prepared by reacting 4-chloro-6-iodofuro[2,3-d]pyrimidines of formula (11) with a boronic acid (or the equivalent boronate ester) of formula (6) under Suzuki Coupling conditions described herein, known to those skilled in the art, or widely available in the literature. Compounds of formula (12) can be treated with N-bromosuccinimide to provide compounds of formula (13). The reaction is typically performed at ambient temperature in a solvent, such as, but not limited to, N,N-dimethylformamide.

(21)

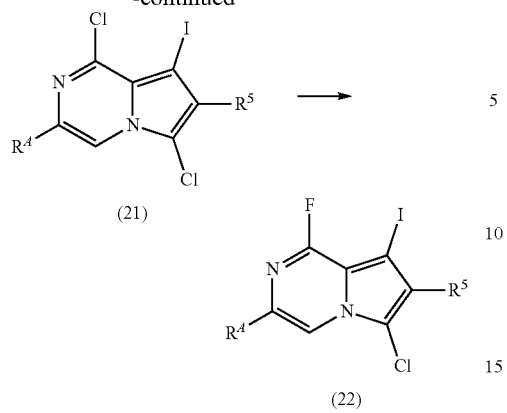

(22)

Scheme 4 describes the synthesis of pyrrolopyrazine intermediates of the formula (22), wherein $R^4$ and $R^5$ are as described herein. Compounds of the formula (15) can be prepared by reacting methyl 4-bromo-1H-pyrrole-2-carboxylate (14) with a boronic acid (or the equivalent boronate ester) of formula (6) under Suzuki Coupling conditions described herein, known to those skilled in the art, or widely available in the literature. Compounds of formula (15) can be heated in the presence of an aqueous ammonium hydroxide solution to provide compounds of formula (16). Compounds of the formula (17) can be prepared by treatment of pyrroles of formula (16) with 2-bromo-1,1-dimethoxyethane in the presence of a base such as, but not limited to, cesium carbonate. The reaction is typically performed in a solvent such as, but not limited to, N,N-dimethylformamide at elevated temperatures ranging from 80° C. to 90° C. Compounds of formula (17) can be treated with hydrogen chloride in a solvent such as, but not limited to, dichloromethane to provide compounds of the formula (18). Compounds of the formula (19) can be prepared by reacting intermediates (18) with phosphorous oxychloride in the presence of a base such as, but not limited to, N,N-diisopropylethylamine. The reaction is typically performed at elevated temperatures such as ranging from 100° C. to 115° C. Compounds of formula (19) can be treated with N,N-chlorosuccinimide in a solvent system such as, but not limited to, tetrahydrofuran to provide compounds of formula (20). The reaction is typically performed at an elevated temperature. Compounds of formula (21) can be prepared by reacting compounds of formula (20) with N-iodosuccinimide at an elevated temperature in a solvent such as, but not limited to, N,N-dimethylformamide. Compounds of formula (21) can be treated with tetramethylammonium fluoride to provide compounds of formula (22). The reaction is typically performed at ambient temperature in a solvent such as, but not limited to, N,N-dimethylformamide.

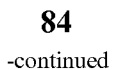

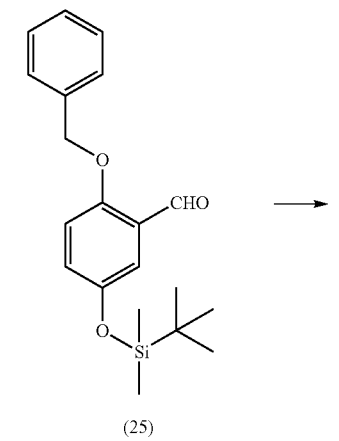

(25)

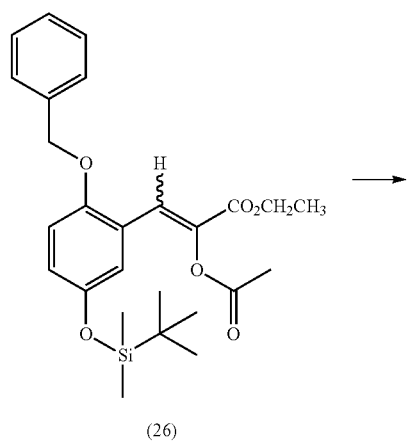

(26)

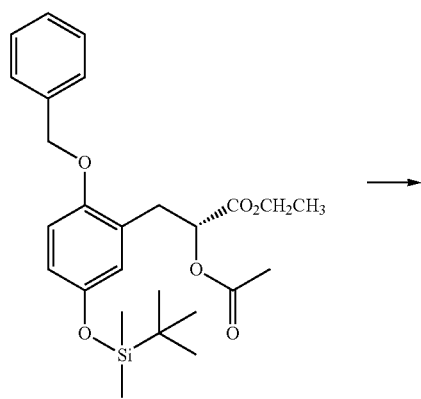

(27)

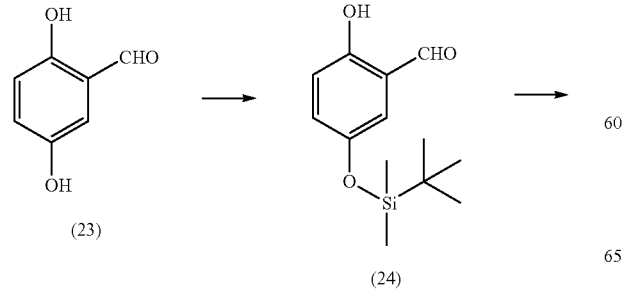

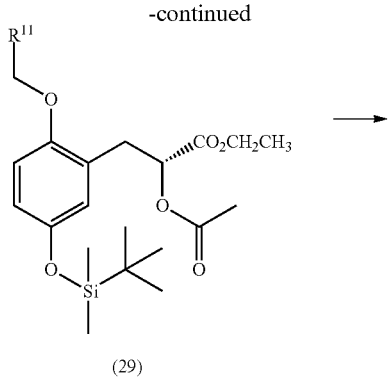

(29)

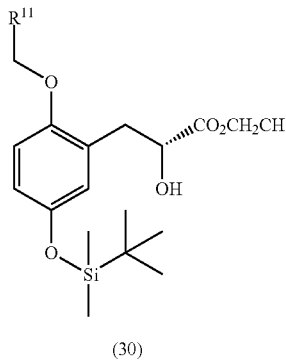

(30)

Scheme 5 describes the synthesis of propanoate intermediates of formula (30). 2,5-Dihydroxybenzaldehyde (23) can be treated with tert-butylchlorodimethylsilane to provide mono-silylated intermediate (24). The reaction is typically conducted at ambient temperature in the presence of a base such as, but not limited to, imidazole in a solvent such as, but not limited to, dichloromethane. The mono-silylated intermediate can be reacted with benzyl bromide to provide 2-(benzyloxy)-5-((tert-butyldimethylsilyl)oxy)benzaldehyde (2S). The reaction is typically performed in the presence of a base such as, but not limited to, potassium carbonate, and in a solvent such as, but not limited to acetone. N,N-dimethylformamide, or mixtures thereof. The reaction is typically initiated at room temperature followed by heating to an elevated temperature. 2-(Benzyloxy)-5-((tert-butyldimethylsilyl)oxy)benzaldehyde (25) can be treated with ethyl 2-acetoxy-2-(diethoxyphosphoryl)acetate to provide (E)/(Z)-ethyl 2-acetoxy-3-(2-<benzyloxy)-5-((tert-butyldimethylsilyl)oxy)phenyl)acrylates (26). The reaction is typically run in the presence a base such as, but not limited to, cesium carbonate in a solvent such as, but not limited to, tetrahydrofuran, toluene, or mixtures thereof. (E)/(Z)-Ethyl 2-acetoxy-3-(2-(benzyloxy)-5-((tert-butyldimethylsilyl)oxy)phenyl)acrylates (26) can be reacted with the catalyst (R,R)—Rh EtDuPhos (1,2-bis[(2R,5R)-2,5-diethylphospholano]benzene(1,5-cyclooctadiene)rhodium (I) trifluoromethanesulfonate) under an atmosphere of hydrogen gas in a solvent such as, but not limited to, methanol, to provide (R)-ethyl 2-acetoxy-3-(2-(benzyloxy)-5-((tert-butyldimethylsilyl)oxy)phenyl)propanoate (27). The reaction is typically performed at 35° C. under 50 psi of hydrogen gas. Ethyl (R)-2-acetoxy-3-(5-((tert-butyldimethylsilyl)oxy)-2-hydroxyphenylpropanoate (28) can be provided by reacting (R)-ethyl 2-acetoxy-3-(2-(benzyloxy)-5-((tert-butyldimethylsilyl)oxy)phenyl)propanoate (27) under hydrogenolysis conditions, such as in the presence of 5% palladium on carbon under 50 psi of hydrogen gas in a solvent such as, but not limited to, ethanol at an elevated temperature, such as, but not limited to, 35° C. Ethyl (R)-2-acetoxy-3-(5-((tert-butyldimethylsilyl)oxy)-2-hydroxyphenyl)propanoate (28) can be reacted with compounds of formula (31), wherein $R^{11}$ is as described herein, under Mitsunobu conditions described herein, known to those skilled in the art, or widely available in the literature, to provide compounds of formula (29). Compounds of the formula (29) can be treated with ethanol in the presence of a base such as, but not limited to, potassium carbonate or sodium ethoxide, to provide compounds of the formula (30).

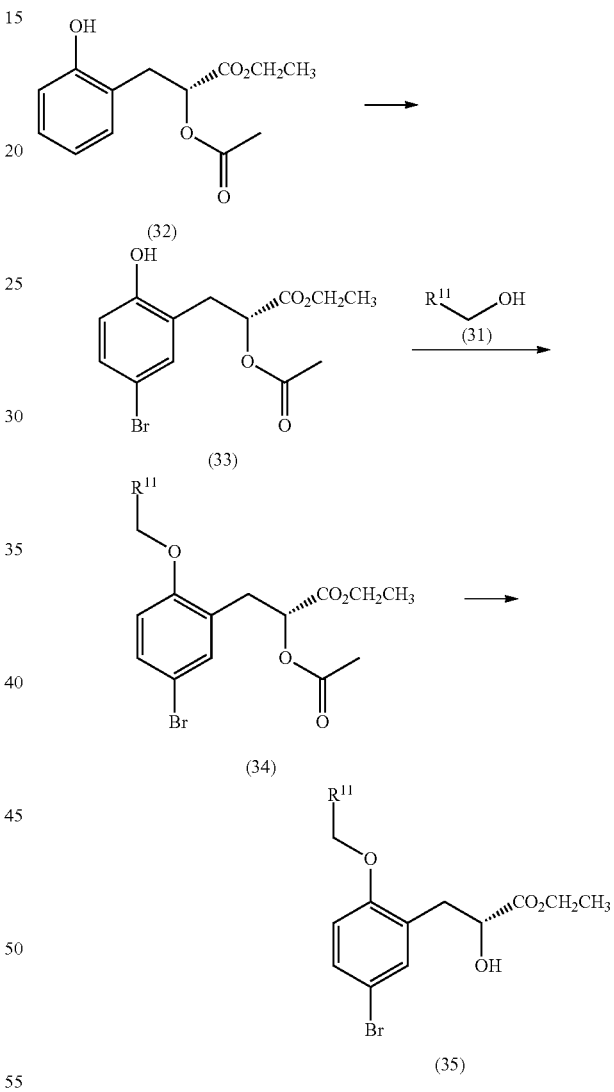

Scheme 6 describes the synthesis of propanoate intermediates of formula (35). (R)-Ethyl 2-acetoxy-3-(2-hydroxyphenyl)propanoate (32), which can be prepared using methods similar to those described for compounds of formula (28) in Scheme 5 or using methods described herein, can be treated with a brominating agent such as N-bromosuccinimide to provide (R)-ethyl 2-acetoxy-3-(5-bromo-2-hydroxyphenyl)propanoate (33). The reaction is typically performed in a solvent such as, but not limited to, tetrahydrofuran, at a low temperature, such as −30° C. to 0° C., before warming to ambient temperature. (R)-Ethyl 2-acetoxy-3-(5-bromo-2-hydroxyphenyl)propanoate (33) can be reacted with compounds of formula (31), wherein $R^{11}$ is as described herein, under Mitsunobu conditions described herein or in the literature to provide compounds of formula (34). Compounds of formula (34) can be treated with ethanol in the presence of a base such as, but not limited to, potassium carbonate or sodium ethoxide at ambient temperature to provide compounds of formula (35).

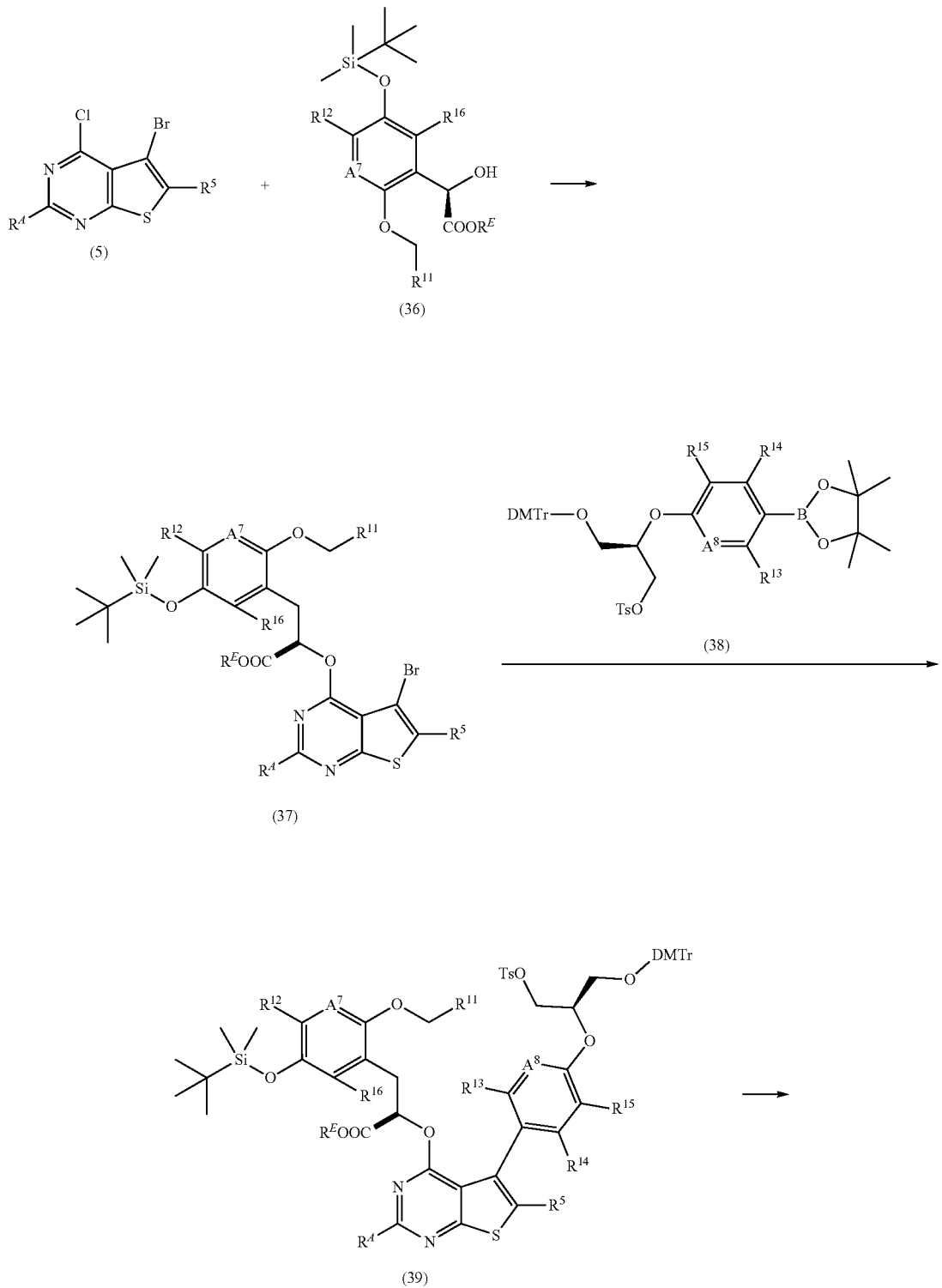

Scheme 7

-continued
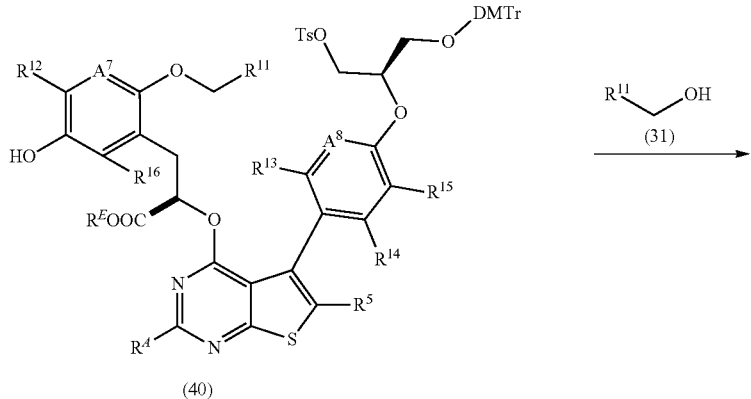
(40)
R¹¹—OH
(31)
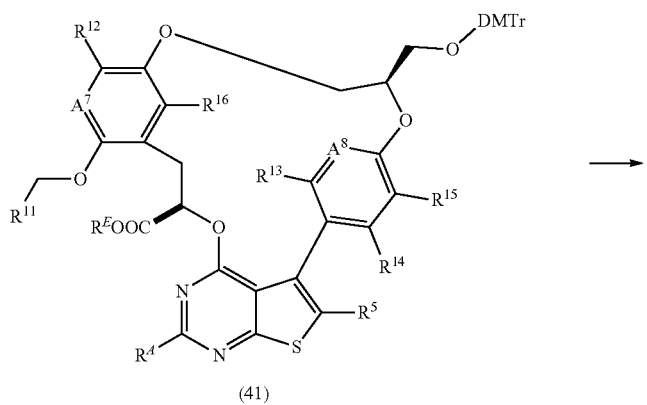
(41)
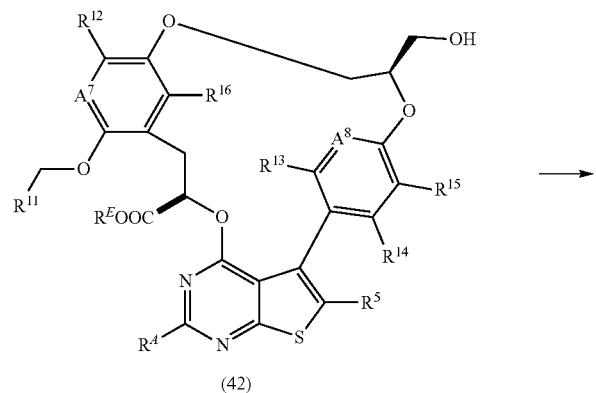
(42)
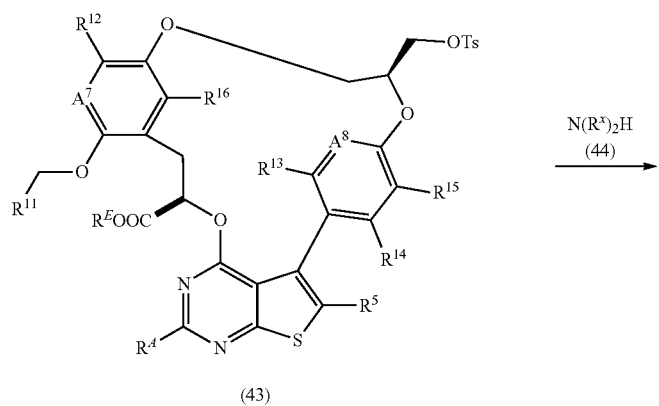
(43)
N(Rˣ)₂H
(44)

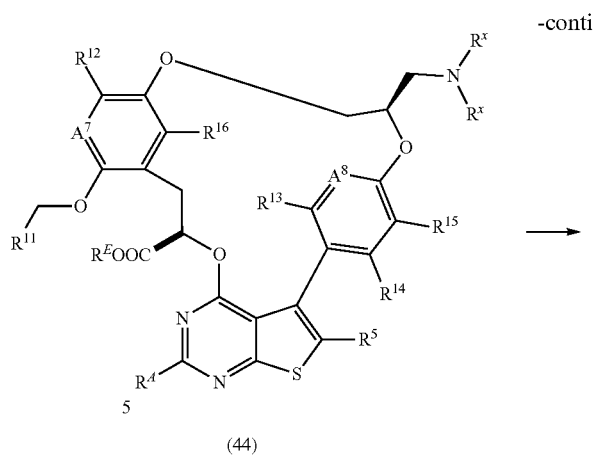

(44)

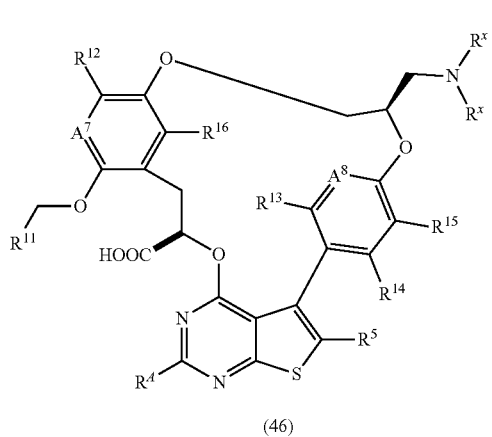

(46)

Scheme 7 describes the synthesis of macrocyclic compounds of the formula (46), which are representative of compounds of formula (I). Intermediates of the formula (5) can be reacted with compounds of the formula (36), wherein $A^7$, $R^{11}$, $R^{12}$, $R^{16}$ are as described herein and $R^E$ is alkyl, in the presence of base such as, but not limited to, cesium carbonate, to provide compounds of the formula (37). The reaction is typically conducted at an elevated temperature, such as, but not limited to 65° C., in a solvent such as but not limited to tert-butanol, N,N-dimethylformamide, or mixtures thereof. Compounds of formula (39) can be prepared by reacting compounds of formula (37) with a boronate ester (or the equivalent boronic acid) of formula (38) under Suzuki Coupling conditions described herein or in the literature. Compounds of formula (39) can be treated with tetrabutylammonium fluoride in a solvent system such as dichloromethane, tetrahydrofuran or mixtures thereof to provide compounds of formula (40). Treatment of compounds of formula (40) with a base such as, but not limited to, cesium carbonate in a solvent such as, but not limited to, N,N-dimethylformamide, will provide compounds of formula (41). The reaction is typically performed at an elevated temperature, or more preferably at ambient temperature. Compounds of the formula (41) can be deprotected to give compounds of the formula (42) using procedures described herein or available in the literature. For example, compounds of formula (41) can be treated with formic acid at ambient temperature in a solvent system such as, but not limited to, dichloromethane and methanol, to provide compounds of the formula (42). Compounds of the formula (42) can be treated with para-toluenesulfonyl chloride in the presence of a base such as, but not limited to, triethylamine or DABCO (1,4-diazabicyclo[2.2.2]octane) to provide compounds of formula (43). The reaction is typically performed at low temperature before warming to room temperature in a solvent such as, but not limited to, dichloromethane. Compounds of formula (43) can be reacted with amine nucleophiles of formula (44), wherein two $R^x$, together with the nitrogen to which they are attached, optionally form a heterocycle, to provide intermediates of formula (45). The reaction is typically performed in a solvent such as, but not limited to, N,N-dimethylformamide, at ambient temperature before heating to 35° C. to 40° C. Compounds of formula (46) can be prepared by treating compounds of formula (45) with lithium hydroxide. The reaction is typically performed at ambient temperature in a solvent such as, but not limited to, tetrahydrofuran, methanol, water, or mixtures thereof.

Scheme 8

Scheme 8 describes an alternative synthesis of intermediates of the formula (39). Compounds of formula (48) can be prepared by reacting compounds of formula (37) with a boronate ester (or the equivalent boronic acid) of formula (47) under Suzuki Coupling conditions described herein or available in the literature. Compounds of the formula (48) can be reacted with compounds of formula (49) under Mitsunobu conditions described herein or available in the literature to provide compounds of the formula (39). Compounds of the formula (39) can be further treated as described in Scheme 7 or using methods described herein to provide macrocyclic compounds of the formula (46), which are representative of compounds of formula (I).

Scheme 9

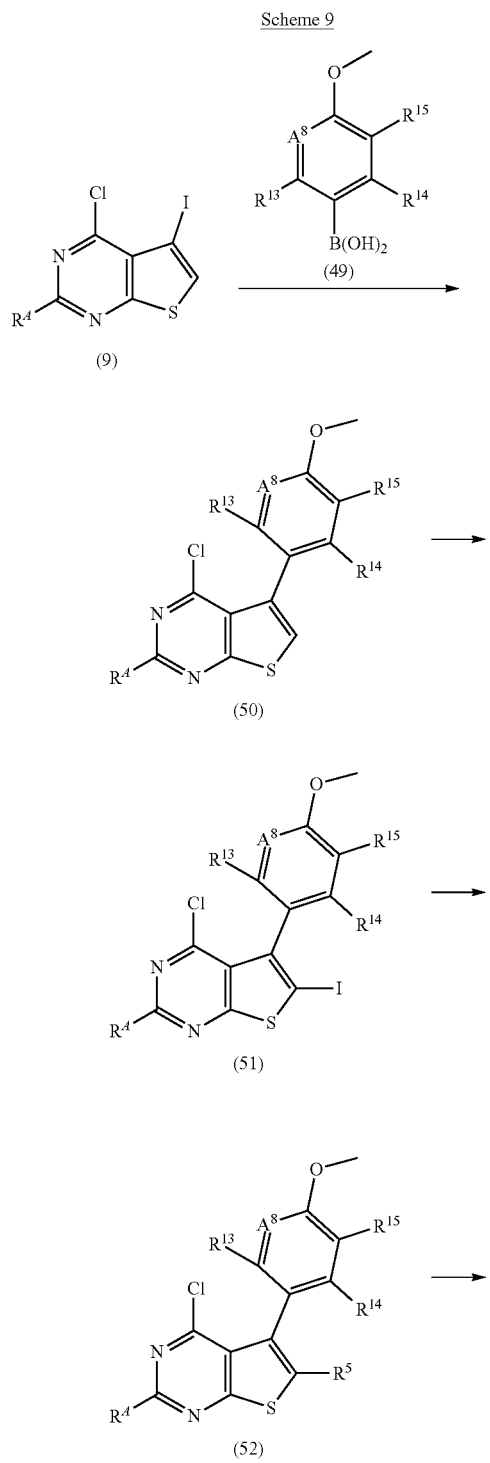

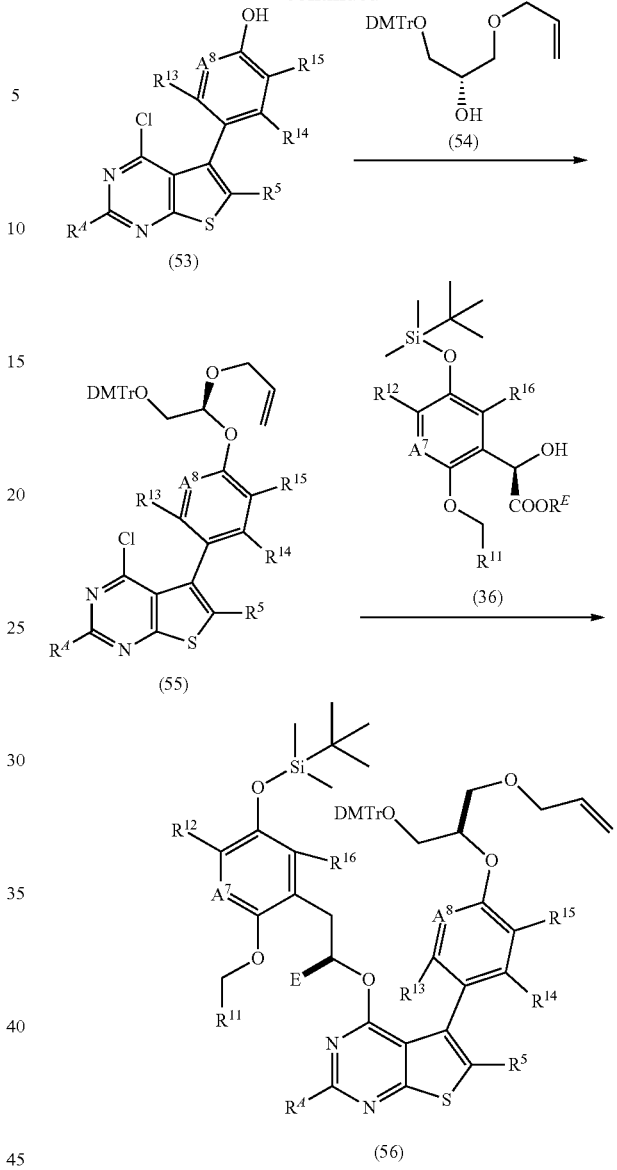

Scheme 9 describes the synthesis of compounds of formula (56). Compounds of formula (50) can be prepared by reacting compounds of formula (9) with a boronate ester (or the equivalent boronic acid) of formula (49) under Suzuki Coupling conditions described herein or available in the literature. Compounds of formula (50) can be treated with a strong base such as, but not limited to lithium diisopropylamide, followed by the addition of iodine to provide compounds of the formula (51). The reaction is typically performed in a solvent such as, but not limited to, tetrahydrofuran, at a reduced temperature before warming to ambient temperature. Compounds of formula (52) can be prepared by reacting compounds of formula (51) with a boronate ester (or the equivalent boronic acid) of formula (6) under Suzuki Coupling conditions described herein or known in the literature. Compounds of formula (52) can be treated with aluminum trichloride to provide compounds of formula (53). The reaction is typically performed at an elevated temperature, for example from 60° C. to 70° C., in a solvent, such as but not limited to, 1,2-dichloroethane.

Compounds of formula (53) can be treated with compounds of formula (54) under Mitsunobu conditions described herein or available in the literature to provide compounds of the formula (55). Compounds of formula (55) can be reacted with compounds of formula (36) in the presence of a base such as, but not limited to, cesium carbonate to provide compounds of formula (56). The reaction is typically performed at an elevated temperature in a solvent such as tert-butanol. N,N-dimethylformamide, or mixtures thereof. Compounds of formula (56) can be used as described in subsequent steps herein to provide compounds of formula (I).

It should be appreciated that the synthetic schemes and specific examples as illustrated in the synthetic examples section are illustrative and are not to be read as limiting the scope of the present disclosure as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Specific procedures are provided in the Synthetic Examples section. Reactions can be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Manipulation of the reaction conditions, reagents and sequence of the synthetic route, protection of any chemical functionality that can not be compatible with the reaction conditions, and deprotection at a suitable point in the reaction sequence of the method are included in the scope of the present disclosure. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the present disclosure can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

When employed as a pharmaceutical, a compound of the present disclosure is typically administered in the form of a pharmaceutical composition. One embodiment pertains to a pharmaceutical composition comprising a therapeutically effective amount of a compound of formula (I) according to claim 1, or a pharmaceutically acceptable salt thereof, in combination with a pharmaceutically acceptable carrier. The phrase "pharmaceutical composition" refers to a composition suitable for administration in medical or veterinary use.

The term "pharmaceutically acceptable carrier" as used herein, means a non-toxic, inert solid, semi-solid or liquid filler, diluent, encapsulating material or formulation auxiliary.

Methods of Use

The compounds of formula (I), or pharmaceutically acceptable salts thereof, and pharmaceutical compositions comprising a compound of formula (I), or a pharmaceutically acceptable salt thereof, may be administered to a subject suffering from a disorder or condition associated with MCL-1 overexpression or up-regulation. The term "administering" refers to the method of contacting a compound with a subject. Disorders or conditions associated with MCL-1 overexpression or up-regulation may be treated prophylactically, acutely, and chronically using compounds of formula (I), depending on the nature of the disorder or condition. Typically, the host or subject in each of these methods is human, although other mammals may also benefit from the administration of a compound of formula (I).

A "MCL-1-mediated disorder or condition" is characterized by the participation of MCL-1 in the inception, manifestation of one or more symptoms or disease markers, maintenance, severity, or progression of a disorder or condition. In embodiments, the present disclosure provides a method for treating multiple myeloma. The method comprises the step of administering to a subject in need thereof a therapeutically effective amount of a compound of formula (I) or a preferred embodiment thereof, with or without a pharmaceutically acceptable carrier.

In embodiments, the present disclosure provides compounds of the disclosure, or pharmaceutical compositions comprising a compound of the disclosure, for use in medicine. In embodiments, the present disclosure provides compounds of the disclosure, or pharmaceutical compositions comprising a compound of the disclosure, for use in the treatment of diseases or disorders as described herein above.

One embodiment is directed to the use of a compound according to formula (I), or a pharmaceutically acceptable salt thereof in the preparation of a medicament. The medicament optionally can comprise at least one additional therapeutic agent. In some embodiments the medicament is for use in the treatment of diseases and disorders as described herein above.

This disclosure is also directed to the use of a compound according to formula (I), or a pharmaceutically acceptable salt thereof in the manufacture of a medicament for the treatment of the diseases and disorders as described herein above. The medicament optionally can comprise at least one additional therapeutic agent.

The compounds of formula (I) may be administered as the sole active agent or may be co-administered with other therapeutic agents, including other compounds that demonstrate the same or a similar therapeutic activity and that are determined to be safe and efficacious for such combined administration. The term "co-administered" means the administration of two or more different therapeutic agents or treatments (e.g., radiation treatment) that are administered to a subject in a single pharmaceutical composition or in separate pharmaceutical compositions. Thus co-administration involves administration at the same time of a single pharmaceutical composition comprising two or more different therapeutic agents or administration of two or more different compositions to the same subject at the same or different times.

EXAMPLES

The following Examples may be used for illustrative purposes and should not be deemed to narrow the scope of the present disclosure.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), triplet (t), quartet (q), quintuplet (quin), multiplet (m) and broad (br).

Example 1

(7R,16R)-19,23-dichloro-10-{[2-(4-{[(4S)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 1A thieno[2,3-d]pyrimidin-4(3H)-one A mixture of 2-amino-3-cyanothiophene (50 g) in formic acid (100 mL) and H$_2$SO$_4$ (22 mL) was heated in a sealed tube for 2 hours at 100° C. The mixture was cooled to 20° C. and was diluted with water (1 L). The resulting precipitate was collected by filtration, washed with water twice (2×1 L) and dried under reduced pressure to provide the title compound. $^1$H NMR (400 MHz, dimethyl sulfoxide-d$_6$) δ ppm 12.16 (br s, 1H), 8.09 (s, 1H), 7.54 (d, 1H), 7.35 (d, 1H).

Example 1B 5,6-diiodothieno[2,3-d]pyrimidin-4(3H)-one

To an ice-cooled 4-neck 2 L flask fit with a mechanical stirrer, reflux condenser and thermocouple/JKEM was added acetic acid (160 mL), sulfuric acid (8 mL) and water (80 mL) with stirring. Example 1A (40.0 g), periodic acid (30.0 g) and iodine (133 g) were added sequentially and the mixture became slightly endothermic. The ice bucket was removed and a heating mantle was added. The reaction mixture was ramped up to 60° C. and was stirred for 20 minutes. The temperature climbed to 95° C. The heating mantle was removed and reaction mixture was allowed to cool to room temperature. The resulting suspension was poured into saturated aqueous sodium sulfite solution, filtered, and washed with water. The organic layer was dried under vacuum to provide the title compound.

Example 1C 4-chloro-5,6-diiodothieno[2,3-d]pyrimidine

A 250 mL flask equipped with magnetic stirring, heating mantle, temperature probe and reflux condenser to a nitrogen bubbler was charged with phosphorus oxychloride (57.3 mL) and N,N-dimethylaniline (17.64 mL). To the mixture was added Example 1B (56.22 g) over 5 minutes. The resulting suspension was heated at 105° C. for 30 minutes. After cooling, the resulting material was broken up and transferred to a funnel with heptane. The material was washed with heptane to remove most of the phosphorus oxychloride. The material was slowly scooped into rapidly stirring ice water (600 mL) and stirred for 30 minutes. The material was collected by filtration, washed with water and ether (200 mL), dried over Na$_2$SO$_4$, and filtered to provide the title compound which was used in the next step without further purification.

Example 1D 4-chloro-5-iodothieno[2,3-d]pyrimidine

A 500 mL 3-neck jacketed flask with magnetic stirring under nitrogen was charged with Example 1C (23 g) and tetrahydrofuran (200 mL). The resulting suspension was cooled to −16° C. using a Huber chiller set to −17° C. To the mixture was added tert-butylmagnesium chloride (40.8 mL, 2 M in ether) dropwise over 40 minutes, keeping the temperature between −15° C. and −16° C. The temperature was slowly raised to 0° C. and was stirred for 30 minutes. The reaction mixture was cooled to −20° C. and was quenched by the very slow dropwise addition (initially about 1 drop/minute) of water (23 mL) over 35 minutes, maintaining the temperature at about −20° C. and then slowly warmed to ambient temperature over 1 hour. The stirring was stopped and the supernatant was decanted from the remaining residue. To the residue was added tetrahydrofuran (200 mL). The mixture was stirred briefly, and after standing, the supernatant was decanted from the remaining residue. This was repeated two times. The combined organics were concentrated. The crude material was purified by chromatography on silica gel eluting with isocratic methylene chloride. The title compound was precipitated from a minimum of hot heptanes.

Example 1E 4-chloro-5-(4-methoxy-2,6-dimethylphenyl)thieno[2,3-d]pyrimidine

To a suspension of Example 1D (5 g). (4-methoxy-2,6-dimethylphenyl)boronic acid (6.07 g) and cesium carbonate (10.99 g) in degassed toluene (50.0 mL) and water (12.5 mL) was added bis(di-tert-butyl(4-dimethylaminophenyl)phosphine)dichloropalladium(1) (597 mg). The mixture was heated to 100° C. overnight. After cooling to room temperature, the mixture was diluted with ethyl acetate (200 mL). The organic layer was washed with water and brine, dried over anhydrous sodium sulfate, filtered and concentrated under vacuum. The residue was purified by silica gel chromatography on a CombiFlash® Teledyne Isco system eluting with 0-20% ethyl acetate in heptanes to provide the title compound. $^1$H NMR (501 MHz, CDCl$_3$) δ ppm 8.88 (s, 1H), 7.35 (s, 1H), 6.70 (s, 2H), 3.85 (s, 3H), 1.99 (s, 6H). MS (ESI) m/z 305.1 (M+H)$^+$.

Example 1F 4-chloro-6-iodo-5-(4-methoxy-2,6-dimethylphenyl) thieno[2,3-d]pyrimidine To a mixture of diisopropylamine (4.15 mL) in tetrahydrofuran (50 mL) cooled to −78° C. was added n-butyllithium (9.71 mL, 2.5 M in hexanes) dropwise. The mixture was stirred for 1 minute before Example 1E (3.7 g) was added as a mixture in tetrahydrofuran (50 mL). The resulting mixture was stirred at −78° C. for 15 minutes. Iodine (6.16 g) was added in one portion and the mixture was warmed to room temperature. The reaction mixture was quenched with saturated aqueous ammonium chloride mixture (100 mL) and was extracted with ethyl acetate (50 mL×3). The combined organic layers were washed sequentially with a sodium thiosulfate mixture and brine, dried over anhydrous sodium sulfate, filtered and concentrated onto silica gel. Purification by flash chromatography on a silica gel column eluting with 0-20% ethyl acetate in heptanes provided crude product, which was triturated with heptanes to obtain the title compound. $^1$H NMR (501 MHz, CDCl$_3$) δ ppm 8.82 (s, 1H), 6.72 (s, 2H), 3.87 (s, 3H), 1.94 (s, 6H). MS (ESI) m/z 431.1 (M+H)$^+$.

Example 1G 4-chloro-6-(4-fluorophenyl)-5-(4-methoxy-2,6-dimethylphenyl)thieno[2,3-d]pyrimidine To a mixture of Example 1F (3.3 g), (4-fluorophenyl) boronic acid (2.144 g) di-tert-butyl(2',4',6'-triisopropyl-[1,1'-biphenyl]-2-yl)phosphine (0.179 g) and potassium phosphate tribasic (3.25 g) in degassed tetrahydrofuran (60 mL) and water (15 mL) was added tris(dibenzylideneacetone) dipalladium(0) (0.175 g). The mixture was heated to 60° C. overnight. After cooling to room temperature, the mixture was diluted with ethyl acetate (100 mL). The organic layer was washed with brine, dried over anhydrous sodium sulfate, filtered and concentrated under vacuum. The residue was purified by flash chromatography on a silica gel column eluting with 0-20% ethyl acetate in heptanes to give crude product, which was triturated with heptanes to obtain the title compound. $^1$H NMR (501 MHz, CDCl$_3$) δ ppm 8.84 (s, 1H), 7.31-7.23 (m, 2H), 7.02-6.93 (m, 2H), 6.65 (d, 2H), 3.83 (s, 3H), 1.92 (d, 6H). MS (ESI) m/z 399.1 (M+H)$^+$.

Example 1H 4-chloro-5-(3,5-dichloro-4-methoxy-2,6-dimethylphenyl)-6-(4-fluorophenyl)thieno[2,3-d]pyrimidine To a suspension of Example 1G (2.13 g) in acetonitrile (50 mL) was added N-chlorosuccinimide (2.85 g). The mixture was heated to reflux for 1 hour. The mixture was concentrated under vacuum and the residue was redissolved in ethyl acetate (50 mL). The mixture was washed with brine, dried over anhydrous sodium sulfate, filtered and concentrated under vacuum. The residue was purified by silica gel chromatography on a CombiFlash® Teledyne Isco system eluting with 0-10% ethyl acetate in heptanes to provide the title compound. $^1$H NMR (400 MHz, CDCl$_3$) δ ppm 8.89 (s, 1H), 7.28-7.18 (m, 2H), 7.08-6.97 (m, 2H), 3.96 (s, 3H), 2.02 (s, 6H). MS (ESI) m/z 469.1 (M+H)$^+$.

Example 11

2,6-dichloro-4-(4-chloro-6-(4-fluorophenyl)thieno[2,3-d]pyrimidin-5-yl)-3,5-dimethylphenol To Example 1H (5 g) in 1,2-dichloroethane (200 mL) was added aluminum trichloride (4.28 g), and the mixture was heated to 68° C. for 6 hours and was cooled to room temperature. Saturated aqueous NaHCO$_3$ (3 mL) was added and the mixture was stirred for 2 minutes. Saturated aqueous NH$_4$Cl (15 mL) was added. The mixture was diluted with ethyl acetate and the layers were separated. The aqueous layer was extracted once with ethyl acetate. The organic layers were combined and washed with water and brine, dried over Na$_2$SO$_4$, filtered, and concentrated to provide the title compound. $^1$H NMR (400 MHz, dimethylsulfoxide-d$_6$) δ ppm 10.10 (br s, 1H), 9.00 (s, 1H), 7.35 (m, 2H), 7.28 (m, 2H), 1.96 (s, 6H). MS (ESI) m/z 452.9 (M−H)$^-$.

Example 1J (R)-3-(allyloxy)propane-1,2-diol

To a 250 mL round bottom containing (S)-4-((allyloxy)methyl)-2,2-dimethyl-1,3-dioxolane (7.08 g) was added methanol (100 mL) and p-toluenesulfonic acid monohydrate (0.782 g). The mixture was heated to 50° C. for 18 hours, and at 60° C. for 4 hours. The mixture was cooled to room temperature, and potassium carbonate (1.704 g) and MgSO$_4$ (5 g) were added. The material was filtered and washed with ethyl acetate. The mixture was concentrated, and the residue was chromatographed on silica gel using 20-80% ethyl acetate in heptanes as the eluent, to provide the title compound. $^1$H NMR (400 MHz, dimethyl sulfoxide-d$_6$) δ ppm 5.87 (tdd, 1H), 5.25 (dd, 1H), 5.13 (dd, 1H), 4.62 (d, 1H), 4.46 (t, 1H), 3.94 (ddd, 2H), 3.58 (m, 1H), 3.39 (m, 1H), 3.30 (m, 3H).

Example 1K (S)-1-(allyloxy)-3-(bis(4-methoxyphenyl)(phenyl) methoxy)propan-2-ol

To a mixture of Example 1J (2.25 g) and 4,4'-(chloro (phenyl)methylene)bis(methoxybenzene) (DMTrCl) (6.06 g) in dichloromethane (68.1 mL) cooled to 0° C., was added N,N-diisopropylethylamine (3.27 mL). The mixture was allowed to warm to room temperature and was stirred for 30 minutes. The reaction mixture was quenched with saturated aqueous ammonium chloride mixture (50 mL). The organic layer was washed with brine, dried over anhydrous sodium sulfate, filtered and concentrated under vacuum. The residue was purified by silica gel chromatography on a CombiFlash® Teledyne Isco system, eluting with 0-50% ethyl acetate in heptanes to provide the title compound. $^1$H NMR (400 MHz, CDCl$_3$) δ ppm 7.45-7.40 (m, 2H), 7.35-7.24 (m, 6H), 7.24-7.17 (m, 1H), 6.86-6.77 (m, 4H), 5.95-5.79 (m, 1H), 5.24 (dq, 1H), 5.17 (dq, 1H), 4.00 (dt, 2H), 3.98-3.91 (m, 1H), 3.78 (s, 6H), 3.55 (dd, 1H), 3.49 (dd, 1H), 3.24-3.16 (m, 2H), 2.40 (bs, 1H). MS (ESI) m/z 457.1 (M+Na)$^+$.

Example 1L (R)-5-(4-((1-(allyloxy)-3-(bis(4-methoxyphenyl)(phenyl)methoxy)propan-2-yl)oxy)-3,5-dichloro-2,6-dimethylphenyl)-4-chloro-6-(4-fluorophenyl)thieno[2,3-d]pyrimidine Triphenylphosphine (1.561 g), Example 1I (1.5 g), and Example 1K (1.580 g) were taken up in 18 mL tetrahydrofuran and di-tert-butylazodicarboxylate (1.370 g) was added and the reaction was stirred overnight. The material was filtered off and rinsed with 1:1 ether/ethyl acetate, and the organics were concentrated. The crude material was chromatographed on silica gel using 1-40% ethyl acetate in heptanes as eluent to provide the title compound. MS (ESI) m/z 891.1 (M+Na)$^+$.

Example 1M 2-(benzyloxy)-5-((tert-butyldimethylsilyl)oxy)benzaldehyde

A 2 L round bottom flask was charged with 2,5-dihydroxybenzaldehyde (30 g), imidazole (29.6 g) and dichloromethane (543 mL). The flask was placed in a water bath and solid tert-butylchlorodimethylsilane (32.7 g) was added. The reaction mixture was stirred at ambient temperature for 15 minutes at which point thin-layer chromatography indicated complete consumption of starting material. The reaction mixture was poured into a separatory funnel with 200 mL water. The biphasic mixture was shaken and the layers were separated. The aqueous layer was washed with 100 mL dichloromethane and the organic layers were combined. The organic layer was dried over sodium sulfate, filtered, and concentrated and the material was used in the next step. A 1 L three-necked round bottom flask equipped with an internal temperature probe, a reflux condenser, and a stir bar was charged with 5-((tert-butyldimethylsilyl)oxy)-2-hydroxybenzaldehyde (45 g, 178 mmol) in acetone (297 mL). Solid K$_2$CO$_3$ (27.1 g) was added followed by dropwise addition of neat benzyl bromide (21.21 mL). The mixture was stirred at ambient temperature for 10 minutes and heated to 55° C. The reaction mixture was stirred overnight. The reaction mixture was cooled to ambient temperature then poured over cold water (200 mL). The mixture was then transferred to a 1 L separatory funnel. The crude product was extracted with ethyl acetate (3×250 mL). The combined organic layers were dried over sodium sulfate, filtered, and concentrated. The crude material was purified by silica gel chromatography over a 330 g column on a Grace Reveleris system (0-5% ethyl acetate/heptanes elution gradient). Fractions containing the desired product were combined, concentrated and dried under vacuum to obtain the title compound. $^1$H NMR (501 MHz, dimethyl sulfoxide-d$_6$) δ ppm 10.35 (s, 1H), 7.51-7.47 (m, 2H), 7.42-7.37 (m, 2H), 7.35-7.31 (m, 1H), 7.22 (d, 1H), 7.15 (dd, 1H), 7.11 (d, 1H), 5.21 (s, 2H), 0.93 (s, 9H), 0.16 (s, 6H).

Example 1N tert-butyl 2-acetoxy-2-(diethoxyphosphoryl)acetate

A 3 L jacketed round bottom flask equipped with an overhead stirrer was charged with glyoxylic acid monohydrate (15 g) and diethyl phosphite (20.82 mL) and was heated to a 60° C. jacket temperature with stirring. The flask headspace was continuously purged with a nitrogen sweep. After stirring overnight, dichloromethane (250 mL) was added, the reaction was cooled to an internal temperature of 5° C., and pyridine (13.05 mL) was added dropwise. After stirring for 1 hour at the same temperature, acetyl chloride (11.47 mL) was added dropwise over 20 minutes. The reaction was warmed to 20° C., stirred for 1.5 hours, and cooled to 5° C. internal temperature. Pyridine (19.57 mL) was added slowly. Tert-butanol (15.43 mL) was added in one portion followed by dropwise addition of 2,4,6-tripropyl-1,3,5,2,4,6-trioxatriphosphinane 2,4,6-trioxide (144 mL, 50% by weight in ethyl acetate) over 20 minutes. After stirring for 1 hour, the reaction was warmed to 20° C. and was stirred overnight. The reactor was then cooled to 5° C. and 1 N aqueous hydrochloric acid (200 mL) was added slowly. The biphasic mixture was stirred for 30 minutes at 20° C., and was poured into a separatory funnel. Dichloromethane (400 mL) and 1N aqueous hydrochloric acid (250 mL) were added and the mixture was separated. The aqueous layer was extracted with dichloromethane (400 mL), and the combined organic layers were washed with a mixture of water (300 mL) and saturated aqueous sodium chloride solution (300 mL). The combined organics were dried over anhydrous magnesium sulfate, filtered and concentrated under reduced pressure. The crude material was purified by plug filtration on silica gel eluting with 1:1 ethyl acetate/heptanes to give the title compound after concentration under reduced pressure. $^1$H NMR (400 MHz, Chloroform-d) δ ppm 5.32 (d, 1H), 4.29-4.18 (m, 4H), 2.21 (s, 3H), 1.37 (tdd, 6H). MS (ESI) m/z 255.0 (M-tert-butyl+2H)$^+$.

Example 1O (E)-tert-butyl 2-acetoxy-3-(2-(benzyloxy)-5-((tert-butyldimethylsilyl)oxy)phenyl)acrylate An oven dried 2 L 3-neck round bottomed flask equipped with overhead stirring was charged with anhydrous lithium chloride (5.55 g). The flask was purged with a sweep of argon for 10 minutes and anhydrous tetrahydrofuran (350 mL) was added. A solution of Example 1N (40.6 g) in tetrahydrofuran (50 mL) was added. A solution of 1,8-diazabicyclo[5.4.0]undec-7-ene) (19.72 mL) in tetrahydrofuran (50 mL) was added dropwise. The stirring mixture became cloudy and was cooled in an ice-water bath to an internal temperature of 15° C. A mixture of Example 1M (32 g) in tetrahydrofuran (50 mL) was added over 30 minutes. The reaction was stirred overnight, cooled to an internal temperature of 5° C., and quenched by addition of 1% by weight aqueous citric acid (700 mL). Ethyl acetate (400 mL) was added and the layers were separated. The combined organic layers were washed with saturated aqueous sodium chloride solution (400 mL), dried over anhydrous magnesium sulfate, filtered and concentrated under reduced pressure. The crude material was purified by flash column chromatography on a Grace Reveleris system using a Teledyne Isco RediSep Gold 330 g column, eluting with a 0-25% ethyl acetate/heptanes gradient to give the title compound in a 9:1 mixture of E- and Z-isomers. E-isomer $^1$H NMR (501 MHz, Chloroform-d) δ ppm 7.39 (ddt, 2H), 7.36 (ddd, 2H), 7.32-7.27 (m, 1H), 6.88 (dd, 1H), 6.85 (d, 1H), 6.76 (d, 1H), 6.71 (ddd, 1H), 5.01 (s, 2H), 2.22 (s, 3H), 1.34 (s, 9H), 0.97 (s, 9H), 0.17 (s, 6H). MS (ESI) m/z 515.9 (M+NH$_4$)$^+$. This isomer was assigned E by 2D NOE experiments. Z-isomer: $^1$H NMR (501 MHz, Chloroform-d) δ ppm 7.74 (s, 1H), 7.45 (ddt, 2H), 7.38 (ddd, 2H), 7.35-7.30 (m, 1H), 7.29-7.26 (m, 1H), 6.83 (d, 1H), 6.79 (dd, 1H), 5.06 (s, 2H), 2.30 (d, 3H), 1.53 (s, 9H), 0.99 (s, 9H), 0.18 (s, 6H). MS (ESI) m/z 515.9 (M+NH$_4$)$^+$. This isomer was assigned Z by 2D NMR experiments.

Example 1P (R)-tert-butyl 2-acetoxy-3-(2-(benzyloxy)-5-((tert-butyldimethylsilyl)oxy)phenyl)propanoate A 600 mL stainless steel reactor was charged with (1,2-bis[(2R,5R)-2,5-diethylphospholano]benzene(1,5-cyclooctadiene)rhodium(I) trifluoromethanesulfonate (1.88 g), followed by a solution of Example 1O (34.86 g) in methanol (350 mL). The reactor was purged with nitrogen 3 times and 2 times with hydrogen. The mixture was stirred at 1200 RPM under 120 psi of hydrogen with no external heating for 24 hours. The mixture was concentrated under reduced pressure, suspended in 5:1 heptanes/dichloromethane (70 mL) and filtered through a pad of diatomaceous earth. The filtrate was concentrated under reduced pressure and purified on a Grace Reveleris system using a 750 g Teledyne Isco Redisep gold column eluting with an ethyl acetate/heptanes gradient (0-25%). The title compound was concentrated under reduced pressure. $^1$H NMR (500 MHz, Chloroform-d) δ ppm 7.45 (d, 2H), 7.42-7.34 (m, 2H), 7.34-7.28 (m, 1H), 6.77 (d, 1H), 6.70 (d, 1H), 6.67 (dd, 1H), 5.19 (dd, 1H), 5.05 (d, 1H), 5.01 (d, 1H), 3.29 (dd, 1H), 2.92 (dd, 1H), 2.03 (s, 3H), 1.40 (s, 9H), 0.97 (s, 9H), 0.16 (s, 6H). MS (DCI) m/z 518.2 (M+NH$_4$)$^+$.

Example 1Q (R)-tert-butyl 3-(2-(benzyloxy)-5-((tert-butyldimethylsilyl)oxy)phenyl)-2-hydroxypropanoate An oven dried 250 mL 3-neck flask was charged with Example 1P (27.46 g). The flask was equipped with a magnetic star bar and rubber septa, and vacuum purged with nitrogen gas twice. Anhydrous ethanol (274 mL) was added, and the mixture was stirred. To the stirring solution was added dropwise sodium ethoxide (21% wt in ethanol, 1.024 mL). The reaction was stirred for three hours at ambient temperature and was quenched by addition of acetic acid (0.3 mL). The bulk of the solvents were removed by rotary evaporation, and the material was diluted with ethyl acetate (300 mL). Saturated aqueous sodium bicarbonate was added (300 mL). The layers were separated and the aqueous layer was extracted with ethyl acetate (300 mL). The combined organic layers were washed with saturated aqueous sodium chloride, dried over MgSO$_4$, treated with activated charcoal (0.5 g) and stirred for 1 hour before filtering through diatomaceous earth to give the title compound after concentration under reduced pressure. $^1$H NMR (400 MHz, chloroform-d) δ ppm 7.48-7.42 (m, 2H), 7.42-7.36 (m, 2H), 7.36-7.29 (m, 1H), 6.79 (d, 1H), 6.75 (d, 1H), 6.67 (dd, 1H), 5.10-4.99 (m, 2H), 4.39 (ddd, 1H), 3.16 (dd, 1H), 2.91 (d, 1H), 2.86 (dd, 1H), 1.41 (s, 9H), 0.99 (s, 9H), 0.18 (s, 6H). MS (DCI) m/z 476.2 (M+NH$_4$)$^+$.

Example 1R tert-butyl (R)-2-((5-(4-(((R)-1-(allyloxy)-3-(bis(4-methoxyphenyl)(phenyl)methoxy)propan-2-yl)oxy)-3,5-dichloro-2,6-dimethylphenyl)-6-(4-fluorophenyl)thieno[2,3-d]pyrimidin-4-yl)oxy)-3-(2-(benzyloxy)-5-((tert-butyldimethylsilyl)oxy)phenyl)propanoate Example 1L (14.7 g), Example 1Q (8.52 g), and cesium carbonate (11.01 g) were added to a three-necked flask equipped with an overhead stirrer and 2.2 g of 4 mm glass beads. Tert-butanol (145 mL) was added and the mixture was heated to 65° C. for 3 hours. Additional cesium carbonate (5.50 g) was added the reaction was stirred at 65° C. overnight. The reaction mixture was cooled and was diluted with ethyl acetate (300 mL). The resulting solution was filtered through diatomaceous earth, and washed through with 200 mL ethyl acetate. The mixture was concentrated, taken up in toluene and purified by silica gel chromatography using 10-30% ethyl acetate in heptanes as eluent to give the title compound. MS (ESI) m/z 1293.3 (M+H)$^+$.

Example 1S tert-butyl (R)-2-((5-(4-(((S)-1-(allyloxy)-3-hydroxypropan-2-yl)oxy)-3,5-dichloro-2,6-dimethylphenyl)-6-(4-fluorophenyl)thieno[2,3-d]pyrimidin-4-yl)oxy)-3-(2-(benzyloxy)-5-((tert-butyldimethylsilyl)oxy)phenyl)propanoate Example 1R (17.11 g) in dichloromethane (65 mL) and methanol (65 mL) was cooled to 0° C. Formic acid (38 mL) was added and the solution was stirred for 15 minutes at 0° C. The mixture was slowly added to 1 L of vigorously stirred saturated aqueous sodium bicarbonate. The resulting mixture was extracted with ethyl acetate (2×500 mL). The combined organics were washed with brine (100 mL), dried over Na$_2$SO$_4$, filtered, and concentrated. The crude material was purified by silica gel chromatography using 10-30% ethyl acetate in heptanes as eluent to give the title compound. MS (ESI) m/z 988.9 (M+H)$^+$.

Example 1T (R)-tert-butyl 2-((5-(4-(((R)-1-(allyloxy)-3-(tosyloxy)propan-2-yl)oxy)-3,5-dichloro-2,6-dimethylphenyl)-6-(4-fluorophenyl)thieno[2,3-d]pyrimidin-4-yl)oxy)-3-(2-(benzyloxy)-5-((tert-butyldimethylsilyl)oxy)phenyl)propanoate Example 1S (13.04 g) was dissolved in dichloromethane (125 mL) and cooled to 0° C. para-Toluenesulfonyl chloride (3.77 g), and 1,4-diazabicyclo[2.2.2]octane (2.95 g) were added, and the reaction was stirred at 0° C. for 30 minutes. The mixture was diluted with 55 mL dichloromethane, and quenched with 55 mL saturated aqueous NH$_4$Cl. The layers were separated and the organic layer was washed with brine, dried over Na$_2$SO$_4$, filtered, and concentrated. The crude material was purified by silica gel chromatography using 10-25% ethyl acetate in heptanes to provide the title compound. MS (ESI) m/z 1145.1 (M+H)$^+$.

Example 1U (R)-tert-butyl 2-((5-(4-(((R)-1-(allyloxy)-3-(tosyloxy)propan-2-yl)oxy)-3,5-dichloro-2,6-dimethylphenyl)-6-(4-fluorophenyl)thieno[2,3-d]pyrimidin-4-yl)oxy)-3-(2-(benzyloxy)-5-hydroxyphenyl)propanoate To Example 1T (14.15 g) in tetrahydrofuran (120 mL) was added acetic acid (0.779 mL), and tetrabutylammonium fluoride (13.60 mL, 1M in tetrahydrofuran). The reaction mixture was stirred for 20 minutes. The mixture was quenched with 20 mL saturated aqueous sodium bicarbonate solution. The mixture was diluted with 20% ethyl acetate/heptanes (150 mL). The layers were separated and the organic layer was washed with water and brine, dried over Na$_2$SO$_4$, filtered, and concentrated. The crude material was purified by silica gel chromatography using 10-50% ethyl acetate in heptanes to provide the title compound. $^1$H NMR (400 MHz, dimethylsulfoxide-d$_6$) δ ppm 8.90 (s, 1H), 8.64 (s, 1H), 7.70 (d, 2H), 7.40 (d, 2H), 7.30 (m, 71), 7.21 (m, 2H), 7.05 (t, 1H), 6.81 (d, 1H), 6.57 (m, 1H), 6.17 (d, 1H), 5.65 (m, 1H), 5.20 (t, 1H), 5.00 (m, 2H), 4.50 (m, 1H), 4.25 (m, 2H), 3.72 (m, 2H), 3.56 (m, 2H), 2.66 (m, 1H), 2.39 (s, 3H), 2.14 (s, 3H), 1.82 (s, 3H), 1.21 (s, 9H). MS (ESI) m/z 1030.7 (M+H)$^+$.

Example 1V tert-butyl (7R,16R)-10-(benzyloxy)-19,23-dichloro-1-(4-fluorophenyl)-20,22-dimethyl-16-{[(prop-2-en-1-yl)oxy]methyl}-7,8,15,16-tetrahydro-18,21-etheno-13,9-(metheno)-6,14,17-trioxa-2-thia-3,5-diazacyclononadeca[1,2,3-cd]indene-7-carboxylate To Example 1U (11.88 g) in N,N-dimethylformamide (1160 mL) was added cesium carbonate (18.79 g) and the reaction was stirred for 2 hours. The solution was poured into water (3600 mL), and the aqueous solution was extracted with ethyl acetate (4×300 mL). The combined organics were washed with water (2×800 mL), and brine (500 mL), dried over Na$_2$SO$_4$, filtered, and concentrated. The crude material was purified by silica gel chromatography using 10-50% ethyl acetate in heptanes to provide the title compound. $^1$H NMR (500 MHz, dimethylsulfoxide-d$_6$) δ ppm 8.75 (s, 1H), 7.40 (m, 5H), 7.20 (m, 4H), 6.90 (m, 2H), 5.98 (m, 1H), 5.92 (m, 1H), 5.68 (s, 1H), 5.30 (d, 1H), 5.19 (d, 1H), 5.02 (q, 2H), 4.81 (m, 1H), 4.51 (dd, 1H), 4.36 (d, 1H), 4.03 (m, 2H), 3.75 (m, 2H), 3.58 (m, 1H), 2.81 (m, 1H), 2.05 (s, 3H), 1.91 (s, 3H), 1.09 (s, 9H). MS (ESI) m/z 857.0 (M+H)$^+$.

Example 1W tert-butyl (7R,16R)-10-(benzyloxy)-19,23-dichloro-1-(4-fluorophenyl)-16-(hydroxymethyl)-20,22-dimethyl-7,8,15,16-tetrahydro-18,21-etheno-13,9-(metheno)-6,14,17-trioxa-2-thia-3,5-diazacyclononadeca[1,2,3-cd]indene-7-carboxylate A solution of Example 1V (8.75 g) in tetrahydrofuran (120 mL) and methanol (80 mL) was degassed and flushed with nitrogen three times. Tetrakis(triphenylphosphine)palladium (0) (1.179 g), and then 1,3-dimethylpyrimidine-2,4,6(1H,3H,5H)-trione (3.98 g) were added, and the solution was degassed and flushed with nitrogen once. The reaction mixture was stirred overnight. Pyrrolidine-1-carbodithioic acid, ammonia salt (0.251 g) was added as a palladium scavenger, and the reaction was stirred for 30 minutes. Ethyl acetate (100 mL) was added and the mixture was filtered through diatomaceous earth, washing with more ethyl acetate. The crude material was concentrated and used without further purification. MS (ESI) m/z 819.2 (M+H)$^+$.

Example 1X tert-butyl (7R,16S)-0-(benzyloxy)-19,23-dichloro-1-(4-fluorophenyl)-20,22-dimethyl-16-{[(4-methylbenzene-1-sulfonyl)oxy]methyl}-7,8,15,16-tetrahydro-18,21-etheno-13,9-(metheno)-6,14,17-trioxa-2-thia-3,5-diazacyclononadeca[1,2,3-cd]indene-7-carboxylate Example 1W (8.09 g) in dichloromethane (95 mL) was cooled to 0° C. To the mixture was added p-toluenesulfonyl chloride (4.9 g), and 1,4-diazabicyclo[2.2.2]octane (3.9 g). The reaction was stirred at 0° C. for 1 hour. The mixture was diluted with 50 mL dichloromethane, and quenched with 50 mL saturated aqueous NH$_4$Cl. Water (50 mL) was added and the layers were separated. The organic layer was washed with brine, dried over Na$_2$SO$_4$, filtered, and concentrated. The crude material was purified by silica gel chromatography using 10-35% ethyl acetate in heptanes to provide the title compound. MS (ESI) m/z 971.2 (M+H)$^+$.

Example 1Y tert-butyl (7R,16R)-10-(benzyloxy)-19,23-dichloro-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To an ambient solution of Example 1X (2.98 g) in N,N-dimethylformamide (10 mL) was added 1-methylpiperazine (10.20 mL). The reaction was heated to 40° C. for 24 hours. Another 2 mL 1-methyl-piperazine was added and the reaction was heated at 35° C. overnight. The reaction was cooled to room temperature, and the solvents were removed by rotary evaporation. The crude material was cooled in an ice bath, stirred, and diluted sequentially with ethyl acetate (100 mL) and water (100 mL). The layers were separated, and the aqueous layer was extracted with additional ethyl acetate (2×100 mL). The combined organics were washed with brine (2×100 mL), dried over anhydrous sodium sulfate, filtered and concentrated under reduced pressure. The residue was diluted with toluene (5 mL) and was purified by normal phase MPLC (Biotage® Isolera, 100 g Biotage® Ultra SiO$_2$ column), eluting with a gradient of 0-6% methanol in dichloromethane to provide the title compound. $^1$H NMR (500 MHz, dimethylsulfoxide-d$_6$) δ ppm 8.74 (s, 1H), 7.41 (m, 2H), 7.39 (m, 2H), 7.35 (m, 1H), 7.20 (m, 4H), 6.90 (m, 1H), 6.81 (m, 1H), 6.00 (m, 1H), 5.67 (s, 1H), 5.02 (q, 2H), 4.75 (m, 1H), 4.44 (m, 2H), 3.60 (m, 1H), 3.58 (m, 1H), 2.80 (m, 1H), 2.48 (m, 3H), 2.40 (m, 4H), 2.30 (m, 4H), 2.15 (s, 3H), 2.08 (s, 3H), 1.89 (s, 3H), 1.09 (s, 9H). MS (ESI) m/z 899.4 (M+H)$^+$.

Example 1Z tert-butyl (7R,16R)-19,23-dichloro-1-(4-fluorophenyl)-10-hydroxy-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 1Y (1.943 g) in tetrahydrofuran (11 mL) was added to 5% Pd/C (1.801 g) in a 20 mL Barnstead Hast C pressure reactor. The reactor was purged with argon gas. The mixture was stirred at 1600 rpm under 50 psi of hydrogen at 25° C. After 17.3 hours, the reaction was vented. The mixture was filtered through a filter funnel with a polyethylene frit packed with diatomaceous earth. The mixture was concentrated, and the crude material was taken up in ether and a small amount of dichloromethane. The mixture was filtered through diatomaceous earth, washing with ether/dichloromethane. The solvent was removed on a rotovap, and the material was placed on high vacuum overnight to provide the title compound. $^1$H NMR (500 MHz, dimethylsulfoxide-d$_6$) δ ppm 9.11 (s, 1H), 8.72 (s, 1H), 7.20 (m, 4H), 6.67 (m, 2H), 5.96 (m, 1H), 5.50 (s, 1H), 4.69 (m, 1H), 4.41 (m, 1H), 4.37 (m, 1H), 3.54 (dd, 1H), 3.58 (m, 1H), 2.62 (m, 2H), 2.22-2.50 (m, 9H), 2.18 (s, 6H), 1.88 (s, 3H), 1.09 (s, 9H). MS (ESI) m/z 811.2 (M+H)+.

Example 1AA methyl 2-(4-((tert-butyldimethylsilyl)oxy)phenyl) pyrimidine-4-carboxylate A mixture of methyl 2-chloropyrimidine-4-carboxylate (3.57 g) and 4-(tert-butyldimethylsilyloxy)phenylboronic acid (15.7 g) were suspended in previously degassed 1,4-dioxane. (140 mL). Potassium carbonate (10.75 g) was solubilized in previously degassed water (21.5 mL), and was added to the reaction mixture. 1,1'-Bis(diphenylphosphino) ferrocene-palladium(II)dichloride dichloromethane complex (2.050 g) was then added and the reaction mixture was placed under an argon atmosphere, then heated at 80° C. for 7 hours. The reaction mixture was diluted with 250 mL of dichloromethane and 200 mL of water and the layers were separated. The aqueous layer was extracted with 3×150 mL of dichloromethane. The combined organic layers were dried over MgSO$_4$, filtered, and concentrated to provide the crude material. Purification was performed by flash chromatography on a Biotage® silica gel cartridge (KPSil 340 g), eluting from 5-20% ethyl acetate in cyclohexane to afford the title compound. LCMS (APCI) m/z 345.0 (M+H)+.

Example 1AB (2-(4-((tert-butyldimethylsilyl)oxy)phenyl)pyrimidin-4-yl)methanol To a solution of Example 1AA (14.06 g) in tetrahydrofuran (100 mL) and methanol (200 mL) was added at −10° C., sodium borohydride (5.40 g) and the reaction was stirred at 0° C. for 30 minutes. The reaction was quenched at 0° C. with 400 mL saturated aqueous NH$_4$Cl and the organic solvents were evaporated. The remaining mixture was diluted with 300 mL dichloromethane. The organic layer was collected and the aqueous phase was extracted with 3×200 mL dichloromethane. The organic layers were combined, dried with MgSO$_4$, filtered and concentrated. The crude material was purified on a silica gel column eluting with 5-20% ethyl acetate in cyclohexane to afford the title compound. LCMS (APCI) m/z 317.0 (M+H)+.

Example 1AC 4-(4-(hydroxymethyl)pyrimidin-2-yl)phenol

To an ambient solution of Example 1AB (1.5 g) in tetrahydrofuran (60 mL) was added tetrabutylammonium fluoride (5.21 mL, 1.0 M in tetrahydrofuran) via syringe. The reaction was stirred overnight and was quenched by the addition of methanol (30 mL). The mixture was concentrated under reduced pressure. The residue was purified by silica gel chromatography (50 g), eluting with a gradient of 0-5% methanol in dichloromethane to give the title compound. $^1$H NMR (300 MHz, dimethyl sulfoxide-d$_6$) δ ppm 9.92 (s, 1H), 8.78 (d, 1H), 8.23 (d, 2H), 7.37 (d, 1H), 6.86 (d, 2H), 5.62 (t, 1H), 4.59 (d, 2H).

Example 1AD (S)-(2-(4-((2,2-dimethyl-1,3-dioxolan-4-yl)methoxy) phenyl)pyrimidin-4-yl)methanol To a solution of Example 1AC (238 mg) in N,N-dimethylformamide (3.5 mL) was added (R)-(2,2-dimethyl-1,3-dioxolan-4-yl)methyl 4-methylbenzenesulfonate (371 mg) and cesium carbonate (460 mg). The mixture was stirred at 50° C. for 24 hours. Ethyl acetate was added and the solution was washed with water, dried over Na$_2$SO$_4$, filtered, and concentrated. The crude residue was purified by silica gel flash chromatography (Biotage® 25 g silica gel column, eluting with 30-80% ethyl acetate in hexanes) to give the title compound.

Example 1AE tert-butyl (7R,16R)-19,23-dichloro-10-{[2-(4-{[(4S)-2,2-dimethyl-1,3-dioxolan-4-yl] methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 4 mL vial, equipped with stir bar, was charged with Example 1Z (100 mg), Example 1AD (78 mg), triphenylphosphine (68.0 mg) and di-tert-butylazodicarboxylate (56.9 mg). The vial was capped with a septum, then evacuated and backfilled with nitrogen gas. Toluene (1.2 mL) was added, and the vial was evacuated and backfilled with nitrogen gas again. The reaction mixture was stirred overnight. The mixture was concentrated and purification by flash chromatography on an AnaLogix IntelliFlash$^{280}$ system (10 g silica gel cartridge (eluting with 0-8% methanol/dichloromethane)) afforded the title compound. MS (ESI) m/z 1107.4 (M+H)+.

Example 1AF (7R,16R)-19,23-dichloro-10-[(2-{4-[(2R)-2,3-dihydroxypropoxy]phenyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 1AE (120 mg) in dichloromethane (0.7 mL) was added trifluoroacetic acid (TFA) (0.700 mL). The mixture was stirred for 4 hours, concentrated in vacuo, and dissolved in acetonitrile. The solution was made basic with saturated aqueous NaHCO$_3$, and was filtered to remove solids. The filtrate was purified by reverse phase preparative LC using a Gilson 2020 system (Luna C-18, 250×50 mm column, mobile phase A: 0.1% TFA in water; B: acetonitrile; 20-75% B to A gradient at 70 mL/minute) to afford the title compound. $^1$H NMR (500 MHz, dimethylsulfoxide-d$_6$) δ ppm 8.85 (s, 1H), 8.76 (s, 1H), 8.35 (d, 2H), 7.42 (d, 1H), 7.19 (m, 4H), 7.05 (d, 2H), 6.90 (d, 1H), 6.81 (m, 1H), 6.24 (m, 1H), 5.80 (s, 1H), 5.21 (q, 2H), 4.92 (m, 1H), 4.41 (m, 2H), 4.08 (dd, 1H), 3.95 (dd, 1H), 3.81 (m, 1H), 3.48 (m, 1H), 3.40 (m, 2H), 3.21 (m, 1H), 2.92-3.08 (m, 8H), 2.82 (m, 2H), 2.80 (s, 3H), 1.99 (s, 3H), 1.96 (s, 3H). MS (ESI) m/z 1011.4 (M+H)+.

Example 1AG (7R,16R)-19,23-dichloro-10-{[2-(4-{[(4S)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 1 AF (36 mg) and 2,2-dimethoxypropane (30.2 mg) in dichloromethane (1.2 mL) was added p-toluenesulfonic acid monohydrate (5.52 mg). The mixture was stirred for 1 hour. The mixture was purified by reverse phase preparatory LC using a Gilson 2020 system (Luna C-18, 250×50 mm column, mobile phase A: 0.1% TFA in water, B: acetonitrile; 20-75% B to A gradient at 70 mL/minute) to afford the title compound. $^1$H NMR (500 MHz, dimethylsulfoxide-$d_6$) δ ppm 8.82 (s, 1H), 8.76 (s, 1H), 8.35 (d, 2H), 7.42 (d, 1H), 7.19 (m, 4H), 7.06 (d, 2H), 6.88 (d, 1H), 6.80 (m, 1H), 6.25 (m, 1H), 5.78 (s, 1H), 5.20 (q, 2H), 4.90 (m, 1H), 4.41 (m, 2H), 4.08 (dd, 2H), 3.79 (dd, 1H), 3.62 (m, 1H), 3.21 (m, 1H), 2.88-3.12 (m, 10H), 2.82 (m, 2H), 2.80 (s, 3H), 1.95 (s, 3H), 1.95 (s, 3H), 1.37 (s, 3H), 1.30 (s, 3H). MS (ESI) m/z 1051.3 (M+H)$^+$.

Example 2

(7R,16R)-19,23-dichloro-10-{[2-(4-{[(2R)-1,4-dioxan-2-yl]methoxy}phenyl)pyrimidin-4-yl]methoxy})-1-(4-fluorophenyl)-20,22-dimethyl-16-[(4-piperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 2A (R)-2-(4-((1,4-dioxan-2-yl)methoxy)phenyl)-4,4,5,5-tetramethyl-1,3,2-dioxaborolane (S)-(1,4-dioxan-2-yl)methanol (160 mg) was dissolved in dichloromethane (6 mL). The mixture was cooled to 0° C. Triethylamine (0.217 mL) was added. Methanesulfonyl chloride (0.116 mL) was then added dropwise. The mixture was allowed to warm to room temperature. After two hours, saturated aqueous sodium bicarbonate (3 mL) was added. The layers were separated and the organic portion was washed with brine (5 mL). The aqueous portions were combined and back-extracted with dichloromethane (10 mL). The organic portions were combined and dried over anhydrous sodium sulfate, and filtered. The solvent was removed under vacuum. To this material was added 4-(4,4,5,5-tetramethyl-1,3,2-dioxaborolan-2-yl)phenol (200 mg) and N,N-dimethylformamide (5 mL). Cesium carbonate (592 mg) was added, and the mixture was heated to 90° C. for 16 hours. The mixture was cooled and saturated aqueous ammonium chloride (2 mL) was added. The mixture was diluted with ethyl acetate (20 mL) and washed with water (10 mL) twice. The organic portion was washed with brine (10 mL) and dried on anhydrous sodium sulfate. After filtration, the mixture was concentrated under vacuum and was purified by flash column chromatography on silica gel using a 30-60% gradient of ethyl acetate in heptanes to provide the title compound. $^1$H NMR (500 MHz, dimethylsulfoxide-$d_6$) δ ppm 7.60 (d, 2H), 6.94 (d, 2H), 3.98 (d, 2H), 3.88-3.74 (m, 3H), 3.68-3.59 (m, 2H), 3.52-3.46 (m, 1H), 3.42-3.37 (m, 1H), 1.27 (s, 12H). MS (ESI) m/z 221.3 (M-tert-butyl carboxylate)$^+$.

Example 2B (R)-(2-(4-((1,4-dioxan-2-yl)methoxy)phenyl)pyrimidin-4-yl)methanol Example 2A (138 mg) and (2-bromopyrimidin-4-yl)methanol (94 mg) were dissolved in 1,4-dioxane (2 mL). Aqueous sodium carbonate (2 M, 0.65 mL) was added. The mixture was degassed and flushed with nitrogen three times. Dichloro[1,1'-bis(diphenylphosphino)ferrocene]palladium (II) dichloromethane adduct (35 mg) was added, and the mixture was degassed and flushed with nitrogen once. The mixture was stirred at 75° C. for 16 hours. The mixture was cooled, diluted with ethyl acetate (10 mL), washed with water (10 mL), washed with brine (10 mL), and dried over anhydrous sodium sulfate. The mixture was concentrated and purified by flash column chromatography on silica gel using a 30-60% gradient of ethyl acetate in heptanes to provide the title compound. $^1$H NMR (500 MHz, dimethylsulfoxide-$d_6$) δ ppm 8.81 (d, 1H), 8.33 (d, 2H), 7.42 (d, 1H), 7.07 (d, 2H), 5.65 (t, 1H), 4.61 (d, 2H), 4.04 (d, 2H), 3.92-3.76 (m, 3H), 3.69-3.61 (m, 2H), 3.54-3.48 (m, 1H), 3.45-3.40 (m, 1H). MS (ESI) m/z 303.2 (M+H)$^+$.

Example 2C tert-butyl (7R,16R)-19,23-dichloro-10-{[2-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 2B for Example 1AD in Example 1AE. MS (ESI) m/z 1093.1 (M+H)$^+$.

Example 2D (7R,16R)-19,23-dichloro-10-{[2-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 2C for Example 1AE in Example 1AF. $^1$H NMR (500 MHz, dimethylsulfoxide-$d_6$) δ ppm 9.42 (bs, 1H), 8.84 (d, 1H), 8.76 (s, 1H), 8.32 (d, 2H), 7.44 (d, 1H), 7.21-7.15 (m, 4H), 7.08 (d, 2H), 6.91 (d, 1H), 6.83 (dd, 1H), 6.28 (m, 1H), 5.79 (d, 1H), 5.21 (q, 2H), 4.93 (m, 1H), 4.51-4.42 (m, 2H), 4.05 (m, 2H), 3.92-3.88 (m, 1H), 3.87 (dd, 1H), 3.78 (dd, 1H), 3.71-3.62 (m, 3H), 3.53 (m, 1H), 3.24 (m, 4H), 3.12-2.91

(m, 6H), 2.89-2.81 (m, 2H), 2.80 (s, 3H), 1.99 (s, 3H), 1.96 (s, 3H). MS (ESI) m/z 1037.1 (M+H)$^+$.

Example 3

(7R,16R)-19,23-dichloro-10-{[2-(2-{[(4R)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 3A (S)-2-(2-((2,2-dimethyl-1,3-dioxolan-4-yl)methoxy)phenyl)-4,4,5,5-tetramethyl-1,3,2-dioxaborolane To a solution of 2-(4,4,5,5-tetramethyl-1,3,2-dioxaborolan-2-yl)phenol (1000 mg) in N,N-dimethylformamide (10 mL) was added (R)-(2,2-dimethyl-1,3-dioxolan-4-yl)methyl 4-methylbenzenesulfonate (1431 mg) and cesium carbonate (1777 mg). The mixture was stirred at 120° C. for 24 hours, cooled, and diluted with ethyl acetate and washed with water. The organic layer was dried over Na$_2$SO$_4$, filtered, and concentrated. The residue was purified by silica gel flash chromatography (Biotage® 25 g silica gel column, eluting with 30-80% ethyl acetate in hexanes) to give the title compound. $^1$H NMR (500 MHz, dimethylsulfoxide-d$_6$) δ ppm 7.39 (m, 2H), 6.95 (m, 2H), 4.31 (m, 1H), 4.00 (m, 4H), 1.34 (s, 6H), 1.24 (s, 6H), 1.21 (s, 6H).

Example 3B (S)-(2-(2-((2,2-dimethyl-1,3-dioxolan-4-yl)methoxy)phenyl)pyrimidin-4-yl)methanol To a solution of (2-chloropyrimidin-4-yl)methanol (143 mg) and Example 3A (330 mg) in a mixture of tetrahydrofuran (5.712 mL) and saturated aqueous sodium bicarbonate solution (3.26 mL) was added Pd(PPh$_3$)$_4$ (114 mg). The reaction was heated to 75° C. overnight. The reaction was then cooled to room temperature and was diluted with water (20 mL) and dichloromethane (20 mL). The layers were separated, and the aqueous layer was extracted with additional dichloromethane (2×25 mL). The combined organics were dried with anhydrous sodium sulfate, filtered and concentrated under reduced pressure. The crude product was purified by MPLC (Biotage® Isolera, 10 g silica column, 37 mL/min flow), eluting with a gradient of 0-50% ethyl acetate in heptane over 20 minutes to give the title compound. MS (ESI) m, 317.2 (M+H)$^+$.

Example 3C tert-butyl (7R,16R)-19,23-dichloro-10-{[2-(2-{[(4S)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A solution of Example 1Z (100 mg), Example 3B (17 mg), triphenylphosphine (97.0 mg) and di-tert-butylazodicarboxylate (85 mg) in toluene (2 mL) was stirred overnight. The solution was directly purified by MPLC (Biotage® Isolera, 10 g silica, 36 mL/min flow), eluting with a gradient of 0-6% CH$_3$OH in dichloromethane over 25 minutes to give the title compound. MS (ESI) m/z 1107.5 (M+H)$^+$.

Example 3D (7R,16R)-19,23-dichloro-10-[(2-{2-1[(2R)-2,3-dihydroxypropoxy]phenyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 3C for Example 1AE in Example 1AF. $^1$H NMR (500 MHz, dimethylsulfoxide-d$_6$) δ ppm 9.43 (s, 1H), 8.87 (d, 1H), 8.77 (s, 1H), 7.67 (dd, 1H), 7.54 (d, 1H), 7.51-7.45 (m, 1H), 7.24-7.13 (m, 6H), 7.09 (t, 1H), 6.88 (d, 1H), 6.84 (dd, 1H), 6.28 (dd, 1H), 5.79 (d, 1H), 5.23 (d, 1H), 5.17 (d, 1H), 4.98-4.85 (m, 1H), 4.55-4.39 (m, 2H), 4.12 (dd, 1H), 4.01 (dd, 1H), 3.77 (p, 1H), 3.67 (dd, 1H), 3.27-3.16 (m, 2H), 3.13-2.94 (m, 8H), 2.85 (qd, 2H), 2.80 (s, 3H), 2.01 (s, 3H), 1.95 (s, 3H). MS (ESI) m/z 1011.3 (M+H)$^+$.

Example 3E (7R,16R)-19,23-dichloro-10-{[2-(2-{[(4R)-2,2-dimethyl-1,3-dioxolan-4-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 3D for Example 1 AF in Example 1AG. $^1$H NMR (400 MHz, dimethylsulfoxide-d$_6$) δ ppm 9.44 (s, 1H), 8.88 (d, 1H), 8.77 (s, 1H), 7.59 (dd, 1H), 7.52 (d, 1H), 7.49-7.41 (m, 1H), 7.24-7.12 (m, 6H), 7.08 (t, 1H), 6.89 (d, 1H), 6.83 (dd, 1H), 6.28 (dd, 1H), 5.80 (d, 1H), 5.24-5.11 (m, 2H), 4.98-4.90 (m, 1H), 4.53-4.39 (m, 2H), 4.35-4.27 (m, 1H), 4.10 (dd, 1H), 4.04 (dd, 1H), 4.00 (dd, 1H), 3.86 (dd, 1H), 3.64 (dd, 1H), 3.13-2.94 (m, 8H), 2.91-2.82 (m, 2H), 2.80 (s, 3H), 1.99 (s, 3H), 1.97 (s, 3H), 1.23 (s, 3H), 1.15 (s, 3H). MS (ESI) m/z 1051.4 (M+H)$^+$.

Example 4

(7R,16R,21S)-19-chloro-10-{[2-(1,4-dioxan-2-yl)pyrimidin-4-yl]methoxy}-1-(4-fluorophenyl)-20-methyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 4A 6-iodothieno[2,3-d]pyrimidin-4(3H)-one

Acetic acid (312 mL), sulfuric acid (9.37 mL) and water (63 mL) were combined with stirring. Thieno[2,3-d]pyrimidin-4(3H)-one (50 g), periodic acid (37.4 g) and iodine (75 g) were added sequentially, and the mixture became slightly endothermic. A heating mantle was added and the reaction mixture was ramped up to 60° C. Midway through, the temperature climbed to 68-69° C. The heating mantle was removed and the temperature was maintained at 70° C. by self-heating for about 45 minutes. The reaction mixture was cooled to room temperature. The resulting suspension was filtered, washed with 5:1 acetic acid:water (three times), and washed with diethyl ether (five times) to provide the title compound which was used in the next step without further purification. $^1$H NMR (400 MHz, dimethylsulfoxide-d$_6$) δ ppm 12.80-12.41 (m, 1H), 8.10 (s, 1H), 7.66 (s, 1H). MS (ESI) m/z 277.9 (M–H)$^-$.

Example 4B 4-chloro-6-iodothieno[2,3-d]pyrimidine

Phosphorous oxychloride (37 mL) and N,N-dimethylaniline (11.5 mL) were combined, and Example 4A (25 g) was added over a few minutes. The reaction mixture was stirred at 105° C. for 1.5 hours. The suspension was cooled to 5-10° C. filtered, and washed with heptanes. The crude filter cake was dumped into ice water with rapid stirring. The mixture was stirred for about 30 minutes, filtered, and washed with three times with water and three times with diethyl ether. The material was dried on the filter bed overnight to provide the title compound which was used in the next step without further purification. $^1$H NMR (400 MHz, dimethylsulfoxide-d$_6$) δ ppm 8.89 (s, 1H), 7.95 (s, 1H).

Example 4C 5-bromo-4-chloro-6-iodothieno[2,3-d]pyrimidine

Example 4B (20.5 g) was taken up in acetonitrile (173 mL) and N-bromosuccinimide (13.54 g) was added followed by tetrafluoroboric acid-dimethyl ether complex (2 mL). While the reaction mixture was stirring, the temperature slowly climbed, reaching 25.5° C. after 30 minutes. The reaction mixture was allowed to stir overnight at room temperature. An additional 0.4 equivalents of N-bromosuccinimide was added followed by tetrafluoroboric acid-dimethyl ether complex (2 mL), and the reaction mixture was stirred for an additional 5 hours. The reaction mixture was cooled in an ice bath to about 5° C. (internal) and was filtered. The material was washed with acetonitrile (twice) and dried on the filter bed overnight. The title compound was used in the next step without further purification. $^1$H NMR (400 MHz, dimethylsulfoxide-d$_6$) δ ppm 8.93 (s, 1H).

Example 4D 5-bromo-4-chloro-6-(4-fluorophenyl)thieno[2,3-d]pyrimidine (Tris(dibenzylideneacetone)dipalladium(0)) (7.32 g), di-tert-butyl(2',4',6'-triisopropyl-[1,1'-biphenyl]-2-yl)phosphine (7.47 g), tripotassium phosphate (181 g), (4-fluorophenyl)boronic acid (89 g), and Example 4C (200 g) were combined in a three neck, 5 L round bottom flask, fitted with a water condenser, thermocouple/JKEM, overhead stirring and an argon gas inlet. The material was flushed with argon for 40 minutes. Tetrahydrofuran (1705 mL) and water (426 mL) were combined into a 3 L round bottom flask. The contents were sparged with argon for 30 minutes. The solvent mixture was cannulated into the flask containing the solids. A sharp temperature increase to 37° C. was observed. The temperature was set to 64° C. (internal), and the reaction mixture was stirred overnight (16 hours) at 64° C. under a light positive flow of argon. The reaction mixture was cooled to 38° C. and 200 mL water was added with stirring (overhead). Stirring was continued for 2 hours, and the material was filtered and washed with water. A second crop was obtained from the filtrate and was combined with the first crop. The combined material was taken up in hot tetrahydrofuran (2 L), stirred with 20 g thiosilica gel and 20 g charcoal for 30 minutes, and filtered through a pad of diatomaceous earth. The filtrate was concentrated to provide the title compound. $^1$H NMR (400 MHz, chloroform-d) δ ppm 8.86 (s, 1H), 7.75-7.58 (m, 2H), 7.22 (t, 2H). MS (ESI) m/z 344.8 (M+H)$^+$.

Example 4E (R)-tert-butyl 3-(2-(benzyloxy)-5-((tert-butyldimethylsilyl)oxy)phenyl)-2-((5-bromo-6-(4-fluorophenyl)thieno[2,3-d]pyrimidin-4-yl)oxy)propanoate A 1 L flask containing Example 1Q (24.03 g) and Example 4D (19.08 g) was equipped with a stir bar, thermocouple for internal temperature monitoring and sealed with a rubber septum. The flask was flushed with argon, and warm tert-butanol (262 mL) was added via cannula. Cesium carbonate (51.2 g) was added in one portion. The reaction was heated to an internal temperature of 65° C. After four hours at 65° C., the reaction was allowed to cool to ambient temperature, diluted with methyl tert-butyl ether (100 mL) and filtered through a pad of diatomaceous earth. The filter pad was washed with ethyl acetate (2×100 mL). The solvents were evaporated, and the crude material was dissolved in ethyl acetate (500 mL). The mixture was washed with water (300 mL) and saturated aqueous sodium chloride solution (300 mL), dried over anhydrous magnesium sulfate, filtered, and concentrated. The crude residue was purified on a Grace Reveleris instrument using a Teledyne Isco Redisep® Gold 750 g column, eluting with a 0-30% ethyl acetate/heptanes gradient. The desired fractions were combined and concentrated to give the title compound. $^1$H NMR (501 MHz, chloroform-d) δ ppm 8.49 (s, 1H), 7.68-7.59 (m, 2H), 7.48-7.44 (m, 2H), 7.39-7.32 (m, 2H), 7.32-7.27 (m, 1H), 7.21-7.13 (m, 2H), 6.91 (d 1H), 6.77 (d, 1H), 6.65 (dd, 1H), 5.76 (dd, 1H), 5.07 (d, 1H), 5.04 (d, 1H), 3.49 (dd, 1H), 3.26 (dd, 1H), 1.40 (s, 9H), 0.93 (s, 9H), 0.11 (s, 3H), 0.10 (s, 3H). MS (ESI) m/z 765.2 (M+H)$^+$.

Example 4F (3-chloro-4-hydroxy-2-methylphenyl)boronic acid

A 5 L 3 neck jacketed flask equipped with overhead stirring and thermocouple for internal temperature monitoring was charged with Example 1R (50 g), chloro[(tri-tert-butylphosphine)-2-(2-aminobiphenyl)]palladium(II) (5.78 g), tetrahydroxydiboron (60.7 g), and potassium acetate (55.4 g) which had been dried overnight under vacuum at 50° C. The flask was flow purged with a N$_2$ gas sweep for 2 hours, and cooled until the internal temperature of the material reached −6° C. An oven dried 2 L round bottomed flask was charged with anhydrous methanol (1129 mL) and anhydrous ethylene glycol (376 mL). The stirring solvents were degassed by subsurface sparging with nitrogen gas for two hours and were cooled to −8° C. in an ice/ethanol bath. The solvent mixture was transferred to the reaction flask via cannula over 10 minutes. The reaction was stirred at −7° C. for 2.5 hours, quenched by addition of water (1 L), and allowed to stir at 0° C. for 1 hour. The mixture was filtered through a large pad of diatomaceous earth and the filter pad was washed with 1:1 water/methanol (2×500 mL). The filtrate was concentrated on a rotary evaporator until approximately 1.5 L of solvent had been removed. The mixture was extracted with ethyl acetate (2×1 L). The combined organic extracts were washed with brine, dried over anhydrous magnesium sulfate, filtered, and concentrated under reduced pressure. The crude material was treated with dichloromethane (200 mL), and the title compound was collected by filtration. $^1$H NMR (400 MHz, dimethylsulfoxide-$d_6$/deuterium oxide) δ ppm 7.19 (d, 1H), 6.75 (d 1H), 2.38 (s, 3H). MS (ESI) m/z 412.9 (M−H)$^−$.

Example 4G (R)-tert-butyl 3-(2-(benzyloxy)-5-((tert-butyldimethylsilyl)oxy)phenyl)-2-(((1S)-5-(3-chloro-4-hydroxy-2-methylphenyl)-6-(4-fluorophenyl 1)thieno[2,3-d]pyrimidin-4-yl)oxy)propanoate A 1 L 3 neck flask equipped with overhead stirring was charged with Example 4E (30.2 g), 4-(di-tert-butylphosphino)-N,N-dimethylaniline (1.15 g), (tris(dibenzylideneacetone)dipalladium(0)) (1.806 g), and Example 4F (14.70 g). The flask was sealed with a rubber septa and was flushed with argon for 15 minutes. A separate 500 mL round bottomed flask equipped with a magnetic stir bar was charged with cesium carbonate (25.7 g) and was sealed with a septum. The flask was flushed with argon for 10 minutes and water (46.9 mL) and 1,4-dioxane (235 mL) were added. The flask was degassed by subsurface sparging with stirring for 30 minutes and the contents were transferred to the reaction flask via cannula. The reaction was stirred for 60 hours and was quenched by addition of ammonium pyrrolidine-1-carbodithioate (1.296 g). The reaction was stirred for 1 hour at which point ethyl acetate (200 mL) and water (100 mL) were added. The biphasic mixture was filtered through a pad of diatomaceous earth, washing with ethyl acetate (100 mL) and water (50 mL). The layers were separated and the aqueous layer was extracted with ethyl acetate (200 mL). The combined organic layers were washed with a solution of saturated aqueous sodium chloride, dried over anhydrous magnesium sulfate, filtered and concentrated under reduced pressure. The crude material was purified by flash column chromatography using a Grace Reveleris system using a Teledyne Isco Redisep® Gold 750 g column eluting with a 0-30% ethyl acetate/heptanes gradient. The pure fractions were collected and concentrated under reduced pressure to give the title compound. $^1$H NMR (501 MHz, dimethylsulfoxide-$d_6$) δ ppm 10.10 (s, 1H), 8.61 (s, 1H), 7.43-7.38 (m, 2H), 7.36-7.24 (m, 5H), 7.24-7.18 (m, 2H), 6.92 (d, 1H), 6.89 (d, 1H), 6.80 (d, Hz, 1H), 6.68 (dd, 1H), 6.43 (d, 1H), 5.34 (t, 1H), 5.03 (s, 2H), 2.70-2.60 (m, 2H), 1.91 (s, 3H), 1.17 (s, 9H), 0.89 (s, 9H), 0.09 (s, 3H), 0.08 (s, 3H). MS (ESI) m/z 827.1 (M+H)$^+$.

Example 4H (S)-3-(allyloxy)-2-hydroxypropyl 4-methylbenzenesulfonate

A 1 L 3 necked round bottomed flask equipped with a magnetic stir bar was charged with a solution of Example 1J (45.8 g) in dichloromethane (500 mL). 4-Dimethylaminopyridine (0.572 g) and N-ethyl-N-isopropylpropan-2-amine (60.3 mL) were added sequentially. Solid 4-methylbenzene-1-sulfonyl chloride (33 g) was added portionwise and the reaction was heated to an internal temperature of 40° C. overnight. Upon cooling to ambient temperature, a solution of saturated aqueous ammonium chloride was added (300 mL). The layers were separated, and the organic layer was washed with a solution of saturated sodium chloride (200 mL), dried over anhydrous magnesium sulfate, filtered and concentrated under reduced pressure. The crude material was purified by flash column chromatography on a Grace Reveleris System using a Teledyne Isco Redisep® Gold 750 g column eluting with a 0-40% ethyl acetate/heptanes gradient to give the title compound. $^1$H NMR (4(00 MHz, chloroform-d) δ ppm 7.79 (d, 2H), 7.35 (d, 2H), 5.82 (ddt, 1H), 5.22 (dq,), 5.16 (dq, 1H), 4.10 (dd, 1H), 4.04 (dd, 1H), 3.98 (dd, 1H), 3.94 (dt, 2H), 3.47 (dd, 1H), 3.43 (dd, 1H), 2.87 (d, 1H), 2.44 (s, 3H). MS (ESI) m/z 304.0 (M+NH$_4$)$^+$.

Example 4I (R)-tert-butyl 2-(((1S)-5-(4-(((R)-1-(allyloxy)-3-(tosyloxy)propan-2-yl)oxy)-3-chloro-2-methylphenyl)-6-(4-fluorophenyl)thieno[2,3-d]pyrimidin-4-yl)oxy)-3-(2-(benzyloxy)-5-((tert-butyldimethylsilyl)oxy)phenyl)propanoate An oven dried 250 mL 3-necked flask was charged with Example 4H (3.11 g) and Example 4G (5.0 g). The flask was equipped with a magnetic stir bar, sealed with rubber septa, and purged with an argon sweep for 15 minutes. Toluene (30 mL) was added and upon dissolution, the flask was cooled in an ice bath to an internal temperature of 5° C. Triphenylphosphine (3.17 g) was added and the reaction mixture was stirred for 5 minutes at which point di-tert-butyl azodicarboxylate (2.78 g) was added. After 30 minutes, the cooling bath was removed and the flask was allowed to warm to ambient temperature and was stirred overnight. The reaction mixture was loaded onto a 400 mL Buchner funnel packed with silica gel which had been equilibrated with heptanes. The silica gel plug was eluted with a mixture of 1:3 ethyl acetate/heptanes (600 mL), which was concentrated. The crude product was purified by flash column chromatography on a Teledyne Isco Combiflash® Rf instrument using a Teledyne Isco RediSep® Gold 220 g column. The pure fractions were combined and concentrated to give the title compound. $^1$H NMR (400 MHz, dimethylsulfoxide-$d_6$) δ ppm 8.62 (s, 1H), 7.75 (d, 1H), 7.46-7.33 (m, 5H), 7.33-7.25 (m, 3H), 7.22 (t, 2H), 7.09 (d, 1H), 6.96 (d, 1H), 6.91 (d, 1H), 6.67 (dd, 1H), 6.39 (d, 1H), 5.62 (ddt, 1H), 5.31 (dd, 1H), 5.06-4.99 (m, 3H), 4.97 (dq, 1H), 4.69 (dt, 1H), 4.28 (dd, 1H), 4.18 (dd, 1H), 3.73 (dq, 2H), 3.45 (d, 2H), 2.58 (qd, 2H), 2.38 (s, 3H), 1.94 (s, 3H), 1.15 (s, 9H), 0.88 (s, 9H), 0.08 (s, 3H), 0.08 (s, 3H). MS (ESI) m/z 1095.3 (M+H)$^+$.

Example 4J (R)-tert-butyl 2-(((1S)-5-(4-(((R)-1-(allyloxy)-3-(tosyloxy)propan-2-yl)oxy)-3-chloro-2-methylphenyl)-6-(4-fluorophenyl)thieno[2,3-d]pyrimidin-4-yl)oxy)-3-(2-(benzyloxy)-5-hydroxyphenyl)propanoate A 100 mL round bottomed flask was charged with Example 4I (3.58 g), sealed with a septum and purged with nitrogen gas for 10 minutes. Tetrahydrofuran (23 mL) was added followed by acetic acid (0.3 mL). The stirring homogeneous solution was cooled in an ice bath to 5° C. internal temperature and a solution of tetra-N-butylammonium fluoride (4.75 mL, 1M) in tetrahydrofuran was added dropwise. After 1 hour, the reaction was quenched by addition of saturated aqueous sodium bicarbonate (40 mL), and diluted with methyl tert-butyl ether (160 mL). The layers were separated and the organic layer was washed sequentially with water and brine, then dried over magnesium sulfate, filtered and concentrated. The crude residue was purified by flash column chromatography on a Teledyne Isco Combiflash® Rf instrument using a Teledyne Isco RediSep® Gold 80 g column eluting with a 0-60% ethyl acetate/heptanes gradient. The desired fractions were collected, combined and concentrated to give the title compound. $^1$H NMR (400 MHz, dimethylsulfoxide-$d_6$) δ ppm 8.78 (s, 1H), 8.61 (s, 1H), 7.80-7.70 (m, 2H), 7.45-7.40 (m, 2H), 7.40-7.33 (m, 4H), 7.32-7.24 (m, 3H), 7.24-7.19 (m, 2H), 7.13 (d, 1H), 7.01 (d, 1H), 6.83 (d, 1H), 6.57 (dd, 1H), 6.17 (d, 1H), 5.63 (ddt, 1H), 5.21 (dd, 1H), 5.04 (dq, 1H), 4.98 (ddt, 3H), 4.73 (dt, 1H), 4.29 (dd, 1H), 4.19 (dd, Hz, 1H), 3.75 (q, 1H), 3.74 (q, 1H), 3.48 (d, 2H), 2.59 (dd, 1H), 2.50 (d, 1H), 2.38 (s, 3H), 1.93 (s, 3H), 1.17 (s, 9H). MS (ESI) m/z 981.1 (M+H)$^+$.

Example 4K tert-butyl (7R,16R,21S)-10-(benzyloxy)-19-chloro-1-(4-fluorophenyl)-16-(allyloxymethyl)-20-methyl-7,8,15,16-tetrahydro-18,21-etheno-13,9-(metheno)-6,14,17-trioxa-2-thia-3,5-diazacyclononadeca[1,2,3-cd]indene-7-carboxylate An oven dried 3 neck 500 mL round bottomed flask was charged with Example 4J (3.13 g), and equipped with a magnetic stir bar and sealed with rubber septa. The flask was purged with an argon flow for 10 minutes. N,N-Dimethylformamide (319 mL) was added and the material was dissolved with stirring at ambient temperature. Cesium carbonate (5.19 g) was added and the suspension was stirred at ambient temperature for 3 hours. Ethyl acetate (100 mL) was added and the mixture was filtered through a pad of diatomaceous earth. The solvents were concentrated under vacuum, and the crude residue was treated with ethyl acetate (200 mL) and water (100 mL). A 1 M aqueous solution of lithium chloride was added (50 mL), and the layers were separated. The organic layer was dried over anhydrous magnesium sulfate, filtered and concentrated under reduced pressure. The crude residue was purified by flash column chromatography on a Teledyne Isco Combiflash® Rf instrument using a Teledyne Isco RediSep® Gold 120 g column eluting with a 0-50% ethyl acetate/heptanes gradient. The desired fractions were collected, combined and concentrated to give the title compound. $^1$H NMR (400 MHz, dimethylsulfoxide-$d_6$) δ ppm 8.70 (s, 1H), 7.49-7.43 (m, 3H), 7.43-7.36 (m, 3H), 7.37-7.29 (m, 1H), 7.26-7.14 (m, 6H), 6.97-6.91 (m, 3H), 6.88 (dd, 1H), 5.97 (dd, 1H), 5.89 (ddt, 1H), 5.52 (d, 1H), 5.27 (dq, 1H), 5.16 (dq, 1H), 5.04 (d, 1H), 4.97 (d, 1H), 4.50 (hept, 1H), 4.46-4.41 (m, 1H), 4.41-4.37 (m, 1H), 4.06-3.97 (m, 1H), 4.01-3.92 (m, 1H), 3.76 (dd, 1H), 3.68 (dd, 1H), 3.62 (dd, 1H), 2.71 (d, 1H), 2.23 (s, 3H), 1.01 (s, 9H). MS (ESI) m/z 809.1 (M+H)$^+$.

Example 4L tert-butyl (7R,16R,21S)-10-(benzyloxy)-19-chloro-1-(4-fluorophenyl)-16-(hydroxymethyl)-20-methyl-7,8,15,16-tetrahydro-18,21-etheno-13,9-(metheno)-6,14,17-trioxa-2-thia-3,5-diazacyclononadeca[1,2,3-cd]indene-7-carboxylate An oven dried 100 mL round bottomed flask was charged with Example 4K (2.23 g), tetrakis(triphenylphosphine) palladium(0) (0.318 g), 1,3-dimethylpyrimidine-2,4,6(1H,3H,5H)-trione (0.946 g), and a magnetic stir bar, and sealed with a septum. The flask was purged with a flow of argon for 15 minutes. A mixture of tetrahydrofuran (18 mL) and methanol (9 mL), which was degassed by subsurface sparging with argon for 30 minutes, was added via cannula. The reaction was stirred at ambient temperature for 40 hours at which point ammonium pyrrolidine-1-carbodithioate (0.181 g) was added and the stirring was continued for 1 hour. The reaction mixture was filtered through a plug of diatomaceous earth, and the filter pad was washed with ethyl acetate (25 mL) and water (25 mL). The filtrate layers were separated and the aqueous layer was extracted once with ethyl acetate (25 mL). The combined organic layers were washed with a solution of saturated aqueous sodium chloride (50 mL), dried over anhydrous magnesium sulfate and concentrated under reduced pressure. The crude residue was purified by flash column chromatography on a Teledyne Isco Combiflash® Rf instrument using a Teledyne Isco RediSep® Gold 80 g column eluting with a 0-50% ethyl acetate/heptanes gradient. The pure fractions were collected, combined and concentrated to give the title compound. $^1$H NMR (400 MHz, dimethylsulfoxide-$d_6$) δ ppm 8.70 (s, 1H), 7.50-7.43 (m, 2H), 7.44-7.36 (m, 2H), 7.37-7.30 (m, 1H), 7.26-7.14 (m, 5H), 6.98-6.90 (m, 2H), 6.86 (dd, 1H), 5.96 (dd, 1H), 5.52 (d, 1H), 5.04 (d, 1H), 4.98 (q, 2H), 4.48-4.31 (m, 3H), 3.76 (dd, 1H), 3.69 (ddd, 1H), 3.56 (dt, 1H), 2.77-2.66 (m, 1H), 2.23 (s, 3H), 1.02 (s, 9H). MS (ESI) m/z 769.2 (M+H)$^+$.

Example 4M tert-butyl (7R,16R,21S)-10-(benzyloxy)-19-chloro-1-(4-fluorophenyl)-20-methyl-16-{[(4-methylbenzene-1-sulfonyl)oxy]methyl}-7,8,15,16-tetrahydro-18,21-etheno-13,9-(metheno)-6,14,17-trioxa-2-thia-3,5-diazacyclononadeca[1,2,3-cd]indene-7-carboxylate A 50 mL round bottomed flask was charged with Example 4L (1.81 g), and a magnetic stir bar. Dichloromethane was added (16 mL), and the mixture was stirred to dissolution. 1,4-Diazabicyclo[2.2.2]octane (0.660 g) and p-toluenesulfonyl chloride (0.673 g) were added sequentially. The reaction was stirred at ambient temperature for 1 hour and quenched by addition of ethylenediamine (0.079 mL). The reaction mixture was stirred for 10 minutes and was diluted with dichloromethane (20 mL). A solution of 1.0 M sodium dihydrogen phosphate NaH$_2$PO$_4$ (30 mL) was added. The layers were separated and the aqueous layer was extracted with dichloromethane (20 mL). The combined organic layers were dried over anhydrous magnesium sulfate, filtered and concentrated to give the title compound which was used without further purification. $^1$H NMR (400 MHz, dimethylsulfoxide-$d_6$) δ ppm 8.70 (s, 1H), 7.84-7.77 (m, 2H), 7.46 (ddd, 4H), 7.44-7.37 (m, 2H), 7.37-7.31 (m, 1H), 7.20 (d, 3H), 7.11-7.04 (m, 1H), 6.94 (d, 1H), 6.92 (d, 1H), 6.87 (dd, 1H), 5.97 (dd, 1H), 5.48 (d, 1H), 5.06 (d, 1H), 4.99 (d, 1H), 4.61-4.49 (m, 1H) 4.39-4.32 (m, 3H), 4.29 (dd, 1H), 3.75 (dd, 1H), 2.75-2.64 (m, 1H) 2.40 (s, 3H), 2.21 (s, 3H), 1.01 (s, 9H). MS (ESI) m/z 923.0 (M+H)$^+$.

Example 4N tert-butyl (7R,16R,21S)-10-(benzyloxy)-19-chloro-1-(4-fluorophenyl)-20-methyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate An oven dried 100 mL round bottomed flask was charged with Example 4M (2.17 g) and a magnetic stir bar then sealed with a rubber septum. The flask was purged with a nitrogen gas sweep for 10 minutes. Dimethylformamide (8 mL) and 1-methylpiperazine (8 mL) were added sequentially. The reaction was stirred for 60 hours at ambient temperature and 16 hours at 30° C. The reaction was cooled in an ice bath, and diluted with ethyl acetate (20 mL) and water (20 mL). The reaction was allowed to warm to ambient temperature and was further diluted with water (80 mL) and ethyl acetate (80 mL). The layers were separated and the aqueous layer was extracted with ethyl acetate (2×50 mL). The combined organic layers were washed sequentially with water and a 0.5 M aqueous solution of lithium chloride, dried over anhydrous magnesium sulfate, and concentrated. The crude residue was purified by flash column chromatography on a Teledyne Isco Combiflash® Rf instrument using a Teledyne Isco RediSep® Gold 80 g column eluting with a 0-10% methanol/dichlormethane gradient to yield the title compound. $^1$H NMR (501 MHz, dimethylsulfoxide-$d_6$) δ ppm 8.71 (s, 1H), 7.47-7.43 (m, 3H), 7.43-7.37 (m, 3H), 7.37-7.29 (m, 2H), 7.26-7.13 (m, 5H), 6.93 (d, J=2.9 Hz, 1H), 6.91 (d, J=3.7 Hz, 1H), 6.82 (dd, J=9.0, 2.9 Hz, 2H), 6.01 (dd, J=5.9, 2.3 Hz, 2H), 5.53 (d, J=2.7 Hz, 1H), 5.06 (d, J=12.1 Hz, 1H), 4.98 (d, J=12.1 Hz, 1H), 4.48 (d, J=13.2 Hz, 1H), 4.44 (dd, J=8.2, 5.5 Hz, 1H), 4.32 (dd, J=13.0, 8.4 Hz, 1H), 3.78 (dd, J=16.7, 5.9 Hz, 1H), 2.75-2.68 (m, 1H), 2.60-2.55 (m, 1H), 2.54 (dd, J=13.0, 7.8 Hz, 1H), 2.31 (d, J=29.0 Hz, 8H), 2.24 (s, 3H), 2.15 (s, 3H), 1.01 (s, 9H). MS (ESI) m/z 851.0 (M+H)$^+$.

Example 4O tert-butyl (7R,16R,2S)-19-chloro-1-(4-fluorophenyl)-10-hydroxy-20-methyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 20 mL Barnstead Hastelloy C reactor was charged with palladium on carbon (0.55 g, 5% weight palladium, wet). A solution of Example 4N in tetrahydrofuran (2.5 mL) was added and the reactor was purged with argon. The mixture was stirred under 50 psi of hydrogen at 25° C. for 48 hours. The mixture was filtered, concentrated under reduced pressure and purified by flash column chromatography on a Teledyne Isco Combiflash® Rf instrument using a Teledyne Isco RediSep® Gold 40 g column eluting with a 0-10% methanol/dichlormethane gradient to yield the title compound. $^1$H NMR (400 MHz, dimethylsulfoxide-$d_6$) δ ppm 9.03 (s, 1H), 8.67 (s, 1H), 7.32-7.04 (m, 7H), 6.88 (d, 1H), 6.78-6.51 (m, 2H), 5.91 (dd, 1H), 5.33 (d, 1H), 4.43-4.32 (m, 2H), 4.24 (dd, 1H), 3.65 (dd, 1H), 2.57 (d, 1H), 2.53-2.47 (m, 3H), 2.36-2.25 (m, 8H), 2.24 (s, 3H), 2.10 (s, 3H), 1.01 (s, 9H). MS (ESI+) m/z 761.5 (M+H)$^+$.

Example 4P 1,4-dioxane-2-carboxamide

In a 1 L recovery flask, 1,4-dioxane-2-carboxylic acid (11.0 g) in tetrahydrofuran (200 mL) was cooled to 3° C., and di(1H-imidazol-1-yl)methanone (16 g) was added all at once. The mixture was stirred cold for 5 minutes, and stirred at room temperature for 2 hours. The mixture was then cooled in an ice-water bath for 15 minutes, concentrated ammonium hydroxide (16 mL) was added, and the reaction was stirred for 1 hour. The cold bath was removed and the reaction was stirred another 1 hour. The mixture was concentrated and left under high vacuum overnight. The material was taken up in 150 mL ethyl acetate and 40 mL 6N aqueous HCl. The layers were separated, and the aqueous layer was extracted with 4×200 mL ethyl acetate. The combined organic layers were dried over sodium sulfate, filtered, and concentrated. The crude product was carried on without further purification.

Example 4Q methyl 1,4-dioxane-2-carbimidate

Example 4P (12.0 g) was added to dichloromethane (225 mL), and the mixture was cooled using an ice-water bath for 15 minutes. Trimethyloxonium tetrafluoroborate (12.0 g) was added all at once. The reaction was allowed to come to room temperature overnight. Saturated aqueous sodium bicarbonate (240 mL) was added and the layers were separated. The aqueous layer was extracted with ethyl acetate (3×180 mL). The combined ethyl acetate layers were dried over sodium sulfate, filtered, and concentrated. The crude product was carried on without further purification.

Example 4R 1,4-dioxane-2-carboximidamide, hydrochloride salt

Example 4Q (7.8 g) was dissolved in methanol (115 mL), and cooled using an ice-water bath for 15 minutes. Ammonium hydrochloride (4.5 g) was added. The reaction was stirred cold for five minutes, at room temperature for 30 minutes, and finally at 70° C. overnight. The reaction was cooled and concentrated, and the residue was stirred in dichloromethane (50 mL) for 45 minutes, and filtered through diatomaceous earth. The filtrate was concentrated to give the title compound which was used in the next step without further purification. MS (DCI) m/z 131.0 (M+H)$^+$.

Example 4S (4-(dimethoxymethyl)-2-(1,4-dioxane-2-yl)pyrimidine

To a mixture of Example 4R (4.6 g) in ethanol (115 mL) was added (E)-4-(dimethylamino)-1,1-dimethoxybut-3-en-2-one (5.4 g) and sodium ethoxide (21 wt. %, 21 mL), and the mixture was stirred at 70° C. for 18 hours. The mixture was cooled to room temperature and was concentrated under reduced pressure. The residue was diluted with ethyl acetate (150 mL) and saturated aqueous ammonium chloride (70 mL), the layers were separated, and the aqueous layer was extracted with ethyl acetate. The combined organic layers were dried over sodium sulfate, filtered and concentrated under reduced pressure to provide the title compound, which was chromatographed on silica gel using 15% ethyl acetate in heptanes as the eluent to give the title compound. $^1$H NMR (400 MHz, chloroform-d) δ ppm 8.81 (d, 1H), 7.47 (d, 1H), 5.29 (d, 1H), 4.92 (dd, 1H), 4.20 (dd, 1H), 4.05 (d, 1H), 3.95 (m, 1H), 3.79 (m, 2H), 3.74 (d, 1H), 3.42 (s, 6H).

Example 4T (2-(1,4-dioxan-2-yl)pyrimidin-4-yl)methanol

A mixture of Example 4S (2.4 g) in 2M HCl in 1,4-dioxane (1:1, 80 mL) was heated to 50° C. for 16 hours. The reaction mixture was cooled to 0° C., and concentrated sodium hydroxide (4.5 mL) was added to adjust the pH to 8. Sodium borohydride (0.75 g) was added. The mixture was stirred for one hour at 0° C. The mixture was extracted with three times with ethyl acetate. The combined organic phases were dried over sodium sulfate, filtered, and concentrated under reduced pressure. The residue was purified by column chromatography on silica gel, eluting with 0.5-10% methanol in dichloromethane to provide the title compound. $^1$H NMR (400 MHz, chloroform-d) δ ppm 8.72 (d, 1H), 7.32 (d, 1H), 4.89 (dd, 1H), 4.78 (d, 2H), 4.19 (dd, 1H), 4.05 (dd, 1H), 3.93 (m, 1H), 3.84-3.71 (m, 3H), 3.48 (dd, 1H).

Example 4U (2-(1,4-dioxan-2-yl)pyrimidin-4-yl)methyl methanesulfonate

To Example 4T (65 mg) in dichloromethane (1.6 mL) was added triethylamine (60 μL), and the mixture was cooled in an ice-water bath for 15 minutes. Methanesulfonyl chloride (33 μL) was added dropwise. The reaction mixture was stirred cold for 5 minutes, and at room temperature for 2 hours. Saturated aqueous sodium bicarbonate solution was added, and the solution was extracted twice with dichloromethane. The extracts were washed with brine, dried over sodium sulfate, filtered, and concentrated. The crude product was carried on without further purification.

Example 4V tert-butyl (7R,16R,21S)-19-chloro-10-{[2-(1,4-dioxan-2-yl)pyrimidin-4-yl]methoxy}-1-(4-fluorophenyl)-20-methyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To Example 4U (59 mg) in dimethylformamide (0.5 mL) was added Example 4O (120 mg), followed by cesium carbonate (103 mg), and the reaction was stirred overnight. The crude mixture was chromatographed on a Reveleris prep LC with a 250×50 mm Luna™ column using 10-80% acetonitrile in 0.1% aqueous TFA over 30 minutes to give the title compound as a mix of diastereomers. MS (ESI) m/z 939.5 (M+H)$^+$.

Example 4W (7R,16R,21S)-19-chloro-10-{[2-(1,4-dioxan-2-yl)pyrimidin-4-yl]methoxy}-1-(4-fluorophenyl)-20-methyl-6-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To Example 4V (68 mg) in dichloromethane (700 μL) was added trifluoroacetic acid (700 μL). The reaction was stirred for 5 hours. The solution was concentrated, dissolved in 1 mL dimethylformamide and 0.5 mL water, and purified by prep liquid chromatography on a Luna™ 250×50 mm column, using 5-75% acetonitrile in 0.1% aqueous TFA over 30 minutes, to give the title compound as a mixture of two diastereomers. $^1$H NMR (400 MHz, dimethylsulfoxide-d$_6$) δ ppm 8.88 (d, 1H), 8.79 (s, 1H), 7.60 (d, 1H), 7.21 (m, 5H), 7.00 (d, 1H), 6.89 (m, 2H), 6.19 (dd, 1H), 5.70 (d, 1H), 5.20 (dd, 2H), 4.75 (d, 1H), 4.61 (dd, 1H), 4.50 (d, 1H), 4.40 (dd, 1H), 4.02 (d, 1H), 3.98-3.75 (m, 6H), 3.61 (m, 1H), 3.41 (m, 2H), 3.12 (m, 4H), 2.90 (d, 1H), 2.82 (s, 3H), 2.80 (m, 1H), 2.48 (m, 2H), 2.21 (s, 3H). MS (ESI+) m/z 883.3 (M+H)$^+$.

Example 5

(7R,16R)-19,23-dicloro-10-{[2-(6-{[(2R)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 5A 2-((1,4-dioxan-2-yl)methoxy)-5-bromopyridine To a solution of (1,4-dioxan-2-yl) methanol (2.4 g) in dimethylsulfoxide (24 mL) was added 5-bromo-2-chloropyridine (3.91 g) and sodium hydride (0.81 g) at 20° C. under nitrogen flow. The reaction mixture was stirred at 60° C. for 10 hours under nitrogen atmosphere. The reaction was diluted with water (40 mL) at 25° C. and extracted with ethyl acetate (3×40 mL). The combined organic layers were washed with brine (5×20 mL) and dried over sodium sulfate. After filtration, the filtrate was concentrated to give a residue which was purified by column chromatography on silica gel (eluted with petroleum ether:ethyl acetate=100:1 to 20:1) to give the title compound. $^1$H NMR (400 MHz, CDCl$_3$) δ ppm 8.15 (d, 1H), 7.63 (dd, 1H), 6.70 (d, 1H) 4.38-4.49 (m, 2H), 3.78-3.85 (m, 2H), 3.59-3.71 (m, 6H), 3.52 (dd, 2H), 3.35 (s, 3H).

Example 5B (6-((1,4-dioxan-2-yl)methoxy)pyridin-3-yl)boronic acid

To a solution of Example 5A (4 g) in 1,4-dioxane (200 mL) was added potassium acetate (2.58 g), 1,1'-bis(diphenylphosphino) ferrocenedichloro palladium(II) dichloromethane (2.15 g) and 4,4,4',4',5,5,5',5'-octamethyl-2,2'-bis (1,3,2-dioxaborolane) (5 g) at 20° C. under nitrogen flow. The reaction mixture was stirred at 100° C. for 12 hours under nitrogen atmosphere. The reaction mixture was cooled and filtered through diatomaceous earth. The filtration was concentrated to provide the title compound. $^1$H NMR (400 MHz, CDCl$_3$) δ ppm 8.51 (br s, 1H), 7.92 (br d, 1H), 6.77 (br d, 1H), 4.35 (br s, 2H), 4.06-3.76 (m, 5H), 3.62-3.45 (m, 2H).

Example 5C 2-(6-((1,4-dioxan-2-yl)methoxy)pyridin-3-yl)pyrimidine-4-carboxylic acid To a solution of 2-chloropyrimidine-4-carboxylic acid (0.81 g) in 1,4-dioxane (120 mL) and water (60 mL) was added sodium bicarbonate (0.85 g), tetrakis (triphenylphosphine) palladium(0) (0.58 g) and Example 5B (8.1 g) at 20° C. The reaction mixture was stirred at 80° C. for 12 hours, cooled down to 20° C. and filtered. The filtrate was concentrated to provide the title compound. $^1$H NMR (400 MHz, D$_2$O) δ ppm 8.39 (br s, 1H), 7.70-7.43 (m, 2H), 6.85 (br s, 1H), 4.36-3.38 (m, 9H).

Example 5D methyl 2-(6-((1,4-dioxan-2-yl)methoxy)pyridin-3-yl)pyrimidine-4-carboxylate To a solution of Example 5C (2.8 g) in methanol (84 mL) was added $H_2SO_4$ (0.7 mL) at 20° C. The reaction was stirred at 80° C. for 2 hours under nitrogen atmosphere, cooled, diluted with water (150 mL) and extracted with ethyl acetate (3×100 mL). The combined organic layers were dried over sodium sulfate, filtered and concentrated. The residue was purified by column chromatography on silica gel (eluted with petroleum ether:ethyl acetate=100:1 to 10:1) to provide the title compound. $^1$H NMR (400 MHz, $CDCl_3$) δ ppm 9.27 (d, 1H), 8.99 (d, 1H), 8.65 (dd, 1H), 7.82 (d, 1H), 6.89 (d, 1H), 4.43 (m, 1H), 4.06-3.96 (m, 4H), 3.94-3.63 (m, 5H), 3.55 (dd, 1H).

Example 5E (R)-(2-(6-((1,4-dioxan-2-yl)methoxy)pyridin-3-yl)pyrimidin-4-yl)methanol To a solution of Example 5D (1.8 g) in dimethyl formamide (27 mL)/methanol (27 mL)/water (2.7 mL) was added sodium borohydride (0.14 g) at 0° C. under nitrogen flow. The reaction mixture was stirred at 25° C. for 10 hours under nitrogen atmosphere. The reaction was quenched by addition of water (30 mL) and extracted with ethyl acetate (3×50 mL). The combined organic layers were dried over sodium sulfate, filtered and concentrated. The residue was purified by column chromatography on silica gel (eluted with petroleum ether:ethyl acetate=100:1 to 100:13) to provide a mixture of two enantiomers. The enantiomeric mixture was separated on a Thar SFC80 preparative SFC instrument (Column: Chiralpak AD-H 250*30 mm i.d. 5 μm, Mobile phase: A for $CO_2$ and B for ethanol (0.1% ammonium hydroxide); Gradient: B %=45%; Flow rate: 85 g/minute; Wavelength: 220 nm; Column temperature: 40° C.; System back pressure: 100 bar; Cycle time: 20 minutes; Injection amount: 25 mg per injection) to provide the title compound. The stereochemistry of the title compound was arbitrarily assigned. $^1$H NMR (400 MHz, $CDCl_3$) δ ppm 9.23 (d, 1H), 8.73 (d, 1H), 8.61 (dd, 1H), 7.17 (d, 1H), 6.91 (d, 1H), 4.81 (br s, 2H), 4.47-4.37 (m, 2H), 4.05 (dtd, 1H), 3.94-3.64 (m, 5H), 3.61-3.54 (m, 2H).

Example 5F tert-butyl (7R,16R)-19,23-dichloro-10-{[2-(6-{[(2R)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A mixture of Example 1Z (40 mg), Example 5E (30 mg) and $Ph_3P$ (38.9 mg) in a 4-mL vial was purged with nitrogen gas for 20 minutes. Tetrahydrofuran (1 mL) was added. The suspension was stirred for 2 minutes and sonicated for 2 minutes. Toluene (1 mL) was added. The mixture was stirred for 3 minutes and (E)-$N^1,N^1,N^2,N^2$-tetramethyldiazene-1,2-dicarboxamide (29.8 mg) was added. The reaction mixture was heated at 50° C. overnight, cooled, diluted with dichloromethane, loaded to a silica gel column, and eluted with 0-10% methanol in dichloromethane to provide the title compound.

Example 5G (7R,16R)-19,23-dichloro-10-{[2-(6-{[(2R)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 5F (48 mg) in dichloromethane (4.5 mL) was treated with trifluoroacetic acid (1.5 mL) overnight and concentrated. The residue was dissolved in ethyl acetate and washed with sodium bicarbonate water solution, and brine/water. The organic layer was dried over sodium sulfate and concentrated. The residue was purified by reverse phase HPLC on a ACCQPrep HP125 system (Column: Luna™ 10 μm C18(2) 100 Å, 250×50 mm), eluting with 40-70% acetonitrile in 5 mM ammonium acetate to provide the title compound. $^1$H NMR (501 MHz, dimethylsulfoxide-$d_6$) δ ppm 9.11 (d, 1H), 8.86 (d, 1H), 8.72 (s, 1H), 8.58 (dd, 1H), 7.54 (d, 1H), 7.25-7.08 (m, 3H), 6.98 (d, 1H), 6.87 (d, 1H), 6.73 (dd, 1H), 6.19 (t, 1H), 5.84 (d, 1H), 5.30-5.13 (m, 2H), 4.88 (d, 1H), 4.49-4.26 (m, 4H), 3.90 (ddt, 1H), 3.82 (dd, 1H), 3.77 (dd, 1H), 3.70-3.58 (m, 3H), 3.56-3.46 (m, 2H), 3.55-3.40 (m, 5H), 3.02-2.90 (m, 1H), 2.74-2.59 (m, 2H), 2.47-2.24 (m, 3H), 2.16 (s, 2H), 1.97 (d, 5H). MS (ESI) m/z 1036.0 (M−H)⁻.

Example 6

(7R,16R)-19,23-dichloro-10-{[2-(6-{[(2S)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 6A (S)-(2-(6-((1,4-dioxan-2-yl)methoxy)pyridin-3-yl)pyrimidin-4-yl)methanol To a solution of Example 5D (1.8 g) in dimethylformamide (27 mL)/methanol (27 mL)/water (2.7 mL) was added sodium borohydride (0.14 g) at 0° C. under nitrogen flow. The reaction mixture was stirred at 25° C. for 10 hours under nitrogen atmosphere. The reaction was quenched by addition of water (30 mL) and extracted with ethyl acetate (3×50 mL). The combined organic layers were dried over sodium sulfate, filtered and concentrated. The residue was purified by column chromatography on silica gel (eluted with petroleum ether:ethyl acetate=100:1 to 100:13) to provide a mixture of two enantiomers. The enantiomeric mixture was separated on a Thar SFC80 preparative SFC instrument (Column: Chiralpak AD-H 250*30 mm i.d. 5 μm; Mobile phase: A for $CO_2$ and B for ethyl acetate (0.1% ammonium hydroxide); Gradient: B %=45%; Flow rate: 85 g/minute; Wavelength: 220 nm; Column temperature: 40° C.; System back pressure: 100 bar; Cycle time: 20 minutes; Injection amount: 25 mg per injection) to provide the title compound. The stereochemistry of the title compound was arbitrarily assigned. ¹H NMR (400 MHz, CDCl₃) δ ppm 9.23 (d, 1H), 8.73 (d, 1H), 8.61 (dd, 1H), 7.17 (d, 1H), 6.91 (d, 1H), 4.81 (s, 2H), 4.49-4.37 (m, 2H), 4.05 (dtd, 1H), 3.95-3.63 (m, 5H), 3.61-3.54 (m, 2H).

Example 6B tert-butyl (7R,16R)-19,23-dichloro-10-{[2-(6-{[(2S)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 6A.

Example 6C (7R,16R)-19,23-dichloro-10-{[2-(6-{[(2S)-1,4-dioxan-2-yl]methoxy}pyridin-3-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 6B. ¹H NMR (500 MHz, dimethylsulfoxide-d₆) δ ppm 9.03 (d, 1H), 8.78 (d, 1H), 8.66 (s, 1H), 8.50 (dd, 1H), 7.46 (d, 1H), 7.16-7.08 (m, 2H), 7.06 (ddd, 2H), 6.90 (d, 1H), 6.80 (d, 1H), 6.66 (dd, 1H), 6.15 (dd, 1H), 5.77 (d, 1H), 5.18 (d, 1H), 5.11 (d, 1H), 4.79 (p, 1H), 4.37 (d, 2H), 4.24 (qd, 2H), 3.83 (dddd, 1H), 3.75 (dd, 1H), 3.69 (dd, 1H), 3.63-3.51 (m, 3H), 3.47-3.39 (m, 1H), 3.34 (dd, 1H), 2.93-2.85 (m, 1H), 2.62 (dd, 1H), 2.56 (dd, 1H), 2.37 (s, 7H), 2.14 (s, 3H), 1.90 (d, 6H).

Example 7

(7R,16R)-19,23-dichloro-10-{[2-(4-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 7A (S)-2-(4-((1,4-dioxan-2-yl)methoxy)phenyl)-4,4,5,5-tetramethyl-1,3,2-dioxaborolane The title compound was prepared by substituting (R)-(1,4-dioxan-2-yl)methanol for (S)-(1,4-dioxan-2-yl)methanol in Example 2A. ¹H NMR (500 MHz, dimethylsulfoxide-d₆) δ ppm 7.59 (d, 2H), 6.92 (d, 2H), 3.96 (d, 2H), 3.87-3.73 (m, 3H), 3.67-3.58 (m, 2H), 3.51-3.46 (m, 1H), 3.41-3.35 (m, 1H), 1.26 (s, 12H). MS (ESI) m/z 338.1 (M+NH₄)⁺.

Example 7B (S)-(2-(4-((1,4-dioxan-2-yl)methoxy)phenyl)pyrimidin-4-yl)methanol

The title compound was prepared by substituting Example 7A for Example 2A in Example 2B. ¹H NMR (500 MHz, dimethylsulfoxide-d₆) δ ppm 8.81 (d, 1H), 8.33 (d, 2H), 7.41 (d, 1H), 7.07 (d, 2H), 5.65 (t, 1H), 4.61 (d, 2H), 4.04 (d, 2H), 3.92-3.76 (m, 3H), 3.69-3.61 (m, 2H), 3.54-3.48 (m, 1H), 3.45-3.40 (m, 1H). MS (ESI) m/z 303.2 (M+H)⁺.

Example 7C tert-butyl (7R,16R)-19,23-dichloro-10-{[2-(4-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 1Z (50 mg). Example 7B (37 mg), and triphenylphosphine (49 mg) were dissolved in toluene (0.3 mL) and tetrahydrofuran (0.3 mL). (E)-N¹,N¹,N²,N²-tetramethyldiazene-1,2-dicarboxamide (32 mg) was added, and the solution was stirred and heated at 50° C. for 90 minutes. The solution was cooled, and the solvent was removed under vacuum. The material was carried on to the next step without further purification. MS (ESI) m/z 1093.5 (M+H)⁺.

Example 7D (7R,16R)-19,23-dichloro-10-{[2-(4-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 7C (66 mg) was dissolved in dichloromethane (0.3 mL). Trifluoroacetic acid was added (0.35 mL), and the solution was stirred overnight. The solvent was removed under vacuum. The material was taken up in dimethylformamide (1 mL) and water (1 mL). The solution was neutralized with minimal 1 M aqueous NaOH and was purified by reverse phase using 30-1(00)% acetonitrile in water (w/10 mM ammonium acetate) over 40 min on a Grace Reveleris equipped with a Luna™ column: C18(2), 100 A, 250×50 mm. Product fractions were pooled, frozen, and placed on a lyophilizer. ¹H NMR (500 MHz, dimethylsulfoxide-d₆) δ ppm 8.81 (d, 1H), 8.69 (s, 1H), 8.33 (d, 2H), 7.47 (d, 1H), 7.20-7.17 (m, 2H), 7.13-7.10 (m, 2H), 7.06 (d, 2H), 6.84 (d, 1H), 6.69 (dd, 1H), 6.20 (m, 1H), 5.92 (s, 1H), 5.19 (q, 2H), 4.92 (m, 1H) 4.48-4.38 (m, 2H), 4.04 (d, 2H), 3.92-3.86 (m, 1H), 3.84 (d, 1H), 3.80-3.74 (m, 1H), 3.70-3.57 (m, 3H), 3.53-3.45 (m, 2H), 2.96 (d, 2H), 2.71-2.62 (m, 3H), 2.46 (m, 2H) 2.36 (m, 4H) 2.15 (s, 3H), 1.94 (s, 3H), 1.92 (s, 3H). MS (ESI) m/z 1037.6 (M+H)⁺.

Example 8

(7R,16R)-19,23-dichloro-10-({2-[4-({[(2S)-1,4-dioxan-2-yl]methoxy}methyl)-4-fluoropiperidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 8A (S)-tert-butyl 4-(((1,4-dioxan-2-yl)methoxy)methyl)-4-fluoropiperidine-1-carboxylate To a solution of tert-butyl 4-fluoro-4-(hydroxymethyl)piperidine-1-carboxylate (200 mg) in dimethylformamide (2.8 mL) at 0° C. was added sodium hydride (43 mg, 60% oil dispersion), and the reaction was allowed to stir for 15 minutes. (S)-(1,4-dioxan-2-yl)methyl 4-methylbenzenesulfonate (410 mg) was added, and the reaction was allowed to warm to room temperature overnight. The reaction was diluted with saturated aqueous ammonium chloride and extracted three times with ethyl acetate. The combined organic layers were washed with water and brine, dried over anhydrous sodium sulfate, filtered and concentrated. The residue was purified by normal phase MPLC on a Teledyne Isco Combiflash®. Rf+ 24 g gold silica gel column eluting with 0-45% ethyl acetate in heptanes to give the title compound. $^1$H NMR (500 MHz, dimethylsulfoxide-$d_6$) δ ppm 3.82-3.36 (m, 12H), 3.26 (dd, 1H), 2.99 (br s, 2H), 1.78-1.66 (m, 2H), 1.63-1.46 (m, 2H), 1.39 (s, 9H).

Example 8B (S)-4-(((1,4-dioxan-2-yl)methoxy)methyl)-4-fluoropiperidine

To a solution of Example 8A (90 mg) in dichloromethane (500 μL) was added trifluoroacetic acid (260 μL), and the reaction was allowed to stand for 2 hours. The reaction was concentrated to give the title compound which was used in the next step without further purification.

Example 8C (S)-(2-(4-(((1,4-dioxan-2-yl)methoxy)methyl)-4-fluoropiperidin-1-yl)pyrimidin-4-yl)methanol A solution of Example 8B (89 mg), (2-chloropyrimidin-4-yl)methanol (30 mg) and N,N-diisopropylethylamine (190 μL) in acetonitrile (540 μL) was stirred at 80° C. for 2.5 hours and at room temperature overnight. The reaction was diluted with water and extracted with ethyl acetate three times. The combined organic layers were dried over anhydrous sodium sulfate, filtered and concentrated. The residue was purified by normal phase MPLC on a Teledyne Isco Combiflash® Rf+ 12 g gold silica gel column eluting with 10-80% ethyl acetate in dichloromethane to give the title compound. $^1$H NMR (400 MHz, dimethylsulfoxide-$d_6$) δ ppm 8.33 (d, 1H), 6.70 (d, 1H), 5.44-5.36 (m, 1H), 4.47-4.31 (m, 4H), 3.74-3.37 (m, 10H), 3.30-3.13 (m, 3H), 1.86-1.73 (m, 2H), 1.70-1.48 (m, 2H).

Example 8D tert-butyl (7R,16R)-19,23-dicloro-10-({2-[4-({[(2S)-1,4-dioxan-2-yl]methoxy}methyl)-4-fluoropiperidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To a vial containing Example 1Z (40 mg), Example 8C (25 mg) and triphenylphosphine (39 mg) in toluene (120 μL) and tetrahydrofuran (120 μL) was added N,N,N',N'-tetramethylazodicarboxamide (26 mg) and the reaction was allowed to stir at 50° C. for 2 hours. The reaction was diluted with ethyl acetate, filtered over diatomaceous earth and concentrated. The residue was purified by normal phase MPLC on a Teledyne Isco Combiflash® Rf+ 4 g gold silica gel column eluting with 0-7% methanol in dichloromethane to give the title compound. $^1$H NMR (400 MHz, dimethyl-sulfoxide-$d_6$) δ ppm 8.74 (s, 1H), 8.36 (s, 1H), 7.28-7.13 (m, 5H), 6.92-6.77 (m, 2H), 6.73 (d, 1H), 6.02 (dd, 1H), 5.67 (dd, 1H), 5.03-4.83 (m, 2H), 4.80-4.69 (m, 1H), 4.53-4.34 (m, 3H), 3.75-3.35 (m, 12H), 3.29-3.17 (m, 3H), 2.86 (d, 1H), 2.80 (s, 3H), 2.73-2.59 (m, 2H), 2.43-2.21 (m, 4H), 2.15 (s, 3H), 2.09 (s, 3H), 1.90 (s, 3H), 1.87-1.75 (m, 2H), 1.73-1.50 (m, 2H), 1.06 (s, 9H).

Example 8E (7R,16R)-19,23-dichloro-10-({2-[4-({[(2S)-1,4-dioxan-2-yl]methoxy}methyl)-4-fluoropiperidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 8D (44 mg) in dichloromethane (190 μL) was added trifluoroacetic acid (190 μL), and the reaction was allowed to stir for 5 hours. The reaction was concentrated under a stream of nitrogen and was taken up in water and acetonitrile. The mixture was purified by RP-HPLC on a Gilson PLC 2020 using a Luna™ column (250×50 mm, 10 mm) (5-85% over 30 minutes with acetonitrile in water containing 10 mM ammonium acetate) to give the title compound after lyophilization. $^1$H NMR (500 MHz, dimethylsulfoxide-$d_6$) δ ppm 8.73 (s, 1H), 8.33 (d 1H), 7.23-7.09 (m, 5H), 6.81 (d, 1H), 6.76-6.69 (m, 2H), 6.25-6.17 (m, 1H), 5.84-5.79 (m, 1H), 5.01-4.81 (m, 3H), 4.49-4.35 (m, 4H), 3.73-3.36 (m, 12H), 3.30-3.17 (m, 5H), 2.98-2.88 (m, 1H), 2.76-2.61 (m, 3H), 2.59-2.33 (m, 6H), 2.25 (s, 3H), 1.97 (s, 6H), 1.86-1.74 (m, 2H), 1.71-1.50 (m, 2H). MS (ESI) m/z 1074.1 (M−H)$^−$.

Example 9

(7R,16R)-19,23-dichloro-10-({2-[(1R,4r)-4-{[(2R)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 9A phenyl(vinyl)selane To a solution of 1,2-diphenyldiselane (7 g) in tetrahydrofuran (75 mL) at 0° C. was added vinylmagnesium bromide (49.3 mL, 1 M in tetrahydrofuran) over 25 minutes, and the reaction was allowed to warm to room temperature and stir overnight. The reaction was slowly diluted with water with water bath cooling and extracted with ethyl acetate three times. The combined organic layers were dried over anhydrous sodium sulfate, filtered and concentrated. The residue was purified by normal phase MPLC on a Teledyne Isco Combiflash® Rf+ 120 g gold silica gel column eluting with heptanes to give the title compound. $^1$H NMR (500 MHz, CDCl$_3$) δ ppm 7.57-7.49 (m, 2H), 7.36-7.27 (m, 3H), 6.91-6.79 (m, 1H), 5.83-5.75 (m, 1H), 5.60-5.50 (m, 1H).

Example 9B (vinylselenonyl)benzene

To a solution of Example 9A (1.2 g) in tetrahydrofuran (120 mL) was added potassium phosphate dibasic (3.4 g)

and magnesium monoperoxyphthalate hexahydrate (8.1 g), and the reaction was allowed to stir for 3 hours. The reaction was diluted with ethyl acetate and washed with 10% aqueous sodium carbonate followed by brine. The organic layer was dried over anhydrous sodium sulfate, filtered and concentrated to give the title compound that was used in the next step without further purification. $^1$H NMR (500 MHz, CDCl$_3$) δ ppm 8.01-7.91 (m, 2H), 7.74-7.60 (m, 3H), 7.08-6.90 (m, 1H), 6.76-6.68 (m, 1H), 6.48-41 (m, 1H).

Example 9C 2-((1r,4r)-4-((1,4-dioxan-2-yl)methoxy)cyclohexyl)-4-(((tert-butyldiphenylsilyl)oxy)methyl)pyrimidine To a solution of Example 14G (480 mg) in dichloromethane (6.1 mL) at room temperature was added sodium hydride (66 mg, 60% oil dispersion), and the reaction was allowed to stir for 10 minutes. A solution of Example 9B (400 mg) in dichloromethane (3 mL) was added, and the reaction was allowed to stir for 5 hours. The reaction was quenched with saturated aqueous ammonium chloride and extracted with ethyl acetate three times. The combined organic layers were dried over anhydrous sodium sulfate, filtered and concentrated. The residue was purified by normal phase MPLC on a Teledyne Isco Combiflash® Rf+ 24 g gold silica gel column eluting with 20-75% ethyl acetate in heptanes to give the title compound as a mixture of isomers. $^1$H NMR (500 MHz, dimethylsulfoxide-d$_6$) δ ppm 8.75 (d, 1H), 7.68-7.60 (m, 4H), 7.51-7.38 (m, 7H), 4.72 (s, 2H), 3.73-3.66 (m, 2H), 3.64-3.50 (m, 3H), 3.47-3.38 (m, 2H), 3.28-3.17 (m, 2H), 2.74-2.63 (m, 1H), 2.06-1.96 (m, 2H), 1.94-1.85 (m, 2H), 1.59-1.46 (m, 2H), 1.29-1.19 (m, 2H), 1.05 (s, 9H).

Example 9D (2-((1R,4r)-4-(((R)-1,4-dioxan-2-yl)methoxy)cyclohexyl)pyrimidin-4-yl)methanol To a solution of Example 9C (370 mg) in tetrahydrofuran (2.2 mL) and methanol (1.1 mL) was added cesium fluoride (500 mg), and the reaction was allowed to stir overnight. The reaction was concentrated, and the residue was taken up in ethyl acetate, filtered over diatomaceous earth and concentrated. The residue was purified by normal phase MPLC on a Teledyne Isco Combiflash® Rf+ 12 g gold silica gel column eluting with 0-6.5% methanol in dichloromethane to give the mixture of enantiomers (160 mg). The mixture was purified by chiral SFC using a Chiralpak AD-H column (30×250 mm, 5 micron) to give the title compound in high enantiomeric excess (>95%). Analytical SFC of the title compound using a Chiralpak AD-H column (5-50% methanol over 10 minutes) gave a retention time of 4.43 minutes. $^1$H NMR (500 MHz, dimethylsulfoxide-4) δ ppm 8.68 (d, 1H), 7.35 (d, 1H), 5.56 (br s, 1H), 4.49 (s, 2H), 3.75-3.66 (m, 2H), 3.65-3.51 (m, 3H), 3.49-3.34 (m, 3H), 3.29-3.20 (m, 2H), 2.78-2.67 (m, 1H), 2.11-2.00 (m, 2H), 1.98-1.88 (m, 2H), 1.66-1.50 (m, 2H), 1.33-1.18 (m, 2H). [α]$_D$=−7°(c 1.0, CHCl$_3$).

Example 9E

The title compound was obtained from the SFC separation described in Example 9D. Analytical SFC of the title compound using a Chiralpak AD-H column (5-50% methanol over 10 minutes) gave a retention time of 4.93 minutes. $^1$H NMR (400 MHz, dimethylsulfoxide-d$_6$) δ ppm 8.68 (d, 1H), 7.35 (d, 1H), 5.56 (br s, 1H), 4.50 (s, 2H), 3.75-3.66 (m, 2H), 3.65-3.51 (m, 3H), 3.49-3.20 (m, 5H), 2.78-2.67 (m, 1H), 2.11-2.00 (m, 2H), 1.98-1.88 (m, 2H), 1.66-1.50 (m, 2H), 1.33-1.16 (m, 2H).

Example 9F tert-butyl (7R,16R)-19,23-dichloro-10-({2-[(1R,4r)-4-{[(2R)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 9D (30 mg) and Example 1Z (26 mg) were azeotroped with toluene/tetrahydrofuran three times. The residue was taken up in toluene (80 μL), and tetrahydrofuran (80 μL) and triphenylphosphine (25 mg) followed by N,N,N',N'-tetramethylazodicarboxamide (17 mg) were added. The reaction was heated to 50° C. for 7 hours and stirred at room temperature overnight. The reaction mixture was diluted with ethyl acetate, filtered over diatomaceous earth and concentrated. The residue was purified by normal phase MPLC on a Teledyne Isco Combiflash® Rf+ 4 g gold silica gel column, eluting with 1.5-10% methanol in dichloromethane to give the title compound. MS (EST) m/z 1099.6 (M+H)$^+$.

Example 9G (7R,16R)-19,23-dichloro-10-({2-[(1R,4r)-4-{[(2R)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 9F (33 mg) in dichloromethane (150 μL) was added trifluoroacetic acid (150 μL), and the reaction was allowed to stir overnight. The reaction was concentrated under a stream of nitrogen and was taken up in water and acetonitrile. The mixture was purified by RP-HPLC on a Gilson PLC 2020 using a Luna™ column (250×50 mm, 10 mm, 30-80% over 30 minutes with acetonitrile in water containing 10 mM ammonium acetate) to give a crude material after lyophilization. The crude material was purified by normal phase MPLC on a Teledyne Isco Combiflash® Rf+ 4 g gold silica gel column eluting with 10-25% methanol in dichloromethane to give the title compound. $^1$H NMR (400 MHz, Methanol-d$_4$) δ 8.66 (d, 1H), 8.60 (s, 1H), 7.60 (d, 1H), 7.16-7.07 (m, 2H), 7.04-6.94 (m, 2H), 6.76-6.63 (m, 2H), 6.17 (dd, 1H), 6.08 (d, 1H), 5.10 (s, 3H), 4.59-4.48 (m, 3H), 4.36 (d, 1H), 3.81-3.74 (m, 2H), 3.73-3.63 (m, 4H), 3.61-3.43 (m, 3H), 3.42-3.33 (m, 2H), 3.06 (dd, 1H), 2.93-2.67 (m, 9H), 2.57 (s, 3H), 2.20-2.12 (m, 5H), 2.06-1.97 (m, 51H), 1.79-1.66 (m, 2H), 1.42-1.27 (m, 21H), exchangeable CO$_2$H not observed. MS (ESI) m/z 1041.0 (M−H)$^-$.

Example 10

(7R,16R)-19,23-dichloro-10-{[2-(4-{[(2R)-1,4-dioxan-2-yl]methoxy}piperidin-1-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 10A tert-butyl (R)-4-((1,4-dioxan-2-yl)methoxy)piperidine-1-carboxylate (S)-(1,4-Dioxan-2-yl)methanol (160 mg) was dissolved in dichloromethane (6 mL). The mixture was cooled to 0° C. Triethylamine (0.217 mL) was added. Methanesulfonyl chloride (0.116 mL) was added dropwise. The mixture was allowed to warm to room temperature. After two hours, saturated aqueous sodium bicarbonate (3 mL) was added. The layers were separated, and the organic layer was washed with brine (5 mL). The aqueous layers were combined and back-extracted with dichloromethane (10 mL). The organic layers were combined, dried over anhydrous sodium sulfate and filtered. The solvent was removed under vacuum. The material was taken up in tetrahydrofuran (1 mL) and added to a solution of tert-butyl 4-hydroxypiperidine-1-carboxylate (300 mg) and sodium hydride (60%, 71.5 mg) that had been pre-stirred for 15 minutes in tetrahydrofuran (7 mL). The solution was stirred at room temperature overnight and quenched with a few drops of saturated aqueous ammonium chloride. The solvent was removed under vacuum. The residue was taken up in ethyl acetate (10 mL), washed with water (2 mL), washed with brine (2 mL), dried with anhydrous sodium sulfate, filtered and concentrated. The material was used without further purification. $^1$H NMR (500 MHz, dimethylsulfoxide-$d_6$) δ ppm 4.70 (d, 1H), 4.19 (q, 1H), 3.814-3.74 (m, 2H), 3.68-3.59 (m, 4H), 3.52-3.45 (m, 1H), 3.20 (s, 2H), 2.95 (m, 2H), 1.71-1.65 (m, 2H), 1.28-1.20 (m, 2H), 1.40 (s, 9H), 1.41 (m, 1H).

Example 10B (R)-4-((1,4-dioxan-2-yl)methoxy)piperidine

Example 10A (448 mg) was dissolved in dichloromethane (1 mL). Trifluoroacetic acid (2 mL) was added, and the solution was stirred at room temperature for 30 minutes. The solvent was removed under vacuum, and the material was carried on in the next step as the trifluoroacetic acid salt without purification.

Example 10C (R)-(2-(4-((1,4-dioxan-2-yl)methoxy)piperidin-1-yl)pyrimidin-4-yl)methanol (2-Chloropyrimidin-4-yl)methanol (170 mg), Example 10B (469 mg) and triethylamine (595 mg) were dissolved in acetonitrile (6.5 mL). The solution was heated to 80° C. for four hours. The solution was cooled, concentrated under vacuum and purified by flash column chromatography on silica gel using a gradient of 30-100% ethyl acetate in heptanes. $^1$H NMR (500 MHz, dimethylsulfoxide-$d_6$) δ ppm 8.70 (d, 1H), 6.67 (d, 1H), 5.36 (t, 1H), 4.70 (d, 1H), 4.34 (d, 2H), 4.26 (dt, 2H), 3.70 (m, 2H), 3.65-3.50 (m, 2H), 3.48-3.35 (m, 1H), 3.21 (m, 2H), 1.75 (m, 4H), 1.29 (m, 4H). MS (ESI) m/z 310.3 (M+H)$^+$.

Example 10D tert-butyl (7R,16R)-19,23-dichloro-10-{[2-(4-{[(2R)-1,4-dioxan-2-yl]methoxy}piperidin-1-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 10C for Example 7B in Example 7C. MS (ESI) m/z 1100.3 (M+H)$^+$.

Example 10E (7R,16R)-19,23-dichloro-10-{[2-(4-{[(2R)-1,4-dioxan-2-yl]methoxy}piperidin-1-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 10D for Example 7C in Example 7D. $^1$H NMR (500 MHz, dimethylsulfoxide-$d_6$) δ ppm 8.69 (bs, 1H), 8.31 (d, 1H), 7.22-7.15 (m, 2H), 7.15-7.08 (m, 2H), 6.79-6.64 (m, 4H), 6.13 (m, 1H), 5.88 (bs, 1H), 4.92 (m, 4H), 4.43 (m, 2H), 4.16 (m, 2H), 3.71 (m 2H), 3.65-3.58 (m, 2H), 3.57-3.52 (m, 2H), 3.47-3.42 (m, 2H), 2.93 (m, 1H), 2.68 (m, 4H), 2.47 (m, 4H), 2.40-2.28 (m, 4H), 2.17 (s, 3H), 2.00 (s, 3H), 1.92-1.90 (m, 4H), 1.88-1.78 (m, 2H), 1.43-1.32 (m, 2H). MS (ESI) m/z 1044.2 (M+H)$^+$.

Example 11

(7R,16R)-19,23-dichloro-10-({2-[1-({[(2S)-1,4-dioxan-2-yl]methoxy}methyl)cyclobutyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 11A 1-(((tert-butyldimethylsilyl)oxy)methyl)cyclobutanecarbonitrile 1-(Hydroxymethyl)cyclobutanecarbonitrile (2 g) was dissolved in dichloromethane (36 mL) and imidazole (2.45 g) and tert-butyldimethylchlorosilane (3.53 g) were added. The resulting mixture was stirred at room temperature for 4 hours. The mixture was concentrated onto silica gel and was purified by flash chromatography on a CombiFlash® Teledyne Isco system using a Teledyne Isco RediSep® Rf gold 80 g silica gel column (eluting with 0-15% ethyl acetate/heptanes) to afford the title compound. MS (APCI) m/z 226.5 (M+H)$^+$.

Example 11B 1-(((tert-butyldimethylsilyl)oxy)methyl)cyclobutanecarboximidamide A 2 M solution of trimethylaluminum in toluene (15.37 mL) was slowly added to a magnetically stirred suspension of ammonium chloride (1.645 g) in toluene (38.0 mL) at 0° C. After the addition, the ice water bath was removed and the mixture was stirred at room temperature for 2 hours until gas evolution had ceased. Example 11A (3.85 g) was added as a toluene (20 mL) solution and the mixture was stirred at 80° C. under nitrogen for 12 hours, cooled with an ice water bath, quenched carefully with 100 mL of methanol, and stirred at room temperature for 2 hours. The material was removed through filtration and washed with methanol. The combined filtrate was concentrated to afford the crude title compound. MS (APCI) m/z 243.4 (M+H)$^+$.

Example 11C 2-(1-(((tert-butyldimethylsilyl)oxy)methyl)cyclobutyl)-4-(dimethoxymethyl)pyrimidine Example 11B (4.12 g) and 4-(dimethylamino)-1,1-dimethoxybut-3-en-2-one (5.89 g) were taken up in ethanol (24 mL) and 21% ethanol solution of sodium ethoxide (33.1 g) was added which warmed the reaction mildly. The mixture was heated at 80° C. for 15 hours, and cooled back to room temperature. The mixture was concentrated, saturated aqueous sodium bicarbonate was added (150 mL) and the mixture was stirred for 2 minutes. The mixture was poured into a 250 mL separatory funnel and was extracted with three portions of dichloromethane. The organic layers were combined and the resulting solution was dried over anhydrous magnesium sulfate, filtered and concentrated onto silica gel. Purification by flash chromatography on a CombiFlash® Teledyne Isco system using a Teledyne Isco RediSep® Rf gold 40 g silica gel column (eluting with 5-80% ethyl acetate/heptanes) afforded the title compound. MS (APCI) m/z 353.4 (M+H)$^+$.

Example 11D (1-(4-(dimethoxymethyl)pyrimidin-2-yl)cyclobutyl)methanol

To a stirring mixture of Example 11C (11.3 g) in 100 mL of tetrahydrofuran was added 96 mL of 1 molar tetra n-butylammonium fluoride and the mixture was stirred at room temperature for 1 hours. The mixture was concentrated onto silica gel and purification by flash chromatography on a CombiFlash® Teledyne Isco system using a Teledyne Isco RediSep® Rf gold 220 g silica gel column (eluting with 30-100% ethyl acetate/heptanes) afforded the title compound. MS (APCI) m/z 239.4 (M+H)$^+$.

Example 11E (R)-(1,4-dioxan-2-yl)methyl methanesulfonate

A mixture of (S)-(1,4-dioxan-2-yl)methanol (500 mg) and triethylamine (1.7 mL) in 10 mL of dichloromethane was stirred at 0° C. and methanesulfonyl chloride (0.5 mL) was added dropwise. Upon completion of the addition, the cooling bath was removed and the mixture was stirred at room temperature for an hour. The mixture was concentrated onto silica gel and purification by flash chromatography on a CombiFlash® Teledyne Isco system using a Teledyne Isco RediSep® Rf gold 40 g silica gel column (eluting with 30-100% ethyl acetate/heptanes) afforded the title compound. $^1$H NMR (400 MHz, dimethylsulfoxide-d$_6$) δ ppm 4.24-4.13 (m, 2H), 3.81-3.71 (m, 3H), 3.67-3.56 (m, 2H), 3.51-3.42 (m, 1H), 3.33-3.27 (m, 1H), 3.19 (s, 3H).

Example 11F (S)-2-(1-(((1,4-dioxan-2-yl)methoxy)methyl)cyclobutyl)-4-(dimethoxymethyl)pyrimidine To a stirring solution of Example 11D (400 mg) and Example 11E (659 mg) in 16 mL of acetonitrile was slowly added sodium hydride (81 mg, 60% in mineral oil) and the mixture was stirred at 45° C. overnight. After cooling to room temperature, a few drops of saturated aqueous ammonium chloride were added and the mixture was concentrated onto silica gel. Purification by flash chromatography on a CombiFlash® Teledyne Isco system using a Teledyne Isco RediSep® Rf gold 40 g silica gel column (eluting with 10-100% ethyl acetate/heptanes) gave the title compound. MS (APCI) m/z 339.4 (M+H)$^+$.

Example 11G (S)-2-(1-(((1,4-dioxan-2-yl)methoxy)methyl)cyclobutyl)pyrimidine-4-carbaldehyde To a stirring mixture of Example 11F (480 mg) in tetrahydrofuran (9 mL) was added 6 molar aqueous HCl (8.5 mL) and the mixture was stirred at 55° C. for 5 hours. After cooling to room temperature, the mixture was poured into a separatory funnel containing saturated aqueous sodium bicarbonate. The mixture was extracted with five portions of dichloromethane, and the organic layers were combined and dried over anhydrous magnesium sulfate, filtered and concentrated onto silica gel. Purification by flash chromatography on a CombiFlash® Teledyne Isco system using a Teledyne Isco RediSep®. Rf gold 24 g silica gel column (eluting with 20-1(0% ethyl acetate/heptanes) afforded the title compound. MS (APCI) m/z 293.3 (M+H)$^+$.

Example 11H (S)-(2-(1-(((1,4-dioxan-2-yl)methoxy)methyl)cyclobutyl)pyrimidin-4-yl)methanol To Example 11G (315 mg) in 7 mL of tetrahydrofuran was added sodium borohydride (82 mg) in one portion followed by 2 mL of methanol. The mixture was stirred at room temperature for 30 minutes and quenched by careful addition of 5 mL of saturated aqueous ammonium chloride solution and stirred for an additional 15 minutes. The resulting mixture was poured into a separatory funnel containing 15 mL of water and was extracted with 3 portions of dichloromethane. The combined organic layer was dried over anhydrous magnesium sulfate, filtered and concentrated onto silica gel. Purification by flash chromatography on a CombiFlash® Teledyne Isco system using a Teledyne Isco RediSep®® Rf gold 24 g silica gel column (eluting with solvent A=2:1 ethyl acetate:ethanol; solvent B=heptane, 10-80% A to B) afforded the title compound. MS (APCI) m/z 295.3 (M+H)$^+$.

Example 11I tert-butyl (7R,16R)-19,23-dichloro-10-({2-[1-({[(2S)-1,4-dioxan-2-yl]methoxy}methyl)cyclobutyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 4 mL vial, equipped with stir bar, was charged with Example 11H (54.5 mg), Example 1Z (75 mg) and triphenylphosphine (51.0 mg). The vial was capped with a septa and evacuated and backfilled with nitrogen twice. Toluene (1 mL) was added and the mixture was cooled with an ice bath. To the stirring mixture, (E)-di-tert-butyl diazene-1,2-dicarboxylate (42.7 mg) was added in one portion. The vial was capped with a septa and the stirring mixture was evacuated and backfilled with nitrogen twice. The stirring continued at 0° C. for 10 minutes, the cooling bath was removed and the mixture was allowed to stir at room temperature overnight. The mixture was concentrated onto silica gel and purification by flash chromatography on a CombiFlash® Teledyne Isco system using a Teledyne Isco RediSep® Rf gold 12 g silica gel column (eluting with 0-20% methanol/dichloromethane) afforded the title compound. MS (APCI) m/z 1087.4 $(M+H)^+$.

Example 11J (7R,16R)-19,23-dichloro-10-({2-[1-({[(2S)-1,4-dioxan-2-yl]methoxy}methyl)cyclobutyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 11I (77 mg) in dichloromethane (0.75 mL) was added trifluoroacetic acid (0.75 mL) and the reaction mixture was stirred at room temperature for 5 hours and concentrated. The crude residue was redissolved into 2 mL of acetonitrile and purified directly by reverse phase prep LC using a Gilson 2020 system (Luna™, C-18, 250×50 mm column, Mobile phase A: 0.1% trifluoroacetic acid in water; B: acetonitrile; 5-75% B to A gradient at 75 mL/minute, 30 minute gradient) to afford the title compound as a trifluoroacetic acid salt. The material obtained was treated with saturated aqueous sodium bicarbonate and dichloromethane and poured into a separatory funnel. The mixture was partitioned between the two phases. The organic layer was removed and the aqueous layer was washed with two more portions of dichloromethane. The organic layers were combined, dried over anhydrous magnesium sulfate, filtered and concentrated to obtain the title compound. MS (APCI) m/z 1029.3 $(M+H)^+$. $^1$H NMR (400 MHz, dimethylsulfoxide-$d_6$) δ ppm 8.75 (d, 1H), 8.73 (s, 1H), 7.42 (d, 1H), 7.24-7.08 (m, 4H), 6.86 (d, 1H), 6.74 (dd, 1H), 6.24 (dd, 1H), 5.82 (d, 1H), 5.11 (q, 2H), 4.87 (m, 1H), 4.44 (d, 2H), 3.86 (s, 2H), 3.67-3.45 (m, 5H), 3.41-3.32 (m, 2H), 3.26 (dd, 1H), 3.16-3.05 (m, 1H), 3.01-2.90 (m, 1H), 2.77-2.60 (m, 2H), 2.57-2.36 (m, 11H), 2.24 (s, 3H), 2.18-2.06 (m, 2H), 2.04-1.89 (m, 7H), 1.87-1.69 (m, 1H).

Example 12

(7R,16R)-19,23-dichloro-10-({2-[3-({[(2S)-1,4-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid

Example 12A tert-butyl (S)-3-(((1,4-dioxan-2-yl)methoxy)methyl)azetidine-1-carboxylate tert-Butyl 3-(hydroxymethyl)azetidine-1-carboxylate (400 mg) was dissolved in N,N-dimethylformamide (10 mL) and cooled to 0° C. Sodium hydroxide (123 mg, 50%) was added and the reaction mixture was stirred at 0° C. for 1 hour. (S)-(1,4-dioxan-2-yl)methyl 4-methylbenzenesulfonate (873 mg) dissolved in N,N-dimethylformamide (10 mL) was added dropwise. The mixture was allowed to warm to ambient temperature and stirred for 1 hour at room temperature. The mixture was diluted with water and dichloromethane. The phases were separated and the organic phase was washed with water. The organic layer was dried over sodium sulfate, filtrated and concentrated. Purification of the residue was performed on a silica gel column (12 g, 0-30% methanol in dichloromethane). The pure fractions were combined and the solvents were removed under reduced pressure to provide the title compound. MS (ESI) m/z 232.1 $(M\text{-tert-Bu})^+$.

Example 12B (S)-3-(((1,4-dioxan-2-yl)methoxy)methyl)azetidine 2,2,2-trifluoroacetate Example 12A (178 mg) was dissolved in dichloromethane (10 mL) and trifluoroacetic acid (0.48 mL) was added. The mixture was stirred for 3 hours at room temperature. An aliquot was analyzed by LC/MS indicating complete conversion. The reaction mixture was concentrated at room temperature and co-distilled with three times dichloromethane to provide the crude title compound, which was directly used in the next step without further purification. $^1$H NMR (500 MHz, chloroform-d) δ ppm 4.54 (d, 1H), 4.39-4.31 (m, 2H), 4.19-4.13 (m, 1H), 4.09-4.04 (m, 1H), 3.95-3.76 (m, 5H), 3.71-3.63 (m, 2H), 3.61 (d, 1H), 3.54-3.46 (m, 2H). MS (ESI) m/z 188.2 $(M+H)^+$.

Example 12C (S)-(2-(3-(((1,4-dioxan-2-yl)methoxy)methyl)azetidin-1-yl)pyrimidin-4-yl)methanol (2-Chloropyrimidin-4-yl)methanol (50 mg). Example 12B (93 mg), and triethylamine (0.19 mL) were dissolved in dioxane (4 mL). The reaction mixture was heated in the microwave to 80° C. and stirred for 2 hours. The mixture was cooled and diluted with dichloromethane. The organic layer was washed with water, dried over sodium sulfate, and concentrated. Purification was performed on a silica gel column (12 g, 0-20% methanol in dichloromethane). The pure fractions were combined and the solvents were removed under reduced pressure to provide the title compound. $^1$H NMR (500 MHz, chloroform-d) δ ppm 8.23 (d, 1H), 6.44 (d, 1H), 4.57 (d, 2H), 4.23 (dd, 2H), 3.90 (dd, 2H), 3.81-3.68 (m, 8H), 3.63-3.59 (m, 1H), 3.51 (dd, 1H), 3.45 (dd, 1H), 3.41 (dd, 1H), 3.01-2.94 (m, 1H). MS (ESI) m/z 296.2 (M+H)$^+$.

Example 12D (S)-(2-(3-(((1,4-dioxan-2-yl)methoxy)methyl)azetidin-1-yl)pyrimidin-4-yl)methyl methanesulfonate Example 12C (0.03 g) and triethylamine (0.04 mL) were dissolved in dichloromethane (0.90 mL) and cooled to 0° C. by an ice-bath. Methanesulfonyl chloride (8.27 μL) was added and the reaction mixture was allowed to warm to ambient temperature and was stirred for 30 minutes at room temperature. Brine was added to the reaction mixture and the phases were separated. The aqueous phase was washed with dichloromethane, dried over sodium sulfate, filtered, and concentrated to yield the crude title compound, which was directly used in the next step. MS (ESI) m/z 374.1 (M+H)$^+$.

Example 12E tert-butyl (7R,16R)-19,23-dichloro-10-({2-[3-({[(2S)-1,4-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate Example 12D (33 mg), Example 1Z (40 mg), cesium carbonate (36 mg), and N,N-dimethylformamide (200 μL) were combined under an argon-atmosphere. The reaction mixture was stirred overnight at room temperature. To the reaction mixture was added dropwise aqueous sodium bicarbonate solution (5%) and dichloromethane. The phases were separated and the aqueous layer was extracted twice with dichloromethane. The combined organic phase was dried over sodium sulfate, filtered, and concentrated. Purification was performed on a silica gel column (4 g, 0-20% methanol in dichloromethane). The pure fractions were combined and the solvents were removed under reduced pressure to provide the title compound. MS (APCI) m/z 1087.4 (M+H)$^+$.

Example 12F (7R,16R)-19,23-dichloro-10-({2-[3-({[(2S)-1,4-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 12E (51 mg) was dissolved in dichloromethane (470 μL) and trifluoroacetic acid (470 μL) was added. The reaction mixture was stirred for 5 hours at room temperature. The reaction mixture was concentrated, dissolved in methanol, diluted with water, and freeze-dried. The crude material was purified by HPLC (Waters X-Bridge C8 19×150 mm 5 m column, gradient 5-100% acetonitrile+0.2% ammonium hydroxide in water+0.2% ammonium hydroxide) to provide the title compound. $^1$H NMR (500 MHz, dimethylsulfoxide-d$_6$) δ ppm 8.72 (s, 1H), 8.29 (d, 1H), 7.21-7.12 (m, 4H), 6.80-6.71 (m, 3H), 6.16 (b, 1H), 5.83 (b, 1H), 4.97-4.86 (m, 3H), 4.46-4.40 (m, 2H), 4.07 (t, 2H), 3.75-3.17 (m, 16H), 2.95-2.85 (m, 3H), 2.72-2.36 (m, 8H), 2.18 (s, 3H), 1.99 (s, 3H), 1.96 (s, 3H). MS (APCI) m/z 1030.3 (M+H)$^+$.

Example 13

(7R,16R)-19,23-dichloro-10-({2-[3-({[(2R)-14-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 13A tert-butyl (R)-3-(((1,4-dioxan-2-yl)methoxy)methyl)azetidine-1-carboxylate The title compound was prepared as described in Example 12A by substituting (S)-(1,4-dioxan-2-yl)methyl 4-methylbenzenesulfonate for (R)-(1,4-dioxan-2-yl)methyl 4-methylbenzenesulfonate. MS (ESI) m/z 232.1 (M-tert-Bu)$^+$.

Example 13B (R)-3-(((1,4-dioxan-2-yl)methoxy)methyl)azetidine 2,2,2-trifluoroacetate The title compound was prepared as described in Example 12B by substituting Example 13A for Example 12A. MS (ESI) m/z 188.1 (M+H)$^+$.

Example 13C ((R)-2-(3-(((1,4-dioxan-2-yl)methoxy)methyl)azetidin-1-yl)pyrimidin-4-yl)methanol The title compound was prepared as described in Example 12C by substituting Example 13B for Example 12B. $^1$H NMR (600 MHz, chloroform-d) δ ppm 8.24 (d, 1H), 6.44 (d, 1H), 4.57 (d, 2H), 4.23 (dd, 2H), 3.90 (dd, 2H), 3.81-3.67 (m, 8H), 3.61 (ddd, 1H), 3.53-3.49 (m, 1H), 3.45 (dd, 1H), 3.41 (dd, 1H), 3.01-2.95 (m, 1H). MS (ESI) m/z 296.4 (M+H)$^+$.

Example 13D (R)-(2-(3-(((1,4-dioxan-2-yl)methoxy)methyl)azetidin-1-yl)pyrimidin-4-yl)methyl methanesulfonate The title compound was prepared as described in Example 12D by substituting Example 13C for Example 12C. MS (ESI) m/z 374.4 (M+H)$^+$.

Example 13E tert-butyl (7R,16R)-19,23-dichloro-10-({2-[3-({[(2R)-1,4-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 12E by substituting Example 13D for Example 12D. MS (APCI) m/z 1086.4 (M+H)$^+$.

Example 13F (7R,16R)-19,23-dichloro-10-({2-[3-({[(2R)-1,4-dioxan-2-yl]methoxy}methyl)azetidin-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 13E (35 mg) was dissolved in dichloromethane (325 μL) and trifluoroacetic acid (325 μL) was added. The reaction mixture was stirred for 5 hours at room temperature. The reaction mixture was concentrated at room temperature. The residue was dissolved in methanol, diluted with water, and freeze-dried. The crude material was purified by HPLC (Waters X-Bridge C8 19×150 mm 5 μm column, gradient 5-100% acetonitrile+0.2% ammonium hydroxide in water+0.2% ammonium hydroxide) to provide the title compound. $^1$H NMR (500 MHz, dimethylsulfoxide-$d_6$) δ ppm 8.72 (s, 1H), 8.29 (d, 1H), 7.21-7.12 (m, 4H), 6.80-6.71 (m, 3H), 6.17 (b, 1H), 5.82 (b, 1H), 4.97-4.86 (m, 3H), 4.46-4.43 (m, 2H), 4.07 (t, 2H), 3.75-3.16 (m, 16H), 2.94-2.84 (m, 2H), 2.72-2.66 (m, 1H), 2.54-2.32 (m, 8H), 2.18 (s, 3H), 1.97 (s, 3H), 1.95 (s, 3H). MS (APCI) m/z 1030.3 (M+H)$^+$.

Example 14

(7R,16R)-19,23-dichloro-10-[(2-{(1r,4r)-4-[(1,3-dioxolan-4-yl)methoxy]cyclohexyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 14A 4-(((tert-butyldiphenylsilyl)oxa)methyl)-2-chloropyrimidine

To a solution of (2-chloropyrimidin-4-yl)methanol (3.8 g) and tert-butylchlorodiphenylsilane (7.23 g) in N,N-dimethylformamide (30 mL) was added imidazole (3.58 g). The mixture was stirred under nitrogen at room temperature overnight. The mixture was diluted with water (50 mL) and ethyl acetate (400 mL). The organic layer was separated, washed with water and brine and dried over sodium sulfate. Filtration and evaporation of the solvent gave crude product which was loaded on a RediSep® Gold 220 g column and eluted with 20% ethyl acetate in heptane to give the title compound. MS (ESI) m/z 383.2 (M+H)$^+$.

Example 14B 4-(((tert-butyldiphenylsilyl)ox)methyl)-2-(1,4-dioxaspiro[4.5]dec-7-en-8-yl)pyrimidine To a solution of 4,4,5,5-tetramethyl-2-(1,4-dioxaspiro[4.5]dec-7-en-8-yl)-1,3,2-dioxaborolane (7.30 g) and Example 14A (10.5 g) in tetrahydrofuran (120 mL) was added Pd(Ph$_3$P)$_4$ (tetrakis(triphenylphosphine)palladium(0), 1.58 g) and aqueous saturated NaHCO$_3$ (60 mL). The mixture was stirred under nitrogen at 70° C. overnight. The mixture was concentrated under vacuum and the residue was diluted with water (120 mL) and ethyl acetate (600 mL). The organic layer was separated, washed with water and brine, dried over sodium sulfate, and filtered. Evaporation of the solvent gave the crude product which was loaded on a RediSep® Gold 220 g column and eluted with 20% ethyl acetate in heptane to give 11.8 g product. MS (ESI) m/z 487.2 (M+H)$^+$.

Example 14C 4-(((tert-butyldiphenylsilyl)oxy)methyl)-2-(1,4-dioxaspiro[4.5]decan-8-yl)pyrimidine To a solution of Example 14B (10 g) in tetrahydrofuran (120 mL) was added Pd/C (10%, 1.5 g). The mixture was stirred under hydrogen (25 psi) at room temperature for 4 hours. The mixture was filtered and concentrated under vacuum to give the title compound. MS (ESI) m/z 489.2 (M+H)$^+$.

Example 14D 4-(4-(((tert-butyldiphenylsilyl)oxy)methyl)pyrimidin-2-yl)cyclohexanone To a solution of Example 14C (10 g) in acetone (70 mL) and water (30 mL) was added pyridinium toluenesulfonate (1.5 g). The mixture was stirred at reflux for 16 hours. The mixture was concentrated under vacuum and the residue was diluted with water (120 mL) and ethyl acetate (600 mL). The organic layer was separated, washed with water and brine and dried over sodium sulfate. Filtration and evaporation of the solvent gave the crude product which was loaded on a RediSep® Gold 220 g column and eluted with 20% ethyl acetate in heptane to give the title compound. MS (ESI) min 445.3 (M+H)$^+$.

Example 14E (1r,4r)-4-(4-(((tert-butyldiphenylsilyl)oxy)methyl)pyrimidin-2-yl)cyclohexanol To a solution of Example 14D (2.2 g) in tetrahydrofuran (20 mL) was added sodium borohydride (0.56 g). The mixture was stirred at room temperature for 3 hours. The mixture was diluted with water (20 mL) and ethyl acetate (300 mL). The organic layer was separated and washed with water and brine and dried over sodium sulfate. Filtration and evaporation of the solvent gave crude product which was loaded on a RediSep® Gold 120 g column and eluted with 40% ethyl acetate in heptane to give the title compound. MS (ESI) m/z 447.3 (M+H)$^+$.

Example 14F 2-((1r,4r)-4-(allyloxy)cyclohexyl)-4-(((tert-butyldiphenylsilyl)oxy)methyl)pyrimidine To a suspension of NaH (60% oil dispersion, 660 mg) in tetrahydrofuran (20 mL), a solution of Example 14E (600 mg) in tetrahydrofuran (5 mL) was added dropwise at room temperature and the resulting suspension was stirred at room temperature for 1 hour under nitrogen. To the mixture, allylbromide (406 mg) was added. The mixture was stirred for 4 hours at room temperature. The mixture was quenched with aqueous ammonium chloride, extracted with ethyl acetate (300 mL), washed with water and brine, and dried over sodium sulfate. Filtration and evaporation of the solvent gave the crude product which was loaded on a RediSep® Gold 40 g column and eluted with 20% ethyl acetate in heptane to give the title compound. MS (ESI) m/z 487.0 (M+H)+.

Example 14G 3-(((1r,4r)-4-(4-(((tert-butyldiphenylsilyl)oxy) methyl)pyrimidin-2-yl)cyclohexyl)oxy)propane-1,2-diol To a solution of Example 14F (340 mg) in tert-butanol (5 mL) and water (5 mL) at 0° C. was added AD-Mix-alpha (1.4 g). The resulting suspension was stirred at 0° C. for 4 hours, and at room temperature overnight. The mixture was quenched with sodium sulfite and extracted with ethyl acetate (three times, 100 mL). The combined organic phases were washed with brine and dried over sodium sulfate. Filtration and evaporation of the solvent gave the title compound. MS (ESI) m/z 521.2 (M+H)+.

Example 14H 2-((1r,4r)-4-((1,3-dioxolan-4-yl)methoxy)cyclohexyl)-4-(((tert-butyldiphenylsilyl)oxy)methyl)pyrimidine To a solution of Example 14G (460 mg) in dichloromethane (10 mL) was added dimethoxymethane (672 mg) and para-toluenesulfonic acid hydrate (168 mg). The resulting mixture was stirred at room temperature for 4 days. The mixture was diluted with ethyl acetate (300 mL), washed with water and brine, and dried over sodium sulfate. Filtration and evaporation of the solvent gave the crude product which was loaded on a RediSep® Gold 40 g column and eluted with 20% ethyl acetate in heptane to give the title compound. MS (ESI) m/z 533.2 (M+H)+.

Example 14I (2-((1r,4r)-4-((1,3-dioxolan-4-yl)methoxy)cyclohexyl)pyrimidin-4-yl)methanol To a solution of Example 14H (50 mg) in tetrahydrofuran (2 mL) was added cesium fluoride (120 mg) and methanol (1 mL). The mixture was stirred at room temperature overnight. The solvent was evaporated under vacuum and the residue was triturated with heptane (30 mL) to get rid of the non-polar material. The residue was triturated with ethyl acetate (30 mL). Evaporation of the solvent gave the title compound. MS (ESI) m/z 295.3 (M+H)+.

Example 14J tert-butyl (7R,16R)-19,23-dichloro-10-[2-{(1r,4r)-4-[(1,3-dioxolan-4-yl)methoxy]cyclohexyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To a 4 mL vial containing Example 1Z (50 mg), Example 14I (28 mg) and triphenylphosphine (52.5 mg) was added toluene (500 µL) and tetrahydrofuran (500 µL) followed by (E)-N1,N1,N2,N2-tetramethyldiazene-1,2-dicarboxamide (34.5 mg). The mixture was purged with argon for 3 minutes and was stirred at 50° C. for 4 hours. The mixture was diluted with dichloromethane (10 mL), loaded on a 40 g column, and eluted with 30% ethyl acetate in heptane (1 L) followed by 5% (7N ammonia in methanol) in dichloromethane (1 L) to give the title compound. MS (ESI) m/z 1085.5 (M+H)+.

Example 14K (7R,16R)-19,23-dichloro-10-[(2-{(1r,4r)-4-[(1,3-dioxolan-4-yl)methoxy]cyclohexyl}pyrimidin-4-yl) methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 14J (89 mg) in dichloromethane (3 mL) was added trifluoroacetic acid (3 mL). The mixture was stirred at room temperature for 6 hours. The mixture was concentrated under vacuum and the residue was dissolved in N,N-dimethylformamide (3 mL) and loaded on HPLC (Gilson 2020 system. Luna™ C-18, 250×50 mm column, mobile phase A: 0.1% trifluoroacetic acid in water; B: acetonitrile; 20-75% B to A gradient at 70 mL/minute in 35 minute) to afford the title compound. $^1$H NMR (400 MHz, dimethylsulfoxide-$d_6$) δ ppm 8.69 (s, 1H), 8.67 (d, 1H), 7.39 (d, 1H), 7.13 (dtt, 6H), 6.80 (d, 1H), 6.70 (dd, 1H), 6.18 (dd, 1H), 5.78 (d, 1H), 5.05 (q, 3H), 4.85 (s, 3H), 4.75 (s, 1H), 4.40 (d, 3H), 4.07 (p, 1H), 3.92-3.84 (m, 1H), 2.91 (dd, 1H), 2.79-2.58 (m, 4H), 2.18 (s, 4H), 2.08-2.01 (m, 3H), 1.57 (qd, 3H), 1.25 (qd, 3H). MS (ESI) m/z 1029.3 (M+H)+.

Example 15

(7R,16R)-19,23-dichloro-10-[(2-{(1s,4s)-4-[(1,4-dioxan-2-yl)methoxy]cyclohexyl}pyrimidin-4-yl) methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 15A 2-((1r,4r)-4-((1,4-dioxan-2-yl)methoxy)cyclohexyl)-4-(((tert-butyldimethylsilyl)oxy)methyl)pyrimidine To a stirred solution of Example 14G (740 mg) in dichloromethane (10 mL) was added NaH (102 mg) at 0° C. The mixture was stirred for 10 minutes. A solution of Example 9B (400 mg) in dichloromethane (5 mL) was added to the mixture and the mixture was stirred at room temperature for 3 hours. The mixture was quenched with aqueous ammonium chloride, extracted with ethyl acetate (twice, 200 mL), washed with water and brine, and dried over sodium sulfate. Filtration and evaporation of the solvent gave crude product which was purified by column chromatography, eluting with 20% ethyl acetate in heptane, to give the title compound. MS (ESI) m/z 547.3 (M+H)+.

Example 15B (2-((1r,4r)-4-((1,4-dioxan-2-yl)methoxy)cyclohexyl) pyrimidin-4-yl)methanol To a solution of Example 15A (430 mg) in tetrahydrofuran (5 mL) was added methanol (5 mL) and cesium fluoride (0.6 g). The mixture was stirred at room temperature overnight. The solvents were evaporated under vacuum and the residue was first triturated with 50 mL of heptane and with ethyl acetate (3×30 mL). The combined ethyl acetate extracts were concentrated under vacuum to give crude product which was loaded on a RediSep® Gold 220 g column and eluted with 5% methanol in dichloromethane (500 mL) to give the title compound. MS (ESI) m/z 309.2 (M+H)$^+$.

Example 15C tert-butyl (7R,16R)-19,23-dichloro-10-[(2-{(1s,4s)-4-[(1,4-dioxan-2-yl)methoxy]cyclohexyl}pyrimidin-4-yl)methoxy]-1-(4-fluorophenyl)-20,22-dimethyl-6-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To a 4 mL vial containing Example 1Z (50 mg). Example 15B (28 mg) and triphenylphosphine (52.5 mg) was added toluene (500 μL) and tetrahydrofuran (500 μL) followed by (E)-N$^1$,N$^1$,N$^2$,N$^2$-tetramethyldiazene-1,2-dicarboxamide (34.5 mg). The mixture was purged with argon for 3 minutes and was stirred at 50° C. for 4 hours. The mixture was diluted with dichloromethane (10 mL) and loaded on a 40 g column and eluted with 30% ethyl acetate in heptane (1 L) followed by 5% (7N ammonia in methanol) in dichloromethane (1 L) to give the title compound. MS (ESI) m/z 1099.5 (M+H)$^+$.

Example 15D (7R,16R)-19,23-dichloro-10-[(2-{(1s,4s)-4-[(1,4-dioxan-2-yl)methoxy]cyclohexyl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 15C (82 mg) in dichloromethane (3 mL) was added trifluoroacetic acid (3 mL). The mixture was stirred at room temperature for 6 hours. The mixture was concentrated under vacuum and the residue was dissolved in N,N-dimethylformamide (3 mL) and loaded on a HPLC (Gilson 2020 system, Luna™ C-18, 250×50 mm column, mobile phase A: 0.1% trifluoroacetic acid in water; B: acetonitrile; 20-75% B to A gradient at 70 mL/minute in 35 minutes) to give the title compound. $^1$H NMR (400 MHz, dimethylsulfoxide-d$_6$) δ ppm 8.69-8.59 (m, 2H), 7.35 (d, 1H), 7.20-7.01 (m, 4H), 6.76 (d, 1H), 6.66 (dd, 1H), 6.12 (dd, 1H), 5.75 (d, 1H), 5.02 (q, 2H), 4.88-4.76 (m, 1H), 4.37 (d, 2H), 3.69-3.62 (m, 2H), 3.52 (dddd, 4H), 2.93-2.80 (m, 1H), 2.77-2.57 (m, 2H), 2.36 (d, 4H), 2.13 (s, 3H), 1.98 (dd, 2H), 1.52 (qd, 2H), 1.29-1.08 (m, 2H). MS (ESI) m/z 1043.5 (M+H)$^+$.

Example 16

(7R,16R)-19,23-dichloro-10-{[6-(4-{[(2R)-1,4-dioxan-2-yl]methoxy}phenyl)pyrazin-2-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 16A (R)-2-(4-((1,4-dioxan-2-yl)methoxy)phenyl)-4,4,5,5-tetramethyl-1,3,2-dioxaborolane To (4-(4,4,5,5-tetramethyl-1,3,2-dioxaborolan-2-yl)phenol (418 mg) and (R)-(1,4-dioxan-2-yl)methyl 4-methylbenzenesulfonate (724 mg) dissolved in dimethylformamide (6.3 mL) was added cesium carbonate (1.24 g) and the reaction mixture was stirred for 90 minutes at ambient temperature and then for 5 hours at 80° C. To the reaction mixture was added aqueous ammonium hydrochloride solution (5 mL) and the aqueous phase was extracted twice with ethyl acetate. The organic phase was washed twice with water, once with brine, dried over MgSO$_4$, filtered and concentrated in vacuo. The residue was purified by normal phase MPLC on a Teledyne-Isco-Combiflash® system (eluting with 0-30% ethyl acetate in n-heptane) to give the title compound. MS (APCI) m/z 321.2 (M+H)$^+$.

Example 16B (R)-(6-(4-((1,4-dioxan-2-yl)methoxy)phenyl)pyrazin-2-yl)methanol

A mixture of (6-chloropyrazin-2-yl)methanol (52.6 mg), Example 16A (106 mg), tris(dibenzylideneacetone)dipalladium(0) (3 mg), (1S,3R,5R,7S)-1,3,5,7-tetramethyl-8-phenyl-2,4,6-trioxa-8 phosphaadamantane (2.9 mg) and tribasic potassium phosphate (141 mg) were purged with argon for 30 minutes. A solution of tetrahydrofuran (1.25 mL) and water (0.3 mL) was degassed and added. The reaction mixture was stirred in a Biotage® microwave unit for 8 hours at 65° C. To the reaction mixture was added ethyl acetate and the mixture was filtrated via a pad of diatomaceous earth. To the filtrate was added ethyl acetate and water. The aqueous phase was extracted twice with ethyl acetate. The combined organic extracts were washed with brine and then dried over MgSO$_4$, filtered, and subsequently concentrated in vacuo. The residue was purified by normal phase MPLC on a Teledyne-Isco-Combiflash® system (eluting with 40-100% ethyl acetate in heptane) to afford the title compound. MS (APCI) m/z 303.2 (M+H)$^+$.

Example 16C tert-butyl (7R,16R)-19,23-dichloro-10-{[6-(4-{[(2R)-1,4-dioxan-2-yl]methoxy}phenyl)pyrazin-2-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 4 mL vial, equipped with stir bar, was charged with Example 1Z (40 mg). Example 16B (17.9 mg), triphenylphosphine (25.9 mg) and tetramethlylazodicarboxamide (17 mg) and the mixture was purged for 15 minutes with argon. A solution of tetrahydrofuran (0.5 mL) and toluene (0.5 mL) was added and the reaction mixture was stirred for 48 hours at room temperature. The material in the reaction mixture were filtered off and to the organic phase was added ethyl acetate. The organic phase was washed with water and brine solution. The organic phase was dried with sodium sulfate, filtered, and subsequently concentrated in vacuo. The residue was purified by normal phase MPLC on a Teledyne-Isco-Combiflash® system (eluting with 10-35% ethanol in ethyl acetate) to afford the title compound. MS (APCI) m/z 1093.4 (M+H)+.

Example 16D (7R,16R)-19,23-dichloro-10-{[6-(4-{[(2R)-1,4-di-oxan-2-yl]methoxy}phenyl)pyrazin-2-yl]methoxy}-1-(4-fluorophenyl)-20,22-dimethyl-16-[(4-methyl-piperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 16C (35 mg) in dichloromethane (250 μL) was added trifluoroacetic acid (99 μL). The reaction mixture was stirred overnight at ambient temperature. The reaction mixture was then concentrated in vacuo. The residue was dissolved in dichloromethane and saturated aqueous NaHCO₃-solution was added. The aqueous phase was extracted twice with dichloromethane. The combined organic phases were dried via DryDisk® and concentrated in vacuo. The residue was purified by HPLC (Waters X-Bridge C8 19×150 mm 5 μm column, gradient 5-100% acetonitrile+0.2% ammonium hydroxide in water+0.2% ammonium hydroxide) to provide the title compound. $^1$H NMR (600 MHz, dimethylsulfoxide-d₆) δ ppm 9.15 (s, 1H), 8.73 (s, 1H), 8.64 (s, 1H), 8.12 (m, 2H), 7.20 (m, 2H), 7.13 (m, 2H), 7.09 (m, 2H), 6.95 (d, 1H), 6.76 (m, 1H), 6.20 (m, 1H), 5.80 (d, 1H), 5.27 (d, 1H), 5.25 (d, 1H), 4.86 (m, 1H), 4.45 (m, 2H), 4.04 (m, 2H), 3.89 (m, 1H), 3.84 (m, 1H) 3.77 (m, 1H), 3.70-3.60 (m, 3H), 3.51 (m, 1H), 3.42 (m, 1H), 2.95 (m, 1H), 2.66 (m, 2H), 2.55-2.25 (m, 8H), 2.16 (s, 3H), 1.97 (s, 3H), 1.95 (s, 3H). MS (ESI) m/z 1037.3 (M+H)+.

Example 17

(7R,16R)-19,23-dichloro-1-cyclohexyl-10-{[2-(4-{[(2S)-1,4-dioxan-2-yl]methoxy}phenyl)pyrimidin-4-yl]methoxy}-20,22-dimethyl-16-[(4-methylpiper-azin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 17A 4-chloro-5-(3,5-dichloro-4-methoxy-2,6-dimethyl-phenyl)thieno[2,3-d]pyrimidine To a suspension of Example 1E (4 g) in acetonitrile (50 mL) was added N-chlorosuccinimide (3.86 g) and tetrafluoroboric acid diethyl ether complex (4.68 g). The reaction mixture was stirred at 15° C. under nitrogen for 16 hours. The reaction mixture was diluted with water (30 mL) and extracted three times with ethyl acetate (200 mL). The organic layer was dried over Na₂SO₄, filtered and concentrated. The residue was purified by column chromatography on silica gel (petroleum ether:ethyl acetate from 200:1 to 20:1) to provide the title compound. $^1$H NMR (400 MHz, dimethylsulfoxide-d₆) δ ppm 9.01 (s, 1H), 8.02 (s, 1H), 3.88 (s, 3H), 2.01 (s, 6H).

Example 17B 6-bromo-4-chloro-5-(3,5-dichloro-4-methoxy-2,6-dimethylphenyl)thieno[2,3-d]pyrimidine To a solution of Example 17A (3.0 g) in tetrahydrofuran (50 mL) cooled to −78° C., was added lithium diisopropylamide (2M in tetrahydrofuran/heptane/ethylbenzene, 6.02 mL) and the mixture was stirred at −78° C. for 90 minutes. 1,2-Dibromotetrachloroethane (3.14 g) was added in three portions over 10 minutes and stirring was continued at −78° C. for 1 hour. The mixture was allowed to warm to −30° C., water (60 mL) was added, and the mixture was extracted twice with ethyl acetate (40 mL). The combined organic extracts washed with brine, dried over magnesium sulfate, filtered and concentrated. Purification by chromatography on silica gel using an ISCO CombiFlash® Companion MPLC (10 g Chromabond® column, eluting with 0-20% heptane/ethyl acetate) provided the title compound. $^1$H NMR (600 MHz, dimethylsulfoxide-d₆) δ ppm 10.22 (bs, 1H), 9.00 (s, 1H), 1.96 (s, 6H). MS (ESI) m/z 450.95 (M+H)+.

Example 17C 4-(6-bromo-4-chlorothieno[2,3-d]pyrimidin-5-yl)-2,6-dichloro-3,5-dimethylphenol To a solution of Example 17B (4.35 g) in 1,2-dichloroethane (60 mL) at 15° C. was added AlCl₃ (3.84 g) in three portions over 5 minutes, and the mixture was stirred for 10 minutes at ambient temperature. Boron trichloride (1 M in dichloromethane-24.03 mL) was added dropwise over 5 minutes, and the mixture was stirred for 2 hours. The mixture was allowed to warm to 5° C., and water (50 mL) was added. The mixture was extracted twice with dichloromethane (40 mL), and the combined organic extracts were washed twice with HCl (1 M aqueous solution-30 mL), dried over magnesium sulfate, filtered, and concentrated to provide the title compound. MS (ESI) m/z 436.8 (M+H)+.

Example 17D (R)-5-(4-((1-(allyloxy)-3-(bis(4-methoxyphenyl) (phenyl)methoxy)propan-2-yl)oxy)-3,5-dichloro-2,6-dimethylphenyl)-6-bromo-4-chlorothieno[2,3-d] pyrimidine The title compound was prepared as described in Example 1L by substituting Example 17C for Example 1L. $^1$H NMR (400 MHz, chloroform-d) δ ppm 8.85 (s, 1H), 7.47-7.41 (m, 2H), 7.36-7.30 (m, 5H), 7.30-7.24 (m, 3H), 7.23-7.15 (m, 1H), 5.82 (ddt, 1H), 5.19 (dq, 1H), 5.11 (dq, 1H), 4.74 (p, 1H), 3.97 (dt, 2H), 3.86-3.81 (m, 2H), 3.79 (s, 6H), 3.59-3.49 (m, 2H), 2.01 (s, 3H), 2.01 (s, 3H). MS (ESI) m/z 877.0 [M+H]+.

Example 17E (R)-tert-butyl 2-((5-(4-(((R)-1-(allyloxy))-3-(bis(4-methoxyphenyl)(phenyl)methoxy)propan-2-yl)oxy)-3,5-dichloro-2,6-dimethylphenyl)-6-bromothieno[2, 3-d]pyrimidin-4-yl)oxy)-3-(2-(benzyloxy)-5-((tert-butyldimethylsilyl)oxy)phenyl)propanoate The title compound was prepared as described in Example 1R by substituting Example 17D for Example 1L. $^1$H NMR (501 MHz, chloroform-d) δ ppm 8.51 (s, 1H), 7.46-7.39 (m, 2H), 7.39-7.32 (m, 2H), 7.35-7.28 (m, 4H), 7.28-7.22 (m, 2H), 7.22-7.15 (m, 1H), 6.83-6.75 (m, 4H), 6.69 (d, 1H), 6.60 (dd, 1H), 6.40 (d, 1H), 5.77 (ddt, 1H), 5.39 (t, 1H), 5.13 (dq, 1H), 5.07 (dq, 1H), 4.98 (d, 1H), 4.94 (d, 1H), 4.60 (p, 1H), 3.90 (ddt, 2H), 3.78 (s, 6H), 3.83-3.72 (m, 2H), 3.59-3.50 (m, 2H), 2.67 (d 2H), 2.13 (s, 3H), 1.93 (s, 3H), 1.31 (s, 1H), 1.35-1.23 (m, 1H), 1.28 (s, 2H), 1.26 (s, 9H), 0.93 (s, 9H), 0.10 (s, 3H), 0.09 (s, 3H). MS (ESI) m/z 1275 [M+H]+.

Example 17F (R)-tert-butyl 2-((5-(4-(((S)-1-(allyloxy)-3-hydroxy-propan-2-yl)oxy)-3,5-dichloro-2,6-dimethylphenyl)-6-bromothieno[2,3-d]pyrimidin-4-yl)oxy)-3-(2-(benzyloxy)-5-((tert-butyldimethylsilyl)oxy)phenyl) propanoate The title compound was prepared as described in Example 1S substituting Example 17E for Example 1R. $^1$H NMR (400 MHz, chloroform-d) δ ppm 8.47 (d, 1H), 7.39-7.31 (m, 2H), 7.31-7.23 (m, 2H), 7.27-7.17 (m, 1H), 6.68 (d, 1H), 6.57 (dd, 1H), 6.35 (d, 1H), 5.78 (ddt, 1H), 5.39 (t, 1H), 5.16 (dt, 1H), 5.08 (dd, 1H), 4.96 (d, 1H), 4.92 (d, 1H), 4.53-4.44 (m, 1H), 3.91 (dddd, 3H), 3.81 (ddd, 1H), 3.79-3.70 (m, 2H), 2.66 (dd, 1H), 2.58 (dd, 1H), 2.31 (dd, 1H), 2.09 (s, 3H), 1.91 (s, 3H), 1.22 (s, 9H), 0.88 (s, 9H), 0.06 (s, 3H), 0.05 (s, 3H). MS (DCI) m/z 973.2 [M+H]+.

Example 17G (R)-tert-butyl 2-((5-(4-(((R)-1-(allyloxy)-3-(tosyloxy)propan-2-yl)oxy)-3,5-dichloro-2,6-dimethyl-phenyl)-6-bromothieno[2,3-d]pyrimidin-4-yl)oxy)-3-(2-(benzyloxy)-5-((tert-butyldimethylsilyl)oxy) phenyl)propanoate The title compound was prepared as described in Example 1T substituting Example 17F for Example 1S. $^1$H NMR (400 MHz, chloroform-di) δ ppm 8.46 (s, 1H), 7.77-7.68 (m, 2H), 7.36-7.28 (m, 2H), 7.28-7.17 (m, 5H), 6.66 (d, 1H), 6.56 (dd, 1H), 6.34 (d, 1H), 5.75-5.61 (m, 1H), 5.35 (t, 1H), 5.13-5.00 (m, 2H), 4.95 (d, 1H), 4.91 (d, 1H), 4.51 (p, 1H), 4.41 (dd, 1H), 4.33 (dd, 1H), 3.87-3.73 (m, 2H), 3.66 (dd, 1H), 3.61 (dd, 1H), 2.64 (dd, 1H) 2.57 (dd, 1H), 2.38 (s, 3H), 2.06 (s, 3H), 1.87 (s, 3H), 1.22 (s, 9H), 0.88 (s, 9H), 0.06 (s, 3H). MS (ESI) m/z 1127.3 [M+H]+.

Example 17H (R)-tert-butyl 2-((5-(4-(((R)-1-(allyloxy)-3-(tosyloxy)propan-2-yl)oxy)-3,5-dichloro-2,6-dimethyl-phenyl)-6-bromothieno[2,3-d]pyrimidin-4-yl)oxy)-3-(2-(benzyloxy)-5-hydroxyphenyl)propanoate The title compound was prepared as described in Example 1U substituting Example 17G for Example 1T. $^1$H NMR (501 MHz, chloroform-d) δ ppm 8.51 (s, 1H), 7.82-7.75 (m, 2H), 7.44-7.38 (m, 2H), 7.37-7.29 (m, 4H), 7.32-7.25 (m, 1H), 6.73 (d, 1H), 6.64 (dd, 1H), 5.96 (d, 1H), 5.76 (ddt, 1H), 5.52 (dd, 1H), 5.16 (dq, 1H), 5.12 (dt, 1H), 5.01 (s, 1H), 4.99 (s, 2H), 4.69-4.61 (m, 1H), 4.48 (dd, 1H), 4.41 (dd, 1H), 3.97-3.82 (m, 2H), 3.78 (dd, 1H), 3.74 (dd, 1H), 2.99 (dd, 1H), 2.43 (s, 3f), 2.39 (dd, 1H), 2.18 (s, 3H), 1.97 (s, 3H), 1.31 (s, 9H). MS (ESI) m/z 1112.8 [M+H]+.

Example 17I tert-butyl (7R,16R)-10-(benzyloxy)-1-bromo-19,23-dichloro-20,22-dimethyl-16-{[(prop-2-en-1-yl)oxy] methyl}-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 1V substituting Example 17H for Example 1U. $^1$H NMR (400 MHz, chloroform-d) ppm 8.59 (s, 1H), 7.47-7.40 (m, 2H), 7.42-7.34 (m, 2H), 7.37-7.28 (m, 1H), 6.80-6.70 (m, 2H), 6.03-5.88 (m, 2H), 5.82 (d, 1H), 5.35 (dq, 1H), 5.24 (dq, 1H), 5.09-5.01 (m, 1H), 5.04-4.94 (m, 2H), 4.63 (dd, 1H), 4.35 (dd, 1H), 4.23-4.07 (m, 2H), 3.91 (dd, 1H), 3.82 (dd, 1H), 3.48 (dd, 1H), 2.91 (dd, 1H), 2.19 (s, 3H), 1.98 (s, 3H), 1.20 (s, 9H). MS (ESI) m/z 841.1 [M+H]+.

Example 17J tert-butyl (7R,16R)-10-(benzyloxy)-1-bromo-19,23-dichloro-16-(hydroxymethyl)-20,22-dimethyl-7,8,15,16-tetrahydro-18,21-etheno-9,13-(metheno)-6,14,17-trioxa-2-thia-3,5-diazacyclononadeca[1,2,3-cd] indene-7-carboxylate The title compound was prepared as described in Example 1W substituting Example 17I for Example 1V. $^1$H NMR (400 MHz, chloroform-d) δ ppm 8.57 (s, 1H), 7.46-7.40 (m, 2H), 7.37 (ddd, 2H), 7.35-7.26 (m, 1H), 6.75 (d, 1H), 6.71 (dd, 1H), 5.86 (dd, 1H), 5.82 (d, 1H), 5.12 (dddd, 1H), 5.01 (d, 1H), 4.97 (d, 1H), 4.61 (dd, 1H), 4.23 (dd, 1H), 4.06 (ddd, 1H), 3.93 (ddd, 1H), 3.35 (dd, 1H), 2.98 (dd, 1H), 2.34 (dd, 1H), 2.21 (s, 3H), 1.95 (s, 3H), 1.22 (s, 9H). MS (ESI) m/z 801.0 [M+H]+.

Example 17K tert-butyl (7R,16S)-10-(benzyloxy)-1-bromo-19,23-dichloro-20,22-dimethyl-16-{[(4-methylbenzene-1-sulfonyl)oxy]methyl}-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 1X substituting Example 17J for Example 1W. $^1$H NMR (501 MHz, Chloroform-d) δ 8.57 (s, 1H), 7.89-7.83 (m, 2H), 7.45-7.40 (m, 2H), 7.40-7.33 (m, 4H), 7.35-7.28 (m, 1H), 6.76 (d, 1H), 6.69 (dd 1H), 5.86 (dd, 1H), 5.77 (d, 1H), 5.09-4.98 (m, 2H), 4.98 (d, 1H), 4.52 (dd, 1H), 4.43 (dd, 1H), 4.37 (dd, 1H), 4.22 (dd, 1H), 3.38 (dd, 1H), 2.93 (dd, 1H), 2.45 (s, 3H), 2.17 (s, 3H), 1.92 (s, 3H), 1.20 (s, 9H). MS (ESI) m/z 955.0 [M+H]+.

Example 17L tert-butyl (7R,16S)-10-(benzyloxy)-1-bromo-19,23-dichloro-20,22-dimethyl-16-{[(4-methylbenzene-1-sulfonyl)oxy]methyl}-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 1Y substituting Example 17K for Example 1X. $^1$H NMR (400 MHz, dimethylsulfoxide-d$_6$) δ ppm 8.68 (s, 1H), 7.41-7.35 (m, 2H), 7.35-7.28 (m, 2H), 7.31-7.22 (m, 1H), 6.87 (d, 1H), 6.79 (dd, 1H), 5.97 (dd, 1H), 5.59 (d, 1H), 5.01 (d, 1H), 4.93 (d, 1H), 4.70 (tt, 1H), 4.51-4.38 (m, 2H), 3.58-3.49 (m, 1H), 2.78-2.65 (m, 1H), 2.66 (d, 2H), 2.41 (s, 4H), 2.28 (s, 4H), 2.11 (s, 3H), 1.98 (s, 3H), 1.93 (s, 3H), 1.03 (s, 9H). MS (ESI) m/z 883.4 [M+H]$^+$.

Example 17M tert-butyl (7R,16R)-19,23-dichloro-1-(cyclohex-1-en-1-yl)-10-hydroxy-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate Example 17L (400 mg), 1,1'-bis(diphenylphosphino)ferrocene-palladium(II)dichloride dichloromethane complex (35.4 mg), I-cyclohexen-yl-boronic acid pinacol ester (160 mg), and cesium carbonate were combined under an argon atmosphere in dioxane/water (degassed, 4 mL/9 mL). The reaction mixture was heated to 90° C. and stirred for 45 minutes. The reaction mixture was partitioned between water and ethyl acetate. The aqueous phase was extracted with ethyl acetate twice. The combined organic layer was washed with brine, dried over anhydrous magnesium sulfate, filtrated and concentrated. The residue was purified on a silica gel column (12 g, 0-10% methanol in dichloromethane). The desired fractions were combined and the solvents were removed under reduced pressure to provide the title compound. MS (ESI) m/z 885.3 (M+H)$^+$.

Example 17N tert-butyl (7R,16R)-19,23-dichloro-1-cyclohexyl-10-hydroxy-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 1Z substituting Example 17M for Example 1Y. $^1$H NMR (600 MHz, dimethylsulfoxide-d$_6$) δ ppm 9.06 (s, 1H), 8.65 (s, 1H), 6.70 (dd, 1H), 6.64 (d, 1H), 5.94 (dd, 1H), 5.49 (d, 1H), 4.68 (q, 1H), 4.50-4.46 (m, 1H), 4.40 (d, 1H), 3.50 (dd, 1H), 2.71-2.65 (m, 2H), 2.57 (d, 1H), 2.51-2.25 (m, 9H), 2.17 (bs, 3H), 2.02 (s, 3H), 1.99 (s, 3H), 1.83 (d, 1H), 1.74-1.58 (m, 4H), 1.49-1.42 (m, 1H), 1.39-1.32 (m, 1H), 1.24-1.08 (m, 3H), 1.07 (s, 9H). MS (ESI) m/z 797.3 (M+H)$^+$.

Example 17O tert-butyl (7R,16R)-19,23-dichloro-1-cyclohexyl-10-{[2-(4-{[(2S)-1,4-dioxan-2-yl]methoxy}phenyl)pyrimidin-4-yl]methoxy}-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate Example 17N (29 mg), Example 7B (35 mg), triphenylphosphine (46 mg), and N,N,N',N'-tetramethylazodicarboxamide (30 mg) were combined and flushed with argon for 15 minutes. Tetrahydrofuran (1.0 mL) and toluene (1.0 mL) were mixed, flushed with argon for 15 minutes, and mixed with the solid reactants. The reaction mixture was stirred over the weekend at room temperature. The reaction mixture was concentrated. Purification was performed on a silica gel column (4 g, 0-30% methanol in dichloromethane). The pure fractions were combined and the solvents were removed under reduced pressure to provide the title compound. MS (APCI) m/z 1081.4 (M+H)$^+$.

Example 17P (7R,16R)-19,23-dichloro-1-cyclohexyl-10-{[2-(4-{[(2S)-1,4-dioxan-2-yl]methoxy}phenyl)pyrimidin-4-yl]methoxy}-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 17O (43 mg) was dissolved in dichloromethane (1.0 mL) and trifluoroacetic acid (0.5 mL) was added. The reaction mixture was stirred for 6 hours at room temperature. The reaction mixture was concentrated. The residue was dissolved in methanol, diluted with water, and freeze-dried. Purification by HPLC (Waters X-Bridge C8 19×150 mm 5 µm column, gradient 5-100% acetonitrile+0.2% ammonium hydroxide in water+0.2% ammonium hydroxide) provided the title compound. $^1$H NMR (500 MHz, dimethylsulfoxide-d$_6$) δ ppm 8.81 (d, 1H), 8.63 (s, 1H), 8.35-8.32 (m, 2H), 7.44 (d, 1H), 7.08-7.06 (m, 2H), 6.86 (d, 1H), 6.75-6.73 (m, 1H), 6.21 (b, 1H), 5.84 (b, 1H), 5.23 (d, 1H), 5.16 (d, 1H), 4.89-4.88 (m, 1H), 4.52-4.46 (m, 2H), 4.06-4.02 (m, 2H), 3.91-3.87 (m, 1H), 3.86-3.83 (m, 1H), 3.79-3.77 (m, 1H), 3.69-3.58 (m, 3H), 3.51 (td, 1H), 3.44-3.41 (m, 1H), 2.89-2.86 (m, 1H), 2.73-2.67 (m, 2H), 2.56-2.47 (m, 8H), 2.20-2.16 (m, 1H), 2.15 (s, 3H), 2.04 (s, 3H), 1.89 (s, 3H), 1.77-1.75 (m, 1H), 1.72-1.65 (m, 3H), 1.58-1.56 (m, 1H), 1.44-1.31 (m, 2H), 1.21-1.05 (m, 3H). MS (APCI) m/z 1025.1 (M+H)$^+$.

Example 18

(7R,16R)-19,23-dichloro-1-{[(2R)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 18A 6-bromo-4-chloro-5-(3,5-dichloro-2,6-dimethyl-4-((triisopropylsilyl)oxy)phenyl)thieno[2,3-d]pyrimidine A mixture of Example 17C (4.18 g) and diisopropylethylamine (4.16 mL) in dichloromethane (50 mL) was stirred for 5 minutes at ambient temperature. After cooling to 15° C., triisopropylchlorosilane (2.83 mL) was added, and the stirring was continued at ambient temperature for 24 hours. The mixture was concentrated in vacuo, water (40 mL) and NaHCO$_3$ (saturated aqueous solution, 10 mL) were added, and the mixture was extracted twice with ethyl acetate (20 mL). The combined organic extracts washed with brine, dried over magnesium sulfate, filtered and concentrated. Precipitation from ethanol (20 mL) provided the title compound. MS (ESI) m/z 593.1 (M+H)$^+$.

Example 18B (R)-tert-butyl 2-acetoxy-3-(5-((tert-butyldimethylsilyl)oxy)-2-hydroxyphenyl)propanoate Example 1P (4.5 g) in ethanol (30 mL) was added to 5% Pd/C (wet JM #9) (0.22 g) in a 100 mL pressure bottle. The mixture was stirred under 50 psi of hydrogen (g) at 35° C. for 10 hours. The reaction mixture was cooled to ambient temperature and filtered. The filtrate was concentrated to obtain the title compound. $^1$H NMR (400 MHz, chloroform-d) δ ppm 6.70 (d, 1H), 6.66-6.60 (m, 2H), 5.59 (s, 1H), 5.18 (dd, 1H), 3.12 (dd, 1H), 3.02 (dd, 1H), 2.11 (s, 3H), 1.43 (s, 9H), 0.97 (s, 9H), 0.17 (d, 6H). MS (ESI) m/z 427.8 $[M+NH_4]^+$.

Example 18C 2-methoxybenzimidamide hydrochloride

A dried 12 L five-necked flask equipped with a mechanical stirrer, a gas inlet with tubing leading to a nitrogen regulator, a gas inlet adapter with tubing leading to a bubbler, and an internal temperature probe (J-KEM controlled), was charged with ammonium chloride (86 g). The material was mixed under nitrogen with anhydrous toluene (2 L). The mixture was cooled to −12.3° C. in an ice/methanol bath. To the mixture was added, via cannula, 2.0 M trimethylaluminum in toluene (800 mL). Upon addition of the trimethylaluminum, the mixture started to smoke immediately and gas was evolved. The temperature of the reaction mixture rose to a high of −0.4° C. during the addition, and the addition took a total of about 60 minutes. After all the trimethylaluminum was added, the mixture was allowed to stir at 20° C. for 3 hours. To the mixture was added 2-methoxybenzonitrile (107 g) as a liquid (had been melted in bath at about 45° C.). Once the 2-methoxybenzonitrile was added, the reaction mixture was heated at 90° C. overnight with the use of a heating mantle controlled by a J-KEM. The reaction flask was fitted with a vigreux condenser. Thin-layer chromatography in 50% ethyl acetate/heptane indicated a major baseline product. The reaction mixture was cooled to −8.7° C. in an ice/methanol bath, and to the cold mixture was added 4 L of methanol, dropwise via an addition funnel. The addition evolved gas and was exothermic. The temperature of the reaction mixture reached a high of 7.9° C., and the addition took a total of about one hour. After all the methanol was added, the mixture was allowed to stir for three hours at 20° C. The reaction mixture was filtered through filter paper on a benchtop filter. The material collected were washed with additional methanol (2 L). The filtrate was concentrated. The crude material was mixed with 500 mL of ethyl acetate. The mixture was sonicated for 30 minutes and was stirred for another 30 minutes. The solids material was filtered off and washed with more ethyl acetate. The material collected were air dried for an hour and then dried under high vacuum for two hours to provide the title compound. $^1$H NMR (400 MHz, dimethylsulfoxide-$d_6$) δ ppm 9.23 (bs, 2H), 7.69 (bs, 1H), 7.63 (ddd, 1H), 7.55 (dd, 1H), 7.25 (dd, 1H), 7.12 (td, 1H), 3.87 (s, 3H). MS (DCI) m/z 151.0 $(M+H)^+$.

Example 18D 4-(dimethoxymethyl)-2-(2-methoxyphenyl)pyrimidine

An oven-dried 5 L three neck flask equipped with a mechanical stirrer, nitrogen inlet into a reflux condenser and outlet to a bubbler, and an internal temperature probe (J-KEM controlled), was charged with Example 18C (126.9 g) and (E)-4-(dimethylamino)-1,1-dimethoxybut-3-en-2-one (177 g). Anhydrous methanol (1360 mL) was added. To the mixture at room temperature under nitrogen was added solid sodium methoxide (257 g) in portions over 20 minutes. The temperature of the reaction went up from 18.6° C. to 35.7° C. during the addition. Once the exotherm stopped, the reaction mixture was heated to 65° C. overnight. The reaction mixture was cooled, and concentrated. The residue was mixed with ethyl acetate (800 mL), and water (1 L) was added carefully. The two phase mixture was sonicated for about 30 minutes to dissolve all the material. The layers were separated, and organic layer was washed with saturated aqueous $NH_4Cl$ mixture. The combined aqueous extracts were extracted one time with ethyl acetate. The combined organic extracts were washed with brine, dried with $Na_2SO_4$, filtered, and concentrated. The residue was dissolved in a small amount of dichloromethane (30 mL) and loaded onto a 2.0 L plug of silica in a 3 L Buchner funnel that had been equilibrated with 40% ethyl acetate/heptane. The desired product was eluted with 40% to 50% ethyl acetate/heptane. The fractions containing the desired product were combined, and were concentrated to provide the title compound. $^1$H NMR (500 MHz, dimethylsulfoxide-$d_6$) δ ppm 8.93 (d, 1H), 7.54 (dd, 1H), 7.50-7.43 (m, 2H), 7.16 (dd, 1H), 7.06 (td, 1H), 5.31 (s, 1H), 3.76 (s, 3H), 3.38 (s, 6H). MS (DCI) m/z 261.0 $(M+H)^+$.

Example 18E (2-(2-methoxyphenyl)pyrimidin-4-yl)methanol

A mixture of Example 18D (14.7 g) in 110 mL HCl in dioxane (4M mixture) and 110 mL water was heated at 50° C. for 14 hours. The mixture was cooled to 0° C. and ground NaOH (17.60 g) was added in portions. The pH was adjusted to 8 using 10% $K_2CO_3$ aqueous mixture. Sodium borohydride (4.27 g) was added in portions. The mixture was stirred at 0° C. for 45 minutes. The mixture was carefully quenched with 150 mL saturated aqueous $NH_4Cl$ and was stirred at 0° C. for 30 minutes. The mixture was extracted with ethyl acetate (5×150 mL), washed with brine, dried over $MgSO_4$, filtered, and concentrated. The residue was triturated in 30 mL ethanol to give a first crop of the title compound. The filtrate was concentrated and the residue was purified on a silica gel column (120 g, 55-100% ethyl acetate in heptanes, dry load) to give a second crop of the title compound. $^1$H NMR (500 MHz, dimethylsulfoxide-$d_6$) δ ppm 8.84 (d, 1H), 7.49 (m, 2H), 7.44 (ddd, 1H), 7.13 (dd, 1H), 7.04 (td, 1H), 5.65 (t, 1H), 4.60 (dd, 2H), 3.75 (s, 3H). MS (DCI) m/z 217.0 $(M+H)^+$.

Example 18F (R)-tert-butyl 2-acetoxy-3-(5-((tert-butyldimethylsilyl)oxy)-2-((2-(2-methoxyphenyl)pyrimidin-4-yl)methoxy)phenyl)propanoate To an oven dried 500 mL round bottom flask was added Example 18B (14.7 g), triphenylphosphine (27.4 g). Example 18E (20 g) and tetrahydrofuran (105 mL). The reaction flask was cooled in an ice bath. Solid (E)-N,N,N',N'-tetramethyldiazene-1,2-dicarboxamide (18 g) was added and the reaction mixture was allowed to warm up to ambient temperature and was stirred overnight. The mixture was filtered and the filter cake was washed with tetrahydrofuran.

The filtrate was concentrated. The residue was taken up in 200 mL of 15% ethyl acetate in heptanes, shaken, and filtered through 200 g silica gel. The filtrate was concentrated and purified by silica gel chromatography on a Grace Reveleris X2 MPLC system using a Teledyne Isco RediSep® Rf gold 330 g silica column with 20-50% ethyl acetate/heptanes. Fractions containing desired product were combined and concentrated to obtain the title compound. $^1$H NMR (501 MHz, chloroform-d) δ ppm 8.89 (d, 1H), 7.70 (dd, 1H), 7.63 (d, 1H), 7.47-7.41 (m, 1H), 7.09 (tt, 1H), 7.05 (d, 1H), 6.79-6.73 (m, 2H), 6.70 (dd, 1H), 5.25 (dd, 1H), 5.20 (d, 2H), 3.88 (s, 3H), 3.40 (dd, 1H), 3.00 (dd, 1H), 2.06 (s, 3H), 1.47 (s, 9H), 0.99 (s, 9H), 0.18 (s, 6H). MS (ESI) m/z 609.2 [M+H]$^+$.

Example 18G (R)-tert-butyl 3-(5-((tert-butyldimethylsilyl)oxy)-2-((2-(2-methoxyphenyl)pyrimidin-4-yl)methoxy)phenyl)-2-hydroxy propanoate To a mixture of Example 18F (24.4 g) in anhydrous ethanol (210 mL) was added sodium ethoxide solution (21% in ethanol, 0.78 mL), and the mixture was stirred at room temperature for 2 hours. Acetic acid (0.24 mL) was added and the solution was concentrated and purified by silica gel chromatography on a Grace Reveleris X2 MPLC system using a Teledyne Isco RediSep® Rf gold 330 g silica column with 30-60% ethyl acetate/heptanes. Fractions containing desired product were combined and concentrated to obtain the title compound. $^1$H NMR (400 MHz, chloroform-d) δ ppm 8.88 (d, 1H), 7.70 (dd, 1H), 7.58 (dt, 1H), 7.44 (ddd, 1H), 7.09 (td, 1H), 7.05 (dd, 1H), 6.78 (d, 1H), 6.75 (d, 1H), 6.68 (dd, 1H), 5.20 (s, 2H), 4.44 (ddd, 1H), 3.88 (s, 3H), 3.24 (dd, 1H), 2.95 (dd, 1H), 2.92 (d, 1H), 1.47 (s, 9H), 0.98 (s, 9H), 0.18 (s, 6H). MS (ESI) m/z 567.2 [M+H]$^+$.

Example 18H tert-butyl (R)-2-((6-bromo-5-(3,5-dichloro-2,6-dimethyl-4-((triisopropylsilyl)oxy)phenyl)thieno[2,3-d]pyrimidin-4-yl)oxy)-3-(5-((tert-butyldimethylsilyl)oxy)-2-((2-(2-methoxyphenyl)pyrimidin-4-yl)methoxy)phenyl)propanoate A mixture of Example 18A (5.3 g), Example 18G (26.4 g) and cesium carbonate (6.62 g) in tert-butanol (75 mL) was stirred at 70° C. for 7 hours. After cooling to 10° C., water (200 mL) was added, and the mixture was extracted twice with ethyl acetate (70 mL). The combined organic extracts were washed with brine, dried over magnesium sulfate, filtered and concentrated. Purification by chromatography on silica gel using an ISCO CombiFlash® Companion MPLC (220 g Chromabond® column, eluting with 0-60%/o heptane/ethyl acetate) provided the title compound. $^1$H NMR (600 MHz, dimethylsulfoxide-d$_6$) δ ppm 8.86 (d, 1H), 8.64 (s, 1H), 7.49 (dd, 1H), 7.48-7.42 (m, 2H), 7.14 (dd, 1H), 7.02 (td, 1H), 6.95 (d, 1H), 6.70 (dd, 1H), 6.53 (d, 1H), 5.45 (dd, 1H), 5.16 (d, 1H), 5.05 (d, 1H), 3.75 (s, 3H), 2.78 (dd, 1H), 2.61-2.56 (m, 1H), 2.08 (s, 3H), 1.97 (s, 3H), 1.39 (h, 3H), 1.18 (s, 9H), 1.05 (dd, 18H), 0.98 (d, 1H), 0.90 (s, 9H), 0.90 (d, 1H), 0.10 (d, 6H).

Example 18I (R)-2-((6-bromo-5-(3,5-dichloro-4-hydroxy-2,6-dimethylphenyl)thieno[2,3-d]pyrimidin-4-yl)oxy)-3-(5-((tert-butyldimethylsilyl)oxy)-2-((2-(2-methoxyphenyl)pyrimidin-4-yl)methoxy)phenyl)propanoate To a solution of Example 18H (9.3 g) in N,N-dimethylformamide (70 mL) cooled to 15° C., potassium carbonate (0.077 g) dissolved in 3.7 mL water was added and the reaction mixture was stirred for 4 hours at ambient temperature. Water (100 mL) and NaHCO$_3$ (saturated aqueous solution, 30 mL) were added, and the resulting mixture was extracted twice with ethyl acetate (80 mL). The combined organic extracts were washed with brine, dried over magnesium sulfate, filtered and concentrated. Purification by chromatography on silica gel using an ISCO CombiFlash® Companion MPLC (220 g Chromabond® column, eluting with 5-70% heptane/ethyl acetate) provided the title compound. MS (ESI) m/z 967.2 (M+H)$^+$.

Example 18J (S)-2,3-dihydroxypropyl 4-methylbenzenesulfonate

To a stirring mixture of (S)-(2,2-dimethyl-1,3-dioxolan-4-yl)methyl 4-methylbenzenesulfonate (9 g) in 36 mL of methanol was slowly added 42 mL of 1 M aqueous HCl mixture, and the reaction mixture was stirred at ambient temperature overnight. The mixture was concentrated under reduced pressure to remove most of the methanol. The mixture was carefully poured into 225 mL of saturated aqueous sodium bicarbonate mixture. The mixture was extracted with three portions of ethyl acetate. The combined organic layers were washed with saturated aqueous brine, dried over anhydrous magnesium sulfate, filtered and concentrated onto silica gel. Purification by silica gel flash chromatography on a CombiFlash® Teledyne Isco system using a Teledyne Isco RediSep® Rf gold 330 g silica gel column (eluting with 10-80% of 2:1 ethyl acetate:ethanol in heptane) provided the title compound, which was quickly carried through to the next step before it solidified. $^1$H NMR (400 MHz dimethylsulfoxide-d$_6$) δ ppm 2.42 (s, 3H), 3.18-3.27 (m, 1H), 3.29-3.34 (m, 1H), 3.61 (ttd, 1H), 3.84 (dd, 1H), 3.97-4.05 (m, 1H), 4.68 (t, 1H), 5.10 (d, 1H), 7.48 (d, 2H), 7.73-7.85 (m, 2H). LC/MS (APCI) m/z 247.3 (M+H)$^+$.

Example 18K (S)-3-(bis(4-methoxyphenyl)(phenyl)methoxy)-2-hydroxypropyl 4-methylbenzenesulfonate To a stirring mixture of Example 18J (6.3 g) in 128 mL of dichloromethane at 0° C. was added 4,4'-dimethoxytrityl chloride (9.10 g) in one portion. To the mixture was added N,N-diisopropylethylamine (4.69 mL) dropwise over 15 minutes. The reaction mixture was stirred at 0° C. for an hour and was quenched with saturated aqueous ammonium chloride (100 mL). The layers were separated, and the aqueous layer was extracted with two portions of dichloromethane. The combined organic extracts was dried over anhydrous magnesium sulfate, filtered and concentrated onto silica gel. Purification by flash chromatography on a CombiFlash® Teledyne Isco system using a Teledyne Isco RediSep® Rf gold 330 g silica gel column (eluting 0-50% ethyl acetate/heptane) provided the title compound. $^1$H NMR (400 MHz, dimethylsulfoxide-d$_6$) δ ppm 2.39 (s, 3H), 2.84 (dd, 1H), 2.94 (dd, 1H), 3.74 (s, 6H), 3.76-3.81 (m, 1H), 3.96 (dd, 1H), 4.02-4.09 (m, 1H), 5.28 (d, 1H), 6.82-6.92 (m, 4H), 7.12-7.18 (m, 4H), 7.19-7.25 (m, 1H), 7.28 (d, 4H), 7.45 (d, 2H), 7.71-7.79 (m, 2H).

Example 18L tert-butyl (R)-2-((5-(4-(((R)-1-(bis(4-methoxyphenyl)(phenyl)methoxy)-3-(tosyloxy)propan-2-yl)oxy)-3,5-dichloro-2,6-dimethylphenyl)-6-bromothieno[2,3-d]pyrimidin-4-yl)oxy)-3-(5-((tert-butyldimethylsilyl)oxy)-2-((2-(2-methoxyphenyl)pyrimidin-4-yl)methoxy)phenyl)propanoate Example 18I (7.3 g). Example 18K (4.55 g), triphenylphosphine (2.96 g) and di-tert-butyl azodicarboxylate (2.6 g) were added together in a reaction flask and flushed for 10 minutes with nitrogen. Freshly degassed toluene (60 mL) was added and the reaction mixture was stirred for 90 minutes at ambient temperature. The mixture was concentrated on Telos Bulk Sorbent and was purified twice by chromatography on silica gel using an ISCO CombiFlash® Companion MPLC (330 g RediSep® Gold and 120 Chromabond® column, eluting with 0-70% heptane/ethyl acetate) providing the title compound. MS (ESI) m/z 1497.4 (M+H)$^+$.

Example 18M tert-butyl (R)-2-((5-(4-((R)-3-(bis(4-methoxyphenyl)(phenyl)methoxy)-2-((tosyloxy)methyl)propyl)-3,5-dichloro-2,6-dimethylphenyl)-6-bromothieno[2,3-d]pyrimidin-4-yl)oxy)-3-(5-hydroxy-2-((2-(2-methoxyphenyl)pyrimidin-4-yl)methoxy)phenyl)propanoate Example 18L (2.24 g) in tetrahydrofuran (20 mL) cooled to 5° C., was treated with tetrabutylammonium fluoride (1 M in tetrahydrofuran, 3 mL) for 20 minutes. Water (60 mL) was added and the mixture was extracted twice with ethyl acetate (40 mL). The combined organic extracts were washed with brine, dried over magnesium sulfate, filtered and concentrated. Purification by chromatography on silica gel using an ISCO CombiFlash® Companion MPLC (80 g Chromabond® column, eluting with 0-100% heptane/ethyl acetate) provided the title compound. MS (ESI) m/z 1383.2 (M+H)$^+$.

Example 18N tert-butyl (7R,16S)-16-{[bis(4-methoxyphenyl)(phenyl)methoxy]methyl}-1-bromo-19,23-dichloro-10-{[2-(2-methoxyphenyl)pyrimidin-4-yl]methoxy}-20,22-dimethyl-7,8,15,16-tetrahydro-18,21-etheno-9,13-(metheno)-6,14,17-trioxa-2-thia-3,5-diazacyclononadeca[1,2,3-cd]indene-7-carboxylate A mixture of Example 18M (2.0 g) and cesium carbonate (2.35 g) in dimethylformamide (150 mL) was stirred at ambient temperature for 2 hours. After cooling to 5° C., the reaction mixture was poured into water (300 mL) and ethyl acetate (100 mL). The layers were separated and the aqueous layer was extracted with ethyl acetate (50 mL). The combined organic extracts were washed with brine, dried over magnesium sulfate, filtered and concentrated. Purification by chromatography on silica gel using an ISCO CombiFlash® Companion MPLC (40 g Chromabond®, column, eluting with 0-70% heptane/ethyl acetate) provided the title compound. $^1$H NMR (600 MHz, dimethylsulfoxide-d$_6$) δ ppm 8.90 (d, 1H), 8.76 (s, 1H), 7.56 (d, 1H), 7.53 (dd, 1H), 7.46 (m, 3H), 7.37-7.29 (m, 6H), 7.27-7.21 (m, 1H), 7.15 (dd, 1H), 7.05 (td, 1H), 6.98 (d, 1H), 6.95-6.87 (m, 5H), 6.05 (dd, 1H), 5.69 (d, 1H), 5.21 (d, 1H), 5.14 (d, 1H), 4.89 (m, 1H), 4.59 (dd, 1H), 4.40 (d, 1H), 3.75 (s, 9H), 3.63 (dd, 1H), 3.45-3.30 (m, 3H), 2.90 (m, 1H), 2.07 (s, 3H), 2.00 (s, 3H), 1.10 (s, 9H). MS (ESI) m/z 1211.4 (M+H)$^+$.

Example 18O tert-butyl (7R,16R)-1-bromo-19,23-dichloro-16-(hydroxymethyl)-10-{[2-(2-methoxyphenyl)pyrimidin-4-yl]methoxy}-20,22-dimethyl-7,8,15,16-tetrahydro-18,21-etheno-9,13-(metheno)-6,14,17-trioxa-2-thia-3,5-diazacyclononadeca[1,2,3-cd]indene-7-carboxylate To a solution of Example 18N (856 mg) in methanol (3 mL) and dichloromethane (3 mL) was added formic acid (2.2 mL) and the mixture was stirred at ambient temperature for 1 hour. The reaction mixture was cooled to 5° C. water (40 mL) was added, and the mixture was extracted twice with dichloromethane (30 mL). The combined organic extracts were washed with NaHCO$_3$ (saturated aqueous solution, 30 mL) and water, dried over magnesium sulfate, filtered and concentrated. Purification by chromatography on silica gel using an ISCO CombiFlash® Companion MPLC (25 g Chromabond® column, eluting with 0-100% heptane/ethyl acetate) provided the title compound. MS (ESI) m/z 909.2 (M+H)$^+$.

Example 18P tert-butyl (7R,16S)-1-bromo-19,23-dichloro-10-{[2-(2-methoxyphenyl)pyrimidin-4-yl]methoxy}-20,22-dimethyl-16-{[(4-methylbenzene-1-sulfonyl)oxy]methyl}-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 1X substituting Example 18O for Example 1W. MS (ESI) m/z 1063.2 (M+H)$^+$.

Example 18Q tert-butyl (7R,16R)-1-bromo-19,23-dichloro-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 1Y substituting Example 18P for Example 1Y. MS (ESI) m/z 1063.2 (M+H)$^+$.

Example 18R tert-butyl (7R,16R)-19,23-dichloro-1-{[(2R)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A pre-catalyst stock solution was prepared using a dry microwave vial charged with NiCl$_2$ dimethoxyethane adduct (1.107 mg), 4,4'-di-tert-butyl-2,2'-bipyridine (1.35 mg) and dimethoxyethane (0.5 mL) and the solution was sonicated for 5 minutes. To a dry 5 mL microwave vial, which was dried for 24 hours at 70° C. under vacuum and stored in a glove box, was added Example 18Q (50 mg), (S)-2-bromomethyl)-1,4-dioxane (40 mg), Ir[dF(CF$_3$)ppy]$_2$(dtbbpy) (5.65 mg), and Na$_2$CO$_3$ (8 mg) in a glove box. Dry dimethoxyethane (0.5 mL degassed with nitrogen) and tris(trimethylsilyl)silane (20 μL) was added, pre-catalyst stock solution (0.5 mL) was syringed into the vial, and the reaction mixture was exposed to blue light (34 W Blue LED KESSIL Light, EvoluChem™ PhotoRedOx Box) under stirring at 25° C. for 20 hours. Water (5 mL) was added to the mixture and the mixture was extracted twice with dichloromethane. The combined organic extracts were dried over magnesium sulfate, filtered and concentrated in vacuo. Purification by chromatography using an ISCO CombiFlash® Companion MPLC (4 g Chromabond® silica gel column, eluting with 0-10% dichloromethane/methanol) provided a mixture of the title compound and the corresponding des-bromo analogue. MS (ESI) m/z 1013.4 (M+H)$^+$.

Example 18S (7R,16R)-19,23-dichloro-1-{[(2R)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 18R (120 mg) in dichloromethane (1 mL) was added trifluoroacetic acid (0.1 mL). The mixture was stirred for 20 hours and concentrated in vacuo. Purification by HPLC (Gemini NX C18 21.2×150 mm 5 μm column, gradient 5-100% acetonitrile+0.2% ammonium hydroxide in water+0.1% ammonium hydroxide) provided the title compound. $^1$H NMR (600 MHz, dimethylsulfoxide-d$_6$) δ ppm 13.0 (s, 1H), 8.86 (d, 1H), 8.63 (s, 1H), 7.54 (dd, 1H), 7.46 (ddd, 1H), 7.15 (dd, 1H), 7.04 (td, 1H), 6.87 (d, 1H), 6.74 (s, 1H), 6.19 (sb, 1H), 5.81 (s, 1H), 5.20 (d, 1H), 5.12 (d, 1H), 4.91 (s, 1H), 4.49 (m, 2H), 3.76 (s, 3H), 3.69 (m, 1H), 3.61-3.49 (m, 4H), 3.40-3.30 (m, 8H), 3.08 (dd, 1H), 2.87 (dd, 1H), 2.72 (m, 2H), 2.55-2.35 (m, 4H), 2.16 (s, 3H), 2.03 (s, 3H), 1.88 (s, 3H). MS (ESI) m/z 957.4 (M+H)$^+$.

Example 19

(7R,16R)-19,23-dichloro-1-{[(2S)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 19A tert-butyl (7R,16R)-19,23-dichloro-1-{[(2S)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 18R by replacing (S)-2-bromomethyl)-1,4-dioxane with (R)-2-bromomethyl)-1,4-dioxane. MS (ESI) m/z 1013.4 (M+H)$^+$.

Example 19B (7R,16R)-19,23-dichloro-1-{[(2S)-1,4-dioxan-2-yl]methyl}-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 18S by replacing Example 18R with Example 19A. $^1$H NMR (600 MHz, dimethylsulfoxide-d$_6$) δ ppm 8.86 (d, 1H), 8.66 (s, 1H), 7.56-7.51 (m, 2H), 7.46 (ddd, 1H), 7.15 (dd, 1H), 7.04 (td, 1H), 6.89 (d, 1H), 6.77 (dd, 1H), 6.23 (s, 1H), 5.82 (s, 1H), 5.20 (d, 1H), 5.12 (d, 1H), 4.89 (m, 1H), 4.50 (m, 2H), 3.76 (s, 3H), 3.72 (m, 1H), 3.64-3.49 (m, 5H), 3.42-3.25 (m, 7H), 3.09 (dd, 1H), 2.91 (dd, 1H), 2.72 (m, 2H), 2.55.-2.35 (m, 4H), 2.17 (s, 3H), 2.02 (s, 3H), 1.90 (s, 3H). MS (ESI) m/z 957.4 (M+H)$^+$.

Example 20

(7R,16R)-19,23-dichloro-10-({2-[(2R)-2-({[(1,4-dioxan-2-yl)methoxy]methyl}morpholin-4-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 20A (R)-(4-(4-(((tert-butyldimethylsilyl)oxy)methyl)pyrimidin-2-yl)morpholin-2-yl)methanol A solution of (R)-morpholin-2-ylmethanol, trifluoroacetic acid (210 mg), 4-(((tert-butyldimethylsilyl)oxy)methyl)-2-chloropyrimidine (200 mg) and N,N-diisopropylethylamine (800 μL) in acetonitrile (1.9 mL) was heated to 80° C. overnight. The reaction was cooled, diluted with water and extracted with ethyl acetate three times. The combined organic layers were dried over anhydrous sodium sulfate, filtered and concentrated. The residue was purified by normal phase MPLC on a Teledyne Isco Combiflash® Rf+ 12 g gold silica gel column eluting with 0-70% ethyl acetate in dichloromethane to give the title compound. $^1$H NMR (400 MHz, dimethylsulfoxide-d$_6$) δ ppm 8.38 (d, 1H), 6.70 (d, 1H), 4.85-4.74 (m, 1H), 4.60-4.50 (m, 3H), 4.43-4.34 (m, 1H), 3.95-3.86 (m, 1H), 3.55-3.35 (m, 4H), 2.99-2.85 (m, 1H), 2.72-2.58 (m, 1H), 0.91 (s, 9H), 0.09 (s, 6H).

Example 20B (R)-2-((allyloxy)methyl)-4-(4-(((tert-butyldimethylsilyl)oxy)methyl)pyrimidin-2-yl)morpholine To a solution of Example 20A (200 mg) and 3-bromoprop-1-ene (100 μL) in tetrahydrofuran (3 mL) was added sodium hydride (48 mg, 60% oil dispersion), and the reaction was warmed to 40° C. after bubbling subsided. After 4 hours, the reaction was cooled, diluted with saturated aqueous ammonium chloride and extracted with ethyl acetate three times. The combined organic layers were dried over anhydrous sodium sulfate, filtered and concentrated. The residue was purified by normal phase MPLC on a Teledyne Isco Combiflash® Rf+ 12 g gold silica gel column eluting with 0-25% ethyl acetate in dichloromethane to give the title compound. ¹H NMR (400 MHz, dimethylsulfoxide-$d_6$) δ ppm 8.38 (d, 1H), 6.70 (d, 1H), 5.97-5.81 (m, 1H), 5.31-5.21 (m, 1H), 5.20-5.10 (m, 1H), 4.55 (s, 2H), 4.53-4.45 (m, 1H), 4.42-4.32 (m, 1H), 4.01-3.94 (m, 2H), 3.93-3.86 (m, 1H), 3.62-3.38 (m, 4H), 2.99-2.86 (m, 1H), 2.77-2.66 (m, 1H), 0.91 (s, 9H), 0.09 (s, 6H).

Example 20C 3-(((R)-4-(4-(((tert-butyldimethylsilyl)oxy)methyl)pyrimidin-2-yl)morpholin-2-yl)methoxy)propane-1,2-diol To a solution of Example 20B (190 mg) in tert-butanol (2.5 mL) and water (2.5 mL) at 0° C. was added AD-Mix alpha (1.1 g), and the reaction was stirred for 4 hours at 0° C. The reaction was warmed to room temperature and stirred overnight. The reaction was quenched with solid sodium sulfite, diluted with water and extracted with ethyl acetate three times. The combined organic layers were washed with brine, dried over anhydrous sodium sulfate, filtered and concentrated to give the title compound as a mixture of diastereomers that was used in the next step without further purification.

Example 20D (2R)-2-(((1,4-dioxan-2-yl)methoxy)methyl)-4-(4-(((tert-butyldimethylsilyl)oxy)methyl)pyrimidin-2-yl)morpholine To a solution of Example 20C (210 mg) in dichloromethane (3.3 mL) at room temperature was added sodium hydride (36 mg, 60% oil dispersion), and the reaction was allowed to stir for 10 minutes. A solution of Example 9B (220 mg) in dichloromethane (1.7 mL) was added, and the reaction was allowed to stir for 5 hours. The reaction was quenched with saturated aqueous ammonium chloride and extracted with ethyl acetate three times. The combined organic layers were dried over anhydrous sodium sulfate, filtered and concentrated. The residue was purified by normal phase MPLC on a Teledyne Isco Combiflash® Rf+ 12 g gold silica gel column eluting with 0-50% ethyl acetate in dichloromethane to give the title compound as a mixture of diastereomers. ¹H NMR (400 MHz, dimethylsulfoxide-$d_6$) δ ppm 8.38 (d, 1H), 6.70 (d, 1H), 4.55 (s, 2H), 4.51-4.42 (m, 1H), 4.41-4.30 (m, 1H), 3.96-3.81 (m, 2H), 3.76-3.35 (m, 11H), 3.30-3.19 (m, 1H), 3.00-2.85 (m, 1H), 2.78-2.62 (m, 1H), 0.91 (s, 9H), 0.09 (s, 6H).

Example 20E (2-((2R)-2-(((1,4-dioxan-2-yl)methoxy)methyl)morpholino)pyrimidin-4-yl)methanol To a solution of Example 20D (110 mg) in tetrahydrofuran (860 μL) and methanol (430 μL) was added cesium fluoride (200 mg), and the reaction was allowed to stir for 5.5 hours. The reaction mixture was concentrated, and the residue was taken up in ethyl acetate with sonication, filtered over diatomaceous earth, and concentrated. The residue was purified by normal phase MPLC on a Teledyne Isco Combiflash® Rf+ 4 g gold silica gel column eluting with 10-100% ethyl acetate in dichloromethane to give the title compound as a mixture of diastereomers. ¹H NMR (500 MHz, dimethylsulfoxide-$d_6$) δ ppm 8.35 (d, 1H), 6.75 (d, 1H), 5.45-5.36 (m, 1H), 4.51-4.43 (m, 1H), 4.41-4.32 (m, 3H), 3.95-3.86 (m, 1H), 3.74-3.36 (m, 12H), 3.30-3.21 (m, 1H), 2.97-2.86 (m, 1H), 2.74-2.64 (m, 1H).

Example 20F tert-butyl (7R,16R)-19,23-dichloro-10-({2-[(2R)-2-{[(1,4-dioxan-2-yl)methoxy]methyl}morpholin-4-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,23-cd]indene-7-carboxylate A vial containing Example 20E (42 mg), Example 1Z (35 mg), triphenylphosphine (34 mg) and N,N',N'-tetramethylazodicarboxamide (22 mg) in toluene (110 μL) and tetrahydrofuran (110 μL) was allowed to stir at 50° C. for 4 hours. The reaction was cooled, diluted with ethyl acetate, filtered over diatomaceous earth and concentrated. The residue was purified by normal phase MPLC on a Teledyne Isco Combiflash® Rf+ 4 g gold silica gel column eluting with 0.5-9% methanol in dichloromethane to give the title compound as a mixture of diastereomers. ¹H NMR (400 MHz, dimethylsulfoxide-$d_6$) δ ppm 8.74, (s, 1H), 8.39 (d, 1H), 7.29-7.12 (m, 5H), 6.90-6.74 (m, 3H), 6.06-5.99 (m, 1H), 5.69-5.63 (m, 1H), 5.04-4.85 (m, 2H), 4.79-4.68 (m, 1H), 4.56-4.34 (m, 4H), 3.97-3.87 (m, 1H), 3.75-3.36 (m, 14H), 3.30-3.21 (m, 1H), 3.02-2.57 (m, 8H), 2.44-2.20 (m, 4H), 2.14 (s, 3H), 2.10 (s, 3H), 1.06 (s, 9H).

Example 20G (7R,16R)-19,23-dichloro-10-({2-[(2R)-2-{[(1,4-dioxan-2-yl)methoxy]methyl}morpholin-4-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 20F (41 mg) in dichloromethane (190 μL) was added trifluoroacetic acid (190 μL), and the reaction was allowed to stir for 4 hours. The reaction was concentrated under a stream of nitrogen and taken up in water and acetonitrile. The mixture was purified by RP-HPLC on a Gilson PLC 2020 using a Luna™ column (250×50 mm, 10 mm, 5-85% over 30 minutes with acetonitrile in water containing 10 mM ammonium acetate) to give the title compound after lyophilization as a mixture of diastereomers. ¹H NMR (500 MHz, dimethylsulfoxide-$d_6$) δ ppm 8.73 (s, 1H), 8.35 (d, 1H), 7.23-7.09 (m, 5H), 6.83-6.68 (m, 3H), 6.25-6.16 (m, 1H), 5.85-5.77 (m, 1H), 5.03-4.81 (m, 3H), 4.54-4.33 (m, 3H), 3.95-3.86 (m, 1H), 3.74-3.22 (m, 11H), 3.00-2.87 (m, 2H), 2.77-2.59 (m, 2H), 2.48-2.35 (m, 2H), 2.22 (s, 3H), 2.02-1.93 (m, 6H). MS (ESI) m/z 1060.4 (M+H)⁺.

Example 21

(7R,16R)-19,23-dichloro-10-{[2-(3-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 21A (R)-2-(3-((1,4-dioxan-2-yl)methoxy)phenyl)-4,4,5,5-tetramethyl-1,3,2-dioxaborolane The title compound was prepared by substituting 3-(4,4,5,5-tetramethyl-1,3,2-dioxaborolan-2-yl)phenol for 4-(4,4,5,5-tetramethyl-1,3,2-dioxaborolan-2-yl)phenol in Example 2A. $^1$H NMR (500 MHz, dimethylsulfoxide-$d_6$) δ ppm 7.30 (m, 1H), 7.26 (d, 1H), 7.15 (d, 1H), 7.07 (dd, 1H), 3.96 (d, 2H), 3.86-3.80 (m, 2H), 3.77-3.75 (m, 1H), 3.69-3.58 (m, 2H), 3.50 (td, 1H), 3.42 (t, 1H), 1.29 (s, 12H). MS (ESI) m/z 338.1 (M+NH$_4$)$^+$.

Example 21B (R)-(2-(3-((1,4-dioxan-2-yl)methoxy)phenyl)pyrimidin-4-yl)methanol The title compound was prepared by substituting Example 21A for Example 2A in Example 2B. $^1$H NMR (500 MHz, dimethylsulfoxide-$d_6$) δ ppm 8.88 (d, 1H), 7.99 (d, 1H), 7.92 (t, 1H), 7.50 (d, 1H), 7.43 (t, 1H), 7.11 (dd, 1H), 5.68 (t, 1H), 4.64 (d, 2H), 4.04 (d, 2H), 3.91-3.77 (m, 3H), 3.69-3.62 (m, 2H), 3.53 (dd, 1H), 3.45 (t, 1H). MS (ESI) m/z 303.1 (M+H)$^+$.

Example 21C tert-butyl (7R,16R)-19,23-dichloro-10-{[2-(3-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 21B for Example 7B in Example 7C. MS (ESI) m/z 1095.4 (M+H)$^+$.

Example 21D (7R,16R)-19,23-dichloro-10-{[2-(3-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 21C for Example 7C in Example 7D. $^1$H NMR (500 MHz, dimethylsulfoxide-$d_6$) δ ppm 8.89 (d, 1H), 8.74 (s, 1H), 8.00 (d, 1H), 7.94 (d, 1H), 7.54 (d, 1H), 7.44 (t, 1H), 7.23-7.10 (m, 5H), 6.90 (d, 1H), 6.76 (dd, 1H), 6.24 (m, 1H), 5.81 (d, 1H), 5.24 (q, 2H), 4.86 (m, 1H), 4.45 (m, 2H), 4.04 (d, 2H), 3.92-3.84 (m, 2H), 3.79-3.75 (m, 1H), 3.69-3.61 (m, 3H), 3.54-3.45 (m, 2H), 2.98 (d, 2H), 2.73-2.61 (m, 3H), 2.48-2.28 (m, 6H), 2.18 (s, 3H), 1.99 (s, 3H), 1.95 (s, 3H). MS (ESI) m/z 1037.5 (M+H)$^+$.

Example 22

(7R,16R)-19,23-dichloro-10-{[2-(3-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 22A (S)-2-(3-((1,4-dioxan-2-yl)methoxy)phenyl)-4,4,5,5-tetramethyl-1,3,2-dioxaborolane The title compound was prepared by substituting 3-(4,4,5,5-tetramethyl-1,3,2-dioxaborolan-2-yl)phenol for 4-(4,4,5,5-tetramethyl-1,3,2-dioxaborolan-2-yl)phenol and (R)-(1,4-dioxan-2-yl)methanol for (S)-(1,4-dioxan-2-yl)methanol in Example 2A. $^1$H NMR (500 MHz, dimethylsulfoxide-$d_6$) δ ppm 7.30 (m, 1H), 7.26 (d, 1H), 7.15 (d, 1H), 7.06 (dd, 1H), 3.96 (d, 2H), 3.86-3.79 (m, 2H), 3.77-3.75 (m, 1H), 3.67-3.59 (m, 2H), 3.50 (td, 1H), 3.42 (t, 1H), 1.29 (s, 12H). MS (ESI) m/z 337.9 (M+NH$_4$)$^+$.

Example 22B (S)-(2-(3-((1,4-dioxan-2-yl)methoxy)phenyl)pyrimidin-4-yl)methanol The title compound was prepared by substituting Example 22A for Example 2A in Example 2B. $^1$H NMR (500 MHz, dimethylsulfoxide-$d_6$) δ ppm 8.88 (d, 1H), 7.99 (d, 1H), 7.92 (dd, 1H), 7.50 (d, 1H), 7.43 (t, 1H), 7.11 (dd, 1H), 5.67 (t, 1H), 4.64 (d, 2H), 4.04 (d, 2H), 3.91-3.82 (m, 2H), 3.81-3.76 (m, 1H), 3.70-3.61 (m, 2H), 3.53 (dd, 1H), 3.45 (t, 1H). MS (ESI) m/z 303.1 (M+H)$^+$.

Example 22C tert-butyl (7R,16R)-19,23-dichloro-10-{[2-(3-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 22B for Example 7B in Example 7C. MS (ESI) m/z 1093.3 (M+H)$^+$.

Example 22D (7R,16R)-19,23-dichloro-10-{[2-(3-{[(2S)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 22C for Example 7C in Example 7D. $^1$H NMR (500 MHz, dimethylsulfoxide-d$_6$) δ ppm 8.89 (d, 1H), 8.73 (s, 1H), 8.00 (d, 1H), 7.94 (s, 1H), 7.54 (d, 1H), 7.43 (t, 1H), 7.22-7.12 (m, 5H), 6.89 (d, 1H), 6.75 (dd, 1H), 6.24 (m, 1H), 5.83 (s, 1H), 5.23 (q, 2H), 4.87 (m, 1H), 4.45 (bs, 2H), 4.04 (d, 2H), 3.93-3.84 (m, 2H), 3.79-3.75 (m, 1H), 3.70-3.60 (m, 3H), 3.54-3.45 (m, 2H), 2.98 (d, 2H), 2.73-2.61 (m, 3H), 2.48-2.31 (m, 6H), 2.17 (s, 3H), 1.98 (s, 3H), 1.96 (s, 3H). MS (ESI) m/z 1037.5 (M+H)$^+$.

Example 23

(7R,16R)-19,23-dichloro-10-{[4-(4-{[(2R)-1,4-dioxan-2-yl]methoxy}phenyl)pyrimidin-2-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 23A (R)-(4-(4-((1,4-dioxan-2-yl)methoxy)phenyl)pyrimidin-2-yl)methanol A mixture of (4-chloropyrimidin-2-yl)methanol (36.6 mg), Example 16A (70 mg), tris(dibenzylideneacetone)dipalladium(0) (2 mg), (1S,3R,5R,7S)-1,3,5,7-tetramethyl-8-phenyl-2,4,6-trioxa-8 phosphaadamantane (1.9 mg) and tribasic potassium phosphate (93 mg) were purged with argon for 30 minutes. A solution of tetrahydrofuran (0.87 mL) and water (0.22 mL) was degassed and added. The reaction mixture was stirred in a Biotage® Initiator microwave unit for 8 hours at 65° C. To the reaction mixture was added ethyl acetate and the mixture was filtrated via a pad of diatomaceous earth. To the filtrate was added ethyl acetate and water. The aqueous phase was extracted twice with ethyl acetate. The combined organic extracts were washed with brine and then dried over magnesium sulfate, filtered, and subsequently concentrated in vacuo. The residue was purified by normal phase MPLC on a Teledyne-Isco-Combiflash® system (eluting with 40-100% ethyl acetate in heptane) to afford the title compound. MS (APCI) m/z 303.2 (M+H)$^+$.

Example 23B tert-butyl (7R,16R)-19,23-dichloro-10-{[6-(4-{[(2R)-1,4-dioxan-2-yl]methoxy}phenyl)pyrimidin-2-yl]methoxy}-1-(4-fluorophenyl)-20,22-dimethyl-116-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 4 mL vial, equipped with stir bar, was charged with Example 1Z (35 mg), Example 23A (15.7 mg), triphenylphosphine (22.7 mg) and tetramethylazodicarboxamide (14.9 mg) and purged for 30 minutes with argon. A solution of tetrahydrofuran (0.5 mL) and toluene (0.5 mL) were added and the reaction mixture was stirred for 19 hours at ambient temperature. To the reaction mixture were added triphenylphosphine (11.3 mg) and tetramethylazodicarboxamide (7.5 mg) and stirring was continued for 28 hours at ambient temperature. To the reaction mixture were added triphenylphosphine (11.3 mg) and tetramethylazodicarboxamide (7.5 mg) and stirring was continued for 17 hours at ambient temperature. The material in the reaction mixture were filtered off and to the organic phase was added dichloromethane. The material was washed with dichloromethane. The combined organic phases were washed with water and brine solution. The organic phase was dried via DryDisk® and subsequently concentrated in vacuo. The residue was purified by normal phase MPLC on a Teledyne-Isco-Combiflash® system (eluting with 0-20% methanol in dichloromethane) to afford the title compound. MS (APCI) m/z 1093.3 (M+H)$^+$.

Example 23C (7R,16R)-19,23-dichloro-10-{[4-(4-{[(2R)-1,4-dioxan-2-yl]methoxy}phenyl)pyrimidin-2-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 23B (38 mg) in dichloromethane (270 µL) was added trifluoroacetic acid (268 µL). The reaction mixture was stirred for 24 hours at ambient temperature. The reaction mixture was then concentrated in vacuo. The residue was dissolved in dichloromethane and saturated aqueous NaHCO$_3$-solution was added. The aqueous phase was extracted twice with dichloromethane. The combined organic phases were dried via DryDisk® and concentrated in vacuo. The residue was purified by HPLC (Waters X-Bridge C8 19×150 mm 5 mm column, gradient 5-100% acetonitrile+0.2% ammonium hydroxide in water+0.2% ammonium hydroxide) to provide the title compound. $^1$H NMR (600 MHz, dimethylsulfoxide-d$_6$) δ ppm 8.75 (d, 1H), 8.72 (s, 1H), 8.17 (m, 2H), 7.92 (d, 1H), 7.19 (m, 2H), 7.13 (m, 2H), 7.05 (m, 2H), 6.83 (d, 1H), 6.68 (m, 1H), 6.20 (m, 1H), 5.81 (s, 1H), 5.24 (s, 2H), 4.86 (m, 1H), 4.41 (m, 2H), 4.03 (m, 2H), 3.89 (m, 1H), 3.84 (m, 1H) 3.77 (m, 1H), 3.70-3.60 (m, 3H), 3.51 (m, 1H), 3.43 (m, 1H), 2.98 (m, 1H), 2.63 (m, 2H), 2.55-2.25 (m, 8H), 2.14 (s, 3H), 1.96 (s, 3H), 1.91 (s, 3H). MS (ESI) m/z 1037.1 (M+H)$^+$.

Example 24

(7R,16R)-19,23-dichloro-10-[(2-{[(2S)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 24A (S)-2-((1,4-dioxan-2-yl)methoxy)-4-(((tert-butyldimethylsilyl)oxy)methyl)pyrimidine (R)-(1,4-Dioxan-2-yl)methanol (91 mg), 4-(((tert-butyldimethylsilyl)oxy)methyl)-2-chloropyrimidine (200 mg), and triethylamine (0.4 mL) were dissolved in acetonitrile (2.5 mL) and heated to 80° C. for 3 hours. Sodium hydride (111 mg, 50%) was added at room temperature and the mixture was stirred overnight at room temperature. The reaction mixture was concentrated. The residue was dissolved in dichloromethane and washed with water. The organic layer was dried over sodium sulfate, filtered, and concentrated. Purification was performed on a silica gel column (4 g, 0-20% methanol in dichloromethane). The pure fractions were combined and the solvents were removed under reduced pressure to provide the title compound. MS (ESI) m/z 341.2 (M+H)+.

Example 24B (S)-(2-((1,4-dioxan-2-yl)methoxy)pyrimidin-4-yl)methanol

Example 24A (66.5 mg) was dissolved in tetrahydrofuran (1 mL) and cooled to 0° C. by an ice bath. Tetrabutylammonium fluoride (1M in tetrahydrofuran, 0.39 mL) was added and the mixture was stirred for 2 hours at 0° C. The reaction mixture was partitioned between ethyl acetate and brine. The organic layer was washed with brine, dried over sodium sulfate, filtered, and concentrated. Purification was performed on a silica gel column (4 g, 0-50% methanol in dichloromethane). The pure fractions were combined and the solvents were removed under reduced pressure to provide the title compound. MS (ESI) m/z 227.1 (M+H)+.

Example 24C tert-butyl (7R,16R)-19,23-dichloro-10-[(2-{[(2S)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate Example 24B (42 mg), Example 1Z (25 mg), triphenylphosphine (32 mg), and N,N,N',N'-tetramethylazodicarboxamide (21 mg) were combined and flushed with argon for 15 minutes. Tetrahydrofuran (0.2 mL) and toluene (0.2 mL) were mixed, flushed with argon for 15 minutes, and added to the solid reactants. The reaction mixture was stirred over the weekend at room temperature. The reaction mixture was concentrated. Purification was performed on a silica gel column (4 g, 0-30% methanol in dichloromethane). The pure fractions were combined and the solvents were removed under reduced pressure to provide the title compound. MS (APCI) m/z 1017.3 (M+H)+.

Example 24D (7R,16R)-19,23-dichloro-10-[(2-{[(2S)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 24C (70 mg) was dissolved in dichloromethane (1.0 mL) and trifluoroacetic acid (0.24 mL) was added. The reaction mixture was stirred overnight at room temperature. The reaction mixture was concentrated at 25° C. The residue was dissolved in methanol, diluted with water and freeze-dried. The crude material was purified by HPLC (Waters X-Bridge C8 19×150 mm 5 μm column, gradient 5% to 100% acetonitrile+0.2% ammonium hydroxide in water+0.2% ammonium hydroxide) to provide the title compound. $^1$H NMR (500 MHz, dimethylsulfoxide-$d_6$) δ ppm 8.73 (s, 1H), 8.58 (d, 1H), 7.25 (d, 1H), 7.22-7.18 (m, 2H), 7.16-7.12 (m, 2H), 6.83 (d, 1H), 6.75-6.73 (m, 1H), 6.19 (b, 1H), 5.81 (b, 1H), 5.10 (d, 1H), 5.02 (d, 1H), 4.90-4.86 (m, 1H), 4.47-4.41 (m, 2H), 4.31-4.25 (m, 2H), 3.90-3.85 (m, 1H), 3.78 (ddd, 2H), 3.67-3.57 (m, 3H), 3.49 (td, 1H), 3.42-3.38 (m, 1H), 2.96-2.92 (m, 1H), 2.72-2.65 (m, 2H), 2.55-2.49 (m, 8H), 2.19 (s, 3H), 1.98 (s, 3H), 1.96 (s, 3H). MS (APCI) m/z 961.3 (M+H)+.

Example 25

(7R,16R)-19,23-dichloro-10-[(2-{[(2R)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 25A The title compound was prepared as described in Example 24A by substituting (S)-(1,4-dioxan-2-yl)methanol for (R)-(1,4-dioxan-2-yl)methanol. MS (ESI) m/z 341.2 (M+H)+.

Example 25B (R)-(2-((1,4-dioxan-2-yl)methoxy)pyrimidin-4-yl)methanol

The title compound was prepared as described in Example 24B by substituting Example 25A for Example 24A. MS (ESI) m/z 227.1 (M+H)+.

Example 25C tert-butyl (7R,16R)-19,23-dichloro-10-[(2-{[(2R)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate The title compound was prepared as described in Example 24C by substituting Example 25B for Example 24B. MS (APCI) m/z 1017.3 (M+H)+.

Example 25D (7R,16R)-19,23-dichloro-10-[(2-{[(2R)-1,4-dioxan-2-yl]methoxy}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 25C (67 mg) was dissolved in dichloromethane (1.0 mL) and trifluoroacetic acid (0.23 mL) was added. The reaction mixture was stirred overnight at room temperature. The reaction mixture was concentrated at 25° C. The residue was dissolved in methanol, diluted with water and freeze-dried. The crude material was purified by HPLC (Waters X-Bridge C8 19×150 mm 5 mm column, gradient 5-100% acetonitrile+0.2% ammonium hydroxide in water+0.2% ammonium hydroxide) to provide the title compound. $^1$H NMR (500 MHz, dimethylsulfoxide-$d_6$) δ ppm 8.73 (s, 1H), 8.58 (d, 1H), 7.25 (d, 1H), 7.22-7.18 (m, 2H), 7.16-7.12 (m, 2H), 6.83 (d, 1H), 6.75-6.73 (m, 1H), 6.19 (b, 1H), 5.81 (b, 1H), 5.10 (d, 1H), 5.02 (d, 1H), 4.90-4.86 (m, 1H), 4.47-4.41 (m, 2H), 4.32-4.25 (m, 2H), 3.90-3.86 (m, 1H), 3.78 (ddd, 2H), 3.67-3.56 (m, 3H), 3.49 (td, 1H), 3.42-3.38 (m, 1H), 2.96-2.92 (m, 1H), 2.72-2.63 (m, 2H), 2.55-2.42 (m, 8H), 2.18 (s, 3H), 1.98 (s, 3H), 1.96 (s, 3H). MS (APCI) m/z 961.2 (M+H)$^+$.

Example 26

(7R,16R)-19,23-dichloro-10-[(2-{4-[(1,4-dioxan-2-yl)methanesulfonyl]piperazin-1-yl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 26A tert-butyl 4-(((1,4-dioxan-2-yl)methyl)sulfonyl)piperazine-1-carboxylate tert-Butyl piperazine-1-carboxylate (102 mg) was dissolved in dichloromethane (3 mL). Triethylamine (151 mg) was added, followed by (1,4-dioxan-2-yl)methanesulfonyl chloride (100 mg). The solution was mixed at room temperature overnight. The solvent was removed under vacuum, and the residue was taken up in ethyl acetate (10 mL). The solution was washed with 0.1 M aqueous HCl (3 mL). The solution was washed with brine, dried over anhydrous sodium sulfate, and filtered. The solvent was removed under vacuum, and the material was carried on without further purification. $^1$H NMR (500 MHz, dimethylsulfoxide-d$_6$) δ ppm 3.94 (m, 1H), 3.80 (d, 2H), 3.74-3.63 (m, 2H), 3.57-3.48 (m, 1H), 3.45 (m, 4H), 3.35-3.30 (m, 1H), 3.27-3.23 (m, 2H), 3.18 (m, 4H), 1.47 (s, 9H). MS (ESI) m/z 251.2 (M-tert-butyl carboxylate)$^+$.

Example 26B 1-(((1,4-dioxan-2-yl)methyl)sulfonyl)piperazine

The title compound was prepared by substituting Example 26A for Example 10A in Example 10B. The material was isolated as the trifluoroacetic acid salt and was carried on in the next step without further purification.

Example 26C (2-(4-(((1,4-dioxan-2-yl)methyl)sulfonyl)piperazin-1-yl)pyrimidin-4-yl)methanol The title compound was prepared by substituting Example 26B for Example 10B in Example 10C. $^1$H NMR (500 MHz, dimethylsulfoxide-d$_6$) δ ppm 8.37 (d, 1H), 6.77 (d, 1H), 5.43 (t, 1H), 4.37 (d, 2H), 3.93-3.85 (m, 1H), 3.80 (m, 4H), 3.72 (m, 2H), 3.64-3.55 (m, 2H), 3.48-3.43 (m, 1H), 3.29-3.19 (m, 7H). MS (ESI) m/z 359.2 (M+H)$^+$.

Example 26D tert-butyl (7R,16R)-19,23-dichloro-10-[(2-{4-[(1,4-dioxan-2-yl)methanesulfonyl]piperazin-1-yl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 26C for Example 7B in Example 7C. MS (ESI) m/z 1149.5 (M+H)$^+$.

Example 26E (7R,16R)-19,23-dichloro-10-[(2-{4-[(1,4-dioxan-2-yl)methanesulfonyl]piperazin-1-yl}pyrimidin-4-yl)methoxy]-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 26D for Example 7C in Example 7D. $^1$H NMR (500 MHz dimethylsulfoxide-d$_6$) δ ppm 8.72 (s, 1H), 8.38 (d, 1H), 7.22-7.11 (m, 4H), 6.83-6.77 (m, 2H), 6.74 (dd, 1H), 6.18 (m, 1H), 5.82 (s, 1H), 4.95 (q, 2H), 4.89 (m, 1H), 4.44 (m, 2H), 3.92-3.87 (m, 1H), 3.83 (m, 4H), 3.76-3.68 (m, 3H), 3.65-3.53 (m, 6H), 3.49-3.44 (m, 4H), 2.96 (d, 2H), 2.75-2.65 (m, 3H), 2.47 (m, 2H), 2.42-2.32 (m, 4H), 2.18 (s, 3H), 1.97 (bs, 6H). MS (ESI) m/z 1093.4 (M+H)$^+$.

Example 27

(7R,16R)-19,23-dichloro-1-(5,6-dihydro-1,4-dioxin-2-yl)-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 27A tert-butyl (7R,16R)-19,23-dichloro-1-(5,6-dihydro-1,4-dioxin-2-yl)-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A microwave vial, equipped with stir bar, was charged with Example 18Q (50 mg), 5-(4,4,5,5-tetramethyl-1,3,2-dioxaborolan-2-yl)-2,3-dihydro-1,4-dioxine (20 mg), 1'-bis(di-tert-butylphosphino)ferrocene-palladium dichloride dichloromethane complex (3 mg) and CsCO$_3$ (45 mg) and degassed for 10 minutes with nitrogen. Freshly degassed dioxane (0.8 mL) and water (0.2 mL) were added. The vial was capped and the reaction mixture was heated in a Biotage® Initiator microwave to 90° C. for 90 minutes. Water (2 mL) and dichloromethane (4 mL) were added, the organic layer separated via Chromabond® PTS cartridge, the aqueous layer re-extracted with dichloromethane (2 mL), and the combined organic layers concentrated in vacuo. Purification by chromatography on silica gel using an ISCO CombiFlash® Companion MPLC (5 g Chromabond® column, eluting with 0-10% dichloromethane/methanol) provided the title compound. MS (ESI) m/z 997.4 (M+H)+.

Example 27B (7R,16R)-19,23-dichloro-1-(5,6-dihydro-1,4-dioxin-2-yl)-10-{[2-(2-methoxyphenyl)pyrimidin-4-yl]methoxy}-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 18S by replacing Example 18R with Example 27A. $^1$H NMR (600 MHz, dimethylsulfoxide-$d_6$) δ ppm 8.86 (d, 1H), 8.66 (s, 1H), 7.54 (dd, 1H), 7.52 (d, 1H), 7.46 (ddd, 1H), 7.15 (dd, 1H), 7.05 (td, 1H), 6.90 (d, 1H), 6.78 (dd, 1H), 6.24 (s, 1H), 5.78 (s, 1H), 5.47 (s, 1H), 5.21 (d, 1H), 5.13 (d, 1H), 4.87 (m, 1H), 4.50 (m, 2H), 4.13 (m, 1H), 4.07 (m, 1H), 4.01 (m, 2H), 3.76 (s, 3H), 3.64 (dd, 1H), 2.91 (dd, 1H), 2.71 (m, 2H), 2.55-2.45 (m, 6H), 2.39 (s, 2H), 2.17 (s, 3H), 2.05 (s, 3H), 1.97 (s, 3H). MS (ESI) m/z 941.4 (M+H)+.

Example 28

(7R,16R)-19,23-dichloro-10-({2-[(1R,4s)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 28A (S)-8-(((1,4-dioxan-2-yl)methoxy)methyl)-8-fluoro-1,4-dioxaspiro[4.5]decane To a solution of Example 39D (1.7 g) in dimethylformamide (20 mL) was added sodium hydride (1.1 g, 60% oil dispersion) at 0° C. under nitrogen. After 10 minutes, a solution of (S)-(1,4-dioxan-2-yl)methyl 4-methylbenzenesulfonate (3.8 g) in dimethylformamide (20 mL) was added to the reaction. The reaction was stirred at 50° C. for 12 hours. Two additional reactions were set up as above. All three reactions were combined. The reaction was poured into ice water and exacted with ethyl acetate twice. The combined organic layers were dried over anhydrous sodium sulfate, filtered and concentrated to give a residue which was purified by column chromatography on silica gel (eluting with petroleum ether:ethyl acetate=100:1 to 20:3) to give the title compound. $^1$H NMR (400 MHz, CDCl$_3$) δ ppm 4.03-3.87 (m, 4H), 3.85-3.66 (m, 5H), 3.65-3.37 (m, 6H), 2.02-1.80 (m, 4H), 1.79-1.55 (m, 4H).

Example 28B (S)-4-(((1,4-dioxan-2-yl)methoxy)methyl)-4-fluorocyclohexanone

To a solution of Example 28A (1.8 g) in tetrahydrofuran (54 mL) was added aqueous HCl (54 mL, 6 M) at 0° C. The reaction was stirred at 25° C. for 16 hours under a nitrogen atmosphere. Two additional reactions were set up as above. All three reactions were combined. The pH of the combined mixture was adjusted to 8 by addition of solid NaOH at 0° C., and the mixture was extracted with ethyl acetate eight times. The combined organics were dried over anhydrous sodium sulfate, filtered and concentrated to give the title compound. $^1$H NMR (400 MHz, CDCl$_3$) δ ppm 3.89-3.20 (m, 11H), 2.76-2.57 (m, 2H), 2.40-2.17 (m, 4H), 1.99-1.77 (m, 2H).

Example 28C 4-((((S)-1,4-dioxan-2-yl)methoxy)methyl)-4-fluorocyclohex-1-en-1-yl trifluoromethanesulfonate To a stirred solution of diisopropylamine (1.8 g) in dry tetrahydrofuran (150 mL) was added n-butyllithium (7.3 mL, 1 M) at 0° C. under nitrogen flow. After 5 minutes, a solution of Example 28B (3 g) in dry tetrahydrofuran (150 mL) was added to the reaction mixture. The mixture was stirred for 15 minutes at 0° C. A solution of 1,1,1-trifluoro-N-phenyl-N-((trifluoromethyl)sulfonyl)methanesulfonamide (5.6 g) in tetrahydrofuran (150 mL) was added to the mixture at −78° C. under nitrogen atmosphere, and the reaction was warmed to 20° C. and stirred for 16 hours under nitrogen atmosphere. The reaction was poured into ice water and extracted with ethyl acetate twice. The organic phases were combined and washed with brine, dried over anhydrous magnesium sulfate, filtered, and concentrated. The residue was purified by column chromatography on silica gel (eluting with petroleum ether:ethyl acetate=3:1 to 1:1) to give the title compound. $^1$H NMR (400 MHz, CDCl$_3$) δ ppm 5.68 (br s, 1H), 3.86-3.37 (m, 11H), 2.70-2.27 (m, 4H), 2.17-2.06 (m, 1H), 1.99-1.78 (m, 1H).

Example 28D 2-(4-((((S)-1,4-dioxan-2-yl)methoxy)methyl)-4-fluorocyclohex-1-en-1-yl)-4,4,5,5-tetramethyl-1,3,2-dioxaborolane To a solution of Example 28C (3.4 g) in 1,4-dioxane (102 mL) was added 4,4,4',4',5,5,5',5'-octamethyl-2,2'-bi(1,3,2-dioxaborolane) (2.9 g), potassium acetate (1.6 g) and [1,1-bis(diphenylphosphino)ferrocene]palladium(II) chloride (0.7 g) at 20° C. under nitrogen. The mixture was stirred at 80° C. for 12 hours. The reaction was cooled to 20° C. One additional vial was set up as described above, and both of the two mixtures were combined. The mixture was filtered and concentrated to give a residue. The residue was purified by column chromatography on silica gel (eluted with petroleum ether:ethyl acetate=100:1 to 20:1) to give the title compound. $^1$H NMR (400 MHz, CDCl$_3$) δ ppm 6.44 (br d, 1H), 3.85-3.36 (m, 11H), 2.42-2.11 (m, 5H), 1.95-1.84 (m, 1H), 1.82-1.64 (m, 1H), 1.33-1.20 (m, 15H).

Example 28E (2-(4-((((S)-1,4-dioxan-2-yl)methoxy)methyl)-4-fluorocyclohex-1-en-1-yl)pyrimidin-4-yl)methanol To a solution of Example 28D (1.9 g) and (2-chloropyrimidin-4-yl) methanol (0.6 g) in dioxane (30 mL) was added tetrakis(triphenylphosphine)palladium(0) (0.2 g) and saturated aqueous sodium bicarbonate (10 mL) at 15° C. under nitrogen atmosphere. The mixture was stirred under nitrogen at 100° C. for 16 hours. The reaction mixture was cooled, extracted with ethyl acetate three times, and the combined organic phases were washed with brine twice, dried over anhydrous magnesium sulfate, filtered and concentrated. The residue was purified by prep-HPLC on a Gilson 281 semi-preparative HPLC using a Nano-micro Kromazil C18 column (100×30 mm, 5 micron) eluting with acetonitrile (14-100% over 10 minutes) in water containing 0.075% trifluoroacetic acid to give the title compound. $^1$H NMR (400 MHz, CDCl$_3$) δ ppm 8.63 (d, 1H), 7.22 (br s, 1H), 7.07 (d, 1H), 4.74 (s, 2H), 3.91-3.38 (m, 12H), 2.79 (br d, 2H), 2.70-2.45 (m, 2H), 2.14 (qd, 1H), 1.98-1.81 (m, 1H).

Example 28F (2-((1R,4s)-4-((((S)-1,4-dioxan-2-yl)methoxy) methyl)-4-fluorocyclohexyl)pyrimidin-4-yl)methanol To a solution of Example 28E (0.35 g) and triethylamine (0.2 mL) in dry tetrahydrofuran (10 mL) was added 10% Pd/C (0.1 g), and the suspension was stirred for 16 hours under hydrogen (15 psi) at 25° C. One additional reaction was set up as above. Both of the two reactions were combined. The mixture was filtered and concentrated to get the crude product. The crude material was purified by chiral SFC on a Thar SFC80 preparative SFC using a Chiralpak AS-H column (250×30 mm, 5 micron) with isopropanol containing 0.1% ammonium hydroxide to give the title compound. Analytical SFC of Example 28F on a Thar analytical SFC using a Chiralpak AS-3 (0.46×10 cm, 3 micron) column with isopropanol containing 0.05% isopropylamine from 5-40% in 5 minutes and a flow rate of 4.0 mL/minute gave a retention time of 1.31 minutes. $^1$H NMR (400 MHz, CDCl$_3$) δ ppm 8.63 (d, 1H), 7.10 (d, 1H), 4.74 (s, 2H), 3.88-3.38 (m, 11H), 2.98-2.83 (m, 1H), 2.15-1.91 (m, 7H), 1.69-1.44 (m, 2H).

Example 28G (2-((1R,4s)-4-((((S)-1,4-dioxan-2-yl)methoxy) methyl)-4-fluorocyclohexyl)pyrimidin-4-yl)methanol The title compound was obtained from the SFC separation in Example 28F. Analytical SFC of Example 28G on a Thar analytical SFC using a Chiralpak AS-3 (0.46×10 cm, 3 micron) column with isopropanol containing 0.05% isopropylamine from 5-40% in 5 minutes and a flow rate of 4.0 mL/minute gave a retention time of 1.05 minutes. $^1$H NMR (400 MHz, CDCl$_3$) δ ppm 8.69-8.57 (m, 1H), 7.11 (d, 1H), 4.74 (s, 2H), 3.87-3.36 (m, 11H), 3.16-3.00 (m, 1H), 2.17-1.51 (m, 8H).

Example 28H tert-butyl (7R,16R)-19,23-dichloro-10-({2-[(1R,4s)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 28F (50 mg), Example 1Z (40 mg), triphenylphosphine (39 mg) and N,N,N',N'-tetramethylazodicarboxamide (26 mg) in toluene (120 μL) and tetrahydrofuran (120 μL) was allowed to stir at 50° C. overnight. The reaction was cooled, diluted with ethyl acetate, filtered over diatomaceous earth and concentrated. The residue was purified by normal phase MPLC on a Teledyne Isco Combiflash® Rf+ 4 g gold silica gel column eluting with 0-9.5% methanol in dichloromethane to give the title compound.

Example 281

(7R,16R)-19,23-dichloro-10-({2-[(1R,4s)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl) methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 28H (56 mg) in dichloromethane (250 μL) was added trifluoroacetic acid (250 μL), and the reaction was allowed to stir overnight. The reaction was concentrated under a stream of nitrogen and taken up in water and acetonitrile. The mixture was purified by RP-HPLC on a Gilson PLC 2020 using a Luna™ column (250×50 mm, 10 mm, 5-80% over 30 minutes with acetonitrile in water containing 10 mM ammonium acetate) to give the title compound after lyophilization. $^1$H NMR (400 MHz, dimethylsulfoxide-d$_6$) δ ppm 8.75-8.67 (m, 2H), 7.44 (d, 1H), 7.24-7.08 (m, 5H), 6.84 (d, 1H), 6.76-6.66 (m, 1H), 6.25-6.14 (m, 1H), 5.87-5.78 (m, 1H), 5.20-5.00 (m, 2H), 4.94-4.80 (m, 1H), 4.50-4.37 (m, 2H), 3.76-3.22 (m, 10H), 3.00-2.77 (m, 4H), 2.75-2.58 (m, 3H), 2.45 (br s, 4H), 2.23 (s, 3H), 2.03-1.74 (m, 12H), 1.69-1.40 (m, 4H). MS (ESI) m/z 1073.0 (M–H)$^-$.

Example 29

(7R,16R)-19,23-dichloro-1-cyclobutyl-10-[(2-{(1r,4r)-4-[(1,4-dioxan-2-yl)methoxy] cyclohexyl}pyrimidin-4-yl)methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 29A tert-butyl (7R,16R)-10-(benzyloxy)-19,23-dichloro-1-cyclobutyl-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To a 5 mL microwave vial, which was dried for 24 hours at 70° C. under vacuum and stored in a glove box, was added Example 17L (200 mg), potassium cyclobutyltrifluoroborate (80 mg), Cs$_2$CO$_3$ (150 mg), [Ni(dtbbpy)]Cl$_2$ (9 mg), and Ir[dF(CF$_3$)ppy]$_2$(dtbbpy) (25 mg) in a glove box. Freshly degassed dioxane (1 mL) was added and the reaction mixture was exposed to blue light (34 W Blue LED KESSIL Light, EvoluChem™ PhotoRedOx Box) with stirring at 25° C. for 20 hours. The reaction mixture was concentrated, water (20 mL) was added and the mixture was extracted twice with ethyl acetate (10 mL). The combined organic extracts were washed with brine, dried over MgSO$_4$, filtered and concentrated in vacuo. Purification by chromatography on silica gel using an ISCO CombiFlash® Companion MPLC (4 g Chromabond® silica gel column, eluting with 0-10% dichloromethane/methanol) and subsequent purification by SFC (Viridis PFP 250×19 mm 5 μm column; gradient 5-50% liquid $CO_2$ in methanol+0.2% ammonium hydroxide) provided the title compound. MS (ESI) m/z 859.3 $(M+H)^+$.

Example 29B tert-butyl (7R,16R)-19,23-dichloro-1-cyclobutyl-10-hydroxy-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A Tinyclave steel reactor (Buechi) was charged with Example 29A (165 mg) in tetrahydrofuran (10 mL) and Pd/C (50% wet with water, 50 mg) was added. The reactor was purged with hydrogen gas three times, and stirred under hydrogen first with a pressure of 50 psi for 24 hours and then under a pressure of 100 psi for 96 hours. The reaction was vented, the mixture filtered over a filter funnel packed with diatomaceous earth, and the filtrate then concentrated in vacuo. Purification by chromatography on silica gel using an ISCO CombiFlash® Companion MPLC (4 g Chromabond® silica gel column, eluting with 0-10% dichloromethane/methanol) provided the title compound. MS (ESI) m/z 769.3 $(M+H)^+$.

Example 29C (2-((1R,4r)-4-(((R)-1,4-dioxan-2-yl)methoxy)cyclohexyl)pyrimidin-4-yl)methyl methanesulfonate To a solution of Example 9D (45 mg) in dichloromethane (1 mL) at a temperature of 5° C. was added triethylamine (0.06 mL) and methanesulfonyl chloride (0.017 mL). The reaction was allowed to warm to ambient temperature and was stirred for 1 hour. Dichloromethane (3 mL) and water (4 mL) were added, the organic layer separated via Chromabond® PTS cartridge, the aqueous layer re-extracted with dichloromethane (2 mL), and the combined organic layers concentrated in vacuo to give the title compound. MS (ESI) m/z 387.2 $(M+H)^+$.

Example 29D tert-butyl (7R,16R)-19,23-dichloro-1-cyclobutyl-10-[(2-{(1r,4r)-4-[(1,4-dioxan-2-yl)methoxy]cyclohexyl}pyrimidin-4-yl)methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To a solution of Example 29B (57 mg) and Example 29C (40 mg) in N,N-dimethylformamide, (1 mL) $CsCO_3$ (61.5 mg) was added. The mixture was stirred for 2 hours at ambient temperature. Ethyl acetate (10 mL) and water (20 mL) were added, and the aqueous layer re-extracted with ethyl acetate (10 mL). The combined organic layers were washed with brine, dried over magnesium sulfate, filtered and concentrated in vacuo. Purification of the crude product by chromatography on silica gel using an ISCO CombiFlash® Companion MPLC (4 g Chromabond® silica gel column, eluting with 0-10% dichloromethane/methanol) provided the title compound. MS (ESI) m/z 1059.4 $(M+H)^+$.

Example 29E (7R,16R)-19,23-dichloro-1-cyclobutyl-10-[(2-{(1r,4r)-4-[(1,4-dioxan-2-yl)methoxy]cyclohexyl}pyrimidin-4-yl)methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 18S by replacing Example 18R with Example 29D. $^1$H NMR (600 MHz, dimethylsulfoxide-$d_6$) δ ppm 8.70 (d, 1H), 8.65 (s, 1H), 7.40 (d, 1H), 6.84 (d, 1H), 6.75 (dd, 1H), 6.23 (m, 1H), 5.78 (d, 1H), 5.12 (d, 1H), 5.04 (d, 1H), 4.86 (m, 1H), 4.48 (m, 2H), 3.71 (m, 2H), 3.65-3.52 (m, 4H), 3.44 (m, 2H), 3.38-3.26 (m, 5H), 3.17 (t, 1H), 2.86 (dd, 1H), 2.76 (m, 1H), 2.72 (m, 2H), 2.55.-2.45 (m, 8H), 2.20 (s, 3H), 2.13-1.99 (m, 4H), 1.98 (s, 3H), 1.95-1.93 (m, 2H), 1.88 (s, 3H), 1.92-1.81 (m, 1H), 1.74 (m, 1H), 1.59 (m, 2H), 1.26 (m, 2H). MS (ESI) m/z 1003.4 $(M+H)^+$.

Example 30

(7R,16R)-19,23-dichloro-10-{[2-(1,4-dioxepan-6-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 30A 3,5-dihydro-2H-1,4-dioxepin-6-yl 1,1,2,2,3,3,4,4,4-nonafluorobutane-1-sulfonate To a solution of 1,4-dioxepan-6-one (300 mg) and nonafluorobutanesulfonyl fluoride (900 mg) in dry dimethylformamide (5 mL) was added 2-methyl-N-(tri(pyrrolidin-1-yl)phosphoranylidene)-propan-2-amine (930 mg) dropwise at 0° C. The reaction mixture was stirred at 20° C. for 1 hours. Two additional vials were set up as described above. All three reactions were combined, and the mixture was quenched with saturated aqueous ammonium chloride solution and extracted with petroleum ether three times. The combined organic layers were washed with water and brine, dried over sodium sulfate, filtered and concentrated under reduced pressure to give the title compound which was used directly in the next step without further purification. $^1$H NMR (400 MHz, $CDCl_3$) δ ppm 6.93 (s, 1H), 4.42 (s, 2H), 4.21-4.15 (m, 2H), 3.90-3.84 (m, 2H), 3.27-3.15 (m, 1H).

Example 30B 2-(2,3-dihydro-5H-1,4-dioxepin-6-yl)-4,4,5,5-tetramethyl-1,3,2-dioxaborolane To a solution of Example 30A (400 mg) in dimethoxyethane (5 mL) was added 4,4,4',4',5,5,5',5'-octamethyl-2,2'-bi(1,3,2-dioxaborolane) (280 mg), potassium acetate (300 mg), (1,1'-bis(diphenylphosphino) ferrocenedichloro palladium(II) dichloromethane complex) (37 mg) and (1,1'-bis(diphenylphosphino)ferrocene) (28 mg) under $N_2$ atmosphere. The mixture was stirred at 80° C. for 12 hours under nitrogen atmosphere. Two other vials were set up as described above. All three reactions were combined, and the reaction mixture was concentrated under reduced pressure to give the title compound which was used directly in the next step without further purification.

Example 30C (2-(3,5-dihydro-2H-1,4-dioxepin-6-yl)pyrimidin-4-yl)methanol

To a solution of Example 30B (680 mg) and (2-chloropyrimidin-4-yl)methanol (400 mg) in 1,4-dioxane (4 mL) was added tetrakis[triphenylphosphine]palladium(0) (140 mg) and saturated aqueous sodium bicarbonate solution (1 mL). The mixture was stirred under nitrogen at 110° C. for 12 hours. The reaction liquid was cooled to 25° C., and filtered. The filtrate was exacted with ethyl acetate three times. The organic phases were combined and washed with brine twice. The organic phase was dried over magnesium sulfate, filtered, and concentrated to give the crude product which was purified by column chromatography on silica gel (eluted with dichloromethane:methanol=1:5 to 1:3) to afford the title compound. $^1$H NMR (400 MHz, CDCl$_3$) δ ppm 8.52 (d, 1H), 8.00 (s, 1H), 6.99 (d, 1H), 4.90 (s, 2H), 4.69 (br d, 2H), 4.34-4.30 (m, 2H), 4.03-3.97 (m, 2H), 3.49 (br s, 1H).

Example 30D (2-(1,4-dioxepan-6-yl)pyrimidin-4-yl)methanol

To a mixture of 10% Pd/C (153 mg) in tetrahydrofuran (20 mL) was added Example 30C (300 mg). The reaction mixture was stirred at 25° C. under 15 psi of H$_2$ for 12 hours. The reaction was filtered, and the filtrate was concentrated under reduced pressure to give the crude product. The crude product was purified by column chromatography on silica gel (petroleum ether:ethyl acetate 60:40-40:60) to give the title compound. $^1$H NMR (400 MHz. CD$_3$OD) δ ppm 8.69 (d, 1H), 7.45 (d, 1H), 4.65 (s, 2H), 4.23-4.13 (m, 4H), 3.87-3.79 (m, 4H), 3.70-3.60 (m, 1H).

Example 30E tert-butyl (7R,16R)-19,23-dichloro-10-{[2-(1,4-dioxepan-6-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 30D (31 mg), Example 1Z (40 mg), triphenylphosphine (39 mg) and N,N,N',N'-tetramethylazodicarboxamide (26 mg) in toluene (120 μL) and tetrahydrofuran (120 μL) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 1.5-10°/% methanol in dichloromethane to give the title compound.

Example 30F (7R,16R)-19,23-dichloro-10-{[2-(1,4-dioxepan-6-yl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 30E (45 mg) in dichloromethane (230 μL) was added trifluoroacetic acid (230 μL), and the reaction was allowed to stir for overnight. The reaction was concentrated under a stream of nitrogen and taken up in water and acetonitrile. The mixture was purified by RP-HPLC on a Gilson PLC 2020 using a Luna™ column (250×50 mm, 10 mm, 5-85% over 30 minutes with acetonitrile in water containing 10 mM ammonium acetate) to give the title compound after lyophilization. $^1$H NMR (400 MHz, dimethylsulfoxide-d$_6$) δ ppm 8.78-8.68 (m, 2H), 7.47 (d, 1H), 7.26-7.08 (m, 5H), 6.85 (d, 1H), 6.79-6.68 (m, 1H), 6.27-6.17 (m, 1H), 5.87-5.76 (m, 1H), 5.20-5.00 (m, 2H), 4.93-4.80 (m, 1H), 4.52-4.36 (m, 2H), 4.17-4.02 (m, 4H), 3.81-3.53 (m, 8H), 3.01-2.87 (m, 1H), 2.75-2.59 (m, 2H), 2.49-2.37 (br s, 4H), 2.24 (s, 3H), 1.97 (s, 6H). MS (ESI) m/z 944.25 (M−H)$^-$.

Example 31

(7R,16R)-19,23-dichloro-10-{[6-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 31A (R)-(6-(4-((1,4-dioxan-2-yl)methoxy)phenyl)pyrimidin-4-yl)methanol A mixture of (6-chloropyrimidin-4-yl)methanol (102 mg), Example 16A (200 mg), tris(dibenzylideneacetone)dipalladium(0) (5.7 mg), (1S,3R,5R,7S)-1,3,5,7-tetramethyl-8-phenyl-2,4,6-trioxa-8 phosphaadamantane (5.5 mg) and tribasic potassium phosphate (265 mg) were purged with argon for 30 minutes. A solution of tetrahydrofuran (2.5 mL) and water (0.62 mL) was degassed and added. The reaction mixture was stirred in a Biotage®. Initiator microwave unit for 3 hours at 65° C. To the reaction mixture was added ethyl acetate and the mixture was filtrated through a pad of diatomaceous earth. To the filtrate was added ethyl acetate and water. The aqueous phase was extracted twice with ethyl acetate. The combined organic extracts were washed with brine and then dried over magnesium sulfate, filtered and subsequently concentrated in vacuo. The residue was purified by normal phase MPLC on a Teledyne-Isco-Combiflash® system (eluting with 40-100% ethyl acetate in heptane) to afford the title compound. MS (APCI) m/z 303.2 (M+H)$^+$.

Example 31B tert-butyl (7R,16R)-19,23-dichloro-10-{[6-(4-{[(2R)-1,4-dioxan-2-yl]methoxy}phenyl)pyrimidin-4-yl]methoxy}-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 4 mL vial, equipped with stir bar, was charged with Example 1Z (35 mg), Example 31A (15.7 mg), triphenylphosphine (22.7 mg) and tetramethlylazodicarboxamide (14.9 mg) and purged for 30 minutes with argon. A solution of tetrahydrofuran (0.5 mL) and toluene (0.5 mL) were added and the reaction mixture was stirred for 19 hours at ambient temperature. To the reaction mixture were added triphenylphosphine (22.7 mg) and tetramethlylazodicarboxamide (14.9 mg) and stirring was continued for 21 hours at ambient temperature. The material in the reaction mixture was filtered off and to the organic phase was added dichloromethane. The material was washed with dichloromethane. The combined organic phases were washed with water and brine solution. The organic phase was dried via DryDisk® and subsequently concentrated in vacuo. The residue was purified by normal phase MPLC on a Teledyne-Isco-Combiflash® system (eluting with 0-20% methanol in dichloromethane) to afford the title compound. MS (APCI) m/z 1093.3 (M+H)$^+$.

Example 31C (7R,16R)-19,23-dichloro-10-{[6-(4-{[(2R)-1,4-dioxan-2-yl]methoxy}phenyl)pyrimidin-4-yl]methoxy})-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 31B (44 mg) in dichloromethane (270 µL) was added trifluoroacetic acid (310 µL). The reaction mixture was stirred for 24 hours at ambient temperature. The reaction mixture was then concentrated in vacuo. The residue was dissolved in dichloromethane and saturated aqueous sodium bicarbonate solution was added. The aqueous phase was extracted twice with dichloromethane. The combined organic phases were dried via DryDisk® and concentrated in vacuo. The residue was purified by HPLC (Waters X-Bridge C8 19×150 mm 5 µm column, gradient 5% to 100% acetonitrile+0.2% ammonium hydroxide in water+0.2% ammonium hydroxide) to provide the title compound. $^1$H NMR (600 MHz, dimethylsulfoxide-d$_6$) δ ppm 9.14 (d, 1H), 8.73 (s, 1H), 8.18 (m, 2H), 8.00 (s, 1H), 7.20 (m, 2H), 7.14 (m, 2H), 7.09 (m, 2H), 6.88 (d, 1H), 6.75 (m, 1H), 6.18 (m, 1H), 5.80 (s, 1H), 5.20 (d, 1H), 5.15 (d, 1H), 4.87 (m, 1H), 4.41 (m, 2H), 4.05 (m, 2H), 3.89 (m, 1H), 3.84 (m, 1H) 3.77 (m, 1H), 3.70-3.60 (m, 3H), 3.51 (m, 1H), 3.42 (m, 1H), 3.05 (m, 1H), 2.65 (m, 2H), 2.55-2.25 (m, 8H), 2.18 (s, 3H), 1.97 (s, 3H), 1.95 (s, 3H). MS (ESI) m/z 1037.4 (M+H)$^+$.

Example 32

(7R,16R)-19,23-dichloro-1-(cyclopent-1-en-1-yl)-10-[(2-{(1r,4r)-4-[(1,4-dioxan-2-yl)methoxy]cyclohexyl}pyrimidin-4-yl)methoxy]-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 32A (R)-tert-butyl 2-acetoxy-3-(5-((ter-butyldimethylsilyl)oxy)-2-hydroxyphenyl)propanoate To a solution of Example 1P (12 g) in tetrahydrofuran (300 mL) was added Pd/C (0.210 g) under a nitrogen atmosphere. The suspension was degassed and purged with hydrogen three times. The reaction mixture was stirred under 50 psi of hydrogen at 50° C. for 10 hours. The mixture was cooled, filtered and concentrated to give a residue which was purified by column chromatography on silica gel (eluted with petroleum ether:ethyl acetate=100:1 to 100:5) to give the title compound. $^1$H NMR (400 MHz, CDCl$_3$) ppm 6.71-6.69 (m, 1H), 6.64-6.61 (m, 2H), 5.55 (s, 1H), 5.19-5.15 (dd, 1H), 3.14-3.02 (m, 2H), 2.12 (s, 3H), 1.43 (s, 9H), 0.97 (s, 9H), 0.17 (s, 6H).

Example 32B (R)-tert-butyl 2-acetoxy-3-(5-((tert-butyldimethylsilyl)oxy)-2-((2-(trimethylsilyl)ethoxy)methoxy)phenyl)propanoate To a solution of Example 32A (8.8 g) in tetrahydrofuran (280 mL) was added sodium hydride (0.120 g, 60% dispersion) at 0° C. After 15 minutes. (2-(chloromethoxy)ethyl)-trimethylsilane (0.810 g) was added into the mixture dropwise. The reaction was stirred at 25° C. for 12 hours under a nitrogen atmosphere. One additional vial was set up as described above and both of the two mixtures were combined. The reaction was quenched with water and extracted with ethyl acetate three times. The combined organic layers were washed with brine twice, dried over anhydrous sodium sulfate, filtered and concentrated to give a residue which was purified by column chromatography on silica gel (petroleum ether:ethyl acetate=100:1 to 100:5) to give the title compound. $^1$H NMR (400 MHz, CDCl$_3$) δ ppm 6.97-6.95 (m, 1H), 6.67-6.64 (m, 2H), 5.20-5.12 (m, 3H), 3.79-3.75 (m, 2H), 3.20-3.15 (dd, 1H), 2.97-2.91 (dd, 1H), 2.05 (s, 3H), 1.43 (s, 9H), 0.99-0.94 (m, 11H), 0.17-0.16 (m, 6H), 0.03-0.00 (m, 9H).

Example 32C (R)-tert-butyl 3-(5-((tert-butyldimethylsilyl)oxy)-2-((2-(trimethylsilyl)ethoxy)methoxy)phenyl)-2-hydroxypropanoate To a solution of Example 32B (9 g) in ethyl alcohol (280 mL) was added sodium ethanolate (6.3 mg) at 0° C. under nitrogen flow. After 15 minutes, the reaction mixture was stirred at 25° C. for 1 hour. The reaction was quenched with water and extracted with ethyl acetate three times. The combined organic layers were washed with brine twice, dried over anhydrous sodium sulfate, filtered and concentrated to give a residue which was purified by column chromatography on silica gel (petroleum ether:ethyl acetate=100:1 to 100:5) to give the title compound. $^1$H NMR (400 MHz, CDCl$_3$) δ ppm 6.96 (d, 1H), 6.70-6.63 (m, 2H), 5.18 (s, 2H), 4.36-4.31 (m, 1H), 3.79-3.75 (m, 2H), 3.04-2.90 (m, 3H), 1.43 (s, 9H), 0.99-0.95 (m, 1H), 0.17 (s, 6H), 0.04-0.01 (m, 9H).

Example 32D 4-chloro-5-(3,5-dichloro-4-methoxy-2,6-dimethylphenyl)thieno[2,3-d]pyrimidine To a suspension of Example 1E (25 g) in acetonitrile (300 mL) was added N-chlorosuccinimide (24 g) and HBF$_4$.Et$_2$O (29 g). The reaction mixture was stirred at 15° C. under nitrogen atmosphere for 16 hours. Another reaction was set up as above, and the two reaction mixtures were combined. The reaction mixture was diluted with water and extracted with ethyl acetate three times. The combined organic layers were dried over anhydrous sodium sulfate, filtered and concentrated. The residue was purified by column chromatography on silica gel (petroleum:ethyl acetate from 200:1 to 20:1) to give the title compound. $^1$H NMR (400 MHz, dimethylsulfoxide-d$_6$) δ ppm 9.01 (s, 1H), 8.02 (s, 1H), 3.88 (s, 3H), 2.01 (s, 6H).

Example 32E 4-chloro-5-(3,5-dichloro-4-methoxy-2,6-dimethyl-phenyl)-6-iodothieno[2,3-d]pyrimidine To a suspension of Example 32D (20 g) in tetrahydrofuran (200 mL) was added lithium diisopropylamide (38.1 mL, 2M) at −78° C. under nitrogen, and the reaction was stirred for 0.5 hours. Iodine (19.4 g) in tetrahydrofuran (100 mL) was added, and the reaction mixture was stirred at the same temperature for 0.5 hours. The reaction mixture was warmed to 15° C. under nitrogen atmosphere for 1 hour. Two other vials were set up as described above. The three reactions were combined, and the resulting mixture was treated with saturated aqueous sodium thiosulfate and extracted with ethyl acetate three times. The combined organic layers were dried over anhydrous sodium sulfate, filtered and concentrated. The crude material was purified by column chromatography on silica gel (petroleum ether:ethyl acetate from 100:1 to 40:1) to give the title compound. $^1$H NMR (400 MHz, dimethylsulfoxide-d$_6$) δ ppm 8.96 (s, 1H), 3.90 (s, 3H), 1.95 (s, 6H).

Example 32F 2,6-dichloro-4-(4-chloro-6-iodothieno[2,3-d]pyrimidin-5-yl)-3,5-dimethylphenol To a solution of Example 32E (7.5 g) in dichloroethane (100 mL) was added aluminum chloride (6.0 g) at 0° C. and heated at 68° C. for 6 hours. Two additional vials were set up as described above. The three reactions were combined, and the resulting mixture was quenched with saturated aqueous sodium bicarbonate and saturated aqueous ammonium chloride at 0° C. The mixture was extracted with ethyl acetate/tetrahydrofuran=1:1 three times, and the combined organic phases were washed with brine, dried over anhydrous magnesium sulfate, filtered and concentrated under vacuum. The residue was purified by column chromatography on silica gel (n-hexane/ethyl acetate/tetrahydrofuran=20:1:1 to 10:1:1) to give the title compound. $^1$H NMR (400 MHz, CDCl$_3$) δ ppm 8.85 (s, 1H), 6.23 (s, 1H), 2.00 (s, 6H).

Example 32G 2,6-dichloro-4-(4-chloro-6-(cyclopent-1-en-1-yl)thieno[2,3-d]pyrimidin-5-yl)-3,5-dimethylphenol To a suspension of Example 32F (2.3 g) and 2-(cyclopent-1-en-1-yl)-4,4,5,5-tetramethyl-1,3,2-dioxaborolane (1.3 g) in water (5 mL) and dioxane (50 mL) was added cesium carbonate (3 g) and tetrakis(triphenylphosphine)palladium (0) (0.535 g). The reaction mixture was heated to 80° C. under nitrogen atmosphere for 2 hours. The resulting mixture was diluted with water and extracted with ethyl acetate three times. The combined organic layers were washed with brine, dried over anhydrous sodium sulfate, filtered and concentrated under vacuum. The residue was purified by column chromatography on silica gel (n-hexane/ethyl acetate=100:1 to 15:1) to give the title compound. $^1$H NMR (400 MHz, dimethylsulfoxide-d$_6$) δ ppm 10.13 (br s, 1H), 8.71-9.01 (m, 1H), 6.10 (d, 1H), 2.39 (td, 2H), 2.08-2.17 (m, 2H), 1.94 (s, 6H), 1.80 (quin, 2H).

Example 32H (R)-5-(4-((1-(allyloxy)-3-(bis(4-methoxyphenyl)(phenyl)methoxy)propan-2-yl)oxy)-3,5-dichloro-2,6-dimethylphenyl)-4-chloro-6-(cyclopent-1-en-1-yl)thieno[2,3-d]pyrimidine To a suspension of Example 32G (6.6 g) and Example 1K (9.4 g) in tetrahydrofuran (80 mL) was added triphenylphosphine (8.1 g) and (E)-di-tert-butyl diazene-1,2-dicarboxylate (7.1 g) at 0° C. The reaction mixture was warmed to 25° C. and stirred for 12 hours. The reaction was concentrated to give a residue which was purified by column chromatography on silica gel (eluted with petroleum ether:ethyl acetate=94:6) to give the title compound. $^1$H NMR (400 MHz, CDCl$_3$) δ ppm 8.79 (s, 1H), 7.47 (d, 2H), 7.35 (d, 4H), 7.31-7.25 (m, 3H), 7.19 (dd, 2H), 6.87-6.77 (m, 5H), 5.95 (br s, 1H), 5.88-5.74 (m, 1H), 5.26-5.07 (m, 2H), 4.81-4.70 (m, 1H), 3.96 (d, 2H), 3.90-3.83 (m, 2H), 3.81-3.77 (m, 7H), 3.53 (d, 2H), 2.42-2.32 (m, 2H), 2.19 (br t, 2H), 2.01 (d, 6H), 1.89-1.77 (m, 3H).

Example 32I (R)-tert-butyl 2-((5-(4-(((R)-1-(allyloxy)-3-(bis(4-methoxyphenyl)(phenyl)methoxy)propan-2-yl)oxy)-3,5-dichloro-2,6-dimethylphenyl)-6-(cyclopent-1-en-1-yl)thieno[2,3-d]pyrimidin-4-yl)oxy)-3-(5-((tert-butyldimethylsilyl)oxy)-2-((2-(trimethylsilyl)ethoxy)methoxy)phenyl)propanoate To a suspension of Example 32H (4.8 g) and Example 32C (3.3 g) in tert-butanol (60 mL) was added cesium carbonate (6.6 g) at 25° C. under nitrogen flow. The reaction mixture was stirred at 65° C. for 16 hours. The reaction was quenched with water and extracted with ethyl acetate three times. The combined organic layers were washed with brine twice, dried over anhydrous sodium sulfate, filtered and concentrated to give a residue which was purified by column chromatography on silica gel (eluted with petroleum ether:ethyl acetate=95:5) to give the title compound which was used to the next step without further purification.

Example 32J (R)-tert-butyl 2-((5-(4-(((S)-1-(allyloxy))-3-hydroxypropan-2-yl)oxy)-3,5-dichloro-2,6-dimethylphenyl)-6-(cyclopent-1-en-1-yl)thieno[2,3-d]pyrimidin-4-yl)oxy)-3-(5-((tert-butyldimethylsilyl)oxy)-2-((2-(trimethylsilyl)ethoxy)methoxy)phenyl)propanoate To a solution of Example 32I (3.5 g) in methanol (25 mL) and dichloromethane (25 mL) was added formic acid (4.1 mL) at 0° C. The reaction was stirred at 25° C. for 16 hours. Three additional vials were set up as described above, and all the four reaction mixtures were combined. The combined mixture was poured into saturated aqueous sodium bicarbonate solution at 0° C. and extracted with ethyl acetate three times. The combined organic phases were washed with brine twice, dried over anhydrous sodium sulfate, filtered and concentrated to get the crude product. The crude product was purified by column chromatography on silica gel (eluted with petroleum ether:ethyl acetate=97:3 to 90:10) to give the title compound. ¹H NMR (400 MHz, CDCl₃) δ ppm 8.48 (s, 1H), 7.35-7.24 (m, 2H), 7.21-7.14 (m, 1H), 6.91 (d, 1H), 6.87-6.79 (m, 1H), 6.61 (dd, 1H), 6.38 (d, 1H), 5.94-5.77 (m, 2H), 5.34 (t, 1H), 5.23 (dd, 1H), 5.19-5.09 (m, 3H), 4.59-4.50 (m, 1H), 4.04-3.93 (m, 3H), 3.92-3.79 (n, 5H), 3.78-3.70 (m, 5H), 2.58 (d, 2H), 2.51 (dd, 1H), 2.45-2.36 (m, 2H), 2.27-2.15 (m, 5H), 2.00 (s, 3H), 1.92-1.80 (m, 5H), 1.27 (s, 11H), 1.02-0.82 (m, 14H), 0.10 (d, 6H), 0.01 (s, 9H).

Example 32K (R)-tert-butyl 2-((5-(4-(((R)-1-(allyloxy)-3-(tosyloxy)propan-2-yl)oxy)-3,5-dichloro-2,6-dimethylphenyl)-6-(cyclopent-1-en-1-yl)thieno[2,3-d]pyrimidin-4-yl)oxy)-3-(5-(((tert-butyldimethylsilyl)oxy)-2-((2-(trimethylsilyl)ethoxy)methoxy)phenyl)propanoate To a solution of Example 32J (4.6 g) and triethylamine (2.6 mL) in dichloromethane (100 mL) was added para-toluenesulfonyl chloride (2.6 g) at 0° C., and the reaction was stirred at 25° C. for 40 hours. One additional vial was set up as described above. Both of the two mixtures were combined and poured into water and extracted with dichloromethane three times. The combined organic phases were washed with brine twice, dried over anhydrous magnesium sulfate, filtered and concentrated under reduced pressure to afford the crude product which was purified by column chromatography on silica gel (eluted with petroleum ether:ethyl acetate=97:3 to 90:10) to give the title compound. ¹H NMR (400 MHz, CDCl₃) δ ppm 8.47 (s, 1H), 7.81 (d, 2H), 7.34 (d, 2H), 6.92 (d, 1H), 6.61 (dd, 1H), 6.39 (d, 1H), 5.91 (br s, 1H), 5.82-5.67 (m, 1H), 5.35-5.27 (m, 1H), 5.21-5.06 (m, 4H), 4.67-4.57 (m, 1H), 4.51-4.37 (m, 2H), 4.14 (q, 1H), 3.94-3.79 (m, 3H), 3.78-3.66 (m, 4H), 2.62-2.49 (m, 2H), 2.46-2.37 (m, 5H), 2.23 (br t, 2H), 2.16 (s, 3H), 1.99 (s, 3H), 1.92-1.81 (m, 2H), 1.33-1.15 (m, 12H), 0.93 (s, 11H), 0.10 (d, 6H), 0.00 (s, 9H).

Example 32L (R)-tert-butyl 2-((5-(4-(((R)-1-(allyloxy)-3-(tosyloxy)propan-2-yl)oxy)-3,5-dichloro-2,6-dimethylphenyl)-6-(cyclopent-1-en-1-yl)thieno[2,3-d]pyrimidin-4-yl)oxy)-3-(5-hydroxy-2-((2-(trimethylsilyl)ethoxy)methoxy)phenyl)propanoate To a solution of Example 32K (4.6 g) in dichloromethane (46 mL) was added tetra-N-butylammonium fluoride (5.2 mL, 1M) at 0° C. After the addition, the reaction was stirred at 25° C. for 16 hours under nitrogen atmosphere. One additional vial was set up as described above. Both of the two mixtures were combined, poured into water and extracted with ethyl acetate three times. The combined organic layers were washed with brine twice, dried over anhydrous sodium sulfate, filtered and concentrated to give a residue which was purified by column chromatography on silica gel (petroleum ether:ethyl acetate=100:1 to 100:5) to give the title compound. ¹H NMR (400 MHz, CDCl₃) δ ppm 8.47 (s, 1H), 7.80 (d, 2H), 7.34 (d, 2H), 6.92 (d 1H), 6.65 (dd, 1H), 6.02 (d, 1H), 5.89 (br s, 1H), 5.83-5.68 (m, 1H), 5.39 (dd, 1H), 5.22-5.09 (m, 5H), 4.70 (t, 1H), 4.51-4.41 (m, 2H), 3.98-3.67 (m, 7H), 2.83 (dd, 1H), 2.49-2.34 (m, 6H), 2.28-2.15 (m, 5H), 2.00-1.81 (m, 5H), 1.33 (s, 10H), 0.99-0.91 (m, 2H), 0.04-0.03 (m, 9H).

Example 32M tert-butyl (7R,16R)-19,23-dichloro-1-(cyclopent-1-en-1-yl)-20,22-dimethyl-16-{[(prop-2-en-1-yl)oxy]methyl}-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate To a solution of Example 32L (3.6 g) in dimethylformamide (40 mL) was added cesium carbonate (5.6 g) at 0° C., and the reaction was stirred at 25° C. for 16 hours under nitrogen atmosphere. One additional vial was set up as described above. Both of the mixtures were combined, quenched with water and extracted with ethyl acetate three times. The combined organic layers were washed with brine twice, dried over anhydrous sodium sulfate, filtered and concentrated to give a residue which was purified by column chromatography on silica gel (petroleum ether:ethyl acetate=100:1 to 100:5) to give the title compound. ¹H NMR (400 MHz, CDCl₃) δ ppm 8.55 (s, 1H), 6.95 (d, 1H), 6.74 (dd, 1H), 6.03-5.90 (m, 1H), 5.87 (dd, 1H), 5.79-5.67 (m, 2H), 5.34 (qd, 1H), 5.28-5.20 (m, 1H), 5.15 (s, 2H), 5.03-4.92 (m, 1H), 4.68 (dd, 1H), 4.37-4.29 (m, 1H), 4.21-4.06 (m, 2H), 3.91-3.70 (m, 4H), 3.49 (dd, 1H), 2.87-2.77 (m, 1H), 2.35 (dt, 2H), 2.13 (s, 3H), 2.09-1.99 (m, 5H), 1.79 (m, 2H), 1.13 (s, 10H), 0.01-0.00 (m, 9H).

Example 32N tert-butyl (7R,16R)-19,23-dichloro-1-(cyclopent-1-en-1-yl)-16-(hydroxymethyl)-20,22-dimethyl-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate To a degassed solution of Example 32M (2.3 g) in tetrahydrofuran (50 mL) and methanol (50 mL) under nitrogen atmosphere was added 1,3-dimethylpyrimidine-2,4,6,(1H,3H,5H)-trione (2.5 g) and tetrakis(triphenylphosphine)palladium(0) (2.3 g), and the reaction was stirred at 30° C. for 18 hours. One additional vial was set up as described above. Both of the mixtures were combined, poured into water and extracted with ethyl acetate three times. The combined organic phases were washed with brine twice, dried over anhydrous magnesium sulfate, filtered and concentrated under reduced pressure to afford the crude product which was purified by column chromatography on silica gel (eluted with petroleum ether:ethyl acetate=100:6 to 100:10) to give the title compound which was used in the next step directly.

Example 32O tert-butyl (7R,16S)-19,23-dichloro-1-(cyclopent-1-en-1-yl)-20,22-dimethyl-16-{[(4-methylbenzene-1-sulfonyl)oxy]methyl}-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate To a solution of Example 32N (1.3 g) and triethylamine (1.1 mL) in dichloromethane (50 mL) was added toluenesulfonyl chloride (1.2 g) under nitrogen atmosphere at 0° C., and the reaction was stirred at 25° C. for 12 hours. Three additional vials were set up as described above. The mixtures were combined, quenched with water and extracted with ethyl acetate three times. The combined organic layers were washed with brine twice, dried over anhydrous sodium sulfate, filtered and concentrated to give a residue which was purified by column chromatography on silica gel (petroleum ether:ethyl acetate=100:1 to 100:5) to give the title compound. $^1$H NMR (400 MHz, CDCl$_3$) δ ppm 8.55 (s, 1H), 7.86 (d, 2H), 7.37 (d, 2H), 6.96 (d, 1H) 6.69 (dd, 1H), 5.81 (dd, 1H), 5.76-5.68 (m, 2H), 5.15 (s, 2H), 5.03-4.87 (m, 1H), 4.58 (dd, 1H), 4.46-4.36 (m, 2H), 4.20 (d, 1H), 3.76 (t, 3H), 3.41 (dd, 1H), 2.84 (br d, 1H), 2.47 (s, 3H), 2.36 (br s, 2H), 2.13 (s, 3H), 1.98 (s, 5H), 1.90-1.73 (m, 3H), 1.29 (br d, 2H), 1.14 (s, 9H), 1.00-0.92 (m, 3H), 0.00 (s, 9H).

Example 32P tert-butyl (7R,16R)-19,23-dichloro-1-(cyclopent-1-en-1-yl)-20,22-dimethyl-16-[(4-methylpiperazin-1-yl)methyl]-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate To a solution of Example 32O (1.6 g) in N,N-dimethylformamide (16 mL) was added 1-methylpiperazine (16 mL) under nitrogen atmosphere at 0° C., and the reaction was stirred at 55° C. for 12 hours. Two other vials were set up as described above. The three reaction mixtures were combined and concentrated to a residue. The residue was dissolved in ethyl acetate and washed with brine twice. The organic phase was dried over anhydrous magnesium sulfate, filtered and concentrated to give the crude product. The crude product was purified by column chromatography on silica gel (eluted with petroleum ether:ethyl acetate=1:1) to provide the title compound.

Example 32Q tert-butyl (7R,16R)-19,23-dichloro-1-(cyclopent-1-en-1-yl)-10-hydroxy-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate To a solution of Example 32P (2.1 g) in dichloromethane (75 mL) was added HCl (1.1 mL, 1 M in methanol) under nitrogen atmosphere at 0° C., and the reaction was stirred at 25° C. for 2 hours. Two additional vials were set up as described above. The three reaction mixtures were combined, quenched with saturated aqueous sodium bicarbonate solution at 0° C. and extracted with ethyl acetate three times. The combined organic layers were washed with brine twice, dried over anhydrous sodium sulfate, filtered and concentrated to give the title compound. $^1$H NMR (400 MHz, CDCl$_3$) δ ppm 8.57 (s, 1H), 6.76-6.61 (m, 2H), 5.94 (dd, 1H), 5.73 (br s, 1H), 5.64 (d, 1H), 4.89 (q, 1H), 4.67-4.52 (m, 1H), 4.31 (br d, 1H), 3.66-3.49 (m, 1H), 2.91 (dd, 1H), 2.83-2.67 (m, 3H), 2.66-2.43 (m, 6H), 2.43-2.27 (m, 5H), 2.17-1.99 (m, 8H), 1.81 (m, 2H), 1.11 (s, 9H).

Example 32R (2-((1r,4r)-4-((1,4-dioxan-2-yl)methoxy)cyclohexyl) pyrimidin-4-yl)methanol To a stirred solution of Example 9C (750 mg) in tetrahydrofuran (10 mL) at room temperature was added cesium fluoride (2 g) and methanol (3 mL), and reaction was stirred for 3 days. The reaction was diluted with ethyl acetate, washed with water and brine, dried over anhydrous sodium sulfate, filtered and concentrated. The crude product was purified by normal phase silica gel chromatography eluting with 30% ethyl acetate in dichloromethane, then 5% 7N ammonia in methanol in dichloromethane to give the title compound as a mixture of isomers. $^1$H NMR (500 MHz, CDCl$_3$) δ ppm 8.60 (d, 1H), 7.09 (d, 1H), 4.77-4.66 (m, 2H), 3.86-3.67 (m, 5H), 3.66-3.57 (m, 2H), 3.53 (dd, 1H), 3.49-3.39 (m, 2H), 3.37-3.26 (m, 1H), 2.93-2.82 (m, 1H), 2.23-2.13 (m, 2H), 2.12-2.05 (m, 2H), 1.76-1.61 (m, 2H), 1.48-1.35 (m, 2H).

Example 32S tert-butyl (7R,16R)-19,23-dichloro-1-(cyclopent-1-en-1-yl)-10-[(2-{((1r,4r)-4-[(1,4-dioxan-2-yl) methoxy]cyclohexyl}pyrimidin-4-yl)methoxy]-20, 22-dimethyl-16-[(4-methylpiperazin-1-yl)methyl]-7, 8,15,16-tetrahydro-18,21-etheno-13,9-(metheno)-6, 14,17-trioxa-2-thia-3,5-diazacyclononadeca[1,2,3-cd]indene-7-carboxylate A vial containing Example 32R (47 mg), Example 32Q (40 mg), triphenylphosphine (40 mg) and N,N,N',N'-tetramethylazodicarboxamide (26 mg) in toluene (130 μL) and tetrahydrofuran (130 L) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 0-10% methanol in dichloromethane to give the title compound as a mixture of diastereomers.

Example 32T (7R,16R)-19,23-dichloro-1-(cyclopent-1-en-1-yl)-10-[(2-{(1r,4r)-4-[(1,4-dioxan-2-yl)methoxy] cyclohexyl}pyrimidin-4-yl)methoxy]-20,22-dimethyl-16-[(4-methylpiperazin-1-yl)methyl]-7,8,15, 16-tetrahydro-18,21-etheno-13,9-(metheno)-6,14,17-trioxa-2-thia-3,5-diazacyclononadeca[1,2,3-cd] indene-7-carboxylic acid To a solution of Example 32S (48 mg) in dichloromethane (230 μL) was added trifluoroacetic acid (230 μL), and the reaction was allowed to stir overnight. The reaction was concentrated under a stream of nitrogen and was taken up in water and acetonitrile. The mixture was purified by RP-HPLC on a Gilson PLC 2020 using a Luna™ column (250×50 mm, 10 mm, 5-85% over 30 minutes with acetonitrile in water containing 10 mM ammonium acetate) to give the title compound after lyophilization. $^1$H NMR (400 MHz, dimethylsulfoxide-d$_6$) δ ppm 8.69 (d, 1H), 8.64 (s, 1H), 7.40 (d, 1H), 6.82 (d, 1H), 6.77-6.69 (m, 1H), 6.24-6.15 (m, 1H), 5.85-5.80 (m, 1H), 5.79-5.72 (m, 1H), 5.16-4.98 (m, 2H), 4.94-4.80 (m, 1H), 4.56-4.39 (m, 2H), 3.75-3.66 (m, 2H), 3.65-3.19 (m, 12H), 2.92-2.61 (m, 6H), 2.45 (br s, 4H), 2.36-2.26 (m, 2H), 2.22 (s, 3H), 2.10-1.83 (m, 10H), 1.80-1.67 (m, 2H), 1.65-1.50 (m, 2H), 1.36-1.15 (m, 2H). MS (ESI) m/z 1013.0 (M−H)$^-$.

Example 33

(7R,16R)-19,23-dichloro-1-(cyclopent-1-en-1-yl)-10-({2-[(1R,4s)-4-({[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 33A tert-butyl (7R,16R)-19,23-dichloro-1-(cyclopent-1-en-1-yl)-10-({2-[(1R,4s)-4-({[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 28F (52 mg), Example 32Q (40 mg), triphenylphosphine (40 mg) and N,N,N',N'-tetramethylazodicarboxamide (26 mg) in toluene (130 μL) and tetrahydrofuran (130 μL) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 1-10% methanol in dichloromethane to give the title compound.

Example 33B (7R,16R)-19,23-dichloro-1-(cyclopent-1-en-1-yl)-10-({2-[(1R,4s)-4-({[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,815,16-tetrahydro-18,21-etheno-13,9-(metheno)-6,14,17-trioxa-2-thia-3,5-diazacyclononadeca[1,2,3-cd]indene-7-carboxylic acid To a solution of Example 33A (46 mg) in dichloromethane (210 μL) was added trifluoroacetic acid (210 μL), and the reaction was allowed to stir overnight. The reaction was concentrated under a stream of nitrogen and was taken up in water and acetonitrile. The mixture was purified by RP-HPLC on a Gilson PLC 2020 using a Luna® column (250×50 mm, 10 mm, 5-85% over 30 min with acetonitrile in water containing 10 mM ammonium acetate) to give the title compound after lyophilization. $^1$H NMR (500 MHz, dimethylsulfoxide-$d_6$) δ ppm 8.70 (d, 1H), 8.64 (s, 1H), 7.42 (d, 1H), 6.82 (d, 1H), 6.75-6.69 (m, 1H), 6.23-6.15 (m, 1H), 5.86-5.81 (m, 1H), 5.79-5.73 (m, 1H), 5.18-5.01 (m, 2H), 4.92-4.85 (m, 1H), 4.55-4.43 (m, 2H), 3.75-3.35 (m, 10H), 3.31-3.21 (m, 1H), 2.91-2.60 (m, 6H), 2.44 (br s, 6H), 2.36-2.25 (m, 2H), 2.21 (s, 3H), 2.03 (s, 3H), 1.98-1.66 (m, 9H), 1.66-1.42 (m, 4H). MS (ESI) m/z 1044.9 (M−H)$^-$.

Example 34

(7R,16R)-19,23-dichloro-1-(cyclopent-1-en-1-yl)-10-({2-[(4S)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 34A tert-butyl (7R,16R)-19,23-dichloro-1-(cyclopent-1-en-1-yl)-10-({2-[(4S)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 40A (52 mg). Example 32Q (40 mg), triphenylphosphine (40 mg) and N,N,N',N'-tetramethylazodicarboxamide (26 mg) in toluene (130 μL) and tetrahydrofuran (130 μL) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 1-8.5% methanol in dichloromethane to give the title compound.

Example 34B (7R,16R)-19,23-dichloro-1-(cyclopent-1-en-1-yl)-10-({2-[(4S)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 34A (47 mg) in dichloromethane (210 μL) was added trifluoroacetic acid (210 μL), and the reaction was allowed to stir overnight. The reaction was concentrated under a stream of nitrogen and was taken up in water and acetonitrile. The mixture was purified by RP-HPLC on a Gilson PLC 2020 using a Luna™ column (250×50 mm, 10 mm, 10-95% over 30 minutes with acetonitrile in water containing 10 mM ammonium acetate) to give the title compound after lyophilization. $^1$H NMR (500 MHz, dimethylsulfoxide-$d_6$) δ ppm 8.72 (d, 1H), 8.63 (s, 1H), 7.40 (d, 1H), 7.16-7.08 (m, 1H), 6.84-6.78 (m, 1H), 6.74-6.68 (m, 1H), 6.23-6.15 (m, 1H), 5.86-5.81 (m, 1H), 5.79-5.73 (m, 1H), 5.19-5.02 (m, 2H), 4.90-4.84 (m, 1H), 4.54-4.43 (m, 2H), 3.76-3.35 (m, 12H), 3.32-3.25 (m, 1H), 2.91-2.81 (m, 1H), 2.76-2.61 (m, 4H), 2.48-2.26 (m, 8H), 2.20 (s, 3H), 2.07-1.66 (m, 14H). MS (ESI) m/z 1045.1 (M−H)$^-$.

Example 35

(7R,16R)-19,23-dichloro-1-(cyclopent-1-en-1-yl)-10-({2-[(4S)-4-({[(2S)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 35A tert-butyl (7R,16R)-19,23-dichloro-1-(cyclopent-1-en-1-yl)-10-({2-[(4S)-4-({[(2)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 45A (52 mg), Example 32Q (40 mg), triphenylphosphine (40 mg) and N,N,N',N'-tetramethylazodicarboxamide (26 mg) in toluene (130 μL) and tetrahydrofuran (130 μL) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 0.5-9% methanol in dichloromethane to give the title compound.

Example 35B (7R,16R)-19,23-dichloro-1-(cyclopent-1-en-1-yl)-10-({2-[(4S)-4-({[(2S)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 35A (50 mg) in dichloromethane (230 μL) was added trifluoroacetic acid (230 μL), and the reaction was allowed to stir overnight. The reaction was concentrated under a stream of nitrogen and was taken up in water and acetonitrile. The mixture was purified by RP-HPLC on a Gilson PLC 2020 using a Luna™ column (250×50 mm, 10 mm, 10-95% over 30 minutes with acetonitrile in water containing 10 mM ammonium acetate) to give the title compound after lyophilization. $^1$H NMR (500 MHz, dimethylsulfoxide-d$_6$) δ ppm 8.73 (d, 1H), 8.65 (s, 1H), 7.39 (d, 1H), 7.16-7.08 (m, 1H), 6.83 (d, 1H), 6.77-6.70 (m, 1H), 6.25-6.19 (m, 1H), 5.84-5.79 (m, 1H), 5.78-5.75 (m, 1H), 5.20-5.04 (m, 2H), 4.90-4.81 (m, 1H), 4.54-4.43 (m, 2H), 3.75-3.39 (m, 12H), 3.32-3.25 (m, 1H), 2.92-2.84 (m, 1H), 2.76-2.61 (m, 4H), 2.48-2.26 (m, 8H), 2.22 (s, 3H), 2.06-1.68 (m, 14H). MS (ESI) m/z 1043.0 (M–H)$^-$.

Example 36

(7R,16R)-19,23-dichloro-10-({2-[6-({[(2S)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 36A (S)—N-((1,4-dioxan-2-yl)methyl)-5-(4,4,5,5-tetramethyl-1,3,2-dioxaborolan-2-yl)pyridin-2-amine 2-Fluoro-5-(4,4,5,5-tetramethyl-1,3,2-dioxaborolan-2-yl)pyridine (325 mg) was dissolved in dimethylsulfoxide (5 mL). (S)-(1,4-Dioxan-2-yl)methanamine hydrochloride (246 mg) was added, followed by N-ethyl-N-isopropylpropan-2-amine (753 mg). The solution was heated to 120° C. for six hours and was cooled. The solution was added to water (15 mL) and brine (3 mL). The solution was extracted with dichloromethane (20 mL) three times. The extracts were combined, dried on anhydrous sodium sulfate, filtered, and concentrated. The residue was purified by flash column chromatography on silica gel using a 0% to 10% gradient of methanol in dichloromethane. $^1$H NMR (500 MHz, dimethylsulfoxide-d$_6$) δ ppm 8.22 (d, 1H), 7.52 (dd, 1H), 6.95 (t, 1H), 6.47 (d, 1H), 3.73 (dd, 2H), 3.66-3.61 (m, 2H), 3.55 (td, 1H), 3.46 (td, 1H), 3.31 (m, 2H), 3.23 (dd, 1H), 1.31 (s, 3H), 1.25 (s, 6H), 1.07 (s, 3H). MS (ESI) m/z 321.3 (M+H)$^+$, 319.1 (M–H)$^-$.

Example 36B (S)-(2-(6-(((1,4-dioxan-2-yl)methyl)amino)pyridin-3-yl)pyrimidin-4-yl)methanol The title compound was prepared by substituting Example 36A for Example 2A in Example 2B. $^1$H NMR (500 MHz, dimethylsulfoxide-d$_6$) δ ppm 8.99 (d, 1H), 8.75 (d, 1H), 8.26 (dd, 1H), 7.34 (d, 1H), 7.13 (t, 1H), 6.61 (d, 1H), 5.60 (t, 1H), 4.57 (d, 2H), 3.76 (td, 2H), 3.72-3.63 (m, 2H), 3.58 (td, 1H), 3.48 (td, 1H), 3.38 (m, 2H), 3.27 (m, 1H). MS (ESI) m/z 303.1 (M+H)$^+$.

Example 36C tert-butyl (7R,16R)-19,23-dichloro-10-({2-[6-({[(2S)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 36B for Example 7B in Example 7C. MS (ESI) min 1095.4 (M+H)$^+$.

Example 36D (7R,16R)-19,23-dichloro-10-({2-[6-({[(2S)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 36C for Example 7C in Example 7D. $^1$H NMR (500 MHz, dimethylsulfoxide-$d_6$) δ ppm 9.00 (s, 1H), 8.75 (s, 2H), 8.26 (dd, 1H), 7.36 (d, 1H), 7.24-7.11 (m, 5H), 6.87 (d, 1H), 6.75 (m, 1H), 6.62 (m, 1H), 6.24 (m, 1H), 5.80 (s, 1H), 5.17 (q, 2H), 4.85 (m, 1H), 4.45 (m, 2H), 3.78-3.72 (m, 2H), 3.68-3.59 (m, 4H), 3.58-3.53 (m, 2H), 3.51-3.45 (m, 2H), 2.98 (d, 2H), 2.72-2.62 (m, 3H), 2.50-2.32 (m, 6H), 2.18 (s, 3H), 2.00 (s, 3H), 1.95 (s, 3H). MS (ESI) m/z 1037.5 $(M+H)^+$.

Example 37

(7R,16R)-19,23-dichloro-1-(cyclopent-1-en-1-yl)-10-({2-[(1S,4r)-4-({[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 37A tert-butyl (7R,16R)-19,23-dichloro-1-(cyclopent-1-en-1-yl)-10-({2-[(1S,4r)-4-({[(2S)-1,4-dioxan-2-yl]methoxy}methyl)-4-fluorocyclohexyl]pyrimidin-4-yl}methoxy)-20,22-dimethyl-6-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 28G (33 mg), Example 32Q (30 mg), triphenylphosphine (25 mg) and N,N,N',N'-tetramethylazodicarboxamide (17 mg) in toluene (100 μL) and tetrahydrofuran (100 μL) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 12 g gold silica gel column eluting with 0-9% methanol in dichloromethane to give the title compound.

Example 37B (7R,16R)-19,23-dichloro-1-(cyclopent-1-en-1-yl)-10-({2-[(1S,4r)-4-{[(2S)-1,4-dioxan-2-yl]methoxy}methyl)-4-fluorocyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 37A (21 mg) in dichloromethane (100 μL) was added trifluoroacetic acid (100 μL), and the reaction was allowed to stir overnight. The reaction was concentrated under a stream of nitrogen and was taken up in water and acetonitrile. The mixture was purified by RP-HPLC on a Gilson PLC 2020 using a Lunar® column (250×50 mm, 10 mm, 30-80% over 30 minutes with acetonitrile in water containing 10 mM ammonium acetate) to give the title compound after lyophilization. $^1$H NMR (400 MHz, dimethylsulfoxide-$d_6$) δ ppm 8.71 (d, 1H), 8.63 (s, 1H), 7.43 (d, 1H), 6.83 (d, 1H), 6.77-6.64 (m, 1H), 6.23-6.13 (m, 1H), 5.89-5.80 (m, 1H), 5.79-5.72 (m, 1H), 5.19-5.00 (m, 2H), 4.96-4.82 (m, 1H), 4.58-4.37 (m, 2H), 3.74-3.21 (m, 12H), 3.04-2.92 (m, 1H), 2.91-2.81 (m, 1H), 2.78-2.61 (m, 2H), 2.41 (br s, 6H), 2.35-2.26 (m, 2H), 2.21 (s, 3H), 2.03 (s, 3H), 2.00-1.58 (m, 12H). MS (ESI) m/z 1045.1 $(M-H)^-$.

Example 38

(7R,16R)-19,23-dichloro-1-(cyclopent-1-en-1-yl)-10-({2-[(4R)-4-({[(2S)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 38A tert-butyl (7R,16R)-19,23-dichloro-1-(cyclopent-1-en-1-yl)-10-({2-[(4R)-4-({[(2S)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 42A (52 mg), Example 32Q (40 mg), triphenylphosphine (40 mg) and N,N,N',N'-tetramethylazodicarboxamide (26 mg) in toluene (130 μL) and tetrahydrofuran (130 μL) was allowed to stir at 50° C. overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 0.5-8.5% methanol in dichloromethane to give the title compound.

Example 38B (7R,16R)-19,23-dichloro-1-(cyclopent-1-en-1-yl)-10-({2-[(4R)-4-({[(2S)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 38A (49 mg) in dichloromethane (220 μL) was added trifluoroacetic acid (220 μL), and the reaction was allowed to stir overnight. The reaction was concentrated under a stream of nitrogen and was taken up in water and acetonitrile. The mixture was purified by RP-HPLC on a Gilson PLC 2020 using a Luna™ column (250×50 mm, 10 mm, 30-80% over 30 minutes with acetonitrile in water containing 10 mM ammonium acetate) to give the title compound after lyophilization. $^1$H NMR (500 MHz, dimethylsulfoxide-$d_6$) δ ppm 8.72 (d, 1H), 8.64 (s, 1H), 7.40 (d, 1H), 7.16-7.08 (m, 1H), 6.81 (d, 1H), 6.76-6.68 (m, 1H), 6.23-6.13 (m, 1H), 5.86-5.81 (m, 1H), 5.79-5.73 (m, 1H), 5.20-5.02 (m, 2H), 4.91-4.82 (m, 1H), 4.56-4.40 (m, 2H), 3.78-3.38 (m, 12H), 3.33-3.24 (m, 1H), 2.92-2.81 (m, 1H), 2.78-2.62 (m, 4H), 2.60-2.25 (m, 8H), 2.19 (s, 3H), 2.09-1.65 (m, 14H). MS (ESI) m/z 1042.9 $(M-H)^-$.

Example 39

(7R,16R)-19,23-dichloro-10-({2-[(1S,4s)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 39A 8-methylene-1,4-dioxaspiro[4.5]decane

To a solution of methyltriphenylphosphonium bromide (68.6 g) in tetrahydrofuran (200 mL) was added n-butyllithium (77 mL, 2.5 M in tetrahydrofuran) at −78° C. The reaction mixture was stirred for 10 minutes at −78° C. 30 minutes at 0° C. and cooled to −78° C. A solution of 1,4-dioxaspiro[4.5]decan-8-one (50 g) in tetrahydrofuran (200 mL) was added. The reaction mixture was stirred for 16 hours at 25° C. and filtered. The filtrate was concentrated. The residue was purified by column chromatography on silica gel (eluted with petroleum ether:ethyl acetate=5:1) to provide the title compound. $^1$H NMR (400 MHz, CDCl$_3$) δ ppm 4.67 (s, 2H), 3.97 (s, 4H), 2.31-2.27 (m, 4H), 1.72-1.64 (m, 3H).

Example 39B 8-(bromomethyl)-8-fluoro-1,4-dioxaspiro[4.5]decane

To a mixture of Example 39A (10 g) and 1-bromopyrrolidine-2,5-dione (13.85 g) in dichloromethane (150 mL) was added triethylamine trihydrofluoride (15.68 g) at 0° C. The reaction mixture was stirred at 20° C. for 2 hours, poured into saturated aqueous sodium bicarbonate solution (500 mL) and extracted with dichloromethane (500 mL). The combined organic extracts were washed with 0.1M aqueous HCl (2×200 mL) and 5% aqueous sodium hydrogen carbonate solution (2×200 mL), dried over MgSO$_4$, filtered, and concentrated. The residue was purified by column chromatography on silica gel (eluted with petroleum ether:ethyl acetate=3:1) to provide the title compound. $^1$H NMR (400 MHz, CDCl$_3$) δ ppm 3.99-3.92 (m, 4H), 3.48 (d, 2H), 2.10-2.05 (m, 2H), 1.91-1.64 (m, 6H).

Example 39C (8-fluoro-1,4-dioxaspiro[4.5]decan-8-yl)methyl acetate

To a mixture of Example 39B (10 g) and potassium iodide (0.656 g) in dimethylformamide (100 mL) was added potassium acetate (38.8 g) at 25° C. The mixture was heated at 135° C. for 16 hours, cooled, poured into water and extracted with ethyl acetate. The combined organic layer was washed with brine (2×100 mL). The organic phase was dried over sodium sulfate, filtered, and concentrated. The residue was purified by column chromatography on silica gel (eluted with petroleum ether:ethyl acetate=3:1 to 1:1) to provide the title compound. $^1$H NMR (400 MHz, CDCl$_3$) δ ppm 4.11 (d, 2H), 3.99-3.93 (m, 4H), 2.10 (s, 3H), 1.97-1.63 (m, 8H).

Example 39D (8-fluoro-1,4-dioxaspiro[4.5]decan-8-yl)methanol

To a solution of Example 39C (25 g) in tetrahydrofuran (200 mL) and water (100 mL) was added lithium hydroxide monohydrate (6.78 g) at 0° C. The reaction mixture was stirred for 16 hours at 25° C., poured into H$_2$O (500 mL) and extracted with ethyl acetate (3×500 mL). The combined organic phase was washed with brine (2×100 mL). The organic layers were combined, dried over magnesium sulfate, filtered, and concentrated. The residue was purified by column chromatography on silica gel (eluted with petroleum ether:ethyl acetate=3:1) to provide the title compound. $^1$H NMR (400 MHz, CDCl$_3$) δ ppm 3.99-3.93 (m, 4H), 3.64-3.57 (m, 2H), 2.03-2.01 (m, 2H), 1.89-1.86 (m, 3H), 1.68-1.63 (m, 4H).

Example 39E (R)-8-(((1,4-dioxan-2-yl)methoxy)methyl)-8-fluoro-1,4-dioxaspiro[4.5]decane The title compound was prepared as described in Example 28A by replacing (S)-(1,4-dioxan-2-yl)methyl 4-methylbenzenesulfonate with (R)-(1,4-dioxan-2-yl)methyl 4-methylbenzenesulfonate. $^1$H NMR (400 MHz, CDCl$_3$) δ ppm 4.01-3.89 (m, 4H), 3.84-3.67 (m, 5H), 3.65-3.38 (m, 6H), 2.03-1.83 (m, 4H), 1.80-1.57 (m, 4H).

Example 39F (R)-4-(((1,4-dioxan-2-yl)methoxy)methyl)-4-fluorocyclohexanone

The title compound was prepared as described in Example 28B by replacing Example 28A with Example 39E. $^1$H NMR (400 MHz, CDCl$_3$) δ ppm 3.89-3.29 (m, 11H), 2.67 (dt, 2H), 2.41-2.20 (m, 4H), 2.04-1.75 (m, 2H).

Example 39G 4-((((R)-1,4-dioxan-2-yl)methoxy)methyl)-4-fluorocyclohex-1-en-1-yl trifluoromethanesulfonate The title compound was prepared as described in Example 28C by replacing Example 28B with Example 39F. $^1$H NMR (400 MHz, CDCl$_3$) δ ppm 5.67 (br s, 1H), 3.87-3.32 (m, 11H), 2.68-2.26 (m, 4H), 2.16-2.06 (m, 1H), 1.99-1.78 (m, 1H).

Example 39H 2-(4-((((R)-1,4-dioxan-2-yl)methoxy)methyl)-4-fluorocyclohex-1-en-1-yl)-4,4,5,5-tetramethyl-1,3,2-dioxaborolane The title compound was prepared as described in Example 28D by replacing Example 28C with Example 39G. $^1$H NMR (400 MHz, CDCl$_3$) δ ppm 6.43 (br d, 1H), 3.84-3.38 (m, 11H), 2.42-2.12 (m, 4H), 1.97-1.83 (m, 1H), 1.82-1.57 (m, 1H), 1.26 (s, 17H).

Example 39I (2-(4-((((R)-1,4-dioxan-2-yl)methoxy)methyl)-4-fluorocyclohex-1-en-1-yl)pyrimidin-4-yl)methanol The title compound was prepared as described in Example 28E by replacing Example 28D with Example 39H. $^1$H NMR (400 MHz, CDCl$_3$) δ ppm 8.63 (d, 1H), 7.21 (br s, 1H), 7.07 (d, 1H), 4.73 (s, 2H), 3.87-3.39 (m, 11H), 2.78 (br d, 2H), 2.70-2.45 (m, 2H), 2.20-2.08 (m, 1H), 1.99-1.80 (m, 1H).

Example 39J (2-((1R,4S)-4-((((R)-1,4-dioxan-2-yl)methoxy) methyl)-4-fluorocyclohexyl)pyrimidin-4-yl)methanol The title compound was prepared as described in Example 28F by replacing Example 28E with Example 39I. $^1$H NMR (400 MHz, CDCl$_3$) δ ppm 8.63 (d, 1H), 7.10 (d, 1H), 4.74 (d, 2H), 3.88-3.39 (m, 11H), 2.98-2.85 (m, 1H), 2.20-1.92 (m, 6H), 1.69-1.42 (m, 3H). MS (ESI) m/Z 341.1 (M+H)$^+$.

Example 39K tert-butyl (7R,16R)-19,23-dichloro-10-({2-[(1S,4s)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 39J.

Example 39L (7R,16R)-19,23-dichloro-10-({2-[(1S,4s)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl) methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 39K. $^1$H NMR (400 MHz, dimethylsulfoxide-d$_6$) δ 8.77-8.70 (m, 2H), 7.43 (d, 1H), 7.25-7.10 (m, 4H), 6.87 (d, 1H), 6.76 (dd, 1H), 6.24 (dd, 1H), 5.78 (d, 1H), 5.11 (q, 2H), 4.90-4.83 (m, 1H), 4.45 (d, 2H), 3.78-3.52 (m, 12H), 3.03-2.79 (m, 4H), 2.73-2.65 (m, 3H), 2.24 (s, 3H), 2.00 (s, 3H), 1.97-1.78 (m, 9H), 1.16-1.14 (m, 2H). MS (ESI) m/z 1075.5 (M+H)$^+$.

Example 40

(7R,16R)-19,23-dichloro-10-({2-[(4S)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl) methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 40A (2-((S)-4-((((R)-1,4-dioxan-2-yl)methoxy)methyl)-4-fluorocyclohex-1-en-1-yl)pyrimidin-4-yl)methanol Racemic Example 39I was separated by SFC on a Thar SFC80 preparative SFC (Column: Chiralpak AD-H, 250×30 mm i.d. 5 μm; Mobile phase: A for CO$_2$ and B for methanol (0.1% NH$_3$—H$_2$O); Gradient: B %=45%; Flow rate: 85 g/minute; Wavelength: 220 nm; Column temperature: 40° C.; System back pressure: 100 bar; Cycle time: 22 minutes; Injection amount: 25 mg per injection) to provide the title compound. $^1$H NMR δ ppm 8.63 (d, 1H), 7.22 (br s, 1H), 7.07 (d, 1H), 4.73 (d, 2H), 3.92-3.38 (m, 12H), 2.92-2.41 (m, 4H), 2.21-2.02 (m, 1H), 1.98-1.77 (m, 1H).

Example 40B (2-((R)-4-((((R)-1,4-dioxan-2-yl)methoxy)methyl)-4-fluorocyclohex-1-en-1-yl)pyrimidin-4-yl)methanol The title compound was obtained from the SFC separation in Example 40A. $^1$H NMR (400 MHz, CDCl$_3$) δ ppm 8.63 (d, 1H), 7.21 (br s, 1H), 7.08 (d, 1H), 4.73 (s, 2H), 3.92-3.37 (m, 12H), 2.90-2.43 (m, 4H), 2.18-2.04 (m, 1H), 1.98-1.77 (m, 1H).

Example 40C tert-butyl (7R,16R)-19,23-dichloro-10-({2-[(4S)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 40A. MS (ESI) m/z 1129.5 (M+H)$^+$.

Example 40D (7R,16R)-19,23-dichloro-10-({2-[(4S)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl) methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 40C. $^1$H NMR (400 MHz, dimethylsulfoxide-d$_6$) δ ppm 8.74 (t, 2H), 7.40 (d, 1H), 7.25-7.10 (m, 5H), 6.85 (d, 1H), 6.75 (dd, 1H), 6.23 (dd, 1H), 5.79 (d, 1H), 5.13 (q, 2H), 4.89-4.82 (m, 1H), 4.44 (d, 2H), 3.78-3.44 (m, 15H), 2.96 (d, 2H), 2.72-2.62 (m, 3H), 2.44-2.27 (m, 6H), 2.21 (s, 3H), 2.08-1.92 (m, 14H), 1.88-1.66 (m, 2H). MS (ESI) m/z 1073.5 (M+H)$^+$.

Example 41

(7R,16R)-19,23-dichloro-10-({2-[6-({[(2R)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd] indene-7-carboxylic acid Example 41A (R)—N-((1,4-dioxan-2-yl)methyl)-5-(4,4,5,5-tetramethyl-1,3,2-dioxaborolan-2-yl)pyridin-2-amine The title compound was prepared by substituting (R)-(1, 4-dioxan-2-yl)methanamine hydrochloride for (S)-(1,4-dioxan-2-yl)methanamine hydrochloride in Example 36A. ¹H NMR (500 MHz, dimethylsulfoxide-d₆) δ ppm 8.22 (d, 1H), 7.52 (dd, 1H), 6.95 (t, 1H), 6.47 (d, 1H), 3.73 (dd, 2H), 3.66-3.60 (m, 2H), 3.55 (td, 1H), 3.45 (td, 1H), 3.31 (m, 2H), 3.23 (dd, 1H), 1.31 (s, 3H), 1.25 (s, 6H), 1.07 (s, 3H). MS (ESI) m/z 321.3 (M+H)⁺.

Example 41B (R)-(2-(6-(((1,4-dioxan-2-yl)methyl)amino)pyridin-3-yl)pyrimidin-4-yl)methanol The title compound was prepared by substituting Example 41A for Example 2A in Example 2B. ¹H NMR (500 MHz, dimethylsulfoxide-d₆) δ ppm 8.95 (d, 1H), 8.71 (d, 1H), 8.22 (dd, 1H), 7.30 (d, 1H), 7.09 (t, 1H), 6.57 (d, 1H), 5.56 (t, 1H), 4.53 (d, 2H), 3.73 (td, 2H), 3.68-3.58 (m, 2H), 3.54 (td, 1H), 3.44 (td, 1H), 3.34 (m, 2H), 3.23 (m, 1H). MS (ESI) m/z 303.3 (M+H)⁺.

Example 41C tert-butyl (7R,16R)-19,23-dichloro-10-({2-[6-({[(2R)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared by substituting Example 41B for Example 7B in Example 7C. MS (ESI) m/z 1095.4 (M+H)⁺.

Example 41D (7R,16R)-19,23-dichloro-10-({2-[6-({[(2R)-1,4-dioxan-2-yl]methyl}amino)pyridin-3-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared by substituting Example 41C for Example 7C in Example 7D. ¹H NMR (500 MHz, dimethylsulfoxide-d₆) δ ppm 8.93 (s, 1H), 8.67 (s, 2H), 8.19 (dd, 1H), 7.29 (d, 1H), 7.15-7.04 (m, 5H), 6.80 (d, 1H), 6.68 (dd, 1H), 6.54 (d, 1H), 6.17 (dd, 1H), 5.74 (d, 1H), 5.10 (q, 2H), 4.78 (m, 1H), 4.37 (m, 2H), 3.72-3.65 (m, 2H), 3.63-3.54 (m, 2H), 3.50 (td, 2H), 3.40 (td, 2H), 3.31 (m, 2H), 3.20 (dd, 1H), 2.90 (d, 2H), 2.60 (m, 2H), 2.37 (m, 6H), 2.14 (s, 3H), 1.92 (s, 3H), 1.88 (s, 3H). MS (ESI) m/z 1037.5 (M+H)⁺.

Example 42

(7R,16R)-19,23-dichloro-10-({2-[(4R)-4-({[(2S)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 42A (2-((R)-4-((((S)-1,4-dioxan-2-yl)methoxy)methyl)-4-fluorocyclohex-1-en-1-yl)pyrimidin-4-yl)methanol Racemic Example 28E was separated by SFC on a Thar SFC80 preparative SFC (Column: Chiralpak AD-H, 250×30 mm i.d. 5 μm; Mobile phase: A for CO₂ and B for methanol (0.1% ammonium hydroxide); Gradient: B %=45%; Flow rate: 85 g/min; Wavelength: 220 nm; Column temperature: 40° C.; System back pressure: 100 bar; Cycle time: 22 minutes; Injection amount: 25 mg per injection) to provide the title compound. ¹H NMR δ ppm 8.63 (d, 1H), 7.22 (br s, 1H), 7.07 (d, 1H), 4.73 (d, 2H), 3.92-3.38 (m, 12H), 2.92-2.41 (m, 4H), 2.21-2.02 (m, 1H), 1.98-1.77 (m, 1H).

Example 42B tert-butyl (7R,16R)-19,23-dichloro-10-({2-[(4R)-4-({[(2S)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 42A.

Example 42C (7R,16R)-19,23-dichloro-10-({2-[(4R)-4-({[(2S)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 42B. ¹H NMR (501 MHz, dimethylsulfoxide-d₆) δ 8.74 (t, 2H), 7.40 (d, 1H), 7.24-7.11 (m, 5H), 6.85 (d, 1H), 6.75 (dd, 1H), 6.23 (dd, 1H), 5.78 (d, 1H), 5.20-5.06 (m, 2H), 4.89-4.82 (m, 1H), 4.45 (d, 2H), 3.76-3.68 (m, 3H), 3.66-3.53 (m, 9H), 3.01-2.90 (m, 1H), 2.68 (dd, 3H), 2.45 (s, 1H), 2.39 (s, 2H), 2.20 (s, 3H), 2.00 (s, 4H), 1.95 (s, 3H), 1.86-1.68 (m, 1H). MS (ESI) m/z 1073.5 (M+H)⁺.

Example 43

(7R,16R)-19,23-dichloro-10-({2-[(4R)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 43A tert-butyl (7R,16R)-19,23-dichloro-10-({2-[(4R)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A vial containing Example 40B (63 mg). Example 1Z (50 mg), triphenylphosphine (49 mg) and N,N,N',N'-tetramethylazodicarboxamide (32 mg) in toluene (150 μL) and tetrahydrofuran (150 μL) was allowed to stir at 50° C. for 2.5 hours and at room temperature overnight. The reaction was diluted with ethyl acetate, filtered over diatomaceous earth and concentrated. The residue was purified by normal phase MPLC on a Teledyne Isco Combiflash® Rf+ 4 g gold silica gel column eluting with 0.5-9.5% methanol in dichloromethane to give the title compound.

Example 43B (7R,16R)-19,23-dichloro-10-({2-[(4R)-4-({[(2R)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 43A (49 mg) in dichloromethane (300 μL) was added trifluoroacetic acid (300 μL), and the reaction was allowed to stir for 5 hours. The reaction was concentrated under a stream of nitrogen and was taken up in water and acetonitrile. The mixture was purified by RP-HPLC on a Gilson PLC 2020 using a Luna® column (250×50 mm, 10 mm, 30-80% over 30 minutes with acetonitrile in water containing 10 mM ammonium acetate) to give a residue after lyophilization that was further purified by normal phase MPLC on a Teledyne Isco Combiflash® Rf+ 4 g gold silica gel column eluting with 10-25% methanol in dichloromethane to give the title compound. $^1$H NMR (500 MHz, dimethylsulfoxide-d$_6$) δ ppm 8.77-8.70 (m, 2H), 7.40 (d, 1H), 7.24-7.09 (m, 5H), 6.84 (d, 1H), 6.78-6.70 (m, 1H), 6.27-6.19 (m, 1H), 5.84-5.78 (m, 1H), 5.21-5.03 (m, 2H), 4.91-4.80 (m, 1H), 4.50-4.38 (m, 2H), 3.77-3.39 (m, 12H), 3.32-3.24 (m, 1H), 3.00-2.90 (m, 1H), 2.78-2.60 (m, 4H), 2.58-2.37 (m, 6H), 2.23 (s, 3H), 2.07-1.91 (m, 8H), 1.85-1.66 (m, 2H). MS (ESI) m/z 1073.1 (M–H)$^-$.

Example 44

(7R,16R)-19,23-dichloro-10-({2-[(1S,4r)-4-{[(2S)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 44A tert-butyl (7R,16R)-19,23-dichloro-10-({2-[(1S,4r)-4-{[(2S)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 9E (74 mg) and Example 1Z (65 mg) were azeotroped with toluene and tetrahydrofuran three times. The residue was taken up in toluene (200 μL) and tetrahydrofuran (200 μL), and triphenylphosphine (63 mg) and N,N,N',N'-tetramethylazodicarboxamide (41 mg) were added. The reaction was heated to 50° C. for 6 hours. The reaction was diluted with ethyl acetate, filtered over diatomaceous earth and concentrated. The residue was purified by normal phase MPLC on a Teledyne Isco Combiflash® Rf+ 4 g gold silica gel column eluting with 1-10% methanol in dichloromethane to give the title compound.

Example 44B (7R,16R)-19,23-dichloro-10-({2-[(1S,4r)-4-{[(2S)-1,4-dioxan-2-yl]methoxy}cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 44A (85 mg) in dichloromethane (390 μL) was added trifluoroacetic acid (390 μL), and the reaction was allowed to stir overnight. The reaction was concentrated under a stream of nitrogen and was taken up in water and acetonitrile. The mixture was purified by RP-HPLC on a Gilson PLC 2020 using a Luna™ column (250×50 mm, 10 mm, 30-80% over 30 minutes with acetonitrile in water containing 10 mM ammonium acetate) to give the title compound after lyophilization. $^1$H NMR (500 MHz, dimethylsulfoxide-d$_6$) δ ppm 8.72-8.67 (m, 2H), 7.44 (d, 1H), 7.23-7.09 (m, 5H), 6.81 (d, 1H), 6.71 (dd, 1H), 6.18-6.11 (m, 1H), 5.87-5.80 (m, 1H), 5.17-5.00 (m, 2H), 4.94-4.83 (m, 1H), 4.49-4.36 (m, 2H), 3.75-3.66 (m, 2H), 3.65-3.52 (m, 6H), 3.48-3.22 (m, 6H), 2.97-2.88 (m, 1H), 2.82-2.60 (m, 3H), 2.56-2.28 (br m, 4H), 2.18 (s, 3H), 2.09-2.00 (m, 2H), 1.99-1.91 (m, 8H), 1.66-1.52 (m, 2H), 1.33-1.18 (m, 2H).

Example 45

(7R,16R)-19,23-dichloro-10-({2-[(4S)-4-({[(2)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 45A (2-((S)-4-((((S)-1,4-dioxan-2-yl)methoxy)methyl)-4-fluorocyclohex-1-en-1-yl)pyrimidin-4-yl)methanol Racemic Example 28E was separated by SFC on a Thar SFC80 preparative SFC (Column: Chiralpak AD-H, 250×30 mm i.d. 5 μm; Mobile phase: A for $CO_2$ and B for methanol (0.1% $NH_3$—$H_2O$); Gradient: B %=45%; Flow rate: 85 g/minute; Wavelength: 220 nm; Column temperature: 40° C.; System back pressure: 100 bar; Cycle time: 22 minute; Injection amount: 25 mg per injection) to provide the title compound. $^1$H NMR (400 MHz, $CDCl_3$) δ ppm 8.63 (d, 1H), 7.22 (br s, 1H), 7.07 (d, 1H), 4.73 (br s, 2H), 3.95-3.33 (m, 12H), 2.88-2.39 (m, 4H), 2.20-2.04 (m, 1H), 1.99-1.79 (m, 1H).

Example 45B tert-butyl (7R,16R)-19,23-dichloro-10-({2-[(4S)-4-({[(2S)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 45A. MS (ESI) m/z 1129.6 (M+H)$^+$.

Example 45C (7R,16R)-19,23-dichloro-10-({2-[(4S)-4-({[(2)-1,4-dioxan-2-yl]methoxy}methyl)-4-fluorocyclohex-1-en-1-yl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 45B. $^1$H NMR (400 MHz, dimethylsulfoxide-d$_6$) δ ppm 8.77-8.71 (m, 2H), 7.40 (d, 1H), 7.25-7.10 (m, 5H), 6.85 (d, 1H), 6.75 (dd, 1H), 6.24 (dd, 1H), 5.78 (d, 1H), 5.21-5.05 (m, 2H), 4.85 (q, 1H), 4.45 (d, 2H), 3.78-3.50 (m, 11H), 2.96 (d, 2H), 2.72-2.64 (m, 3H), 2.48-2.29 (m, 9H), 2.23 (s, 3H), 2.00 (s, 4H), 1.95 (s, 3H), 1.88-1.65 (m, 1H). MS (ESI) m/z 1073.4 (M+H)$^+$.

Example 46

(7R,16R)-19,23-dichloro-10-({2-[(1S,4r)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 46A tert-butyl (7R,16R)-19,23-dichloro-10-({2-[(1S,4r)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 28G. MS (ESI) m/z 1131.54 (M+H)$^+$.

Example 46B (7R,16R)-19,23-dichloro-10-({2-[(1S,4r)-4-({[(2S)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 46A. $^1$H NMR (400 MHz, dimethylsulfoxide-d$_6$) δ ppm 8.76-8.69 (m, 2H), 7.45 (d, 1H), 7.24-7.09 (m, 4H), 6.84 (d, 1H), 6.73 (dd, 1H), 6.17 (d, 1H), 5.83 (d, 1H), 5.10 (q, 2H), 4.89 (s, 1H), 4.44 (d, 2H), 3.73-3.51 (m, 13H), 3.51-3.41 (m, 3H), 3.05-2.87 (m, 3H), 2.68 (t, 3H), 2.36 (s, 2H), 2.18 (s, 3H), 1.94 (dd, 9H), 1.85-1.78 (m, 2H), 1.72-1.62 (m, 2H). MS (ESI) m/z 1073.1 (M−H)$^-$.

Example 47

(7R,16R)-19,23-dichloro-10-({2-[(1R,4r)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 47A (2-((1R,4r)-4-((((R)-1,4-dioxan-2-yl)methoxy)methyl)-4-fluorocyclohexyl)pyrimidin-4-yl)methanol The title compound was prepared as described in Example 28F by replacing Example 28E with Example 39I.

Example 47B tert-butyl (7R,16R)-19,23-dichloro-10-({2-[(1R,4r)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 5F by replacing Example 5E with Example 47A. MS (ESI) m/z 1133.5 (M+H)$^+$.

Example 47C (7R,16R)-19,23-dichloro-10-({2-[(1R,4r)-4-({[(2R)-1,4-dioxan-2-yl]methoxy}methyl)-4-fluorocyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 5G by replacing Example 5F with Example 47B. $^1$H NMR (400 MHz, dimethylsulfoxide-d$_6$) δ ppm 8.73 (d, 2H), 7.44 (d, 1H), 7.24-7.09 (m, 4H), 6.85 (d, 1H), 6.74 (dd, 1H), 6.20 (dd, 1H), 5.81 (d, 1H), 5.10 (q, 2H), 4.88 (d, 1H), 4.44 (d, 2H), 3.73-3.38 (m, 5H), 3.01-2.90 (m, 3H), 2.75-2.61 (m, 3H), 2.46 (s, 2H), 2.38 (s, 2H), 2.19 (s, 3H), 1.97 (d, 9H), 1.82 (d, 2H), 1.66 (q, 2H). MS (ESI) m/z 1075.6 (M+H)$^+$.

Example 48

(7R,16R)-19,23-dichloro-1-(cyclopent-1-en-1-yl)-10-({2-[(4R)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 48A tert-butyl (7R,16R)-19,23-dichloro-1-(cyclopent-1-en-1-yl)-10-({2-[(4R)-4-{[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 40B (43 mg) and Example 32P (50 mg) were azeotroped with toluene and tetrahydrofuran three times. The residue was taken up in toluene (160 μL) and tetrahydrofuran (160 μL), and triphenylphosphine (50 mg) and N,N,N',N'-tetramethylazodicarboxamide (33 mg) were added. The reaction mixture was heated to 50° C. overnight. The reaction mixture was diluted with ethyl acetate, filtered over diatomaceous earth, and concentrated. The residue was purified by normal phase MPLC on a Teledyne Isco Combiflash® Rf+ 4 g gold silica gel column eluting with 0-7% methanol in dichloromethane to give the title compound.

Example 48B (7R,16R)-19,23-dichloro-1-(cyclopent-1-en-1-yl)-10-({2-[(4R)-4-({[(2R)-1,4-dioxan-2-yl]methoxy}methyl)-4-fluorocyclohex-1-en-1-yl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 48A (59 mg) in dichloromethane (270 μL) was added trifluoroacetic acid (270 μL), and the reaction mixture was allowed to stir overnight. The reaction mixture was concentrated under a stream of nitrogen and taken up in water and acetonitrile. The mixture was purified by RP-HPLC on a Gilson PLC 2020 using a Luna™ column (250×50 mm, 10 mm, 30-80% over 30 minutes with acetonitrile in water containing 10 mM ammonium acetate) to give the title compound after lyophilyzation. $^1$H NMR (400 MHz, dimethyl sulfoxide-d$_6$) δ ppm 8.72 (d, 1H), 8.64 (s, 1H), 7.40 (d, 1H), 7.17-7.08 (m, 1H), 6.82 (d, 1H), 6.77-6.68 (m, 1H), 6.24-6.15 (m, 1H), 5.87-5.80 (m, 1H), 5.79-5.73 (m, 1H), 5.20-5.02 (m, 2H), 4.93-4.81 (m, 1H), 4.57-4.41 (m, 2H), 3.77-3.38 (m, 16H), 3.33-3.23 (m, 1H), 2.93-2.82 (m, 1H), 2.78-2.60 (m, 3H), 2.58-2.26 (m, 8H), 2.21 (s, 3H), 2.07-1.86 (m, 8H), 1.81-1.65 (m, 2H). MS (ESI) m/z 1043.2 (M−H)$^-$.

Example 49

(7R,16R)-19,23-dichloro-10-({2-[(1S,4r)-4-({[(2R)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid

Example 49A 4-(((tert-butyldiphenylsilyl)oxy)methyl)-2-chloropyrimidine

To a flask containing (2-chloropyrimidin-4-yl)methanol (5.00 g) in N,N-dimethylformamide (40 mL) was added tert-butylchlorodiphenylsilane (9.51 g) followed by imidazole (4.71 g). The resulting mixture was stirred at ambient temperature overnight. The mixture was diluted with water (100 mL) and extracted with ethyl acetate (3×150 mL). The organic layer was separated, washed with water and brine, dried over sodium sulfate, filtered and concentrated. The residue was purified by flash chromatography on AnaLogix IntelliFlash[280] system (100 g silica gel cartridge, eluting with 0-30% ethyl acetate/hexanes) to give the title compound. MS (ESI) m/z 383.2 (M+H)$^+$.

Example 49B

Ethyl 4-(4-(((tert-butyldiphenylsilyl)oxy)methyl)pyrimidin-2-yl)cyclohex-3-enecarboxylate A 250 mL flask, equipped with stir bar, was charged with Example 49A (4.00 g), ethyl 4-(4,4,5,5-tetramethyl-1,3,2- dioxaborolan-2-yl)cyclohex-3-enecarboxylate (3.80 g), [1,1'-bis(diphenylphosphino)ferrocene]dichloropalladium (II) (0.764 gl) and potassium phosphate (5.54 g). The flask was capped then evacuated and backfilled with nitrogen twice. 1,4-Dioxane (55 mL) was added followed by water (13.75 mL) and the stirring mixture was evacuated and backfilled with nitrogen twice again. The mixture was stirred at 80° C. for 16 hours. The mixture was cooled to ambient temperature, poured into a separatory funnel containing water and brine, and extracted three times with ethyl acetate. The organics were combined and concentrated. The residue was purified by flash chromatography on AnaLogix IntelliFlash[280] system (100 g silica gel cartridge, eluting with 0-30% ethyl acetate/hexanes) to give the title compound. MS (ESI) m/z 501.2 (M+H)+.

Example 49C (4-(4-(((tert-butyldiphenylsilyl)oxy)methyl)pyrimidin-2-yl)cyclohex-3-en-1-yl)methanol To a solution of Example 49B (2.081 g) in tetrahydrofuran (5 mL) at 0° C. was added lithium diisobutyl-tert-butoxyaluminum hydride (0.25 M in tetrahydrofuran/hexanes, 66.5 mL). The mixture was stirred at 0° C. for 25 minutes. The reaction mixture was quenched at 0° C. by slow addition of saturated aqueous Rochelle's salt solution (20 mL). The mixture was stirred at ambient temperature for 15 minutes. The mixture was extracted three times with ethyl acetate and the organics were concentrated. The residue was purified by flash chromatography on an AnaLogix IntelliFlash[280] system using a Teledyne Isco RediSep® Rf gold 100 g silica gel column (eluting with 0-100% ethyl acetate/hexanes) to afford the title compound. MS (ESI) m/z 459.4 (M+H)+.

Example 49D ((1r,4r)-4-(4-(((tert-butyldiphenylsilyl)oxy)methyl)pyrimidin-2-yl)cyclohexyl)methanol Example 49C (2.095 g) and tetrahydrofuran (14.5 mL) were added to Ra—Ni 2800 water slurry (2.0 g) in a 25 mL Hast C reactor, and the mixture was stirred at 50 psi hydrogen for one hour. The reaction mixture was filtered and concentrated. The residue was purified by flash chromatography on an AnaLogix IntelliFlash™ system using a Teledyne Isco RediSep® Rf gold 100 g silica gel column (eluting with 20-100% ethyl acetate/hexanes) to afford the title compound. $^1$H NMR (400 MHz, dimethylsulfoxide-$d_6$) δ ppm 8.75 (d, 1H), 7.64 (dt, 4H), 7.43 (dddd, 7H), 4.72 (s, 2H), 4.37 (s, 1H), 3.28-3.15 (m, 2H), 2.65 (tt, 1H), 1.96-1.77 (m, 4H), 1.58-1.31 (m, 3H), 1.05 (s, 9H), 1.04-0.93 (m, 2H). MS (ESI) m/z 461.3 (M+H)+.

Example 49E (S)-(1,4-dioxan-2-yl)methyl trifluoromethanesulfonate

A stirring mixture of (R)-(1,4-dioxan-2-yl)methanol (1.5 g) and pyridine (1.078 mL) in dichloromethane (52.4 mL) was evacuated and back filled with nitrogen twice. The reaction mixture was cooled to −10° C. using a methanol/ice cooling bath. The trifluoromethanesulfonic anhydride (3.76 g) was next added dropwise as a dichloromethane (7.49 mL) solution. Stirring was continued at −10° C. for 2 minutes. The cooling bath was removed and the mixture was stirred for 15 minutes. The mixture was diluted with dichloromethane, washed with 1 M HCl aqueous solution and brine, dried over anhydrous magnesium sulfate, filtered and concentrated to give the title compound. $^1$H NMR (400 MHz, chloroform-d) δ ppm 4.51-4.40 (m, 2H), 3.97-3.88 (m, 1H), 3.88-3.70 (m, 4H), 3.63 (ddd, 1H), 3.46 (dd, 1H).

Example 49F 2-((1R,4r)-4-((((R)-1,4-dioxan-2-yl)methoxy) methyl)cyclohexyl)-4-(((tert-butyldiphenylsilyl)oxy) methyl)pyrimidine To a stirring mixture of Example 49D (200 mg) in anhydrous tetrahydrofuran (2.90 mL) was added sodium hydride (26.0 mg). The mixture was stirred for 5 minutes before being cooled to 0° C. with an ice bath. A mixture of Example 49E (272 mg) in tetrahydrofuran (0.97 mL) was added dropwise. Stirring was continued at 0° C. for 5 minutes, the cooling bath was removed and the mixture was stirred at ambient temperature under nitrogen for 5 hours. Saturated aqueous ammonium chloride solution (15 drops) was added to quench the sodium hydride. The mixture was concentrated onto silica gel and purified by flash chromatography on a CombiFlash® Teledyne Isco system using a Teledyne Isco RediSep® Rf gold 12 g silica gel column (eluting with 20-100% ethyl acetate/hexanes) to afford the title compound. $^1$H NMR (501 MHz, dimethylsulfoxide-$d_6$) δ ppm 8.76 (d, 1H), 7.69-7.61 (m, 4H), 7.52-7.39 (m, 7H), 4.73 (d, 2H), 3.69 (dd, 2H), 3.66-3.58 (m, 2H), 3.55 (td, 1H), 3.43 (td, 1H), 3.36 (dd, 1H), 3.29 (dd, 1H), 3.25 (dd, 1H), 3.22 (d, 2H), 2.73-2.61 (m, 1H), 1.97-1.87 (m, 2H), 1.84-1.74 (m, 2H), 1.59-1.44 (m, 3H), 1.06 (s, 9H), 1.05-0.96 (m, 2H). MS (APCI) m/z 561.4 (M+H)+.

Example 49G (2-((1R,4r)-4-((((R)-1,4-dioxan-2-yl)methoxy) methyl)cyclohexyl)pyrimidin-4-yl)methanol To a stirring mixture of Example 49F (198 mg) in tetrahydrofuran (1.12 mL) was added tetra-N-butylammonium fluoride (1.0 M in tetrahydrofuran, 1.06 mL) and the mixture was stirred for 10 minutes. The mixture was concentrated onto silica gel and purified by flash chromatography on a CombiFlash® Teledyne Isco system using a Teledyne Isco RediSep®® Rf gold 24 g silica gel column (solvent A=2:1 ethyl acetate:ethanol, solvent B=heptane, eluting with 10-100% A to B) to afford the title compound. $^1$H NMR (501 MHz, dimethylsulfoxide-$d_6$) δ ppm 8.69 (d, 1H), 7.36 (dt, 1H), 5.56 (t, 1H), 4.51 (dd, 2H), 3.76-3.67 (m, 2H), 3.67-3.60 (m, 2H), 3.56 (td, 1H), 3.44 (td, 1H), 3.37 (dd, 1H), 3.32-3.26 (m, 2H), 3.26-3.22 (m, 2H), 2.70 (tt, 1H), 1.98-1.88 (m, 2H), 1.87-1.78 (m, 2H), 1.62-1.47 (m, 3H), 1.05 (qd, 2H). MS (APCI) m/z 323.2 (M+H)+.

Example 49H tert-butyl (7R,16R)-19,23-dichloro-10-({2-[(1S,4r)-4-({[(2R)-1,4-dioxan-2-yl]methoxy}methyl)cyclohexyl]pyrimidin-4-yl}methoxy)-1-(4-fluorophenyl)-20,22-dimethyl-6-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A 4 mL vial, equipped with stir bar, was charged with Example 1Z (120 mg). Example 49G (96 mg), and triphenylphosphine (82 mg). The vial was capped with septa, and evacuated and backfilled with nitrogen twice. Toluene (1.48 mL) was added, and the mixture was cooled with an ice bath. (E)-Di-tert-butyl diazene-1,2-dicarboxylate (68.2 mg) was added in one solid portion, and the vial was capped with septa, evacuated and backfilled with nitrogen twice again. The mixture was stirred at 0° C. for 10 minutes, the cooling bath was removed and the mixture was allowed to stir for 7 hours. The reaction mixture was concentrated and purified by flash chromatography on an AnaLogix IntelliFlash® system using a Teledyne Isco RediSep® Rf gold 25 g silica gel column (eluting with 1-20% methanol/dichloromethane over 35 minutes) to afford the title compound. MS (ESI) m/z 1113.3 (M+H)$^+$.

Example 491

(7R,16R)-19,23-dichloro-10-({2-[(1S,4r)-4-({[(2R)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid To a solution of Example 49H (107 mg) in dichloromethane (0.6 mL) was added trifluoroacetic acid (0.9 mL). The mixture was stirred for 2 hours. The mixture was concentrated in vacuo. The residue was purified by reverse phase prep LC using a Phenomenex® Luna™ C-18 250×50 mm column, 70 mL/minute flow, 10 to 95% acetonitrile in 10 mM ammonium acetate in water over 35 minutes. The title compound was obtained after lyophilization. $^1$H NMR (501 MHz, dimethylsulfoxide-d$_6$) δ ppm 8.73 (s, 1H), 8.70 (d, 1H), 7.41 (d, 1H), 7.23-7.16 (m, 2H), 7.16-7.11 (m, 2H), 6.84 (d, 1H), 6.73 (dd, 1H), 6.21 (dd, 1H), 5.81 (d, 1H), 5.17-4.98 (m, 2H), 4.92-4.84 (m, 1H), 4.46-4.40 (m, 2H), 7.72-3.68 (m, 2H), 3.67-3.17 (m, 12H), 2.98-2.91 (m, 1H), 2.79-2.60 (m, 3H), 2.48-2.32 (m, 6H), 2.21 (s, 3H), 1.97 (s, 3H), 1.96 (s, 3H), 1.94-1.92 (m, 2H), 1.86-1.77 (m, 2H), 1.62-1.49 (m, 3H), 1.12-0.98 (m, 2H), exchangeable CO$_2$H not observed. MS (ESI) m/z 1157.6 (M+H)$^+$.

Example 50

(7R,16R)-19,23-dichloro-10-({2-[(1S,4s)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 50A 1,4-dioxaspiro[4.5]decan-8-ylmethyl 4-methylbenzenesulfonate To a stirring solution of 1,4-dioxaspiro[4.5]decan-8-ylmethanol (5.0 g), 4-dimethylaminopyridine (0.177 g) and triethylamine (8.09 mL) in 100 mL of dichloromethane at 0° C. was added para-toluenesulfonyl chloride (6.64 g) in one portion. Stirring was continued at 0° C. for 5 minutes, the cooling bath was removed, and the mixture stirred for 4 hours before it was concentrated onto silica gel. Purification by flash chromatography on a CombiFlash® Teledyne Isco system using a Teledyne Isco RediSep®® Rf gold 220 g silica gel column (eluting with 10-60% ethyl acetate/heptanes) afforded the title compound. MS (APCI) m/z 327.3 (M+H)$^+$.

Example 50B (S)-8-(((1,4-dioxan-2-yl)methoxy)methyl)-1,4-dioxaspiro[4.5]decane

To a stirring mixture of (S)-(1,4-dioxan-2-yl)methanol (2.71 g) in 15 mL of N,N-dimethylformamide was added sodium hydride (0.55 g) in one portion. The flask was capped with septa and stirred for 15 minutes. Example 50A (2.5 g) was added as a solution in 2 mL of N,N-dimethylformamide. The mixture was stirred at 45° C. for 4 hours. After cooling to room temperature, the mixture was quenched by addition of 30 mL of saturated aqueous ammonium chloride. The mixture was poured into a separatory funnel, diluted with water, and extracted with three portions of ethyl acetate. The organic layers were combined, washed twice with brine, dried over anhydrous magnesium sulfate, filtered and concentrated onto silica gel. Purification by flash chromatography on a CombiFlash® Teledyne Isco system using a Teledyne Isco RediSep® Rf gold 220 g silica gel column (eluting with 20-100% ethyl acetate/heptanes) afforded the title compound. MS (APCI) m/z 273.6 (M+H)$^+$.

Example 50C (S)-4-(((1,4-dioxan-2-yl)methoxy)methyl)cyclohexanone

To a solution of Example 50B (1.8 g) in 20 mL of tetrahydrofuran was added 30 mL of a 6 molar aqueous solution of HCl. The reaction mixture was stirred at room temperature for 16 hours. The mixture was poured into a 125 mL separatory funnel and diluted with 50 mL of water. The aqueous layer was extracted with three portions of dichloromethane. The organic layers were combined, dried over anhydrous magnesium sulfate, filtered and concentrated onto silica gel. Purification by flash chromatography on a CombiFlash® Teledyne Isco system using a Teledyne Isco RediSep® Rf gold 40 g silica gel column (eluting 0-60% ethyl acetate/heptanesane) afforded the title compound. MS (APCI) m/z 229.3 (M+H)$^+$.

Example 50D (S)-4-((((S)-1,4-dioxan-2-yl)methoxy)methyl)cyclohex-1-en-1-yl trifluoromethanesulfonate To a stirring solution of Example 50C (1.31 g) in 35 mL of tetrahydrofuran, at −78° C., was slowly added 4.3 mL of a 2 molar solution of lithium diisopropylamide in tetrahydrofuran. The mixture was stirred at −78° C. for 30 minutes, and a solution of N,N-bis(trifluoromethylsulfonyl)aniline (2.67 g) in 18 mL of tetrahydrofuran was slowly added over 20 minutes. The dry ice from the cooling bath was removed to allow for the reaction to slowly warm to room temperature. Stirring was continued at room temperature for 16 hours. The reaction mixture was cooled back to 0° C. and quenched with the addition of 20 mL of saturated aqueous sodium bicarbonate. The mixture was poured into a 250 mL separatory funnel, diluted with water, and extracted with three portions of dichloromethane. The organic layers were combined, dried over anhydrous magnesium sulfate, filtered and concentrated onto silica gel. Purification by flash chromatography on a CombiFlash®. Teledyne Isco system using a Teledyne Isco RediSep® Rf gold 80 g silica gel column (eluting with 10-60% ethyl acetate/heptanes, then 100% ethyl acetate) afforded the title compound. MS (APCI) m/z 360.6 (M+H)+.

Example 50E 2-(4-((((S)-1,4-dioxan-2-yl)methoxy)methyl)cyclohex-1-en-1-yl)-4,4,5,5-tetramethyl-1,3,2-dioxaborolane A 100 mL round bottom flask, equipped with stir bar, was charged with Example 50D (1.260 g), bis(pinacolato)diboron (1.154 g). [1,1'-bis(diphenylphosphino)ferrocene]dichloropalladium(II) (0.256 g) and potassium acetate (0.686 g). The flask was capped and evacuated and backfilled with nitrogen twice. Dioxane (30 mL) was added and the stirring mixture was evacuated and backfilled with nitrogen twice and stirred at 80° C. for 4 hours. After cooling to room temperature, the mixture was filtered through a diatomaceous earth pad and the filter cake was washed with ethyl acetate. The mixture was then concentrated onto silica gel. Purification by flash chromatography on a CombiFlash® Teledyne Isco system using a Teledyne Isco RediSep® Rf gold 80 g silica gel column (eluting 0-60% ethyl acetate/heptanes) afforded the title compound. MS (APCI) m/z 338.1 (M+H)+.

Example 50F 2-(4-((((S)-1,4-dioxan-2-yl)methoxy)methyl)cyclohex-1-en-1-yl)-4-(((tert-butyldiphenylsilyl)oxy)methyl)pyrimidine A 100 mL flask, equipped with stir bar, was charged with Example 14A (525 mg), Example 50E (556 mg), [1,1'-bis(diphenylphosphino)ferrocene]dichloropalladium(I) (100 mg) and potassium phosphate (727 mg). The flask was capped with a septa and evacuated and backfilled with nitrogen twice. Dioxane (7.3 mL) was added followed by water (1.8 mL) and the stirring mixture was evacuated and backfilled with nitrogen twice again before it was heated at 80° C. for 4 hours. After cooling to room temperature, the mixture was poured into a separatory funnel containing water and brine and the mixture was extracted three times with ethyl acetate. The organic layers were combined, dried over anhydrous magnesium sulfate, filtered and concentrated onto silica gel. Purification by flash chromatography on a CombiFlash® Teledyne Isco system using a Teledyne Isco RediSep® Rf gold 40 g silica gel column (eluting with 10-70% ethyl acetate/heptanes) afforded the title compound. MS (APCI) m/z 559.4 (M+H)+.

Example 50G cis-4-((((S)-1,4-dioxan-2-yl)methoxy)methyl)cyclohexyl)-4-(((tert-butyldiphenylsilyl)oxy)methyl)pyrimidine Example 50F (675 mg) was dissolved in 2.5 mL of tetrahydrofuran and loaded onto a RS10 high pressure reactor. Palladium on carbon (5%, 100 mg, wet) was added and the reactor was purged with argon. The mixture was stirred at 1200 RPM under 45 psi of hydrogen at 40° C. for 24 hours. After cooling back to room temperature, the solution obtained was concentrated onto silica gel and purification by flash chromatography on a CombiFlash® Teledyne Isco system using a Teledyne Isco RediSep® Rf gold 80 g silica gel column (eluting 10-100% ethyl acetate/heptanes) afforded the title compound which was the cis isomer and the faster eluting isomer. Example 50H was eluted which was the trans isomer and the slower eluting isomer. MS (APCI) m/z 561.4 (M+H)+.

Example 50H trans-4-((((S)-1,4-dioxan-2-yl)methoxy)methyl)cyclohexyl)-4-(((tert-butyldiphenylsilyl)oxy)methyl)pyrimidine The title compound was also obtained as described in Example 50G. MS (APCI) m/z 561.4 (M+H)+.

Example 50I cis-4-((((S)-1,4-dioxan-2-yl)methoxy)methyl)cyclohexyl)pyrimidin-4-yl)methanol To a stirring mixture of Example 50G (68 mg) in tetrahydrofuran (0.4 mL) was added 0.4 mL of a 1 molar solution of tetra-N-butylammonium fluoride in tetrahydrofuran and the mixture was stirred at room temperature for 10 minutes before it was concentrated onto silica gel. Purification by flash chromatography on a CombiFlash® Teledyne Isco system using a Teledyne Isco RediSep® Rf gold 12 g silica gel column (eluting with solvent A=2:1 ethyl acetate:ethanol, solvent B=heptane, 10-80% A to B) afforded the title compound. MS (APCI) m/z 323.4 (M+H)+.

Example 50J tert-butyl (7R,16R)-19,23-dichloro-10-({2-[(1S,4s)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 50J was synthesized according to the procedure described for Example 11I, substituting Example 50I for Example 11H. MS (APCI) m/z 1114.1 (M+H)+.

Example 50K (7R,16R)-19,23-dichloro-10-({2-[(1S,4s)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 50K was synthesized according to the procedure described for Example 11J, substituting Example 50J for Example 11I. $^1$H NMR (400 MHz, dimethylsulfoxide-$d_6$) δ ppm 8.76-8.64 (m, 2H), 7.37 (d, 1H), 7.22-7.05 (m, 4H), 6.81 (d, 1H), 6.70 (dd, 1H), 6.19 (dd, 1H), 5.77 (d, 1H), 5.06 (q, 2H), 4.83 (p, 1H), 4.40 (d, 2H), 3.68-3.47 (m, 6H), 3.30-3.15 (m, 5H), 3.00-2.86 (m, 2H), 2.74-2.57 (m, 2H), 2.53-2.34 (m, 9H), 2.19 (s, 3H), 2.03-1.88 (m, 8H), 1.82-

1.71 (m, 1H), 1.71-1.56 (m, 2H), 1.58-1.44 (m, 2H), 1.44-1.32 (m, 2H). MS (APCI) m/z 1058.0 (M+H)+.

Example 51

(7R,16R)-19,23-dichloro-10-({2-[(1R,4r)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 51A trans-4-((((S)-1,4-dioxan-2-yl)methoxy)methyl)cyclohexyl)pyrimidin-4-yl)methanol Example 51A was synthesized according to the procedure described for Example 50I, substituting Example 50H for Example 50G. MS (APCI) m/z 323.4 (M+H)+.

Example 51B tert-butyl (7R,16R)-19,23-dichloro-10-({2-[(1R,4r)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate Example 51B was synthesized according to the procedure described for Example 11, substituting Example 51A for Example 11H. MS (APCI) m/z 1114.3 (M+H)+.

Example 51C (7R,16R)-19,23-dichloro-10-({2-[(1R,4r)-4-({[(2S)-1,4-dioxan-2-yl]methoxy}methyl)cyclohexyl]pyrimidin-4-yl}methoxy)-1-(4-fluorophenyl)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 51C was synthesized according to the procedure described for Example 11J, substituting Example 51B for Example ill. $^1$H NMR (400 MHz, dimethylsulfoxide-$d_6$) δ ppm 8.73 (s, 1H), 8.70 (d, 1H), 7.41 (d, 1H), 7.24-7.16 (m, 2H), 7.16-7.10 (m, 2H), 6.84 (d, 1H), 6.74 (dd, 1H), 6.22 (dd, 1H), 5.80 (d, 1H), 5.19-5.02 (m, 2H), 4.86 (p, 1H), 4.44 (d, 2H), 3.70 (dt, 2H), 3.66-3.61 (m, 2H), 3.61-3.52 (m, 1H), 3.47-3.41 (m, 2H), 3.39-3.34 (m, 2H), 3.28-3.22 (m, 2H), 2.99-2.91 (m, 1H), 2.80-2.60 (m, 3H), 2.56-2.35 (m, 9H), 2.23 (s, 3H), 2.03-1.91 (m, 7H), 1.88-1.77 (m, 2H), 1.65-1.48 (m, 4H), 1.15-0.97 (m, 2H). MS (APCI) m/z 1060.0 (M+H)+.

Example 52

(7R,16R)-19,23-dichloro-1-cyclobutyl-10-({2-[(1R,4r)-4-{[(2R)-1,4-dioxan-2-yl]methoxy}cyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid Example 52A (R)-tert-butyl 2-((5-(4-(((R)-1-(allyloxy)-3-(bis(4-methoxyphenyl)(phenyl)methoxy)propan-2-yl)oxy)-3,5-dichloro-2,6-dimethylphenyl)-6-bromothieno[2,3-d]pyrimidin-4-yl)oxy)-3-(5-((tert-butyldimethylsilyl)oxy)-2-((2-(trimethylsilyl)ethoxy)methoxy)phenyl)propanoate The title compound was prepared as described in Example 1R by substituting Example 17D for Example 1L and substituting Example 32C for Example 1Q.

Example 52B (R)-tert-butyl 2-((5-(4-(((S)-1-(allyloxy)-3-hydroxypropan-2-yl)oxy)-3,5-dichloro-2,6-dimethylphenyl)-6-bromothieno[2,3-d]pyrimidin-4-yl)oxy)-3-(5-((tert-butyldimethylsilyl)oxy)-2-((2-(trimethylsilyl)ethoxy)methoxy)phenyl)propanoate The title compound was prepared as described in Example 1S substituting Example 52A for Example 1R. MS (ESI) m/z 1012.8 (M–H)−.

Example 52C (R)-tert-butyl 2-((5-(4-(((R)-1-(allyloxy)-3-(tosyloxy)propan-2-yl)oxy)-3,5-dichloro-2,6-dimethylphenyl)-6-bromothieno[2,3-d]pyrimidin-4-yl)oxy)-3-(5-((tert-butyldimethylsilyl)oxy)-2-((2-(trimethylsilyl)ethoxy)methoxy)phenyl)propanoate The title compound was prepared as described in Example 1T substituting Example 52B for Example 1S. MS (ESI) m/z 1185.0 (M+NH$_4$)+.

Example 52D (R)-tert-butyl 2-((5-(4-(((R)-1-(allyloxy)-3-(tosyloxy)propan-2-yl)oxy)-3,5-dichloro-2,6-dimethylphenyl)-6-bromothieno[2,3-d]pyrimidin-4-yl)oxy)-3-(5-hydroxy-2-((2-(trimethylsilyl)ethoxy)methoxy)phenyl)propanoate The title compound was prepared as described in Example 1U substituting Example 52C for Example 1T. MS (ESI) m/z 1051.4 (M–H)−.

Example 52E tert-butyl (7R,16R)-1-bromo-19,23-dichloro-20,22-dimethyl-16-{[(prop-2-en-1-yl)oxy]methyl)-10-[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 1V substituting Example 52D for Example 1U. MS (ESI) m/z 880.8 (M−H)⁻.

Example 52F tert-butyl (7R,16R)-1-bromo-19,23-dichloro-16-(hydroxymethyl)-20,22-dimethyl-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 1W, substituting Example 52E for Example 1V. MS (ESI) m/z 843.1 (M+H)⁺.

Example 52G tert-butyl (7R,16S)-1-bromo-19,23-dichloro-20,22-dimethyl-16-{[(4-methylbenzene-1-sulfonyl)oxy]methyl}-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 1X, substituting Example 52F for Example 1W. MS (ESI) m/z 997.0 (M+H)⁺.

Example 52H tert-butyl (7R,16R)-1-bromo-19,23-dichloro-20,22-dimethyl-16-[(4-methylpiperazin-1-yl)methyl]-10-{[2-(trimethylsilyl)ethoxy]methoxy}-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 1Y, substituting Example 52G for Example 1X. MS (ESI) m/z 925.4 (M+H)⁺.

Example 512I tert-butyl (7R,16R)-1-bromo-19,23-dichloro-10-hydroxy-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate The title compound was prepared as described in Example 32Q, substituting Example 52H for Example 32P. MS (ESI) m/z 796.0 (M+H)⁺.

Example 52J tert-butyl (7R,16R)-19,23-dichloro-1-bromo-10-({2-[(1R,4r)-4-{[(2R)-1,4-dioxan-2-yl]methoxy}cyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate A microwave vial in a glove box was charged with Example 52I (200 mg) and Example 9D (116 mg). Degassed tetrahydrofuran (1 mL) and toluene (1 mL) were added. In a separate vial N,N,N',N'-tetramethylazodicarboxamide (152 mg) and triphenylphosphine (231 mg) were dissolved in degassed tetrahydrofuran (1 mL) and toluene (1 mL). The resulting solution was stirred for 5 minutes. The solutions were combined, and the mixture stirred for 4 hours at ambient temperature and for 20 hours at 50° C. The crude mixture was concentrated and the residue was purified by chromatography on silica gel using an ISCO CombiFlash® Companion MPLC (12 g RediSep® Gold column, eluting with 0-20% dichloromethane:methanol) to provide the title compound. MS (APCI) m/z 1083.3 (M+H)⁺.

Example 52K tert-butyl (7R,16R)-19,23-dichloro-1-cyclobutyl-10-({2-[(1R,4r)-4-{[(2R)-1,4-dioxan-2-yl]methoxy}cyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylate In a microwave vial Example 52J (45 mg) and dichloro[1,3-bis(2,6-di-3-pentylphenyl)-imidazole-2-ylidene](3-chloropyridyl)palladium (II) (3 mg) were degassed for 10 minutes with nitrogen. Toluene (1 mL, degassed with nitrogen) was added. The mixture was cooled to 5° C., dicyclobutylzinc (0.5 mL, 0.25 molar in tetrahydrofuran) was added and the mixture was stirred for 20 hours at ambient temperature. Water (5 mL) was added, the mixture extracted twice with ethyl acetate (20 mL), and the combined organic layers washed with brine, dried over magnesium sulfate, filtered and concentrated in vacuo. Purification by chromatography on silica gel using an ISCO CombiFlash® Companion MPLC (4 g Chromabond® silica gel column, eluting with 0-10% dichloromethane/methanol) provided the title compound. MS (APCI) m/z 1059.4 (M+H)⁺.

Example 52L (7R,16R)-19,23-dichloro-1-cyclobutyl-10-({2-[(1R,4r)-4-{[(2R)-1,4-dioxan-2-yl]methoxy}cyclohexyl]pyrimidin-4-yl}methoxy)-20,22-dimethyl-16-[(4-methylpiperazin-1-yl)methyl]-7,8,15,16-tetrahydro-18,21-etheno-13,9-(metheno)-6,14,17-trioxa-2-thia-3,5-diazacyclononadeca[1,2,3-cd]indene-7-carboxylic acid The title compound was prepared as described in Example 18S by replacing Example 18R with Example 52K. Purification by HPLC (Waters XBridge C8 150×19 mm, 5 μm column, gradient 5-100% acetonitrile+0.2% ammonium hydroxide in water+0.2% ammonium hydroxide) provided the title compound. ¹H NMR (600 MHz, dimethylsulfoxide-d$_6$) δ ppm 8.70 (d, 1H), 8.60 (s, 1H), 7.43 (d, 1H), 6.79 (d, 1H), 6.69 (m, 1H), 6.15 (bs, 1H), 5.92 (bs, 1H), 5.11 (d, 1H), 5.03 (d, 1H), 4.93 (s, 1H), 4.48 (m, 2H), 3.71 (m, 2H), 3.63-3.54 (m, 2H), 3.44-3.24 (m, 6H), 2.83 (d, 1H), 2.76 (m, 1H), 2.74-2.67 (m, 2H), 2.55-2.30 (m, 9H), 2.18 (s, 3H), 2.11-1.93 (m, 8H), 1.86 (m, 1H), 1.81 (s, 3H), 1.73 (m, 1H), 1.63-1.54 (m, 2H), 1.31-1.21 (m, 5H). MS (APCI) m/z 1003.4 (M+H)$^+$.

Example 53

(7R,16R)-19,23-dichloro-10-{[3-{[(2S)-1,4-dioxan-2-yl]methoxy}-6-(2-methoxyphenyl)pyridin-2-yl]methoxy}-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 53A 3-hydroxy-6-(2-methoxyphenyl)picolinic acid 2-(2-Methoxyphenyl)-4,4,5,5-tetramethyl-1,3,2-dioxaborolane (524 mg), methyl 6-chloro-3-hydroxypicolinate (400 mg) and 1,1'-bis(diphenylphosphino)ferrocene-palladium(II)dichloride dichloromethane complex (139 mg) were combined and flushed with argon for 5 minutes. 1,4-Dioxane (11 mL, degassed with argon) and aqueous sodium carbonate solution (2 M, 3.20 mL, degassed with argon) was added. The reaction mixture was heated at 120° C. in a Biotage® Initiator microwave reactor for 4 hours. The reaction mixture was diluted with dichloromethane and washed with water. The aqueous layer was washed with dichloromethane (twice) and acidified with aqueous hydrochloric acid (1 M) to pH 2. The aqueous layer was extracted with dichloromethane (three times). The organic layer was dried by a PTS-cartridge and concentrated to yield the title compound. MS (ESI) m, 246.4 (M+H)$^+$.

Example 53B methyl 3-hydroxy-6-(2-methoxyphenyl)picolinate

Example 53B (600 mg) was added to methanol (5.0 mL). Sulfuric acid (3.0 mL) was carefully added dropwise. The reaction mixture was stirred at 100° C. in a CEM microwave reactor for 16 hours. The reaction mixture was carefully poured into ice-water. The aqueous phase was extracted with dichloromethane (seven times). The organic layer was dried by a PTS-cartridge. Purification was performed on a silica gel column (12 g, 0-30% methanol in dichloromethane). The pure fractions were combined and the solvents were removed under reduced pressure to provide the title compound. MS (ESI) m/z 260.2 (M+H)$^+$.

Example 53C methyl (S)-3-((1,4-dioxan-2-yl)methoxy)-6-(2-methoxyphenyl)picolinate Example 53B (150 mg) and cesium carbonate (566 mg) were suspended in N,N-dimethyl formamide (5.0 mL). (S)-(1,4-dioxan-2-yl)methyl 4-methylbenzenesulfonate (284 mg) was added. The reaction mixture was stirred at 25° C. for 2 days. Additional (S)-(1,4-dioxan-2-yl)methyl 4-methylbenzenesulfonate (284 mg) and cesium carbonate (566 mg) were added and the reaction mixture was stirred overnight at room temperature. The reaction mixture was diluted with water and the phases were separated. The aqueous layer was extracted with dichloromethane (three times) and ethyl acetate (three times). The combined organic phases were dried over magnesium sulfate, filtered, and concentrated. Purification was performed on a silica gel column (4 g, 0-23% methanol in dichloromethane), followed by a second purification (4 g, 0-50% ethyl acetate in n-heptane). The desired fractions were combined and the solvents were removed under reduced pressure to provide the title compound. MS (APCI) m/z 360.2 (M+H)$^+$.

Example 53D (S)-(3-((1,4-dioxan-2-yl)methoxy)-6-(2-methoxyphenyl)pyridin-2-yl)methanol Example 53C (67 mg) was dissolved in tetrahydrofuran (2.0 mL) and cooled by an ice-bath to 0° C. Lithium aluminum hydride (1M in tetrahydrofuran, 0.38 mL) was added dropwise. The reaction mixture was stirred for 10 minutes while warming up to room temperature. The reaction mixture was diluted with dichloromethane and water. The phases were separated. The organic phase was dried over sodium sulfate, filtrated and concentrated. Purification of the residue was performed on a silica gel column (4 g, 0-30% methanol in dichloromethane). The pure fractions were combined and the solvents were removed under reduced pressure to provide the title compound. MS (APCI) m/z 332.1 (M+H)$^+$.

Example 53E tert-butyl (7R,16R)-19,23-dichloro-10-{[3-{[(2S)-1,4-dioxan-2-yl]methoxy}-6-(2-methoxyphenyl)pyridin-2-yl]methoxy}-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylate Example 53D (20 mg), Example 1Z (25 mg), triphenylphosphine (28 mg) and N,N,N',N'-tetramethylazodicarboxamide (19 mg) were combined and flushed with argon for 15 minutes. Toluene (0.7 mL, flushed with argon) was added and the reaction mixture was stirred overnight at room temperature. The reaction mixture was concentrated. Purification was performed on a silica gel column (4 g, 0-30% methanol in dichloromethane). The pure fractions were combined and the solvents were removed under reduced pressure to provide the title compound. MS (APCI) m/z 1122.2 (M+H)$^+$.

Example 53F (7R,16R)-19,23-dichloro-10-{[3-{[(2)-1,4-dioxan-2-yl]methoxy}-6-(2-methoxyphenyl)pyridin-2-yl]methoxy}-1-(4-fluorophenyl)-20,22-dimethyl-16-[(4-methylpiperazin-1-yl)methyl]-7,8,15,16-tetrahydro-18,21-etheno-9,13-(metheno)-6,14,17-trioxa-2-thia-3,5-diazacyclononadeca[1,2,3-cd]indene-7-carboxylic acid Example 53E (57 mg) was dissolved in dichloromethane, trifluoroacetic acid (0.39 mL) was added, and the reaction mixture was stirred overnight at room temperature. All volatiles were evaporated and the crude material was purified by HPLC (Waters XSelect CSH C18 30×150 mm 5 μm column, gradient 5-100% acetonitrile+0.1% TFA in water+ 0.1% TFA) to provide the title compound. $^1$H NMR (600 MHz, dimethylsulfoxide-$d_6$) δ ppm 8.71 (s, 1H), 7.82 (d 1H), 7.71 (dd, 1H), 7.53 (d, 1H), 7.34 (ddd, 1H), 7.21-7.18 (m, 2H), 7.14-7.11 (m, 3H), 7.04-6.99 (m, 2H), 6.74 (dd, 1H), 6.17 (dd, 1H), 5.78 (b, 1H), 5.14 (d 1H), 5.08 (d, 1H), 4.95-4.91 (m, 1H), 4.48-4.40 (m, 2H), 4.10 (qd, 2H), 3.88-3.84 (m, 1H), 3.82 (s, 3H), 3.81-3.80 (m, 1H), 3.75-3.72 (m, 1H), 3.63-3.57 (m, 2H), 3.48-3.40 (m, 3H), 2.88 (dd, 1H), 2.71-2.63 (m, 2H), 2.52-2.29 (m, 8H), 2.18 (s, 3H), 1.94 (s, 3H), 1.92 (s, 3H). MS (APCI) m/z 1066.1 (M+H)$^+$.

BIOLOGICAL EXAMPLES

Exemplary MCL-1 Inhibitors Bind MCL-1

The ability of the exemplary MCL-1 inhibitors of Examples 1 through 151 to bind MCL-1 was demonstrated using the Time Resolved-Fluorescence Resonance Energy Transfer (TR-FRET) Assay. Tb-anti-GST antibody was purchased from Invitrogen (Catalog No. PV4216).

Probe Synthesis

Reagents

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluroniumn hexafluorophosphate (HBTU), N-hydroxybenzotriazole (HOBt) and piperidine were obtained from Applied Biosystems, Inc. (ABI), Foster City, Calif., or American Bioanalytical, Natick, Mass.

Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif.

The peptide synthesis resin (Fmoc-Rink amide MBHA resin) and Fmoc-Lys(Mtt)-OH were obtained from Novabiochem, San Diego, Calif.

Single-isomer 6-carboxyfluorescein succinimidyl ester (6-FAM-NHS) was obtained from Anaspec.

Trifluoroacetic acid (TFA) was obtained from Oakwood Products, West Columbia, S.C.

Thioanisole, phenol, triisopropylsilane (TIS), 3,6-dioxa-1,8-octanedithiol (DODT) and isopropanol were obtained from Aldrich Chemical Co., Milwaukee, Wis.

Matrix-assisted laser desorption ionization mass-spectra (MALDI-MS) were recorded on an Applied Biosystems Voyager DE-PRO MS).

Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of N,N-dimethylformamide (DMF) was flowed through the bed over 15 minutes. The resin was then washed thrice with DMF and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% DIEA/DMF and stirred or shaken at ambient temperature overnight. When complete, the resin was drained, washed thrice with DMF, thrice with (lx dichloromethane and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, Calif.) on a 4.6×250 mm YMC column packed with ODS-AQ 5 μm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/minute.

Synthesis of Probe F-Bak

Peptide probe F-bak, which binds MCL-1, was synthesized as described below. Probe F-Bak is acetylated at the N-terminus, amidated at the C-terminus and has the amino acid sequence GQVGRQLAIIGDKINR (SEQ ID NO:1). It is fluoresceinated at the lysine residue (K) with 6-FAM. Probe F-Bak can be abbreviated as follows: acetvl-GQVGRQLAIIGDK(6-FAM)INR-NH$_2$.

To make probe F-Bak. Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product. This product was purified by RP-HPLC. Fractions across the main peak were tested by analytical RP-HPLC, and the pure fractions were isolated and lyophilized, with the major peak providing the title compound (0.0802 g); MALDI-MS m/z=2137.1 [(M+H)].

Alternative Synthesis of Peptide Probe F-Bak

In an alternative method, the protected peptide was assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in DMF and confirmed complete by ninhydrin testing. The peptide was cleaved from the resin and side-chains deprotected by treating with 80:5:5:5:2.5:2.5 TFA/water/phenol/thioanisole/triisopropylsilane:3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)$^+$).

Time Resolved-Fluorescence Resonance Energy Transfer (TR-FRET) Assay

The ability of exemplary MCL-1 inhibitors Example 1 to Example 3 to compete with probe F-Bak for binding MCL-1 was demonstrated using a Time Resolved Fluorescence Resonance Energy Transfer (TR-FRET) binding assay.

Method

For the assay, an acoustic dispenser was used to prepare dilution series from 10 mM test compounds in 100% DMSO and directly transfer 160 nL into low volume 384-well assay plates. 8 µL of a protein/probe/antibody mix was then added to each well resulting in final concentrations listed below:
Test compound: 11 three-fold dilutions beginning at 25 µM

| Protein: | GST-MCL-1 | 1 nM |
|---|---|---|
| Antibody | Tb-anti-GST | 1 nM |
| Probe: | F-Bak | 100 nM |

The samples were then mixed on a shaker for 1 minute and incubated for an additional 2 hours at room temperature. For each assay plate, a probe/antibody and protein/antibody/probe mixture were included as a negative and a positive control, respectively. Fluorescence was measured on the Envision (Perkin Elmer) using a 340/35 nm excitation filter and 520/525 (F-Bak) and 495/510 nm (Tb-labeled anti-his antibody) emission filters. Dissociation constants ($K_i$) were determined using Wang's equation (Wang, 1995, *FEBS Lett.* 360:111-114). The TR-FRET assay can be performed in the presence of varying concentrations of human serum (HS) or fetal bovine serum (FBS). Compounds were tested both without HS and in the presence of 10% HS.

Results

The results of binding assays ($K_i$ in nanomolar) are provided in Table 2, below, and demonstrate the ability of compounds of the disclosure to bind MCL-1 protein.

TABLE 2

TR-FRET MCL-1 Binding Data

| Example | MCL-1 Binding $K_i$ (nM) | MCL-1 Binding $K_i$ (nM, 10% HS) |
|---|---|---|
| 1 | 0.042 | 0.582 |
| 2 | 0.052 | 1.04 |
| 3 | 0.033 | 0.365 |
| 4 | 0.055 | 0.32 |
| 5 | 0.048 | 0.71 |
| 6 | 0.926 | 6.09 |
| 7 | 0.036 | 0.92 |
| 8 | 0.194 | 2.27 |
| 9 | 0.005 | 0.10 |
| 10 | 0.346 | 3.07 |
| 11 | 0.184 | 0.62 |
| 12 | 0.076 | 0.61 |
| 13 | 0.079 | 1.07 |
| 14 | 0.006 | 0.09 |
| 15 | 0.013 | 0.15 |
| 16 | 0.048 | 0.83 |
| 17 | 0.090 | 4.11 |
| 18 | 0.111 | 0.24 |
| 19 | 0.156 | 0.64 |
| 20 | 0.058 | 0.47 |
| 21 | 0.011 | 1.01 |
| 22 | 0.016 | 0.89 |
| 23 | 4.980 | 41.00 |
| 24 | 0.038 | 0.38 |
| 25 | 0.003 | 0.19 |
| 26 | 0.104 | 1.74 |
| 27 | 0.008 | 0.02 |
| 28 | 0.017 | 0.18 |
| 29 | 0.011 | 0.55 |
| 30 | 0.015 | 0.16 |
| 31 | 0.373 | 5.27 |
| 32 | 0.022 | 0.27 |
| 33 | 0.023 | 0.30 |
| 34 | 0.030 | 0.54 |
| 35 | 0.027 | 0.52 |
| 36 | 0.001 | 0.05 |
| 37 | 0.051 | 0.63 |
| 38 | 0.036 | 0.63 |
| 39 | 0.004 | 0.06 |
| 40 | 0.014 | 0.63 |
| 41 | 0.009 | 0.14 |
| 42 | 0.018 | 0.24 |
| 43 | 0.020 | 0.18 |
| 44 | 0.020 | 0.16 |
| 45 | 0.012 | 0.16 |
| 46 | 0.022 | 0.24 |
| 47 | 0.0133 | 0.521 |
| 48 | 0.026 | 0.648 |
| 49 | <0.01 | 0.128 |
| 50 | 0.022 | 0.249 |
| 51 | <0.01 | 0.131 |
| 52 | <0.01 | 0.72 |
| 53 | 13.7 | 114 |

NT = not tested,
NV = not valid

Exemplary MCL-1 Inhibitors Demonstrate In Vitro Efficacy in Tumor Cell Viability Assays The in vitro efficacy of exemplary MCL-1 inhibitors can be determined in cell-based killing assays using a variety of cell lines and mouse tumor models. For example, their activity on cell viability can be assessed on a panel of cultured tumorigenic and non-tumorigenic cell lines, as well as primary mouse or human cell populations. MCL-1 inhibitory activity of exemplary MCL-1 inhibitors was confirmed in a cell viability assay with AMO-1 and NCI-H929 human multiple myeloma tumor cell lines.

Method

In one exemplary set of conditions, NCI-H929 or AMO-1 (ATCC. Manassas, Va.) were plated 4.000 cells per well in 384-well tissue culture plates (Corning. Corning, N.Y.) in a total volume of 25 μL RPMI tissue culture medium supplemented with 10% fetal bovine serum (Sigma-Aldrich, St. Louis, Mo.) and treated with a 3-fold serial dilution of the compounds of interest with a Labcyte Echo from a final concentration of 10 μM to 0.0005 μM. Each concentration was tested in duplicate at least 3 independent times. A luminescent signal proportional to the number of viable cells following 24 hours of compound treatment was determined using the CellTiter-Glo® Luminescent Cell Viability Assay according to the manufacturer's recommendations (Promega Corp., Madison, Wis.). The plates were read in a Perkin Elmer Envision using a Luminescence protocol. To generate dose response curves the data is normalized to percent viability by setting the averages of the staurosporine (10 uM) and DMSO only control wells to 0% and (00)% viability respectively. The IC50 values for the compounds are generated by fitting the normalized data with Accelrys Assay Explorer 3.3 to a sigmoidal curve model using linear regression. $Y=(100*x^n)/(K^n+x^n)$, where Y is the measured response, x is the compound concentration, n is the Hill Slope and K is the IC50 and the lower and higher asymptotes are constrained to 0 and 100 respectively.

Results

The results of AMO-1 and H929 cell viability assays ($IC_0$ in nanomolar) carried out in the presence of 10% FBS for exemplary MCL-1 inhibitors are provided in Table 3, below. The results demonstrate the ability of compounds of the disclosure to potently inhibit the growth of human tumor cells in vitro.

TABLE 3

MCL-1 Inhibitor In Vitro Cell Efficacy Data

| EXAMPLE | AMO-1 Viability $IC_{50}$ (μM, 10% FBS) | H929 Viability $IC_{50}$ (μM, 10% FBS) |
|---|---|---|
| 1 | 0.00031 | 0.00502 |
| 2 | 0.00019 | 0.0033 |
| 3 | 0.00026 | 0.0037 |
| 4 | 0.00273 | 0.00572 |
| 5 | 0.000178 | 0.00037 |
| 6 | 0.000135 | 0.000359 |
| 7 | 0.000171 | 0.000406 |
| 8 | 0.00086 | 0.00176 |
| 9 | 0.000165 | 0.000245 |
| 10 | 0.000502 | 0.00217 |
| 11 | 0.000188 | 0.000545 |
| 12 | 0.00104 | 0.00208 |
| 13 | 0.00126 | 0.00311 |
| 14 | 0.000114 | 0.000236 |
| 15 | 0.000156 | 0.000294 |
| 16 | 0.000245 | 0.000592 |
| 17 | 0.0010 | 0.00565 |
| 18 | 0.00612 | 0.00995 |
| 19 | 0.00974 | 0.0152 |
| 20 | 0.000286 | 0.000513 |
| 21 | 0.0000488 | 0.000168 |
| 22 | 0.000142 | 0.000333 |
| 23 | 0.00315 | 0.00849 |
| 24 | 0.000687 | 0.00197 |
| 25 | 0.000629 | 0.00188 |
| 26 | 0.00020 | 0.000241 |
| 27 | 0.000435 | 0.0015 |
| 28 | 0.000211 | 0.000337 |
| 29 | 0.0000812 | 0.000346 |
| 30 | 0.000285 | 0.000974 |
| 31 | 0.00419 | 0.011 |
| 32 | 0.00017 | 0.000296 |
| 33 | 0.000222 | 0.000586 |
| 34 | 0.000235 | 0.0010 |
| 35 | 0.000261 | 0.00111 |
| 36 | 0.0000488 | 0.000183 |
| 37 | 0.000187 | 0.00053 |
| 38 | 0.000267 | 0.000748 |
| 39 | 0.000235 | 0.000239 |
| 40 | 0.000352 | 0.000271 |
| 41 | 0.000589 | 0.000595 |
| 42 | 0.000404 | 0.000356 |
| 43 | 0.000346 | 0.000365 |
| 44 | 0.000268 | 0.000286 |
| 45 | 0.000249 | 0.000258 |
| 46 | 0.000579 | 0.000418 |
| 47 | 0.000463 | 0.000344 |
| 48 | 0.000641 | 0.000593 |
| 49 | 0.000172 | 0.000314 |
| 50 | 0.000249 | 0.000255 |
| 51 | 0.000267 | 0.000299 |
| 52 | 0.000448 | 0.00118 |
| 53 | 0.311 | >1.0 |

NT = not tested,
NV = not valid

The ability of certain exemplary compounds of the present disclosure to inhibit the growth of tumor cells in mice was demonstrated in xenograft models derived from a human multiple myeloma cell line. AMO-1.

Evaluation of Efficacy in Xenograft Models Methods

AMO-1 cells were obtained from the Deutsche Sammlung von Microorganismen und Zellkulturen (DSMZ, Braunschweig, Germany). The cells were cultured as monolayers in RPMI-1640 culture media (Invitrogen, Carlsbad, Calif.) that was supplemented with 10% Fetal Bovine Serum (FBS, Hyclone, Logan, Utah). To generate xenografts, $5 \times 10^6$ viable cells were inoculated subcutaneously into the right flank of immune deficient female SCID/bg mice (Charles River Laboratories. Wilmington, Mass.) respectively. The injection volume was 0.2 mL and composed of a 1:1 mixture of S MEM and Matrigel (BD, Franklin Lakes, N.J.). Tumors were size matched at approximately 200 mm³. MCL-1 inhibitors were formulated in 5% DMSO, 20% cremaphor EL and 75% D5W for injection and injected intraperitoneally. Injection volume did not exceed 200 μL. Alternatively, MCL-1 inhibitors were formulated in 5% DMSO, 10% cremaphor and 85% D5W for injection and injected intravenously. Injection volume did not exceed 200 μL. Therapy began within 24 hours after size matching of the tumors. Mice weighed approximately 21 g at the onset of therapy. Tumor volume was estimated two to three times weekly. Measurements of the length (L) and width (W) of the tumor were taken via electronic caliper and the volume was calculated according to the following equation: $V=L \times W^2/2$. Mice were euthanized when tumor volume reached 3,000 mm3 or skin ulcerations occurred. Eight mice were housed per cage. Food and water were available ad libitum. Mice were acclimated to the animal facilities for a period of at least one week prior to commencement of experiments. Animals were tested in the light phase of a 12-hour light: 12-hour dark schedule (lights on at 06:00 hours).

To refer to efficacy of therapeutic agents, parameters of amplitude ($TGI_{max}$), durability (TGD) of therapeutic response are used. $TGI_{max}$ is the maximum tumor growth inhibition during the experiment. Tumor growth inhibition is calculated by $100*(1-T_v/C_v)$ where $T_v$ and $C_v$ are the mean tumor volumes of the treated and control groups, respectively. TGD or tumor growth delay is the extended time of a treated tumor needed to reach a volume of 1 cm³ relative to the control group. TGD is calculated by $100*(T_t/C_t-1)$ where $T_t$ and $C_t$ are the median time periods to reach 1 cm³ of the treated and control groups, respectively.

Results

As shown in Tables 4-6, compounds of the present disclosure are efficacious in an AMO-1 xenograft model of multiple myeloma, rendering significant tumor growth inhibition and tumor growth delay after intraperitoneal (IP) or intravenous (IV) dosing of drug.

TABLE 4

In vivo Efficacy of MCL-1 Inhibitors in AMO-1 Xenograft Model

| Treatment | Dose (mg/kg/day) | Route/ Regimen | $TGI_{max}$ (%) | TGD (%) |
|---|---|---|---|---|
| Vehicle | 0 | IP[(a)]/QDx1 | 0 | 0 |
| Example 1 | 25 | IP/QDx1 | 95* | 133* |
| Example 3 | 25 | IP/QDx1 | 75* | 58* |

[(a)]IP Formulation = 5% DMSO, 20% cremophor EL, 75% D5W
*p < 0.05 as compared to control treatment
7 mice per treatment group

TABLE 5

In vivo Efficacy of MCL-1 Inhibitors in AMO-1 Xenograft Model

| Treatment | Dose (mg/kg/day) | Route/ Regimen | $TGI_{max}$ (%) | TGD (%) |
|---|---|---|---|---|
| Vehicle | 0 | IP[(a)]/QDx1 | 0 | 0 |
| Example 7 | 25 | IP/QDx1 | 99* | 477* |
| Example 8 | 25 | IP/QDx1 | 79* | 46* |

[(a)]IP Formulation = 5% DMSO, 20% cremophor EL, 75% D5W
*p < 0.05 as compared to control treatment
7 mice per treatment group

TABLE 6

In vivo Efficacy of MCL-1 Inhibitors in AMO-1 Xenograft Model

| Treatment | Dose (mg/kg/day) | Route/ Regimen | $TGI_{max}$ (%) | TGD (%) |
|---|---|---|---|---|
| Vehicle | 0 | IV[(a)]/QDx1 | 0 | 0 |
| Example 28 | 6.25 | IV/QDx1 | 89* | 233* |
| Example 30 | 6.25 | IV/QDx1 | 79* | 133* |
| Example 44 | 6.25 | IV/QDx1 | 88 | 156* |
| Example 51 | 6.25 | IV/QDx1 | 74* | 111* |

[(a)]IP Formulation = 5% DMSO, 10% cremophor EL, 85% D5W
*p < 0.05 as compared to control treatment
7 mice per treatment group It is understood that the foregoing detailed description and accompanying examples are merely illustrative and are not to be taken as limitations upon the scope of the present disclosure, which is defined solely by the appended claims and their equivalents. Various changes and modifications to the disclosed embodiments will be apparent to those skilled in the art. All publications, patents, and patent applications cited herein are hereby incorporated by reference in their entirety for all purposes.

We claim:
1. A compound having the structure:
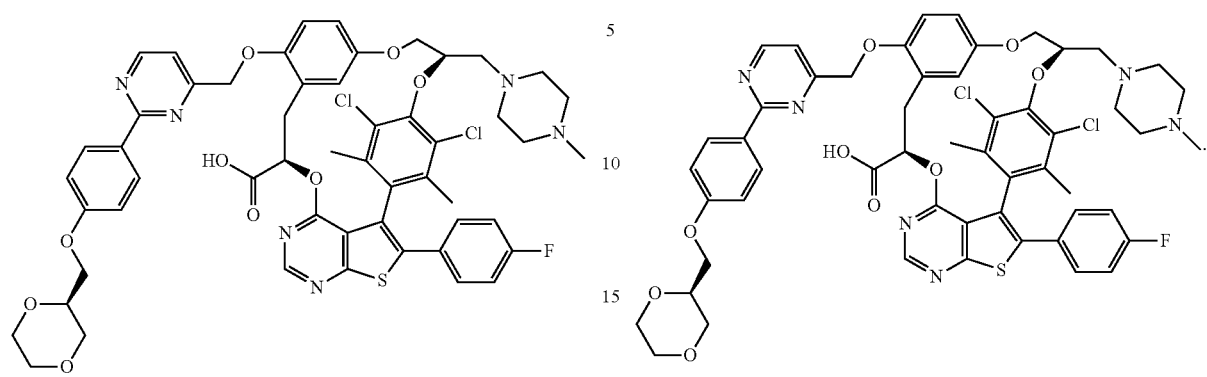
or a pharmaceutically acceptable salt thereof.
2. A compound having the structure:
* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: FLUORESCEINATED WITH 6-FAM
<220> FEATURE:
<221> NAME/KEY: MOD_RES
<222> LOCATION: (16)..(16)
<223> OTHER INFORMATION: AMIDATION

<400> SEQUENCE: 1

Gly Gln Val Gly Arg Gln Leu Ala Ile Ile Gly Asp Lys Ile Asn Arg
1               5                   10                  15
```